United States Patent
Xiong et al.

(10) Patent No.: US 9,714,276 B2
(45) Date of Patent: Jul. 25, 2017

(54) GROWTH DIFFERENTIATION FACTOR 15 (GDF-15) POLYPEPTIDES

(71) Applicant: AMGEN INC, Thousand Oaks, CA (US)

(72) Inventors: Yumei Xiong, San Bruno, CA (US); Yi Zhang, Palo Alto, CA (US); Jackie Zeqi Sheng, Thousand Oaks, CA (US); Agnes Eva Hamburger, Newbury Park, CA (US); Murielle Veniant-Ellison, Thousand Oaks, CA (US); Grant Shimamoto, Westlake Village, CA (US); Xiaoshan Min, Burlingame, CA (US); Zhulun Wang, Palo Alto, CA (US); Jie Tang, Palo Alto, CA (US); Gunasekaran Kannan, Newbury Park, CA (US); Kenneth W. Walker, Newbury Park, CA (US); Bryan Lemon, Mountain View, CA (US)

(73) Assignee: Amgen Inc., Thousand Oaks, CA (US)

( * ) Notice: Subject to any disclaimer, the term of this patent is extended or adjusted under 35 U.S.C. 154(b) by 98 days.

(21) Appl. No.: 14/374,885

(22) PCT Filed: Jan. 28, 2013

(86) PCT No.: PCT/US2013/023465
§ 371 (c)(1),
(2) Date: Jul. 25, 2014

(87) PCT Pub. No.: WO2013/113008
PCT Pub. Date: Aug. 1, 2013

(65) Prior Publication Data
US 2014/0378665 A1    Dec. 25, 2014

Related U.S. Application Data

(60) Provisional application No. 61/591,161, filed on Jan. 26, 2012.

(51) Int. Cl.
C07K 14/00 (2006.01)
C07K 14/475 (2006.01)
A61K 39/00 (2006.01)
C12N 15/62 (2006.01)

(52) U.S. Cl.
CPC ........ *C07K 14/475* (2013.01); *A61K 39/0005* (2013.01); *A61K 2039/6056* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell | |
| 6,737,056 B1 | 5/2004 | Presta | |
| 8,338,569 B2* | 12/2012 | Marshall et al. | 530/351 |
| 8,372,952 B2* | 2/2013 | Smith et al. | 530/350 |
| 9,248,181 B2* | 2/2016 | De Kruif et al. | |
| 2006/0275283 A1* | 12/2006 | van Vlijmen | C07K 16/00 424/130.1 |
| 2010/0087627 A1* | 4/2010 | Marshall et al. | 530/362 |
| 2010/0278843 A1 | 11/2010 | Breit et al. | |
| 2011/0150901 A1* | 6/2011 | Smith et al. | 424/158.1 |
| 2011/0195067 A1 | 8/2011 | Arnason et al. | |
| 2011/0229472 A1 | 9/2011 | Min et al. | |
| 2011/0236375 A1 | 9/2011 | Lazar et al. | |
| 2013/0336981 A1* | 12/2013 | de Kruif et al. | 424/136.1 |
| 2015/0139996 A1* | 5/2015 | De Kruif et al. | 424/136.1 |

FOREIGN PATENT DOCUMENTS

| | | |
|---|---|---|
| EP | 0036776 A2 | 9/1981 |
| EP | 0058481 A1 | 8/1982 |
| EP | 0088046 A2 | 9/1983 |
| EP | 0133988 A2 | 3/1985 |
| EP | 0143949 B1 | 10/1988 |
| EP | 2330197 A2 | 6/2011 |
| WO | 93/15722 A1 | 8/1993 |
| WO | 2005/077981 A2 | 8/2005 |
| WO | 2007/041635 A2 | 4/2007 |
| WO | 2009/089004 A1 | 7/2009 |
| WO | WO2010/017198 * | 2/2010 |
| WO | 2011/063348 A1 | 5/2011 |
| WO | 2012/125850 A1 | 9/2012 |
| WO | 2013/148117 A1 | 10/2013 |
| WO | WO2013/157953 * | 10/2013 |

(Continued)

OTHER PUBLICATIONS

Sino Biological Inc. (http://www.sinobiological.com/GDF-15-Protein-g-570.html; available May 1, 2010.*
Lo et al. (2005, Protein Engineering, Design & Selection 18:1-10).*
Alain et al., Therapeutic Fc-fusion proteins and peptides as successful alternatives to antibodies, MABS, 2011, 3:5, 415-416.
American Diabetes Association Standards of Medical Care in Diabetes Care—2011.
Ansel et al., Pharmaceutical Dosage Forms & Drug Delivery Systems, 7th ed. 2000.
Aulton, Pharmaceutics: The Science of Dosage Form Design, Churchill Livingstone, New York, 1988.
Ausubel et al., eds., Current Protocols in Molecular Biology, Green Publishers Inc. and Wiley and Sons, 1994.
Baek SJ, J. Biol Chemistry, 2001, 276:33384-33392.

(Continued)

*Primary Examiner* — Elizabeth C Kemmerer

(57) ABSTRACT

GDF15 polypeptides, constructs comprising GDF15, and mutants thereof are provided. In various embodiments the GDF15 polypeptides, constructs comprising GDF15, and mutants thereof, can be of use in the treatment or ameliorating a metabolic disorder. In various embodiments the metabolic disease or disorder is type 2 diabetes, obesity, dyslipidemia, elevated glucose levels, elevated insulin levels and diabetic nephropathy.

18 Claims, 68 Drawing Sheets

(56) References Cited

FOREIGN PATENT DOCUMENTS

WO    WO2013/157954    * 10/2013

OTHER PUBLICATIONS

Baek SJ, Gastroenterology, 2006, 131:1553-1560.
Bauskin AR, EMBO J., 2000, 19:2212-2220; NCBI.
Berge et al., "Pharmaceutical Salts", J. Pharm. Science, 1977, 6661, 1-19.
Bootcov MR, 1997, Proc Natl Acad Sci 94:11514-11519.
Bottner M ,Gene, 1999, 237:105-11.
Carrillo et al., Siam J. Applied Math., 1988, 48:1073.
Cekanova M, "Nonsteroidal anti-inflammatory drug-activated gene-1 expression inhibits urethane-induced pulmonary tumorigenesis in transgenic mice", 2009, Cancer Prev Res 2:5, 450-458.
Computational Molecular Biology, Lesk, A. M., ed., 1988, New York: Oxford University Press; Biocomputing Informatics and Genome Projects, Smith, D. W., ed., 1993, New York: Academic Press.
Computer Analysis of Sequence Data, Part I, (Griffin, A. M., and Griffin, H. G., eds., 1994, New Jersey: Humana Press; von Heinje, G., 1987.
Czajkowsky, et al., "Fc-fusion proteins: new developments and future perspectrives". EMBO Mol Med, Epub, 2012 4(10), 1015-1028.
Current Protocols in Molecular Biology (Ausubel et al., eds., Green Publishers Inc. and Wiley and Sons 1994.
Dayhoff et al., Atlas of Protein Sequence and Structure, 1978, 5:345-352.
Devereux et al., Nucl. Acid Res. 1984, 12:387.
Epstein et al., Proc. Natl. Acad. Sci. US, 1985, 82: 3688-3692.
Fairlie WD, Gene, 2000, 254: 67-76.
Freiberg & Zhu, Int. J. Pharm., 2004, 282:1-18.
Goodman and Gilman, Eds., The Pharmacological Basis of Therapeutics, 9th ed., 1996.
Gribskov, M. and Devereux, J., eds., Sequence Analysis Primer, 1991, New York: M. Stockton Press.
Griffin, A. M., and Griffin, H. G., eds., Computer Analysis of Sequence Data, Part I, 1994, New Jersey: Humana Press.
Henikoff et al., Proc. Natl. Acad. Sci. USA 1992, 89:10915-10919.
Hromas R., Biochim Biophys Acta. 1997, 1354:40-44.
Jenson, et al. "A novel Fc gamma receptor ligand augments humoral responses by targeting antigen to Fc gamma receptors", Eur. J. Immunol, 2007, 37:4, 1139-1148.
Johnen H, Nat Med., 2007, 11:1333-1340.
Katoh M, Int J Mol Med, 2006. 17:951-955.
Kempf T, "The Transforming Growth Factor-{szligbeta} Superfamily Member Growth-Differentiation Factor-15 Protects the Heart From Ischemia/Reperfusion Injury", Circ Res., 2006, 98:351-360.
Langer et al., J. Biomed. Mater. Res., 1981, 15:167-277.
Langer, Chem. Tech., 1982, 12: 98-105.
Lawton LN, "Identification of a novel member of the TGF-beta superfamily highly expressed in human placenta", Gene, 1997, 203:17-26.
Lieberman et al., Pharmaceutical Dosage Forms-Disperse Systems, 1998, 2nd Ed., V3.
Mekhaiel, et al. "Polymeric human Fc-fusion proteins with modified effector functions", 2011, Sci Rep. 1:124.
Moore A.G., "The transforming growth factor-ss superfamily cytokine macrophage inhibitory cytokine-1 is present in high concentrations in the serum of pregnant women", J Clin Endocrinol Metab, 2006, 85: 4781-4788.
Needleman et al., J. Mol. Biol., 1970, 48:443-453.
Paralkar VM, "Cloning and characterization of a novel member of the transforming growth factor-beta/bone morphogenetic protein family", J. Biol. Chemistry, 1998, 273:13760- 13767.
Remington: The Science and Practice of Pharmacy, 19th edition, 1995.
Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989.
Sidman et al., Biopolymers 1983, 22: 547-56.
Smith, D. W., ed, Biocomputing Informatics and Genome Projects, 1993, New York: Academic Press.
Strelau J, "Progressive Postnatal Motoneuron Loss in Mice Lacking GDF-15", J Neuroscience, 2009, 29:13640-13648.
Tamary H, "", Blood, 2008, 112:5241-5244.
Tanno T, "High levels of GDF15 in thalassemia suppress expression of the iron regulatory protein hepcidin", Nat Med, 2007, 13:1096-1101.
Van Heeke & Schuster, "Expression of human asparagine synthetase in *Escherichia coli*", J. Biol. Chem., 1989, 264: 5503-5509.
von Heinje, G., Sequence Analysis in Molecular Biology, 1987, New York: Academic Press.
White, "Design and expression of polymeric immunoglobulin fusion proteins: a strategy for target in low-affinity Fogamma receptors", Protein Expr, Purif, 2001, 21:3, 446-455.
Wilson and Gisvolds' Textbook of Organic Medicinal and Pharmaceutical Chemistry, Delgado and Remers, Eds., 10th ed., 1998.
Wischke & Schwendeman, Int. J. Pharm., 2008, 364: 298-327.
Xu J, "GDF15/MIC-1 Functions As a Protective and Antihypertrophic Factor Released From the Myocardium in Association With SMAD Protein Activation", Circ Res., 2006, 98:342-350.
Zimmermann MB, "Iron metabolism in heterozygotes for hemoglobin E (HbE), -thalassemia 1, or -thalassemia and in compound heterozygotes for HbE/ -thalassemia", Am J Clin Nutr, 2008, 88:1026-1031.
K. Gunasekaran et al: "Enhancing Antibody 2-24 Fc Heterodimer Formation through Electrostatic Steering Effects: Applications to Bispecific Molecules and Monovalent IgG", Journal of Biological Chemistry, vol. 285, No. 25, Jun. 18, 2010 (Jun. 18, 2010), pp. 19637-19646.

* cited by examiner

Figure 2

Evaluation of GDF15 constructs in food intake assay

| Protein | ED50 (µg/kg) |
|---|---|
| DhCpmFc(-)-(G4S)4-GDF15:DhCpmFc(+) | 8.4 |
| DhCpmFc(+)-(G4S)4-GDF15:DhCpmFc(-) | 3.6 |
| DhCpmFc(-)-(G4S)4-GDF15(H6D):DhCpmFc(+) | 7.9 |
| DhCpmFc(+)-(G4S)4-GDF15(H6D):DhCpmFc(-) | 15.5 |
| DhCpmFc(+)-(G4S)4-GDF15(N3Q):DhCpmFc(-) | 7.0 |
| DhCpmFc(+)-GDF15:DhCpmFc(-) | 21.8 |
| DhCpmFc(+)-(G4)-GDF15:DhCpmFc(-) | 12.1 |
| DhCpmFc(+)-(G4S)2-GDF15:DhCpmFc(-) | 2.4 |
| DhCpmFc(+)-(G4Q)4-GDF15:DhCpmFc(-) | 16.0 |
| DhCpmFc(+)-(1K)-GDF15:DhCpmFc(-) | 10.7 |
| DhCpmFc(+)(L351C)-G4-GDF15:DhCpmFc(-)(L351C) | 53.4 |
| DhCpmFc(+)( delCP: DhCpmFc(-)-(G4S)4-GDF15:DhCpmFc(+)
hemi: Fc(G4S)8-Fc-GS(G4S)4-GDF15 delCP: DhCpmFc(-)-(G4S)4-GDF15:DhCpmFc(+)
hemi: Fc(G4S)8-Fc-GS(G4S)4-GDF15 delCP: DhCpmFc(-)-(G4S)4-GDF15:DhCpmFc(+)
hemi: Fc(G4S)8-Fc-GS(G4S)4-GDF15 delCP: DhCpmFc(-)-(G4S)4-GDF15:DhCpmFc(+)
hemi: Fc(G4S)8-Fc-GS(G4S)4-GDF15 delCP: DhCpmFc(-)-(G4S)4-GDF15:DhCpmFc(+)
hemi: Fc(G4S)8-Fc-GS(G4S)4-GDF15 delCP: DhCpmFc(−)-(G4S)4-GDF15:DhCpmFc(+)
hemi: Fc(G4S)8-Fc-GS(G4S)4-GDF15 delCP: DhCpmFc(-)-(G4S)4-GDF15:DhCpmFc(+)
hemi: Fc(G4S)8-Fc-GS(G4S)4-GDF15 delCP: DhCpmFc(-)-(G4S)4-GDF15:DhCpmFc(+)
hemi: Fc(G4S)8-Fc-GS(G4S)4-GDF15 delCP: DhCpmFc(-)-(G4S)4-GDF15:DhCpmFc(+)
CP: CpmFc(-)-(G4S)4-GDF15:CpmFc(+)

delCP: DhCpmFc(-)-(G4S)4-GDF15:DhCpmFc(+)
CP: CpmFc(-)-(G4S)4-GDF15:CpmFc(+)

delCP: DhCpmFc(-)-(G4S)4-GDF15:DhCpmFc(+)
CP: CpmFc(-)-(G4S)4-GDF15:CpmFc(+)

delCP: DhCpmFc(-)-(G4S)4-GDF15:DhCpmFc(+)
CP: CpmFc(-)-(G4S)4-GDF15:CpmFc(+)

delCP: DhCpmFc(-)-(G4S)4-GDF15:DhCpmFc(+)
CP: CpmFc(-)-(G4S)4-GDF15:CpmFc(+)

Glucose AUC – OGTT (acclimation)

Glucose AUC – OGTT (treatment, week 5)

Glucose AUC – OGTT (washout, week 8)

Insulin AUC – OGTT (acclimation)

                        SEQUENCE LISTING

<160> NUMBER OF SEQ ID NOS: 130

<210> SEQ ID NO 1
<211> LENGTH: 4
<212> TYPE: PRT
<213> ORGANISM: Unknown
<220> FEATURE:
<223> OTHER INFORMATION: Description of Unknown: Rodent
      mature GDF15 cleavage site peptide

<400> SEQUENCE: 1

Arg Gly Arg Arg
1

<210> SEQ ID NO 2
<211> LENGTH: 7
<212> TYPE: PRT
<213> ORGANISM: Homo sapiens

<400> SEQUENCE: 2

Arg Gly Arg Arg Arg Ala Arg
1               5

<210> SEQ ID NO 3
<211> LENGTH: 927
<212> TYPE: DNA
<213> ORGANISM: Homo sapiens

<400> SEQUENCE: 3
atgcccgggc aagaactcag gacggtgaat ggctctcaga tgctcctggt gttgctggtg      60
ctctcgtggc tgccgcatgg gggcgccctg tctctggccg aggcgagccg cgcaagtttc     120
ccgggaccct cagagttgca ctccgaagac tccagattcc gagagttgcg gaaacgctac     180
gaggacctgc taaccaggct gcgggccaac cagagctggg aagattcgaa caccgacctc     240
gtcccggccc ctgcagtccg gatactcacg ccagaagtgc ggctgggatc cggcggccac     300
ctgcacctgc gtatctctcg ggccgccctt cccgaggggc tccccgaggc ctcccgcctt     360
caccgggctc tgttccggct gtccccgacg gcgtcaaggt cgtgggacgt gacacgaccg     420
ctgcggcgtc agctcagcct tgcaagaccc caggcgcccg cgctgcacct gcgactgtcg     480
ccgccgccgt cgcagtcgga ccaactgctg gcagaatctt cgtccgcacg gccccagctg     540
gagttgcact tgcggccgca agccgccagg gggcgccgca gagcgcgtgc gcgcaacggg     600
gaccactgtc cgctcgggcc cgggcgttgc tgccgtctgc acacggtccg cgcgtcgctg     660
gaagacctgg gctgggccga ttgggtgctg tcgccacggg aggtgcaagt gaccatgtgc     720
atcggcgcgt gcccgagcca gttccggcg gcaaacatgc acgcgcagat caagacgagc     780
ctgcaccgcc tgaagcccga cacggtgcca gcgccctgct gcgtgcccgc cagctacaat     840
cccatggtgc tcattcaaaa gaccgacacc ggggtgtcgc tccagaccta tgatgacttg     900
ttagccaaag actgccactg catatga                                         927

<210> SEQ ID NO 4
<211> LENGTH: 308
<212> TYPE: PRT
<213> ORGANISM: Homo sapiens
```

<400> SEQUENCE: 4

```
Met Pro Gly Gln Glu Leu Arg Thr Val Asn Gly Ser Gln Met Leu Leu
1               5                   10                  15
Val Leu Leu Val Leu Ser Trp Leu Pro His Gly Gly Ala Leu Ser Leu
            20                  25                  30
Ala Glu Ala Ser Arg Ala Ser Phe Pro Gly Pro Ser Glu Leu His Ser
        35                  40                  45
Glu Asp Ser Arg Phe Arg Glu Leu Arg Lys Arg Tyr Glu Asp Leu Leu
    50                  55                  60
Thr Arg Leu Arg Ala Asn Gln Ser Trp Glu Asp Ser Asn Thr Asp Leu
65                  70                  75                  80
Val Pro Ala Pro Ala Val Arg Ile Leu Thr Pro Glu Val Arg Leu Gly
                85                  90                  95
Ser Gly Gly His Leu His Leu Arg Ile Ser Arg Ala Ala Leu Pro Glu
            100                 105                 110
Gly Leu Pro Glu Ala Ser Arg Leu His Arg Ala Leu Phe Arg Leu Ser
        115                 120                 125
Pro Thr Ala Ser Arg Ser Trp Asp Val Thr Arg Pro Leu Arg Arg Gln
    130                 135                 140
Leu Ser Leu Ala Arg Pro Gln Ala Pro Ala Leu His Leu Arg Leu Ser
145                 150                 155                 160
Pro Pro Pro Ser Gln Ser Asp Gln Leu Leu Ala Glu Ser Ser Ser Ala
                165                 170                 175
Arg Pro Gln Leu Glu Leu His Leu Arg Pro Gln Ala Ala Arg Gly Arg
            180                 185                 190
Arg Arg Ala Arg Ala Arg Asn Gly Asp His Cys Pro Leu Gly Pro Gly
        195                 200                 205
Arg Cys Cys Arg Leu His Thr Val Arg Ala Ser Leu Glu Asp Leu Gly
    210                 215                 220
Trp Ala Asp Trp Val Leu Ser Pro Arg Glu Val Gln Val Thr Met Cys
225                 230                 235                 240
Ile Gly Ala Cys Pro Ser Gln Phe Arg Ala Ala Asn Met His Ala Gln
                245                 250                 255
Ile Lys Thr Ser Leu His Arg Leu Lys Pro Asp Thr Val Pro Ala Pro
            260                 265                 270
Cys Cys Val Pro Ala Ser Tyr Asn Pro Met Val Leu Ile Gln Lys Thr
        275                 280                 285
Asp Thr Gly Val Ser Leu Gln Thr Tyr Asp Asp Leu Leu Ala Lys Asp
    290                 295                 300
Cys His Cys Ile
305
```

<210> SEQ ID NO 5
<211> LENGTH: 912
<212> TYPE: DNA
<213> ORGANISM: Mus sp.

<400> SEQUENCE: 5

```
atggccccgc cgcgctcca ggcccagcct ccaggcggct ctcaactgag gttcctgctg      60
ttcctgctgc tgttgctgct gctgctgtca tggccatcgc agggggacgc cctggcaatg     120
cctgaacagc gaccctccgg ccctgagtcc caactcaacg ccgacgagct acggggtcgc     180
ttccaggacc tgctgagccg gctgcatgcc aaccagagcc gagaggactc gaactcagaa     240
ccaagtcctg acccagctgt ccggatactc agtccagagg tgagattggg gtcccacggc     300
```

```
cagctgctac tccgcgtcaa ccgggcgtcg ctgagtcagg gtctccccga agcctaccgc    360
gtgcaccgag cgctgctcct gctgacgccg acggcccgcc cctgggacat cactaggccc    420
ctgaagcgtg cgctcagcct ccggggaccc cgtgctcccg cattacgcct gcgcctgacg    480
ccgcctccgg acctggctat gctgccctct ggcggcacgc agctggaact gcgcttacgg    540
gtagccgccg gcaggggcg ccgaagcgcg catgcgcacc caagagactc gtgcccactg     600
ggtccggggc gctgctgtca cttggagact gtgcaggcaa ctcttgaaga cttgggctgg    660
agcgactggg tgctgtcccc gcgccagctg cagctgagca tgtgcgtggg cgagtgtccc    720
cacctgtatc gctccgcgaa cacgcatgcg cagatcaaag cacgcctgca tggcctgcag    780
cctgacaagg tgcctgcccc gtgctgtgtc ccctccagct acaccccggt ggttcttatg    840
cacaggacag acagtggtgt gtcactgcag acttatgatg acctggtggc ccggggctgc    900
cactgcgctt ga                                                         912
```

<210> SEQ ID NO 6
<211> LENGTH: 303
<212> TYPE: PRT
<213> ORGANISM: Mus sp.

<400> SEQUENCE: 6

```
Met Ala Pro Pro Ala Leu Gln Ala Gln Pro Gly Gly Ser Gln Leu
1               5                   10                  15

Arg Phe Leu Leu Phe Leu Leu Leu Leu Leu Leu Ser Trp Pro
            20                  25                  30

Ser Gln Gly Asp Ala Leu Ala Met Pro Glu Gln Arg Pro Ser Gly Pro
            35                  40                  45

Glu Ser Gln Leu Asn Ala Asp Glu Leu Arg Gly Arg Phe Gln Asp Leu
    50                  55                  60

Leu Ser Arg Leu His Ala Asn Gln Ser Arg Glu Asp Ser Asn Ser Glu
65                  70                  75                  80

Pro Ser Pro Asp Pro Ala Val Arg Ile Leu Ser Pro Glu Val Arg Leu
                85                  90                  95

Gly Ser His Gly Gln Leu Leu Leu Arg Val Asn Arg Ala Ser Leu Ser
            100                 105                 110

Gln Gly Leu Pro Glu Ala Tyr Arg Val His Arg Ala Leu Leu Leu Leu
        115                 120                 125

Thr Pro Thr Ala Arg Pro Trp Asp Ile Thr Arg Pro Leu Lys Arg Ala
    130                 135                 140

Leu Ser Leu Arg Gly Pro Arg Ala Pro Ala Leu Arg Leu Arg Leu Thr
145                 150                 155                 160

Pro Pro Pro Asp Leu Ala Met Leu Pro Ser Gly Gly Thr Gln Leu Glu
                165                 170                 175

Leu Arg Leu Arg Val Ala Ala Gly Arg Gly Arg Arg Ser Ala His Ala
            180                 185                 190

His Pro Arg Asp Ser Cys Pro Leu Gly Pro Gly Arg Cys Cys His Leu
        195                 200                 205

Glu Thr Val Gln Ala Thr Leu Glu Asp Leu Gly Trp Ser Asp Trp Val
    210                 215                 220

Leu Ser Pro Arg Gln Leu Gln Leu Ser Met Cys Val Gly Glu Cys Pro
225                 230                 235                 240

His Leu Tyr Arg Ser Ala Asn Thr His Ala Gln Ile Lys Ala Arg Leu
                245                 250                 255
```

```
His Gly Leu Gln Pro Asp Lys Val Pro Ala Pro Cys Cys Val Pro Ser
            260                 265                 270

Ser Tyr Thr Pro Val Val Leu Met His Arg Thr Asp Ser Gly Val Ser
        275                 280                 285

Leu Gln Thr Tyr Asp Asp Leu Val Ala Arg Gly Cys His Cys Ala
        290                 295                 300

<210> SEQ ID NO 7
<211> LENGTH: 840
<212> TYPE: DNA
<213> ORGANISM: Homo sapiens

<400> SEQUENCE: 7
ctgtctctgg ccgaggcgag ccgcgcaagt ttcccgggac cctcagagtt gcactccgaa      60
gactccagat tccgagagtt gcggaaacgc tacgaggacc tgctaaccag gctgcgggcc     120
aaccagagct gggaagattc gaacaccgac ctcgtcccgg ccctgcagt ccggatactc      180 acgccagaag tgcggctggg atccggcggc cacctgcacc tgcgtatctc tcgggccgcc    240
cttcccgagg ggctccccga ggcctcccgc cttcaccggg ctctgttccg gctgtccccg    300
acggcgtcaa ggtcgtggga cgtgacacga ccgctgcggc gtcagctcag ccttgcaaga    360
ccccaggcgc ccgcgctgca cctgcgactg tcgccgccgc cgtcgcagtc ggaccaactg    420
ctggcagaat cttcgtccgc acggccccag ctggagttgc acttgcggcc gcaagccgcc    480
agggggcgcc gcagagcgcg tgcgcgcaac ggggaccact gtccgctcgg gcccgggcgt    540
tgctgccgtc tgcacacggt ccgcgcgtcg ctggaagacc tgggctgggc cgattgggtg    600
ctgtcgccac gggaggtgca agtgaccatg tgcatcggcg cgtgcccgag ccagttccgg    660
gcggcaaaca tgcacgcgca gatcaagacg agcctgcacc gcctgaagcc cgacacggtg    720
ccagcgccct gctgcgtgcc cgccagctac aatcccatgg tgctcattca aaagaccgac    780
accggggtgt cgctccagac ctatgatgac ttgttagcca aagactgcca ctgcatatga    840

<210> SEQ ID NO 8
<211> LENGTH: 279
<212> TYPE: PRT
<213> ORGANISM: Homo sapiens

<400> SEQUENCE: 8

Leu Ser Leu Ala Glu Ala Ser Arg Ala Ser Phe Pro Gly Pro Ser Glu
1               5                   10                  15

Leu His Ser Glu Asp Ser Arg Phe Arg Glu Leu Arg Lys Arg Tyr Glu
            20                  25                  30

Asp Leu Leu Thr Arg Leu Arg Ala Asn Gln Ser Trp Glu Asp Ser Asn
        35                  40                  45

Thr Asp Leu Val Pro Ala Pro Ala Val Arg Ile Leu Thr Pro Glu Val
    50                  55                  60

Arg Leu Gly Ser Gly Gly His Leu His Leu Arg Ile Ser Arg Ala Ala
65                  70                  75                  80

Leu Pro Glu Gly Leu Pro Glu Ala Ser Arg Leu His Arg Ala Leu Phe
                85                  90                  95

Arg Leu Ser Pro Thr Ala Ser Arg Ser Trp Asp Val Thr Arg Pro Leu
            100                 105                 110

Arg Arg Gln Leu Ser Leu Ala Arg Pro Gln Ala Pro Ala Leu His Leu
        115                 120                 125

Arg Leu Ser Pro Pro Ser Gln Ser Asp Gln Leu Leu Ala Glu Ser
        130                 135                 140
```

```
Ser Ser Ala Arg Pro Gln Leu Glu Leu His Leu Arg Pro Gln Ala Ala
145                 150                 155                 160

Arg Gly Arg Arg Ala Arg Ala Arg Asn Gly Asp His Cys Pro Leu
            165                 170                 175

Gly Pro Gly Arg Cys Cys Arg Leu His Thr Val Arg Ala Ser Leu Glu
            180                 185                 190

Asp Leu Gly Trp Ala Asp Trp Val Leu Ser Pro Arg Glu Val Gln Val
            195                 200                 205

Thr Met Cys Ile Gly Ala Cys Pro Ser Gln Phe Arg Ala Ala Asn Met
210                 215                 220

His Ala Gln Ile Lys Thr Ser Leu His Arg Leu Lys Pro Asp Thr Val
225                 230                 235                 240

Pro Ala Pro Cys Cys Val Pro Ala Ser Tyr Asn Pro Met Val Leu Ile
                245                 250                 255

Gln Lys Thr Asp Thr Gly Val Ser Leu Gln Thr Tyr Asp Asp Leu Leu
            260                 265                 270

Ala Lys Asp Cys His Cys Ile
            275
```

```
<210> SEQ ID NO 9
<211> LENGTH: 816
<212> TYPE: DNA
<213> ORGANISM: Mus sp.

<400> SEQUENCE: 9 tcgcagggggg acgccctggc aatgcctgaa cagcgaccct ccggccctga gtcccaactc      60
aacgccgacg agctacgggg tcgcttccag gacctgctga gccggctgca tgccaaccag     120
agccgagagg actcgaactc agaaccaagt cctgacccag ctgtccggat actcagtcca     180
gaggtgagat tggggtccca cggccagctg ctactccgcg tcaaccgggc gtcgctgagt     240
cagggtctcc ccgaagccta ccgcgtgcac cgagcgctgc tcctgctgac gccgacggcc     300
cgcccctggg acatcactag gccctgaag cgtgcgctca gcctcgggg accccgtgct      360 cccgcattac gcctgcgcct gacgccgcct ccggacctgg ctatgctgcc ctctggcggc     420
acgcagctgg aactgcgctt acgggtagcc gccggcaggg ggcgccgaag cgcgcatgcg     480
cacccaagag actcgtgccc actgggtccg gggcgctgct gtcacttgga gactgtgcag     540
gcaactcttg aagacttggg ctggagcgac tgggtgctgt ccccgcgcca gctgcagctg     600
agcatgtgcg tgggcgagtg tccccacctg tatcgctccg cgaacacgca tgcgcagatc     660
aaagcacgcc tgcatggcct gcagcctgac aaggtgcctg ccccgtgctg tgtcccctcc     720
agctacaccc cggtggttct tatgcacagg acagacagtg gtgtgtcact gcagacttat     780
gatgacctgg tggcccgggg ctgccactgc gcttga                              816
```

```
<210> SEQ ID NO 10
<211> LENGTH: 271
<212> TYPE: PRT
<213> ORGANISM: Mus sp.

<400> SEQUENCE: 10

Ser Gln Gly Asp Ala Leu Ala Met Pro Glu Gln Arg Pro Ser Gly Pro
1               5                   10                  15

Glu Ser Gln Leu Asn Ala Asp Glu Leu Arg Gly Arg Phe Gln Asp Leu
            20                  25                  30

Leu Ser Arg Leu His Ala Asn Gln Ser Arg Glu Asp Ser Asn Ser Glu
```

```
                35                  40                  45
Pro Ser Pro Asp Pro Ala Val Arg Ile Leu Ser Pro Glu Val Arg Leu
 50                      55                  60

Gly Ser His Gly Gln Leu Leu Leu Arg Val Asn Arg Ala Ser Leu Ser
 65                  70                  75                  80

Gln Gly Leu Pro Glu Ala Tyr Arg Val His Arg Ala Leu Leu Leu Leu
                     85                  90                  95

Thr Pro Thr Ala Arg Pro Trp Asp Ile Thr Arg Pro Leu Lys Arg Ala
                100                 105                 110

Leu Ser Leu Arg Gly Pro Arg Ala Pro Ala Leu Arg Leu Arg Leu Thr
            115                 120                 125

Pro Pro Pro Asp Leu Ala Met Leu Pro Ser Gly Gly Thr Gln Leu Glu
            130                 135                 140

Leu Arg Leu Arg Val Ala Ala Gly Arg Gly Arg Ser Ala His Ala
145                 150                 155                 160

His Pro Arg Asp Ser Cys Pro Leu Gly Pro Gly Arg Cys Cys His Leu
                165                 170                 175

Glu Thr Val Gln Ala Thr Leu Glu Asp Leu Gly Trp Ser Asp Trp Val
                180                 185                 190

Leu Ser Pro Arg Gln Leu Gln Leu Ser Met Cys Val Gly Glu Cys Pro
            195                 200                 205

His Leu Tyr Arg Ser Ala Asn Thr His Ala Gln Ile Lys Ala Arg Leu
            210                 215                 220

His Gly Leu Gln Pro Asp Lys Val Pro Ala Pro Cys Cys Val Pro Ser
225                 230                 235                 240

Ser Tyr Thr Pro Val Val Leu Met His Arg Thr Asp Ser Gly Val Ser
                245                 250                 255

Leu Gln Thr Tyr Asp Asp Leu Val Ala Arg Gly Cys His Cys Ala
            260                 265                 270

<210> SEQ ID NO 11
<211> LENGTH: 339
<212> TYPE: DNA
<213> ORGANISM: Homo sapiens

<400> SEQUENCE: 11
gcgcgcaacg gggaccactg tccgctcggg cccgggcgtt gctgccgtct gcacacggtc      60
cgcgcgtcgc tggaagacct gggctgggcc gattgggtgc tgtcgccacg ggaggtgcaa     120
gtgaccatgt gcatcggcgc gtgcccgagc cagttccggg cggcaaacat gcacgcgcag     180
atcaagacga gcctgcaccg cctgaagccc gacacggtgc cagcgccctg ctgcgtgccc     240
gccagctaca tcccatggt gctcattcaa aagaccgaca ccggggtgtc gctccagacc     300
tatgatgact tgttagccaa agactgccac tgcatatga                           339

<210> SEQ ID NO 12
<211> LENGTH: 112
<212> TYPE: PRT
<213> ORGANISM: Homo sapiens

<400> SEQUENCE: 12

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
```

```
                35                  40                  45
Pro Ser Gln Phe Arg Ala Ala Asn Met His Ala Gln Ile Lys Thr Ser
     50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110

<210> SEQ ID NO 13
<211> LENGTH: 351
<212> TYPE: DNA
<213> ORGANISM: Mus sp.

<400> SEQUENCE: 13
atgagcgcgc atgcgcaccc aagagactcg tgcccactgg gtccggggcg ctgctgtcac      60
ctggagactg tgcaggcaac tcttgaagac ttgggctgga cgactgggt gttgtccccg      120 cgccagctgc agctgagcat gtgcgtgggc gagtgtcccc acctgtatcg ctccgcgaac     180
acgcatgcgc agatcaaagc acgcctgcat ggcctgcagc ctgacaaggt gcctgccccg     240
tgctgtgtcc cctccagcta caccccggtg gttcttatgc acaggacaga cagtggtgtg     300
tcactgcaga cttatgatga cctggtggcc cggggctgcc actgcgcttg a              351

<210> SEQ ID NO 14
<211> LENGTH: 116
<212> TYPE: PRT
<213> ORGANISM: Mus sp.

<400> SEQUENCE: 14

Met Ser Ala His Ala His Pro Arg Asp Ser Cys Pro Leu Gly Pro Gly
  1               5                  10                  15

Arg Cys Cys His Leu Glu Thr Val Gln Ala Thr Leu Glu Asp Leu Gly
             20                  25                  30

Trp Ser Asp Trp Val Leu Ser Pro Arg Gln Leu Gln Leu Ser Met Cys
         35                  40                  45

Val Gly Glu Cys Pro His Leu Tyr Arg Ser Ala Asn Thr His Ala Gln
     50                  55                  60

Ile Lys Ala Arg Leu His Gly Leu Gln Pro Asp Lys Val Pro Ala Pro
 65                  70                  75                  80

Cys Cys Val Pro Ser Ser Tyr Thr Pro Val Val Leu Met His Arg Thr
                 85                  90                  95

Asp Ser Gly Val Ser Leu Gln Thr Tyr Asp Asp Leu Val Ala Arg Gly
            100                 105                 110

Cys His Cys Ala
115

<210> SEQ ID NO 15
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atggaatgga gctgggtctt tctcttcttc ctgtcagtaa cgaccggtgt ccactccgcg      60
```

```
cgcaacgggg accactgtcc gctcgggccc gggcgttgct gccgtctgca cacggtccgc    120
gcgtcgctgg aagacctggg ctgggccgat tgggtgctgt cgccacggga ggtgcaagtg    180
accatgtgca tcggcgcgtg cccgagccag ttccgggcgg caaacatgca cgcgcagatc    240
aagacgagcc tgcaccgcct gaagcccgac acggtgccag cgccctgctg cgtgcccgcc    300
agctacaatc ccatggtgct cattcaaaag accgacaccg gggtgtcgct ccagacctat    360
gatgacttgt tagccaaaga ctgccactgc atatga                              396
```

<210> SEQ ID NO 16
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Glu Trp Ser Trp Val Phe Leu Phe Phe Leu Ser Val Thr Thr Gly
1               5                   10                  15

Val His Ser Ala Arg Asn Gly Asp His Cys Pro Leu Gly Pro Gly Arg
            20                  25                  30

Cys Cys Arg Leu His Thr Val Arg Ala Ser Leu Glu Asp Leu Gly Trp
        35                  40                  45

Ala Asp Trp Val Leu Ser Pro Arg Glu Val Gln Val Thr Met Cys Ile
    50                  55                  60

Gly Ala Cys Pro Ser Gln Phe Arg Ala Ala Asn Met His Ala Gln Ile
65                  70                  75                  80

Lys Thr Ser Leu His Arg Leu Lys Pro Asp Thr Val Pro Ala Pro Cys
                85                  90                  95

Cys Val Pro Ala Ser Tyr Asn Pro Met Val Leu Ile Gln Lys Thr Asp
            100                 105                 110

Thr Gly Val Ser Leu Gln Thr Tyr Asp Asp Leu Leu Ala Lys Asp Cys
        115                 120                 125

His Cys Ile
    130

<210> SEQ ID NO 17
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
atggaatgga gctgggtctt tctcttcttc ctgtcagtaa cgactggtgt ccactccgca    60
cctgaactcc tggggggacc gtcagtcttc ctcttccccc caaaacccaa ggacaccctc   120
atgatctccc ggacccctga ggtcacatgc gtggtggtgg acgtgagcca cgaagaccct   180
gaggtcaagt tcaactggta cgtggacggc gtggaggtgc ataatgccaa gacaaagccg   240
cgggaggagc agtacaacag cacgtaccgt gtggtcagcg tcctcaccgt cctgcaccag   300
gactggctga atggcaagga gtacaagtgc aaggtctcca acaaagccct cccagccccc   360
atcgagaaaa ccatctccaa agccaaaggg cagccccgag aaccacaggt gtacaccctg   420
cccccatccc ggaaggagat gaccaagaac caggtcagcc tgacctgcct ggtcaaaggc   480
ttctatccca gcgacatcgc cgtggagtgg gagagcaatg ggcagccgga gaacaactac   540
```

```
aagaccacgc ctcccgtgct gaagtccgac ggctccttct tcctctatag caagctcacc    600
gtggacaaga gcaggtggca gcagggaac gtcttctcat gctccgtgat gcatgaggct    660
ctgcacaacc actacacgca gaagagcctc tccctgtctc cgggtaaatg a            711
```

<210> SEQ ID NO 18
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 19
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Gly Ser Gly Gly Gly Gly Ser Gly Gly Gly Gly Ser Gly
1               5                   10                  15

Gly Gly Gly Ser
            20

<210> SEQ ID NO 21
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atggaatgga gctgggtctt tctcttcttc ctgtcagtaa cgactggtgt ccactccgca    60
cctgaactcc tggggggacc gtcagtcttc ctcttccccc caaaacccaa ggacaccctc   120
atgatctccc ggacccctga ggtcacatgc gtggtggtgg acgtgagcca cgaagaccct   180
gaggtcaagt tcaactggta cgtggacggc gtggaggtgc ataatgccaa gacaaagccg   240
cgggaggagc agtacaacag cacgtaccgt gtggtcagcg tcctcaccgt cctgcaccag   300
gactggctga atggcaagga gtacaagtgc aaggtctcca acaaagccct cccagccccc   360
atcgagaaaa ccatctccaa agccaaaggg cagccccgag aaccacaggt gtacaccctg   420
cccccatccc gggaggagat gaccaagaac caggtcagcc tgacctgcct ggtcaaaggc   480
ttctatccca gcgacatcgc cgtggagtgg gagagcaatg ggcagccgga gaacaactac   540

```
gacaccacgc ctcccgtgct ggactccgac ggctccttct tcctctatag cgacctcacc    600
gtggacaaga gcaggtggca gcaggggaac gtcttctcat gctccgtgat gcatgaggct    660
ctgcacaacc actacacgca aaagagcctc tccctgtctc cgggtggagg tggtggatcc    720
ggaggcggtg aagcggagg tggtggatct ggaggcggtg aagcgcgcg caacggagac    780 cactgtccgc tcgggcccgg gcgttgctgc cgtctgcaca cggtccgcgc gtcgctggaa    840
gacctgggct gggccgattg ggtgctgtcg ccacgggagg tgcaagtgac catgtgcatc    900
ggcgcgtgcc cgagccagtt ccgggcggca acatgcacg cgcagatcaa gacgagcctg    960
caccgcctga gcccgacac ggtgccagcc cctgctgcg tgcccgccag ctacaatccc   1020
atggtgctca ttcaaaagac cgacaccggg gtgtcgctcc agacctatga tgacttgtta   1080
gccaaagact gccactgcat atga                                          1104
```

<210> SEQ ID NO 22
<211> LENGTH: 367
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Glu Trp Ser Trp Val Phe Leu Phe Phe Leu Ser Val Thr Thr Gly
1               5                   10                  15

Val His Ser Ala Pro Glu Leu Leu Gly Gly Pro Ser Val Phe Leu Phe
                20                  25                  30

Pro Pro Lys Pro Lys Asp Thr Leu Met Ile Ser Arg Thr Pro Glu Val
            35                  40                  45

Thr Cys Val Val Val Asp Val Ser His Glu Asp Pro Glu Val Lys Phe
        50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
                100                 105                 110

Ser Asn Lys Ala Leu Pro Ala Pro Ile Glu Lys Thr Ile Ser Lys Ala
            115                 120                 125

Lys Gly Gln Pro Arg Glu Pro Gln Val Tyr Thr Leu Pro Pro Ser Arg
        130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Asp Thr Thr Pro Pro Val Leu Asp Ser Asp Gly Ser
                180                 185                 190

Phe Phe Leu Tyr Ser Asp Leu Thr Val Asp Lys Ser Arg Trp Gln Gln
            195                 200                 205

Gly Asn Val Phe Ser Cys Ser Val Met His Glu Ala Leu His Asn His
        210                 215                 220

Tyr Thr Gln Lys Ser Leu Ser Leu Ser Pro Gly Gly Gly Gly Gly Ser
225                 230                 235                 240

Gly Gly Gly Gly Ser Gly Gly Gly Ser Gly Gly Gly Gly Ser Ala
                245                 250                 255
```

```
Arg Asn Gly Asp His Cys Pro Leu Gly Pro Gly Arg Cys Cys Arg Leu
            260                 265                 270

His Thr Val Arg Ala Ser Leu Glu Asp Leu Gly Trp Ala Asp Trp Val
        275                 280                 285

Leu Ser Pro Arg Glu Val Gln Val Thr Met Cys Ile Gly Ala Cys Pro
    290                 295                 300

Ser Gln Phe Arg Ala Ala Asn Met His Ala Gln Ile Lys Thr Ser Leu
305                 310                 315                 320

His Arg Leu Lys Pro Asp Thr Val Pro Ala Pro Cys Cys Val Pro Ala
                325                 330                 335

Ser Tyr Asn Pro Met Val Leu Ile Gln Lys Thr Asp Thr Gly Val Ser
            340                 345                 350

Leu Gln Thr Tyr Asp Asp Leu Leu Ala Lys Asp Cys His Cys Ile
        355                 360                 365

<210> SEQ ID NO 23
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Asp Thr Thr Pro Pro
                165                 170                 175

Val Leu Asp Ser Asp Gly Ser Phe Phe Leu Tyr Ser Asp Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 24
```

<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

| | | |
|---|---|---|
| atggaatgga gctgggtctt tctcttcttc ctgtcagtaa cgactggtgt ccactccgac | 60 |
| aaaactcaca catgcccacc gtgcccagca cctgaactcc tggggggacc gtcagtcttc | 120 |
| ctcttccccc caaaacccaa ggacaccctc atgatctccc ggacccctga ggtcacatgc | 180 |
| gtggtggtgg acgtgagcca cgaagaccct gaggtcaagt tcaactggta cgtggacggc | 240 |
| gtggaggtgc ataatgccaa gacaaagccg cgggaggagc agtacaacag cacgtaccgt | 300 |
| gtggtcagcg tcctcaccgt cctgcaccag gactggctga atggcaagga gtacaagtgc | 360 |
| aaggtctcca acaaagccct cccagccccc atcgagaaaa ccatctccaa agccaaaggg | 420 |
| cagccccgag aaccacaggt gtacaccctg cccccatccc gggaggagat gaccaagaac | 480 |
| caggtcagcc tgacctgcct ggtcaaaggc ttctatccca gcgacatcgc cgtggagtgg | 540 |
| gagagcaatg ggcagccgga gaacaactac gacaccacgc ctcccgtgct ggactccgac | 600 |
| ggctccttct tcctctatag cgacctcacc gtggacaaga gcaggtggca gcaggggaac | 660 |
| gtcttctcat gctccgtgat gcatgaggct ctgcacaacc actacacgca gaagagcctc | 720 |
| tccctgtctc cgggtggagg tggtggatcc ggaggcggtg aagcggagg tggtggatct | 780 |
| ggaggcggtg aagcgcgcg caacggagac cactgtccgc tcgggcccgg gcgttgctgc | 840 |
| cgtctgcaca cggtccgcgc gtcgctggaa gacctgggct gggccgattg ggtgctgtcg | 900 |
| ccacgggagg tgcaagtgac catgtgcatc ggcgcgtgcc cgagccagtt ccgggcggca | 960 |
| aacatgcacg cgcagatcaa gacgagcctg caccgcctga gcccgacac ggtgccagcg | 1020 |
| ccctgctgcg tgcccgccag ctacaatccc atggtgctca ttcaaaagac cgacaccggg | 1080 |
| gtgtcgctcc agacctatga tgacttgtta gccaaagact gccactgcat atga | 1134 |

<210> SEQ ID NO 25
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Glu Trp Ser Trp Val Phe Leu Phe Phe Leu Ser Val Thr Thr Gly
1               5                   10                  15

Val His Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

```
Leu Asn Gly Lys Glu Tyr Lys Cys Lys Val Ser Asn Lys Ala Leu Pro
            115                 120                 125
Ala Pro Ile Glu Lys Thr Ile Ser Lys Ala Lys Gly Gln Pro Arg Glu
        130                 135                 140
Pro Gln Val Tyr Thr Leu Pro Pro Ser Arg Glu Glu Met Thr Lys Asn
145                 150                 155                 160
Gln Val Ser Leu Thr Cys Leu Val Lys Gly Phe Tyr Pro Ser Asp Ile
                165                 170                 175
Ala Val Glu Trp Glu Ser Asn Gly Gln Pro Glu Asn Asn Tyr Asp Thr
            180                 185                 190
Thr Pro Pro Val Leu Asp Ser Asp Gly Ser Phe Phe Leu Tyr Ser Asp
        195                 200                 205
Leu Thr Val Asp Lys Ser Arg Trp Gln Gln Gly Asn Val Phe Ser Cys
    210                 215                 220
Ser Val Met His Glu Ala Leu His Asn His Tyr Thr Gln Lys Ser Leu
225                 230                 235                 240
Ser Leu Ser Pro Gly Gly Gly Gly Ser Gly Gly Gly Gly Ser Gly
                245                 250                 255
Gly Gly Ser Gly Gly Gly Ser Ala Arg Asn Gly Asp His Cys
            260                 265                 270
Pro Leu Gly Pro Gly Arg Cys Cys Arg Leu His Thr Val Arg Ala Ser
        275                 280                 285
Leu Glu Asp Leu Gly Trp Ala Asp Trp Val Leu Ser Pro Arg Glu Val
    290                 295                 300
Gln Val Thr Met Cys Ile Gly Ala Cys Pro Ser Gln Phe Arg Ala Ala
305                 310                 315                 320
Asn Met His Ala Gln Ile Lys Thr Ser Leu His Arg Leu Lys Pro Asp
                325                 330                 335
Thr Val Pro Ala Pro Cys Cys Val Pro Ala Ser Tyr Asn Pro Met Val
            340                 345                 350
Leu Ile Gln Lys Thr Asp Thr Gly Val Ser Leu Gln Thr Tyr Asp Asp
        355                 360                 365
Leu Leu Ala Lys Asp Cys His Cys Ile
    370                 375

<210> SEQ ID NO 26
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atggaatgga gctgggtctt tctcttcttc ctgtcagtaa cgactggtgt ccactccgac      60
aaaactcaca catgcccacc gtgcccagca cctgaactcc tggggggacc gtcagtcttc     120
ctcttccccc caaaacccaa ggacaccctc atgatctccc ggacccctga ggtcacatgc     180
gtggtggtgg acgtgagcca cgaagaccct gaggtcaagt tcaactggta cgtggacggc     240
gtggaggtgc ataatgccaa gacaaagccg cgggaggagc agtacaacag cacgtaccgt     300
gtggtcagcg tcctcaccgt cctgcaccag gactggctga atggcaagga gtacaagtgc     360
aaggtctcca acaaagccct cccagccccc atcgagaaaa ccatctccaa agccaaaggg     420
cagccccgag aaccacaggt gtacaccctg cccccatccc ggaaggagat gaccaagaac     480
caggtcagcc tgacctgcct ggtcaaaggc ttctatccca gcgacatcgc cgtggagtgg     540
```

```
gagagcaatg ggcagccgga gaacaactac aagaccacgc ctcccgtgct gaagtccgac    600
ggctccttct tcctctatag caagctcacc gtggacaaga gcaggtggca gcagggggaac  660 gtcttctcat gctccgtgat gcatgaggct ctgcacaacc actacacgca gaagagcctc   720
tccctgtctc cgggtaaatg a                                              741
```

```
<210> SEQ ID NO 27
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Glu Trp Ser Trp Val Phe Leu Phe Phe Leu Ser Val Thr Thr Gly
 1               5                  10                  15

Val His Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Lys Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Lys Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 28
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28
```

```
Gly Gly Gly Glu Arg Lys Ser Ser Val Glu Cys Pro Pro Cys Pro Ala
1               5                   10                  15

Pro Pro Val Ala Gly Pro Ser Val Phe Leu Phe Pro Lys Pro Lys
            20                  25                  30

Asp Thr Leu Met Ile Ser Arg Thr Pro Glu Val Thr Cys Val Val Val
            35                  40                  45

Asp Val Ser His Glu Asp Pro Glu Val Gln Phe Asn Trp Tyr Val Asp
50                  55                  60

Gly Val Glu Val His Asn Ala Lys Thr Lys Pro Arg Glu Glu Gln Phe
65                  70                  75                  80

Asn Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Leu
                100                 105                 110

Pro Ala Pro Ile Glu Lys Thr Ile Ser Lys Thr Lys Gly Gln Pro Arg
            115                 120                 125

Glu Pro Gln Val Tyr Thr Leu Pro Pro Ser Arg Glu Glu Met Thr Lys
            130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
210                 215                 220

Leu Ser Leu Ser Pro
225
```

<210> SEQ ID NO 29
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Gly Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser
            35                  40
```

<210> SEQ ID NO 30
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Glu Arg Lys Ser Ser Val Glu Cys Pro Pro Cys Pro Ala Pro Pro Val
1               5                   10                  15
```

```
Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
                35                  40                  45

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro
225

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ser Gly Gly Gly Gly Ser Gly Gly Gly Gly Ser Gly Gly Gly Gly
 1               5                   10                  15

Ser Gly Gly Gly Gly Ser
            20

<210> SEQ ID NO 32
<211> LENGTH: 1893
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
ggaggtggag agcgcaaatc ttctgtcgag tgcccaccgt gcccagcacc acctgtggca      60
ggaccgtcag tcttcctctt ccccccaaaa cccaaggaca ccctcatgat ctcccggacc     120
cctgaggtca cgtgcgtggt ggtggacgtg agccacgaag accccgaggt ccagttcaac     180
tggtacgtgg acggcgtgga ggtgcataat gccaagacaa aaccgcggga ggagcagttc     240
aacagcacgt tccgtgtggt cagcgtcctc accgttgtgc accaggactg gctgaacggc     300
```

```
aaggagtaca agtgcaaggt ctccaacaaa ggcctcccag cccccatcga gaaaaccatc    360
tccaaaacca aagggcagcc ccgagaacca caggtgtaca ccctgccccc atcccgggag    420
gagatgacca agaaccaggt cagcctgacc tgcctggtca aaggcttcta ccccagcgac    480
atcgccgtgg agtgggagag caatgggcag ccggagaaca actacaagac acacctccc    540 atgctggact ccgacggctc cttcttcctc tacagcaagc tcaccgtgga caagagcagg    600
tggcagcagg ggaacgtctt ctcatgctcc gtgatgcatg aggctctgca caaccactac    660
acgcagaaga gcctctcct gtctccgggt ggaggtggcg gtagcggtgg cggaggttca    720
ggtggtggcg gttctggcgg aggtggcagt ggcggtggcg gatcaggtgg cggtggcagc    780
ggtggcggcg gaagcggtgg aggaggttca gagcggaaat ccagcgttga atgtcctccg    840
tgccctgctc cacccgtcgc ggggcctagt gtcttccttt tccctccaaa accaaaggat    900
acactgatga tcagccggac ccccgaggtt acgtgcgtcg tcgtcgatgt ctcccacgag    960
gatccagagg tccaattcaa ctggtacgtg acggggtcg aggtgcataa tgcaaagaca   1020
aagccacggg aagagcagtt taactctact ttccgcgtgg tttctgtgct gaccgtggtg   1080
caccaagatt ggctcaacgg caaggagtac aagtgcaagg taagcaataa ggggctccct   1140 gccccccattg agaagactat ctccaagaca aagggacagc cacgcgagcc acaagtctat   1200
acactccccc cttcccgcga gaaaatgacc aagaatcagg ttagcctgac atgcttggtt   1260 aagggttct accccctctga catagccgtg gagtgggaga gcaatggaca accagagaac   1320
aactacaaga ccaccccacc catgctggat agcgacggtt cattctttct gtatagtaag   1380
cttaccgtgg acaagtcccg gtggcaacaa ggaaatgtct tttcatgctc tgtgatgcac   1440
gaggccttgc ataatcacta tactcagaag agcttgagcc tcagcccggg atctggaggt   1500
ggcggatccg ggggcggtgg aagcggaggt ggtggatcgg gaggcggtgg aagcgcgcgc   1560
aacggcgacc actgtccgct cgggcccgga cgttgctgcc gtctgcacac ggtccgcgcg   1620
tcgctggaag acctgggctg ggccgattgg gtgctgtcgc cacgggaggt gcaagtgacc   1680
atgtgcatcg gcgcgtgccc gagccagttc cgggcggcaa acatgcacgc gcagatcaag   1740
acgagcctgc accgcctgaa gcccgacacg gtgccagcgc cctgctgcgt gcccgccagc    1800
tacaatccca tggtgctcat tcaaaagacc gacaccgggg tgtcgctcca gacctatgat   1860
gacttgttag ccaaagactg ccactgcata tga                                 1893
```

<210> SEQ ID NO 33
<211> LENGTH: 630
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 33

Gly Gly Gly Glu Arg Lys Ser Ser Val Glu Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Gln Phe Asn Trp Tyr Val Asp
    50                  55                  60

Gly Val Glu Val His Asn Ala Lys Thr Lys Pro Arg Glu Glu Gln Phe

```
                65                  70                  75                  80
           Asn Ser Thr Phe Arg Val Val Ser Val Leu Thr Val His Gln Asp
                            85                  90                  95

Trp Leu Asn Gly Lys Glu Tyr Lys Cys Lys Val Ser Asn Lys Gly Leu
                           100                 105                 110

Pro Ala Pro Ile Glu Lys Thr Ile Ser Lys Thr Lys Gly Gln Pro Arg
                           115                 120                 125

Glu Pro Gln Val Tyr Thr Leu Pro Pro Ser Arg Glu Glu Met Thr Lys
           130                 135                 140

Asn Gln Val Ser Leu Thr Cys Leu Val Lys Gly Phe Tyr Pro Ser Asp
           145                 150                 155                 160

Ile Ala Val Glu Trp Glu Ser Asn Gly Gln Pro Glu Asn Asn Tyr Lys
                           165                 170                 175

Thr Thr Pro Pro Met Leu Asp Ser Asp Gly Ser Phe Phe Leu Tyr Ser
                           180                 185                 190

Lys Leu Thr Val Asp Lys Ser Arg Trp Gln Gln Gly Asn Val Phe Ser
                           195                 200                 205

Cys Ser Val Met His Glu Ala Leu His Asn His Tyr Thr Gln Lys Ser
                           210                 215                 220

Leu Ser Leu Ser Pro Gly Gly Gly Gly Ser Gly Gly Gly Gly Ser
           225                 230                 235                 240

Gly Gly Gly Gly Ser Gly Gly Gly Gly Ser Gly Gly Gly Gly Ser Gly
                           245                 250                 255

Gly Gly Gly Ser Gly Gly Gly Gly Ser Gly Gly Gly Gly Ser Glu Arg
                           260                 265                 270

Lys Ser Ser Val Glu Cys Pro Pro Cys Pro Ala Pro Pro Val Ala Gly
                           275                 280                 285

Pro Ser Val Phe Leu Phe Pro Pro Lys Pro Lys Asp Thr Leu Met Ile
                           290                 295                 300

Ser Arg Thr Pro Glu Val Thr Cys Val Val Val Asp Val Ser His Glu
           305                 310                 315                 320

Asp Pro Glu Val Gln Phe Asn Trp Tyr Val Asp Gly Val Glu Val His
                           325                 330                 335

Asn Ala Lys Thr Lys Pro Arg Glu Glu Gln Phe Asn Ser Thr Phe Arg
                           340                 345                 350

Val Val Ser Val Leu Thr Val Val His Gln Asp Trp Leu Asn Gly Lys
                           355                 360                 365

Glu Tyr Lys Cys Lys Val Ser Asn Lys Gly Leu Pro Ala Pro Ile Glu
                           370                 375                 380

Lys Thr Ile Ser Lys Thr Lys Gly Gln Pro Arg Glu Pro Gln Val Tyr
           385                 390                 395                 400

Thr Leu Pro Pro Ser Arg Glu Glu Met Thr Lys Asn Gln Val Ser Leu
                           405                 410                 415

Thr Cys Leu Val Lys Gly Phe Tyr Pro Ser Asp Ile Ala Val Glu Trp
                           420                 425                 430

Glu Ser Asn Gly Gln Pro Glu Asn Asn Tyr Lys Thr Thr Pro Pro Met
                           435                 440                 445

Leu Asp Ser Asp Gly Ser Phe Phe Leu Tyr Ser Lys Leu Thr Val Asp
                           450                 455                 460

Lys Ser Arg Trp Gln Gln Gly Asn Val Phe Ser Cys Ser Val Met His
           465                 470                 475                 480

Glu Ala Leu His Asn His Tyr Thr Gln Lys Ser Leu Ser Leu Ser Pro
                           485                 490                 495
```

Gly Ser Gly Gly Gly Ser Gly Gly Gly Ser Gly Gly Gly
            500                 505                 510

Ser Gly Gly Gly Ser Ala Arg Asn Gly Asp His Cys Pro Leu Gly
        515                 520                 525

Pro Gly Arg Cys Cys Arg Leu His Thr Val Arg Ala Ser Leu Glu Asp
    530                 535                 540

Leu Gly Trp Ala Asp Trp Val Leu Ser Pro Arg Glu Val Gln Val Thr
545                 550                 555                 560

Met Cys Ile Gly Ala Cys Pro Ser Gln Phe Arg Ala Ala Asn Met His
                565                 570                 575

Ala Gln Ile Lys Thr Ser Leu His Arg Leu Lys Pro Asp Thr Val Pro
            580                 585                 590

Ala Pro Cys Cys Val Pro Ala Ser Tyr Asn Pro Met Val Leu Ile Gln
        595                 600                 605

Lys Thr Asp Thr Gly Val Ser Leu Gln Thr Tyr Asp Asp Leu Leu Ala
    610                 615                 620

Lys Asp Cys His Cys Ile
625                 630

<210> SEQ ID NO 34
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Ser
        35                  40

<210> SEQ ID NO 35
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atggaatgga gctgggtctt tctcttcttc ctgtcagtaa cgaccggtgt ccactccgcg      60
cgcaacgggg acgattgtcc gctcgggccc gggcgttgct gccgtctgca cacggtccgc    120
gcgtcgctgg aagacctggg ctgggccgat tgggtgctgt cgccacggga ggtgcaagtg    180
accatgtgca tcggcgcgtg cccgagccag ttccgggcgg caaacatgca cgcgcagatc    240
aagacgagcc tgcaccgcct gaagcccgac acggtgccag cgccctgctg cgtgcccgcc    300
agctacaatc ccatggtgct cattcaaaag accgacaccg gggtgtcgct ccagacctat    360
gatgacttgt tagccaaaga ctgccactgc atatga                              396

<210> SEQ ID NO 36
<211> LENGTH: 131
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 36

Met Glu Trp Ser Trp Val Phe Leu Phe Phe Leu Ser Val Thr Thr Gly
1               5                   10                  15

Val His Ser Ala Arg Asn Gly Asp Asp Cys Pro Leu Gly Pro Gly Arg
            20                  25                  30

Cys Cys Arg Leu His Thr Val Arg Ala Ser Leu Glu Asp Leu Gly Trp
        35                  40                  45

Ala Asp Trp Val Leu Ser Pro Arg Glu Val Gln Val Thr Met Cys Ile
    50                  55                  60

Gly Ala Cys Pro Ser Gln Phe Arg Ala Ala Asn Met His Ala Gln Ile
65                  70                  75                  80

Lys Thr Ser Leu His Arg Leu Lys Pro Asp Thr Val Pro Ala Pro Cys
                85                  90                  95

Cys Val Pro Ala Ser Tyr Asn Pro Met Val Leu Ile Gln Lys Thr Asp
            100                 105                 110

Thr Gly Val Ser Leu Gln Thr Tyr Asp Asp Leu Leu Ala Lys Asp Cys
        115                 120                 125

His Cys Ile
    130

<210> SEQ ID NO 37
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gcgcgcaacg gggacgattg tccgctcggg cccgggcgtt gctgccgtct gcacacggtc       60
cgcgcgtcgc tggaagacct gggctgggcc gattgggtgc tgtcgccacg ggaggtgcaa      120
gtgaccatgt gcatcggcgc gtgcccgagc cagttccggg cggcaaacat gcacgcgcag      180
atcaagacga gcctgcaccg cctgaagccc gacacggtgc cagcgccctg ctgcgtgccc      240
gccagctaca atcccatggt gctcattcaa aagaccgaca ccggggtgtc gctccagacc      300
tatgatgact tgttagccaa agactgccac tgcatatga                             339

<210> SEQ ID NO 38
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Arg Asn Gly Asp Asp Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro

```
                65                  70                  75                  80
Ala Ser Tyr Asn Pro Met Val Leu Ile Gln Lys Thr Asp Thr Gly Val
                    85                  90                  95

Ser Leu Gln Thr Tyr Asp Asp Leu Leu Ala Lys Asp Cys His Cys Ile
                    100                 105                 110
```

<210> SEQ ID NO 39
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
atggaatgga gctgggtctt tctcttcttc ctgtcagtaa cgaccggtgt ccactccgcg    60
cgccagggag accactgtcc gctcgggccc gggcgttgct gccgtctgca cacggtccgc   120
gcgtcgctgg aagacctggg ctgggccgat tgggtgctgt cgccacggga ggtgcaagtg   180
accatgtgca tcggcgcgtg cccgagccag ttccggcgg caaacatgca cgcgcagatc    240
aagacgagcc tgcaccgcct gaagcccgac acggtgccag cgccctgctg cgtgcccgcc   300
agctacaatc ccatggtgct cattcaaaag accgacaccg gggtgtcgct ccagacctat   360
gatgacttgt tagccaaaga ctgccactgc ata                               393
```

<210> SEQ ID NO 40
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Met Glu Trp Ser Trp Val Phe Leu Phe Phe Leu Ser Val Thr Thr Gly
1               5                   10                  15

Val His Ser Ala Arg Gln Gly Asp His Cys Pro Leu Gly Pro Gly Arg
                20                  25                  30

Cys Cys Arg Leu His Thr Val Arg Ala Ser Leu Glu Asp Leu Gly Trp
            35                  40                  45

Ala Asp Trp Val Leu Ser Pro Arg Glu Val Gln Val Thr Met Cys Ile
        50                  55                  60

Gly Ala Cys Pro Ser Gln Phe Arg Ala Ala Asn Met His Ala Gln Ile
65                  70                  75                  80

Lys Thr Ser Leu His Arg Leu Lys Pro Asp Thr Val Pro Ala Pro Cys
                85                  90                  95

Cys Val Pro Ala Ser Tyr Asn Pro Met Val Leu Ile Gln Lys Thr Asp
                100                 105                 110

Thr Gly Val Ser Leu Gln Thr Tyr Asp Asp Leu Leu Ala Lys Asp Cys
            115                 120                 125

His Cys Ile
    130
```

<210> SEQ ID NO 41
<211> LENGTH: 336
<212> TYPE: DNA
<213> ORGANISM: Homo sapiens

<400> SEQUENCE: 41

```
gcgcgccagg gagaccactg tccgctcggg cccgggcgtt gctgccgtct gcacacggtc    60
cgcgcgtcgc tggaagacct gggctgggcc gattgggtgc tgtcgccacg ggaggtgcaa   120
gtgaccatgt gcatcggcgc gtgcccgagc cagttccggg cggcaaacat gcacgcgcag   180
atcaagacga gcctgcaccg cctgaagccc gacacggtgc cagcgccctg ctgcgtgccc   240
gccagctaca atcccatggt gctcattcaa aagaccgaca ccggggtgtc gctccagacc   300
tatgatgact tgttagccaa agactgccac tgcata                             336
```

<210> SEQ ID NO 42
<211> LENGTH: 112
<212> TYPE: PRT
<213> ORGANISM: Homo sapiens

<400> SEQUENCE: 42

```
Ala Arg Gln Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
             20                  25                  30

Val Leu Ser Pro Arg Glu Val Gln Val Thr Met Cys Ile Gly Ala Cys
         35                  40                  45

Pro Ser Gln Phe Arg Ala Ala Asn Met His Ala Gln Ile Lys Thr Ser
     50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110
```

<210> SEQ ID NO 43
<211> LENGTH: 1047
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
gcacctgaac tcctgggggg accgtcagtc ttcctcttcc ccccaaaacc caaggacacc    60
ctcatgatct cccggacccc tgaggtcaca tgcgtggtgg tggacgtgag ccacgaagac   120
cctgaggtca agttcaactg gtacgtggac ggcgtggagg tgcataatgc caagacaaag   180
ccgcgggagg agcagtacaa cagcacgtac cgtgtggtca gcgtcctcac cgtcctgcac   240
caggactggc tgaatggcaa ggagtacaag tgcaaggtct ccaacaaagc cctcccagcc   300
cccatcgaga aaaccatctc caaagccaaa gggcagcccc gagaaccaca ggtgtacacc   360
ctgcccccat cccgggagga gatgaccaag aaccaggtca gcctgacctg cctggtcaaa   420
ggcttctatc ccagcgacat cgccgtggag tgggagagca atgggcagcc ggagaacaac   480
tacgacacca cgcctcccgt gctggactcc gacggctcct tcttcctcta tagcgacctc   540
accgtggaca agagcaggtg gcagcagggg aacgtcttct catgctccgt gatgcatgag   600
gctctgcaca accactacac gcagaagagc ctctccctgt ctccgggtgg aggtggtgga   660
tccggaggcg gtggaagcgg aggtggtgga tctggaggcg gtggaagcgg cgcaacgga   720 gaccactgtc cgctcgggcc cgggcgttgc tgccgtctgc acacggtccg cgcgtcgctg   780
gaagacctgg gctgggccga ttgggtgctg tcgccacggg aggtgcaagt gaccatgtgc   840
```

```
atcggcgcgt gcccgagcca gttccgggcg gcaaacatgc acgcgcagat caagacgagc      900
ctgcaccgcc tgaagcccga cacggtgcca gcgccctgct gcgtgcccgc cagctacaat      960
cccatggtgc tcattcaaaa gaccgacacc ggggtgtcgc tccagaccta tgatgacttg     1020
ttagccaaag actgccactg catatga                                         1047
```

<210> SEQ ID NO 44
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Ser Gly Gly Gly
    210                 215                 220

Gly Ser Gly Gly Gly Gly Ser Gly Gly Gly Ser Ala Arg Asn Gly
225                 230                 235                 240

Asp His Cys Pro Leu Gly Pro Gly Arg Cys Cys Arg Leu His Thr Val
                245                 250                 255

Arg Ala Ser Leu Glu Asp Leu Gly Trp Ala Asp Trp Val Leu Ser Pro
            260                 265                 270

Arg Glu Val Gln Val Thr Met Cys Ile Gly Ala Cys Pro Ser Gln Phe
        275                 280                 285

Arg Ala Ala Asn Met His Ala Gln Ile Lys Thr Ser Leu His Arg Leu
    290                 295                 300

Lys Pro Asp Thr Val Pro Ala Pro Cys Cys Val Pro Ala Ser Tyr Asn
305                 310                 315                 320
```

Pro Met Val Leu Ile Gln Lys Thr Asp Thr Gly Val Ser Leu Gln Thr
            325                 330                 335

Tyr Asp Asp Leu Leu Ala Lys Asp Cys His Cys Ile
            340                 345

<210> SEQ ID NO 45
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Glu Trp Ser Trp Val Phe Leu Phe Phe Leu Ser Val Thr Thr Gly
1               5                   10                  15

Val His Ser Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140

Lys Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Lys Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
225                 230                 235

<210> SEQ ID NO 46
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gcacctgaac tcctgggggg accgtcagtc ttcctcttcc ccccaaaacc caaggacacc      60
ctcatgatct cccggacccc tgaggtcaca tgcgtggtgg tggacgtgag ccacgaagac     120
cctgaggtca agttcaactg gtacgtggac ggcgtggagg tgcataatgc caagacaaag     180

```
ccgcgggagg agcagtacaa cagcacgtac cgtgtggtca gcgtcctcac cgtcctgcac      240
caggactggc tgaatggcaa ggagtacaag tgcaaggtct ccaacaaagc cctcccagcc      300
cccatcgaga aaaccatctc caaagccaaa gggcagcccc gagaaccaca ggtgtacacc      360
ctgcccccat cccggaagga gatgaccaag aaccaggtca gcctgacctg cctggtcaaa      420
ggcttctatc ccagcgacat cgccgtggag tgggagagca atgggcagcc ggagaacaac      480
tacaagacca cgcctcccgt gctgaagtcc gacggctcct tcttcctcta tagcaagctc      540
accgtggaca agagcaggtg gcagcagggg aacgtcttct catgctccgt gatgcatgag      600
gctctgcaca accactacac gcagaagagc ctctccctgt ctccgggtaa atga           654

<210> SEQ ID NO 47
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
atggaatgga gctgggtctt tctcttcttc ctgtcagtaa cgactggtgt ccactccgca       60
cctgaactcc tggggggacc gtcagtcttc ctcttccccc caaaacccaa ggacaccctc      120
atgatctccc ggaccctga ggtcacatgc gtggtggtgg acgtgagcca cgaagaccct      180
gaggtcaagt tcaactggta cgtggacggc gtggaggtgc ataatgccaa gacaaagccg      240
cgggaggagc agtacaacag cacgtaccgt gtggtcagcg tcctcaccgt cctgcaccag      300
gactggctga atggcaagga gtacaagtgc aaggtctcca acaaagccct cccagccccc      360
atcgagaaaa ccatctccaa agccaagggg cagccccgag aaccacaggt gtacaccctg      420
cccccatccc ggaaggagat gaccaagaac caggtcagcc tgacctgcct ggtcaaaggc      480
ttctatccca gcgacatcgc cgtggagtgg gagagcaatg gcagccgga gaacaactac      540 aagaccacgc ctcccgtgct gaagtccgac ggctccttct tcctctatag caagctcacc      600
gtggacaaga gcaggtggca gcaggggaac gtcttctcat gctccgtgat gcatgaggct      660
ctgcacaacc actacacgca gaagagcctc tccctgtctc cgggtggagg tggtggatcc      720
ggaggcggtg gaagcggagg tggtggatct ggaggcggtg gaagcgcgcg caacggagac      780
cactgtccgc tcgggcccgg cgttgctgc cgtctgcaca cggtccgcgc gtcgctggaa      840
gacctgggct gggccgattg ggtgctgtcg ccacgggagg tgcaagtgac catgtgcatc      900
ggcgcgtgcc cgagccagtt ccgggcggca acatgcacg cgcagatcaa gacgagcctg      960
caccgcctga agcccgacac ggtgccagcc cctgctgcg tgcccgccag ctacaatccc     1020
atggtgctca ttcaaaagac cgacaccggg gtgtcgctcc agacctatga tgacttgtta     1080
gccaaagact gccactgcat atga                                           1104

<210> SEQ ID NO 48
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Glu Trp Ser Trp Val Phe Leu Phe Phe Leu Ser Val Thr Thr Gly
1               5                   10                  15
```

Val His Ser Ala Pro Glu Leu Leu Gly Gly Pro Ser Val Phe Leu Phe
         20                  25                  30

Pro Pro Lys Pro Lys Asp Thr Leu Met Ile Ser Arg Thr Pro Glu Val
         35                  40                  45

Thr Cys Val Val Val Asp Val Ser His Glu Asp Pro Glu Val Lys Phe
 50                  55                  60

Asn Trp Tyr Val Asp Gly Val Glu Val His Asn Ala Lys Thr Lys Pro
 65                  70                  75                  80

Arg Glu Glu Gln Tyr Asn Ser Thr Tyr Arg Val Val Ser Val Leu Thr
                 85                  90                  95

Val Leu His Gln Asp Trp Leu Asn Gly Lys Glu Tyr Lys Cys Lys Val
             100                 105                 110

Ser Asn Lys Ala Leu Pro Ala Pro Ile Glu Lys Thr Ile Ser Lys Ala
         115                 120                 125

Lys Gly Gln Pro Arg Glu Pro Gln Val Tyr Thr Leu Pro Pro Ser Arg
130                 135                 140

Lys Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                 165                 170                 175

Glu Asn Asn Tyr Lys Thr Thr Pro Pro Val Leu Lys Ser Asp Gly Ser
             180                 185                 190

Phe Phe Leu Tyr Ser Lys Leu Thr Val Asp Lys Ser Arg Trp Gln Gln
         195                 200                 205

Gly Asn Val Phe Ser Cys Ser Val Met His Glu Ala Leu His Asn His
210                 215                 220

Tyr Thr Gln Lys Ser Leu Ser Leu Ser Pro Gly Gly Gly Gly Ser
225                 230                 235                 240

Gly Gly Gly Gly Ser Gly Gly Gly Ser Gly Gly Gly Gly Ser Ala
                 245                 250                 255

Arg Asn Gly Asp His Cys Pro Leu Gly Pro Gly Arg Cys Cys Arg Leu
             260                 265                 270

His Thr Val Arg Ala Ser Leu Glu Asp Leu Gly Trp Ala Asp Trp Val
         275                 280                 285

Leu Ser Pro Arg Glu Val Gln Val Thr Met Cys Ile Gly Ala Cys Pro
290                 295                 300

Ser Gln Phe Arg Ala Ala Asn Met His Ala Gln Ile Lys Thr Ser Leu
305                 310                 315                 320

His Arg Leu Lys Pro Asp Thr Val Pro Ala Pro Cys Cys Val Pro Ala
                 325                 330                 335

Ser Tyr Asn Pro Met Val Leu Ile Gln Lys Thr Asp Thr Gly Val Ser
             340                 345                 350

Leu Gln Thr Tyr Asp Asp Leu Leu Ala Lys Asp Cys His Cys Ile
         355                 360                 365

<210> SEQ ID NO 49
<211> LENGTH: 1047
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gcacctgaac tcctgggggg accgtcagtc ttcctcttcc ccccaaaacc caaggacacc    60

-continued

```
ctcatgatct cccggacccc tgaggtcaca tgcgtggtgg tggacgtgag ccacgaagac      120
cctgaggtca agttcaactg gtacgtggac ggcgtggagt gcataatgc caagacaaag      180
ccgcgggagg agcagtacaa cagcacgtac cgtgtggtca gcgtcctcac cgtcctgcac      240
caggactggc tgaatggcaa ggagtacaag tgcaaggtct ccaacaaagc cctcccagcc      300
cccatcgaga aaccatctc caaagccaaa gggcagcccc gagaaccaca ggtgtacacc      360
ctgcccccat cccggaagga gatgaccaag aaccaggtca gcctgacctg cctggtcaaa      420
ggcttctatc ccagcgacat cgccgtggag tgggagagca atgggcagcc ggagaacaac      480
tacaagacca cgcctcccgt gctgaagtcc gacggctcct tcttcctcta tagcaagctc      540
accgtggaca gagcaggtg gcagcagggg aacgtcttct catgctccgt gatgcatgag      600
gctctgcaca accactacac gcagaagagc ctctccctgt ctccggtgg aggtggtgga      660
tccggaggcg gtggaagcgg aggtggtgga tctggaggcg gtggaagcgc gcaacgga      720
gaccactgtc cgctcgggcc cgggcgttgc tgccgtctgc acacggtccg cgcgtcgctg      780
gaagacctgg gctgggccga ttgggtgctg tcgccacggg aggtgcaagt gaccatgtgc      840
atcggcgcgt gcccgagcca gttccgggcg gcaaacatgc acgcgcagat caagacgagc      900
ctgcaccgcc tgaagcccga cacggtgcca gcgccctgct gcgtgcccgc cagctacaat      960
cccatggtgc tcattcaaaa gaccgacacc ggggtgtcgc tccagaccta tgatgacttg    1020
ttagccaaag actgccactg catatga                                        1047
```

<210> SEQ ID NO 50
<211> LENGTH: 348
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175
```

```
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
        195                 200                 205
Lys Ser Leu Ser Leu Ser Pro Gly Gly Gly Gly Ser Gly Gly Gly
    210                 215                 220
Gly Ser Gly Gly Gly Ser Gly Gly Gly Ser Ala Arg Asn Gly
225                 230                 235                 240
Asp His Cys Pro Leu Gly Pro Gly Arg Cys Cys Arg Leu His Thr Val
                245                 250                 255
Arg Ala Ser Leu Glu Asp Leu Gly Trp Ala Asp Trp Val Leu Ser Pro
            260                 265                 270
Arg Glu Val Gln Val Thr Met Cys Ile Gly Ala Cys Pro Ser Gln Phe
        275                 280                 285
Arg Ala Ala Asn Met His Ala Gln Ile Lys Thr Ser Leu His Arg Leu
    290                 295                 300
Lys Pro Asp Thr Val Pro Ala Pro Cys Cys Val Pro Ala Ser Tyr Asn
305                 310                 315                 320
Pro Met Val Leu Ile Gln Lys Thr Asp Thr Gly Val Ser Leu Gln Thr
                325                 330                 335
Tyr Asp Asp Leu Leu Ala Lys Asp Cys His Cys Ile
                340                 345
```

<210> SEQ ID NO 51
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

```
atggaatgga gctgggtctt tctcttcttc ctgtcagtaa cgactggtgt ccactccgca    60
cctgaactcc tgggggggacc gtcagtcttc ctcttccccc caaaacccaa ggacaccctc   120
atgatctccc ggacccctga ggtcacatgc gtggtggtgg acgtgagcca cgaagaccct   180
gaggtcaagt tcaactggta cgtggacggc gtggaggtgc ataatgccaa gacaaagccg   240
cgggaggagc agtacaacag cacgtaccgt gtggtcagcg tcctcaccgt cctgcaccag   300
gactggctga atggcaagga gtacaagtgc aaggtctcca acaaagccct cccagccccc   360
atcgagaaaa ccatctccaa agccaaaggg cagccccgag aaccacaggt gtacaccctg   420
cccccatccc gggaggagat gaccaagaac caggtcagcc tgacctgcct ggtcaaaggc   480
ttctatccca gcgacatcgc cgtggagtgg gagagcaatg ggcagccgga gaacaactac   540
gacaccacgc ctcccgtgct ggactccgac ggctccttct tcctctatag cgacctcacc   600
gtggacaaga gcaggtggca gcaggggaac gtcttctcat gctccgtgat gcatgaggct   660
ctgcacaacc actacacgca gaagagcctc tccctgtctc cgggtaaatg a            711
```

<210> SEQ ID NO 52
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Met Glu Trp Ser Trp Val Phe Leu Phe Phe Leu Ser Val Thr Thr Gly
1               5                   10                  15

Val His Ser Ala Pro Glu Leu Leu Gly Gly Pro Ser Val Phe Leu Phe
                20                  25                  30

Pro Pro Lys Pro Lys Asp Thr Leu Met Ile Ser Arg Thr Pro Glu Val
            35                  40                  45

Thr Cys Val Val Val Asp Val Ser His Glu Asp Pro Glu Val Lys Phe
        50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Asp Thr Thr Pro Pro Val Leu Asp Ser Asp Gly Ser
            180                 185                 190

Phe Phe Leu Tyr Ser Asp Leu Thr Val Asp Lys Ser Arg Trp Gln Gln
        195                 200                 205

Gly Asn Val Phe Ser Cys Ser Val Met His Glu Ala Leu His Asn His
210                 215                 220

Tyr Thr Gln Lys Ser Leu Ser Leu Ser Pro Gly Lys
225                 230                 235

<210> SEQ ID NO 53
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gcacctgaac tcctgggggg accgtcagtc ttcctcttcc ccccaaaacc caaggacacc      60
ctcatgatct cccggacccc tgaggtcaca tgcgtggtgg tggacgtgag ccacgaagac     120
cctgaggtca agttcaactg gtacgtggac ggcgtggagg tgcataatgc caagacaaag     180
ccgcgggagg agcagtacaa cagcacgtac cgtgtggtca gcgtcctcac cgtcctgcac     240
caggactggc tgaatggcaa ggagtacaag tgcaaggtct ccaacaaagc cctcccagcc     300
cccatcgaga aaaccatctc caaagccaaa gggcagcccc gagaaccaca ggtgtacacc     360
ctgcccccat cccgggagga gatgaccaag aaccaggtca gcctgacctg cctggtcaaa     420
ggcttctatc ccagcgacat cgccgtggag tgggagagca atgggcagcc ggagaacaac     480
tacgacacca cgcctcccgt gctggactcc gacggctcct tcttcctcta tagcgacctc     540
accgtggaca agagcaggtg gcagcagggg aacgtcttct catgctccgt gatgcatgag     600
gctctgcaca accactacac gcagaagagc ctctccctgt ctccgggtaa atga           654
```

<210> SEQ ID NO 54
<211> LENGTH: 1104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
atggaatgga gctgggtctt tctcttcttc ctgtcagtaa cgactggtgt ccactccgca      60
cctgaactcc tgggggggacc gtcagtcttc ctcttccccc caaaacccaa ggacaccctc    120
atgatctccc ggacccctga ggtcacatgc gtggtggtgg acgtgagcca cgaagaccct    180
gaggtcaagt tcaactggta cgtggacggc gtggaggtgc ataatgccaa gacaaagccg    240
cgggaggagc agtacaacag cacgtaccgt gtggtcagcg tcctcaccgt cctgcaccag    300
gactggctga atggcaagga gtacaagtgc aaggtctcca acaaagccct cccagccccc    360
atcgagaaaa ccatctccaa agccaaaggg cagccccgag aaccacaggt gtacaccctg    420
cccccatccc gggaggagat gaccaagaac caggtcagcc tgacctgcct ggtcaaaggc    480
ttctatccca gcgacatcgc cgtggagtgg gagagcaatg gcagccggga gaacaactac    540
gacaccacgc ctcccgtgct ggactccgac ggctccttct cctctatagc gacctcacc     600
gtggacaaga gcaggtggca gcagggggaac gtcttctcat gctccgtgat gcatgaggct    660
ctgcacaacc actacacgca gaagagcctc tccctgtctc cgggtggagg tggtggatcc    720
ggaggcggtg gaagcggagg tggtggatct ggaggcggtg gaagcgcgcg caacggagac    780
gactgtccgc tcgggcccgg cgttgctgc cgtctgcaca cggtccgcgc gtcgctggaa    840
gacctgggct gggccgattg ggtgctgtcg ccacggggagg tgcaagtgac catgtgcatc    900
ggcgcgtgcc cgagccagtt ccgggcggca aacatgcacg cgcagatcaa gacgagcctg    960
caccgcctga agcccgacac ggtgccagcg ccctgctgcg tgcccgccag ctacaatccc   1020
atggtgctca ttcaaaagac cgacaccggg gtgtcgctcc agacctatga tgacttgtta   1080
gccaaagact gccactgcat atga                                          1104
```

<210> SEQ ID NO 55
<211> LENGTH: 367
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Met Glu Trp Ser Trp Val Phe Leu Phe Phe Leu Ser Val Thr Thr Gly
1               5                   10                  15

Val His Ser Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110
```

```
Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Asp Thr Thr Pro Pro Val Leu Asp Ser Asp Gly Ser
            180                 185                 190

Phe Phe Leu Tyr Ser Asp Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Gly Gly Gly Gly Ser
225                 230                 235                 240

Gly Gly Gly Gly Ser Gly Gly Gly Ser Gly Gly Gly Gly Ser Ala
                245                 250                 255

Arg Asn Gly Asp Asp Cys Pro Leu Gly Pro Gly Arg Cys Cys Arg Leu
            260                 265                 270

His Thr Val Arg Ala Ser Leu Glu Asp Leu Gly Trp Ala Asp Trp Val
        275                 280                 285

Leu Ser Pro Arg Glu Val Gln Val Thr Met Cys Ile Gly Ala Cys Pro
    290                 295                 300

Ser Gln Phe Arg Ala Ala Asn Met His Ala Gln Ile Lys Thr Ser Leu
305                 310                 315                 320

His Arg Leu Lys Pro Asp Thr Val Pro Ala Pro Cys Cys Val Pro Ala
                325                 330                 335

Ser Tyr Asn Pro Met Val Leu Ile Gln Lys Thr Asp Thr Gly Val Ser
            340                 345                 350

Leu Gln Thr Tyr Asp Asp Leu Leu Ala Lys Asp Cys His Cys Ile
        355                 360                 365

<210> SEQ ID NO 56
<211> LENGTH: 1047
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gcacctgaac tcctgggggg accgtcagtc ttcctcttcc ccccaaaacc caaggacacc      60
ctcatgatct cccggacccc tgaggtcaca tgcgtggtgg tggacgtgag ccacgaagac     120
cctgaggtca agttcaactg gtacgtggac ggcgtggagg tgcataatgc caagacaaag     180
ccgcgggagg agcagtacaa cagcacgtac cgtgtggtca gcgtcctcac cgtcctgcac     240
caggactggc tgaatggcaa ggagtacaag tgcaaggtct ccaacaaagc cctcccagcc     300
cccatcgaga aaaccatctc caaagccaaa gggcagcccc gagaaccaca ggtgtacacc     360
ctgcccccat cccgggagga gatgaccaag aaccaggtca gcctgacctg cctggtcaaa     420
ggcttctatc ccagcgacat cgccgtggag tgggagagca atgggcagcc ggagaacaac     480
tacgacacca cgcctcccgt gctggactcc gacggctcct tcttcctcta tagcgacctc     540
accgtggaca agagcaggtg gcagcagggg aacgtcttct catgctccgt gatgcatgag     600
```

```
gctctgcaca accactacac gcagaagagc ctctccctgt ctccgggtgg aggtggtgga        660
tccggaggcg gtggaagcgg aggtggtgga tctggaggcg gtggaagcgc gcgcaacgga        720
gacgactgtc cgctcgggcc cgggcgttgc tgccgtctgc acacggtccg cgcgtcgctg        780
gaagacctgg gctgggccga ttgggtgctg tcgccacggg aggtgcaagt gaccatgtgc        840
atcggcgcgt gcccgagcca gttccgggcg gcaaacatgc acgcgcagat caagacgagc        900
ctgcaccgcc tgaagcccga cacggtgcca gcgccctgct gcgtgcccgc cagctacaat        960
cccatggtgc tcattcaaaa gaccgacacc ggggtgtcgc tccagaccta tgatgacttg       1020
ttagccaaag actgccactg catatga                                            1047
```

<210> SEQ ID NO 57
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Ser Gly Gly Gly
    210                 215                 220

Gly Ser Gly Gly Gly Ser Gly Gly Gly Ser Ala Arg Asn Gly
225                 230                 235                 240

Asp Asp Cys Pro Leu Gly Pro Gly Arg Cys Cys Arg Leu His Thr Val
                245                 250                 255

Arg Ala Ser Leu Glu Asp Leu Gly Trp Ala Asp Trp Val Leu Ser Pro
            260                 265                 270
```

```
Arg Glu Val Gln Val Thr Met Cys Ile Gly Ala Cys Pro Ser Gln Phe
            275                 280                 285
Arg Ala Ala Asn Met His Ala Gln Ile Lys Thr Ser Leu His Arg Leu
        290                 295                 300
Lys Pro Asp Thr Val Pro Ala Pro Cys Cys Val Pro Ala Ser Tyr Asn
305                 310                 315                 320
Pro Met Val Leu Ile Gln Lys Thr Asp Thr Gly Val Ser Leu Gln Thr
                325                 330                 335
Tyr Asp Asp Leu Leu Ala Lys Asp Cys His Cys Ile
                340                 345
```

<210> SEQ ID NO 58
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
atggaatgga gctgggtctt tctcttcttc ctgtcagtaa cgactggtgt ccactccgca    60
cctgaactcc tggggggacc gtcagtcttc ctcttccccc caaaacccaa ggacaccctc   120
atgatctccc ggacccctga ggtcacatgc gtggtggtgg acgtgagcca cgaagaccct   180
gaggtcaagt tcaactggta cgtggacggc gtggaggtgc ataatgccaa gacaaagccg   240
cgggaggagc agtacaacag cacgtaccgt gtggtcagcg tcctcaccgt cctgcaccag   300
gactggctga atggcaagga gtacaagtgc aaggtctcca acaaagccct cccagccccc   360
atcgagaaaa ccatctccaa agccaaaggg cagccccgag aaccacaggt gtacaccctg   420
cccccatccc ggaaggagat gaccaagaac caggtcagcc tgacctgcct ggtcaaaggc   480
ttctatccca gcgacatcgc cgtggagtgg gagagcaatg ggcagccgga gaacaactac   540
aagaccacgc ctcccgtgct ggagtccgac ggctccttct cctctatagc aagctcacc    600
gtggacaaga gcaggtggca gcaggggaac gtcttctcat gctccgtgat gcatgaggct   660
ctgcacaacc actacacgca gaagagcctc tccctgtctc cgggtggagg tggtggatcc   720
ggaggcggtg gaagcggagg tggtggatct ggaggcggtg gaagcgcgcg caacggagac   780
gactgtccgc tcgggccgg cgttgctgc cgtctgcaca cggtccgcgc gtcgctggaa    840
gacctgggct gggccgattg ggtgctgtcg ccacgggagg tgcaagtgac catgtgcatc   900
ggcgcgtgcc cgagccagtt ccgggcggca aacatgcacg cgcagatcaa gacgagcctg   960
caccgcctga agcccgacac ggtgccagcg ccctgctgcg tgcccgccag ctacaatccc  1020
atggtgctca ttcaaaagac cgacaccggg gtgtcgctcc agacctatga tgacttgtta  1080
gccaaagact gccactgcat atga                                         1104
```

<210> SEQ ID NO 59
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Met Glu Trp Ser Trp Val Phe Leu Phe Phe Leu Ser Val Thr Thr Gly
1               5                   10                  15
Val His Ser Ala Pro Glu Leu Leu Gly Gly Pro Ser Val Phe Leu Phe
```

```
                20                  25                  30
Pro Pro Lys Pro Lys Asp Thr Leu Met Ile Ser Arg Thr Pro Glu Val
            35                  40                  45

Thr Cys Val Val Val Asp Val Ser His Glu Asp Pro Glu Val Lys Phe
 50                  55                  60

Asn Trp Tyr Val Asp Gly Val Glu Val His Asn Ala Lys Thr Lys Pro
 65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
            115                 120                 125

Lys Gly Gln Pro Arg Glu Pro Gln Val Tyr Thr Leu Pro Pro Ser Arg
130                 135                 140

Lys Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Lys Ser Asp Gly Ser
            180                 185                 190

Phe Phe Leu Tyr Ser Lys Leu Thr Val Asp Lys Ser Arg Trp Gln Gln
            195                 200                 205

Gly Asn Val Phe Ser Cys Ser Val Met His Glu Ala Leu His Asn His
            210                 215                 220

Tyr Thr Gln Lys Ser Leu Ser Leu Ser Pro Gly Gly Gly Gly Ser
225                 230                 235                 240

Gly Gly Gly Gly Ser Gly Gly Gly Ser Gly Gly Gly Gly Ser Ala
                245                 250                 255

Arg Asn Gly Asp Asp Cys Pro Leu Gly Pro Gly Arg Cys Cys Arg Leu
            260                 265                 270

His Thr Val Arg Ala Ser Leu Glu Asp Leu Gly Trp Ala Asp Trp Val
            275                 280                 285

Leu Ser Pro Arg Glu Val Gln Val Thr Met Cys Ile Gly Ala Cys Pro
            290                 295                 300

Ser Gln Phe Arg Ala Ala Asn Met His Ala Gln Ile Lys Thr Ser Leu
305                 310                 315                 320

His Arg Leu Lys Pro Asp Thr Val Pro Ala Pro Cys Cys Val Pro Ala
                325                 330                 335

Ser Tyr Asn Pro Met Val Leu Ile Gln Lys Thr Asp Thr Gly Val Ser
            340                 345                 350

Leu Gln Thr Tyr Asp Asp Leu Leu Ala Lys Asp Cys His Cys Ile
            355                 360                 365

<210> SEQ ID NO 60
<211> LENGTH: 1047
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gcacctgaac tcctgggggg accgtcagtc ttcctcttcc ccccaaaacc caaggacacc      60
ctcatgatct cccggacccc tgaggtcaca tgcgtggtgg tggacgtgag ccacgaagac     120
```

```
cctgaggtca agttcaactg gtacgtggac ggcgtggagg tgcataatgc caagacaaag      180
ccgcgggagg agcagtacaa cagcacgtac cgtgtggtca gcgtcctcac cgtcctgcac      240
caggactggc tgaatggcaa ggagtacaag tgcaaggtct ccaacaaagc cctcccagcc      300
cccatcgaga aaaccatctc caaagccaaa gggcagcccc gagaaccaca ggtgtacacc      360
ctgcccccat cccggaagga gatgaccaag aaccaggtca gcctgacctg cctggtcaaa      420
ggcttctatc ccagcgacat cgccgtggag tgggagagca atgggcagcc ggagaacaac      480
tacaagacca cgcctcccgt gctgaagtcc gacggctcct tcttcctcta tagcaagctc      540
accgtggaca gagcaggtg gcagcagggg aacgtcttct catgctccgt gatgcatgag      600
gctctgcaca accactacac gcagaagagc ctctccctgt ctccgggtgg aggtggtgga      660
tccggaggcg gtggaagcgg aggtggtgga tctggaggcg gtggaagcgc gcgcaacgga      720
gacgactgtc cgctcgggcc cgggcgttgc tgccgtctgc acacggtccg cgcgtcgctg      780
gaagacctgg gctgggccga ttgggtgctg tcgccacggg aggtgcaagt gaccatgtgc      840
atcggcgcgt gcccgagcca gttccggcg gcaaacatgc acgcgcagat caagacgagc      900
ctgcaccgcc tgaagcccga cacggtgcca gcgccctgct gcgtgcccgc cagctacaat      960
cccatggtgc tcattcaaaa gaccgacacc ggggtgtcgc tccagaccta tgatgacttg     1020
ttagccaaag actgccactg catatga                                         1047

<210> SEQ ID NO 61
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190
```

```
Phe Ser Cys Ser Val Met His Glu Ala Leu His Asn His Tyr Thr Gln
        195                 200                 205

Lys Ser Leu Ser Leu Ser Pro Gly Gly Gly Gly Ser Gly Gly Gly
    210                 215                 220

Gly Ser Gly Gly Gly Ser Gly Gly Gly Ser Ala Arg Asn Gly
225                 230                 235                 240

Asp Asp Cys Pro Leu Gly Pro Gly Arg Cys Cys Arg Leu His Thr Val
                245                 250                 255

Arg Ala Ser Leu Glu Asp Leu Gly Trp Ala Asp Trp Val Leu Ser Pro
            260                 265                 270

Arg Glu Val Gln Val Thr Met Cys Ile Gly Ala Cys Pro Ser Gln Phe
        275                 280                 285

Arg Ala Ala Asn Met His Ala Gln Ile Lys Thr Ser Leu His Arg Leu
    290                 295                 300

Lys Pro Asp Thr Val Pro Ala Pro Cys Cys Val Pro Ala Ser Tyr Asn
305                 310                 315                 320

Pro Met Val Leu Ile Gln Lys Thr Asp Thr Gly Val Ser Leu Gln Thr
                325                 330                 335

Tyr Asp Asp Leu Leu Ala Lys Asp Cys His Cys Ile
                340                 345
```

<210> SEQ ID NO 62
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
atggaatgga gctgggtctt tctcttcttc ctgtcagtaa cgactggtgt ccactccgca    60
cctgaactcc tggggggacc gtcagtcttc ctcttccccc caaaacccaa ggacaccctc   120
atgatctccc ggacccctga ggtcacatgc gtggtggtgg acgtgagcca cgaagaccct   180
gaggtcaagt tcaactggta cgtggacggc gtggaggtgc ataatgccaa gacaaagccg   240
cgggaggagc agtacaacag cacgtaccgt gtggtcagcg tcctcaccgt cctgcaccag   300
gactggctga atggcaagga gtacaagtgc aaggtctcca caaagccct cccagccccc   360
atcgagaaaa ccatctccaa agccaaaggg cagccccgag aaccacaggt gtacaccctg   420
cccccatccc ggaaggagat gaccaagaac caggtcagcc tgacctgcct ggtcaaaggc   480
ttctatccca gcgacatcgc cgtggagtgg gagagcaatg ggcagccgga gaacaactac   540
aagaccacgc ctcccgtgct gaagtccgac ggctccttct tcctctatag caagctcacc   600
gtggacaaga gcaggtggca gcaggggaac gtcttctcat gctccgtgat gcatgaggct   660
ctgcacaacc actacacgca gaagagcctc tccctgtctc cgggtggagg tggtggatcc   720
ggaggcggtg gaagcggagg tggtggatct ggaggcggtg gaagcgcgcg ccaggagac   780
cactgtccgc tcgggcccgg cgttgctgc cgtctgcaca cggtccgcgc gtcgctggaa   840
gacctgggct gggccgattg ggtgctgtcg ccacggagg tgcaagtgac catgtgcatc   900
ggcgcgtgcc cgagccagtt ccgggcggca aacatgcacg cgcagatcaa gacgagcctg   960
caccgcctga gcccgacac ggtgccagcg ccctgctgcg tgcccgccag ctacaatccc  1020
atggtgctca ttcaaaagac cgacaccggg gtgtcgctcc agacctatga tgacttgtta  1080
gccaaagact gccactgcat atga                                         1104
```

<210> SEQ ID NO 63
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Met Glu Trp Ser Trp Val Phe Leu Phe Phe Leu Ser Val Thr Thr Gly
1               5                   10                  15

Val His Ser Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140

Lys Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Lys Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Gly Gly Gly Gly Ser
225                 230                 235                 240

Gly Gly Gly Gly Ser Gly Gly Gly Ser Gly Gly Gly Gly Ser Ala
                245                 250                 255

Arg Gln Gly Asp His Cys Pro Leu Gly Pro Gly Arg Cys Cys Arg Leu
            260                 265                 270

His Thr Val Arg Ala Ser Leu Glu Asp Leu Gly Trp Ala Asp Trp Val
        275                 280                 285

Leu Ser Pro Arg Glu Val Gln Val Thr Met Cys Ile Gly Ala Cys Pro
    290                 295                 300

Ser Gln Phe Arg Ala Ala Asn Met His Ala Gln Ile Lys Thr Ser Leu
305                 310                 315                 320

His Arg Leu Lys Pro Asp Thr Val Pro Ala Pro Cys Cys Val Pro Ala
                325                 330                 335

Ser Tyr Asn Pro Met Val Leu Ile Gln Lys Thr Asp Thr Gly Val Ser
            340                 345                 350

Leu Gln Thr Tyr Asp Asp Leu Leu Ala Lys Asp Cys His Cys Ile
        355                 360                 365
```

<210> SEQ ID NO 64
<211> LENGTH: 1047
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

```
gcacctgaac tcctgggggg accgtcagtc ttcctcttcc ccccaaaacc caaggacacc      60
ctcatgatct cccggacccc tgaggtcaca tgcgtggtgg tggacgtgag ccacgaagac     120
cctgaggtca agttcaactg gtacgtggac ggcgtggagg tgcataatgc caagacaaag     180
ccgcggagg agcagtacaa cagcacgtac cgtgtggtca gcgtcctcac cgtcctgcac     240
caggactggc tgaatggcaa ggagtacaag tgcaaggtct ccaacaaagc cctcccagcc     300
cccatcgaga aaaccatctc caaagccaaa gggcagcccc gagaaccaca ggtgtacacc     360
ctgcccccat cccggaagga gatgaccaag aaccaggtca gcctgacctg cctggtcaaa     420
ggcttctatc ccagcgacat cgccgtggag tgggagagca atgggcagcc ggagaacaac     480
tacaagacca cgcctcccgt gctgaagtcc gacggctcct tcttcctcta tagcaagctc     540
accgtggaca gagcaggtg gcagcagggg aacgtcttct catgctccgt gatgcatgag     600
gctctgcaca accactacac gcagaagagc ctctccctgt ctccgggtgg aggtggtgga     660
tccggaggcg gtggaagcgg aggtggtgga tctggaggcg gtggaagcgc gcgccaggga     720
gaccactgtc cgctcgggcc cgggcgttgc tgccgtctgc acacggtccg cgcgtcgctg     780
gaagacctgg gctgggccga ttgggtgctg tcgccacggg aggtgcaagt gaccatgtgc     840
atcggcgcgt gcccgagcca gttccggcg gcaaacatgc acgcgcagat caagacgagc     900
ctgcaccgcc tgaagcccga cacggtgcca gcgccctgct gcgtgcccgc cagctacaat     960
cccatggtgc tcattcaaaa gaccgacacc ggggtgtcgc tccagaccta tgatgacttg    1020
ttagccaaag actgccactg catatga                                        1047
```

<210> SEQ ID NO 65
<211> LENGTH: 348
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
```

|  |  |  | 100 |  |  |  | 105 |  |  |  | 110 |  |
|---|---|---|---|---|---|---|---|---|---|---|---|---|
| Pro | Arg | Glu | Pro | Gln | Val | Tyr | Thr | Leu | Pro | Pro | Ser | Arg | Lys | Glu | Met |
|  |  |  | 115 |  |  |  | 120 |  |  |  | 125 |  |

Pro Arg Glu Pro Gln Val Tyr Thr Leu Pro Pro Ser Arg Lys Glu Met
         115             120             125

Thr Lys Asn Gln Val Ser Leu Thr Cys Leu Val Lys Gly Phe Tyr Pro
    130             135             140

Ser Asp Ile Ala Val Glu Trp Glu Ser Asn Gly Gln Pro Glu Asn Asn
145             150             155             160

Tyr Lys Thr Thr Pro Pro Val Leu Lys Ser Asp Gly Ser Phe Phe Leu
         165             170             175

Tyr Ser Lys Leu Thr Val Asp Lys Ser Arg Trp Gln Gln Gly Asn Val
    180             185             190

Phe Ser Cys Ser Val Met His Glu Ala Leu His Asn His Tyr Thr Gln
         195             200             205

Lys Ser Leu Ser Leu Ser Pro Gly Gly Gly Gly Ser Gly Gly Gly
    210             215             220

Gly Ser Gly Gly Gly Ser Gly Gly Gly Ser Ala Arg Gln Gly
225             230             235             240

Asp His Cys Pro Leu Gly Pro Gly Arg Cys Cys Arg Leu His Thr Val
         245             250             255

Arg Ala Ser Leu Glu Asp Leu Gly Trp Ala Asp Trp Val Leu Ser Pro
    260             265             270

Arg Glu Val Gln Val Thr Met Cys Ile Gly Ala Cys Pro Ser Gln Phe
         275             280             285

Arg Ala Ala Asn Met His Ala Gln Ile Lys Thr Ser Leu His Arg Leu
    290             295             300

Lys Pro Asp Thr Val Pro Ala Pro Cys Cys Val Pro Ala Ser Tyr Asn
305             310             315             320

Pro Met Val Leu Ile Gln Lys Thr Asp Thr Gly Val Ser Leu Gln Thr
         325             330             335

Tyr Asp Asp Leu Leu Ala Lys Asp Cys His Cys Ile
    340             345

<210> SEQ ID NO 66
<211> LENGTH: 1044
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 66

```
atggagtggt cttgggtctt tctgttcttc ctctccgtca ccaccggtgt gcattctgcc    60
ccagagctgc ttggtggacc atccgtgttc ctgtttcctc caaagccgaa ggacaccctg   120
atgatctcaa gaactccgga agtgacttgc gtcgtcgtgg acgtgtcaca tgaggatcca   180
gaggtcaagt tcaattggta tgtggacgga gtggaagtgc ataacgccaa gaccaaaccc   240
cgcgaagaac agtacaatag cacctaccgc gtggtgagcg tccttactgt gctccaccag   300
gactggctta atgggaagga atacaagtgt aaggtgtcca acaaggccct cccgctcccc   360
atcgaaaaga ccatctcaaa ggcaaagggg caaccaaggg aacctcaagt gtacaccctg   420
cctccgagca ggaaggagat gaccaagaac caggtcagcc tgacttgtct cgtgaagggc   480
ttctatccca gcgatattgc tgtggaatgg gagtcaaatg ccagcccga gaataactac   540 aaaactaccc cacccgtgct gaaatctgat gggtccttct cctttactc caagctgacc   600 gtggacaaga gccgctggca acaaggcaat gtctttagct gctcagtgat gcatgaggct   660
```

-continued

```
ctccataatc actacactca gaagtcactg tccctgtcac ctggagcacg gaacggggac    720
cattgtcccc tgggacctgg tcggtgctgc cggcttcaca ccgtcagagc ctctctggag    780
gaccttggat gggctgattg ggtgctgagc cctcgggagg tgcaagtcac catgtgcatc    840
ggggcctgcc ctagccagtt ccgcgcagcc aacatgcacg ctcagatcaa aacctctctt    900
cacagactga agcccgacac cgtgccagca ccttgctgtg tgccggcctc ttataacccc    960
atggtcctca ttcagaaaac cgacaccgga gtgtcacttc agacttacga tgacctcctg    1020
gccaaggact gccactgtat ttga                                           1044
```

<210> SEQ ID NO 67
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Met Glu Trp Ser Trp Val Phe Leu Phe Phe Leu Ser Val Thr Thr Gly
1               5                   10                  15

Val His Ser Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140

Lys Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Lys Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Ala Arg Asn Gly Asp
225                 230                 235                 240

His Cys Pro Leu Gly Pro Gly Arg Cys Cys Arg Leu His Thr Val Arg
                245                 250                 255

Ala Ser Leu Glu Asp Leu Gly Trp Ala Asp Trp Val Leu Ser Pro Arg
            260                 265                 270

Glu Val Gln Val Thr Met Cys Ile Gly Ala Cys Pro Ser Gln Phe Arg
        275                 280                 285
```

```
Ala Ala Asn Met His Ala Gln Ile Lys Thr Ser Leu His Arg Leu Lys
            290                 295                 300

Pro Asp Thr Val Pro Ala Pro Cys Cys Val Pro Ala Ser Tyr Asn Pro
305                 310                 315                 320

Met Val Leu Ile Gln Lys Thr Asp Thr Gly Val Ser Leu Gln Thr Tyr
                325                 330                 335

Asp Asp Leu Leu Ala Lys Asp Cys His Cys Ile
            340                 345
```

<210> SEQ ID NO 68
<211> LENGTH: 987
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
gccccagagc tgcttggtgg accatccgtg ttcctgtttc ctccaaagcc gaaggacacc      60
ctgatgatct caagaactcc ggaagtgact tgcgtcgtcg tggacgtgtc acatgaggat     120
ccagaggtca agttcaattg gtatgtggac ggagtggaag tgcataacgc caagaccaaa     180
ccccgcgaag aacagtacaa tagcacctac cgcgtggtga cgtccttac tgtgctccac     240
caggactggc ttaatgggaa ggaatacaag tgtaaggtgt ccaacaaggc cctcccgct     300
cccatcgaaa agaccatctc aaaggcaaag ggcaaccaa gggaacctca agtgtacacc     360
ctgcctccga gcaggaagga gatgaccaag aaccaggtca gcctgacttg tctcgtgaag     420
ggcttctatc ccagcgatat tgctgtggaa tgggagtcaa atggccagcc gagaataac     480
tacaaaacta ccccaccegt gctgaaatct gatgggtcct tcttccttta ctccaagctg     540
accgtggaca gagccgctg gcaacaaggc aatgtcttta gctgctcagt gatgcatgag     600
gctctccata atcactacac tcagaagtca ctgtccctgt cacctggagc acggaacggg     660
gaccattgtc ccctgggacc tggtcggtgc tgccggcttc acaccgtcag agcctctctg     720
gaggaccttg atgggctga ttgggtgctg agccctcggg aggtgcaagt caccatgtgc     780
atcgggccct gccctagcca gttccgcgca gccaacatgc acgctcagat caaaacctct     840
cttcacagac tgaagcccga caccgtgcca gcaccttgct gtgtgccggc ctcttataac     900
cccatggtcc tcattcagaa aaccgacacc ggagtgtcac ttcagactta cgatgacctc     960
ctggccaagg actgccactg tatttga                                         987
```

<210> SEQ ID NO 69
<211> LENGTH: 328
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
```

```
            50                    55                    60
Gln Tyr Asn Ser Thr Tyr Arg Val Val Ser Val Leu Thr Val Leu His
 65                      70                      75                  80

Gln Asp Trp Leu Asn Gly Lys Glu Tyr Lys Cys Lys Val Ser Asn Lys
                    85                      90                  95

Ala Leu Pro Ala Pro Ile Glu Lys Thr Ile Ser Lys Ala Lys Gly Gln
                100                     105                 110

Pro Arg Glu Pro Gln Val Tyr Thr Leu Pro Pro Ser Arg Lys Glu Met
            115                     120                 125

Thr Lys Asn Gln Val Ser Leu Thr Cys Leu Val Lys Gly Phe Tyr Pro
        130                     135                 140

Ser Asp Ile Ala Val Glu Trp Glu Ser Asn Gly Gln Pro Glu Asn Asn
145                     150                 155                 160

Tyr Lys Thr Thr Pro Pro Val Leu Lys Ser Asp Gly Ser Phe Phe Leu
                    165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
            195                 200                 205

Lys Ser Leu Ser Leu Ser Pro Gly Ala Arg Asn Gly Asp His Cys Pro
        210                 215                 220

Leu Gly Pro Gly Arg Cys Cys Arg Leu His Thr Val Arg Ala Ser Leu
225                 230                 235                 240

Glu Asp Leu Gly Trp Ala Asp Trp Val Leu Ser Pro Arg Glu Val Gln
                245                 250                 255

Val Thr Met Cys Ile Gly Ala Cys Pro Ser Gln Phe Arg Ala Ala Asn
                260                 265                 270

Met His Ala Gln Ile Lys Thr Ser Leu His Arg Leu Lys Pro Asp Thr
            275                 280                 285

Val Pro Ala Pro Cys Cys Val Pro Ala Ser Tyr Asn Pro Met Val Leu
        290                 295                 300

Ile Gln Lys Thr Asp Thr Gly Val Ser Leu Gln Thr Tyr Asp Asp Leu
305                 310                 315                 320

Leu Ala Lys Asp Cys His Cys Ile
                325

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gly Gly Gly
1

<210> SEQ ID NO 71
<211> LENGTH: 1056
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
atggagtggt cttgggtctt tctgttcttc ctctccgtca ccaccggtgt gcattctgcc      60
```

```
ccagagctgc ttggtggacc atccgtgttc ctgtttcctc caaagccgaa ggacaccctg    120
atgatctcaa gaactccgga agtgacttgc gtcgtcgtgg acgtgtcaca tgaggatcca    180
gaggtcaagt tcaattggta tgtggacgga gtggaagtgc ataacgccaa gaccaaaccc    240
cgcgaagaac agtacaatag cacctaccgc gtggtgagcg tccttactgt gctccaccag    300
gactggctta atgggaagga atacaagtgt aaggtgtcca acaaggccct ccccgctccc    360
atcgaaaaga ccatctcaaa ggcaaagggg caaccaaggg aacctcaagt gtacaccctg    420
cctccgagca ggaaggagat gaccaagaac caggtcagcc tgacttgtct cgtgaagggc    480
ttctatccca gcgatattgc tgtggaatgg gagtcaaatg gccagcccga gaataactac    540
aaaactaccc cacccgtgct gaaatctgat gggtccttct tcctttactc caagctgacc    600
gtggacaaga gccgctggca acaaggcaat gtctttagct gctcagtgat gcatgaggct    660
ctccataatc actacactca gaagtcactg tccctgtcac ctggcggagg tggaggagca    720
cggaacgggg accattgtcc cctgggacct ggtcggtgct gccggcttca caccgtcaga    780
gcctctctgg aggaccttgg atgggctgat tgggtgctga gccctcggga ggtgcaagtc    840
accatgtgca tcggggcctg ccctagccag ttccgcgcag ccaacatgca cgctcagatc    900
aaaacctctc ttcacagact gaagcccgac accgtgccag caccttgctg tgtgccggcc    960
tcttataacc ccatggtcct cattcagaaa accgacaccg gagtgtcact tcagacttac   1020
gatgacctcc tggccaagga ctgccactgt atttga                             1056

<210> SEQ ID NO 72
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Glu Trp Ser Trp Val Phe Leu Phe Phe Leu Ser Val Thr Thr Gly
1               5                   10                  15

Val His Ser Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140

Lys Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175
```

```
Glu Asn Asn Tyr Lys Thr Thr Pro Pro Val Leu Lys Ser Asp Gly Ser
                180                 185                 190

Phe Phe Leu Tyr Ser Lys Leu Thr Val Asp Lys Ser Arg Trp Gln Gln
            195                 200                 205

Gly Asn Val Phe Ser Cys Ser Val Met His Glu Ala Leu His Asn His
        210                 215                 220

Tyr Thr Gln Lys Ser Leu Ser Leu Ser Pro Gly Gly Gly Gly Gly Ala
225                 230                 235                 240

Arg Asn Gly Asp His Cys Pro Leu Gly Pro Gly Arg Cys Cys Arg Leu
                245                 250                 255

His Thr Val Arg Ala Ser Leu Glu Asp Leu Gly Trp Ala Asp Trp Val
            260                 265                 270

Leu Ser Pro Arg Glu Val Gln Val Thr Met Cys Ile Gly Ala Cys Pro
        275                 280                 285

Ser Gln Phe Arg Ala Ala Asn Met His Ala Gln Ile Lys Thr Ser Leu
        290                 295                 300

His Arg Leu Lys Pro Asp Thr Val Pro Ala Pro Cys Cys Val Pro Ala
305                 310                 315                 320

Ser Tyr Asn Pro Met Val Leu Ile Gln Lys Thr Asp Thr Gly Val Ser
                325                 330                 335

Leu Gln Thr Tyr Asp Asp Leu Leu Ala Lys Asp Cys His Cys Ile
            340                 345                 350

<210> SEQ ID NO 73
<211> LENGTH: 999
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
gccccagagc tgcttggtgg accatccgtg ttcctgtttc ctccaaagcc gaaggacacc      60
ctgatgatct caagaactcc ggaagtgact tgcgtcgtcg tggacgtgtc acatgaggat     120
ccagaggtca agttcaattg gtatgtggac ggagtggaag tgcataacgc caagaccaaa     180
ccccgcgaag aacagtacaa tagcacctac cgcgtggtga gcgtccttac tgtgctccac     240
caggactggc ttaatgggaa ggaatacaag tgtaaggtgt ccaacaaggc cctcccccgct    300 cccatcgaaa agaccatctc aaaggcaaag ggcaaccaa gggaacctca agtgtacacc      360
ctgcctccga gcaggaagga gatgaccaag aaccaggtca gcctgacttg tctcgtgaag     420
ggcttctatc ccagcgatat tgctgtggaa tgggagtcaa atggccagcc cgagaataac     480
tacaaaacta ccccacccgt gctgaaatct gatgggtcct tcttcctta ctccaagctg      540 accgtggaca gagccgctg gcaacaaggc aatgtcttta gctgctcagt gatgcatgag      600
gctctccata tcactacac tcagaagtca ctgtccctgt cacctggcgg aggtggagga     660
gcacggaacg ggaccattg tccctggga cctggtcggt gctgccggct tcacaccgtc      720
agagcctctc tggaggacct tggatgggct gattgggtgc tgagccctcg ggaggtgcaa     780
gtcaccatgt gcatcgggc ctgccctagc cagttccgcg cagccaacat gcacgctcag      840
atcaaaacct ctcttcacag actgaagccc gacaccgtgc cagcaccttg ctgtgtgccg     900
gcctcttata cccccatggt cctcattcag aaaaccgaca ccggagtgtc acttcagact     960
tacgatgacc tcctggccaa ggactgccac tgtatttga                            999
```

<210> SEQ ID NO 74
<211> LENGTH: 332
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Ala Arg Asn Gly
    210                 215                 220

Asp His Cys Pro Leu Gly Pro Gly Arg Cys Cys Arg Leu His Thr Val
225                 230                 235                 240

Arg Ala Ser Leu Glu Asp Leu Gly Trp Ala Asp Trp Val Leu Ser Pro
                245                 250                 255

Arg Glu Val Gln Val Thr Met Cys Ile Gly Ala Cys Pro Ser Gln Phe
            260                 265                 270

Arg Ala Ala Asn Met His Ala Gln Ile Lys Thr Ser Leu His Arg Leu
        275                 280                 285

Lys Pro Asp Thr Val Pro Ala Pro Cys Cys Val Pro Ala Ser Tyr Asn
    290                 295                 300

Pro Met Val Leu Ile Gln Lys Thr Asp Thr Gly Val Ser Leu Gln Thr
305                 310                 315                 320

Tyr Asp Asp Leu Leu Ala Lys Asp Cys His Cys Ile
                325                 330
```

<210> SEQ ID NO 75
<211> LENGTH: 10
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 75

Gly Gly Gly Gly Ser Gly Gly Gly Gly Ser
1               5                   10

<210> SEQ ID NO 76
<211> LENGTH: 1074
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
atggaatgga gctgggtctt tctcttcttc ctgtcagtaa cgactggtgt ccactccgcg      60
ccggaactgc tgggcggccc gagcgtgttt ctgtttccgc cgaaaccgaa agataccctg     120
atgattagcc gcaccccgga agtgacctgc gtggtggtgg atgtgagcca tgaagatccg     180
gaagtgaaat taactggta tgtggatggc gtggaagtgc ataacgcgaa aaccaaaccg     240
cgcgaagaac agtataacag cacctatcgc gtggtgagcg tgctgaccgt gctgcatcag     300
gattggctga acggcaaaga atataaatgc aaagtgagca caaagcgct gccggcgccg     360 attgaaaaaa ccattagcaa agcgaaaggc cagccgcgcg aaccgcaggt gtataccctg     420
ccgccgagcc gcaaagaaat gaccaaaaac caggtgagcc tgacctgcct ggtgaaaggc     480
ttttatccga cgatattgc ggtggaatgg gaaagcaacg gccagccgga aaacaactat     540
aaaaccaccc cgccggtgct gaaaagcgat ggcagctttt ttctgtatag caaactgacc     600
gtggataaaa gccgctggca gcagggcaac gtgtttagct gcagcgtgat gcatgaagcg     660
ctgcataacc attataccca gaaaagcctg agcctgagcc cggcggcgg cggcggcagc     720 ggcggcggcg gcagcgcgcg caacggcgat cattgcccgc tgggcccggg ccgctgctgc     780
cgcctgcata ccgtgcgcgc gagcctggaa gatctgggct gggcggattg ggtgctgagc     840
ccgcgcgaag tgcaggtgac catgtgcatt ggcgcgtgcc cgagccagtt tcgcgcggcg     900
aacatgcatg cgcagattaa aaccagcctg catcgcctga accggatac cgtgccggcg     960 ccgtgctgcg tgccggcgag ctataacccg atggtgctga ttcagaaaac cgataccggc    1020
gtgagcctgc agacctatga tgatctgctg gcgaaagatt gccattgcat ttga          1074
```

<210> SEQ ID NO 77
<211> LENGTH: 357
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Glu Trp Ser Trp Val Phe Leu Phe Phe Leu Ser Val Thr Thr Gly
1               5                   10                  15

Val His Ser Ala Pro Glu Leu Leu Gly Gly Pro Ser Val Phe Leu Phe
                20                  25                  30

Pro Pro Lys Pro Lys Asp Thr Leu Met Ile Ser Arg Thr Pro Glu Val
            35                  40                  45

Thr Cys Val Val Val Asp Val Ser His Glu Asp Pro Glu Val Lys Phe
        50                  55                  60

Asn Trp Tyr Val Asp Gly Val Glu Val His Asn Ala Lys Thr Lys Pro

```
                65                  70                  75                  80
        Arg Glu Glu Gln Tyr Asn Ser Thr Tyr Arg Val Val Ser Val Leu Thr
                        85                  90                  95

Val Leu His Gln Asp Trp Leu Asn Gly Lys Glu Tyr Lys Cys Lys Val
                    100                 105                 110

Ser Asn Lys Ala Leu Pro Ala Pro Ile Glu Lys Thr Ile Ser Lys Ala
                    115                 120                 125

Lys Gly Gln Pro Arg Glu Pro Gln Val Tyr Thr Leu Pro Pro Ser Arg
        130                 135                 140

Lys Glu Met Thr Lys Asn Gln Val Ser Leu Thr Cys Leu Val Lys Gly
        145                 150                 155                 160

Phe Tyr Pro Ser Asp Ile Ala Val Glu Trp Glu Ser Asn Gly Gln Pro
                        165                 170                 175

Glu Asn Asn Tyr Lys Thr Thr Pro Pro Val Leu Lys Ser Asp Gly Ser
                    180                 185                 190

Phe Phe Leu Tyr Ser Lys Leu Thr Val Asp Lys Ser Arg Trp Gln Gln
                    195                 200                 205

Gly Asn Val Phe Ser Cys Ser Val Met His Glu Ala Leu His Asn His
                210                 215                 220

Tyr Thr Gln Lys Ser Leu Ser Leu Ser Pro Gly Gly Gly Gly Ser
        225                 230                 235                 240

Gly Gly Gly Gly Ser Ala Arg Asn Gly Asp His Cys Pro Leu Gly Pro
                        245                 250                 255

Gly Arg Cys Cys Arg Leu His Thr Val Arg Ala Ser Leu Glu Asp Leu
                    260                 265                 270

Gly Trp Ala Asp Trp Val Leu Ser Pro Arg Glu Val Gln Val Thr Met
                    275                 280                 285

Cys Ile Gly Ala Cys Pro Ser Gln Phe Arg Ala Ala Asn Met His Ala
                290                 295                 300

Gln Ile Lys Thr Ser Leu His Arg Leu Lys Pro Asp Thr Val Pro Ala
        305                 310                 315                 320

Pro Cys Cys Val Pro Ala Ser Tyr Asn Pro Met Val Leu Ile Gln Lys
                        325                 330                 335

Thr Asp Thr Gly Val Ser Leu Gln Thr Tyr Asp Asp Leu Leu Ala Lys
                    340                 345                 350

Asp Cys His Cys Ile
                    355

<210> SEQ ID NO 78
<211> LENGTH: 1017
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
gcgccggaac tgctgggcgg cccgagcgtg tttctgtttc gccgaaaccc gaaagatacc      60
ctgatgatta gccgcacccc ggaagtgacc tgcgtggtgg tggatgtgag ccatgaagat     120
ccggaagtga aatttaactg gtatgtggat ggcgtggaag tgcataacgc gaaaaccaaa     180
ccgcgcgaag aacagtataa cagcacctat cgcgtggtga gcgtgctgac cgtgctgcat     240
caggattggc tgaacggcaa agaatataaa tgcaaagtga gcaacaaagc gctgccggcg     300
ccgattgaaa aaaccattag caaagcgaaa ggccagccgc gcgaaccgca ggtgtatacc     360
```

```
ctgccgccga gccgcaaaga aatgaccaaa aaccaggtga gcctgacctg cctggtgaaa    420
ggcttttatc cgagcgatat tgcggtggaa tgggaaagca acggccagcc ggaaaacaac    480
tataaaacca ccccgccggt gctgaaaagc gatggcagct ttttctgtta tagcaaactg    540
accgtggata aaagccgctg gcagcagggc aacgtgttta gctgcagcgt gatgcatgaa    600
gcgctgcata accattatac ccagaaaagc ctgagcctga gcccgggcgg cggcggcggc    660
agcggcggcg gcggcagcgc gcgcaacggc gatcattgcc cgctgggccc gggccgctgc    720
tgccgcctgc ataccgtgcg cgcgagcctg gaagatctgg gctgggcgga ttgggtgctg    780
agcccgcgcg aagtgcaggt gaccatgtgc attggcgcgt gcccgagcca gtttcgcgcg    840
gcgaacatgc atgcgcagat aaaaccagcc tgcatcgcc tgaaaccgga taccgtgccg    900
gcgccgtgct gcgtgccggc gagctataac ccgatggtgc tgattcagaa aaccgatacc    960
ggcgtgagcc tgcagaccta tgatgatctg ctggcgaaag attgccattg catttga     1017
```

<210> SEQ ID NO 79
<211> LENGTH: 338
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Ser Gly Gly Gly
    210                 215                 220

Gly Ser Ala Arg Asn Gly Asp His Cys Pro Leu Gly Pro Gly Arg Cys
225                 230                 235                 240

Cys Arg Leu His Thr Val Arg Ala Ser Leu Glu Asp Leu Gly Trp Ala
```

```
                    245                 250                 255
Asp Trp Val Leu Ser Pro Arg Glu Val Gln Val Thr Met Cys Ile Gly
            260                 265                 270

Ala Cys Pro Ser Gln Phe Arg Ala Ala Asn Met His Ala Gln Ile Lys
        275                 280                 285

Thr Ser Leu His Arg Leu Lys Pro Asp Thr Val Pro Ala Pro Cys Cys
    290                 295                 300

Val Pro Ala Ser Tyr Asn Pro Met Val Leu Ile Gln Lys Thr Asp Thr
305                 310                 315                 320

Gly Val Ser Leu Gln Thr Tyr Asp Asp Leu Leu Ala Lys Asp Cys His
                325                 330                 335

Cys Ile

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Gly Gly Gly Gln Gly Gly Gly Gln Gly Gly Gly Gln Gly
1               5                   10                  15

Gly Gly Gly Gln
            20

<210> SEQ ID NO 81
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
atggagtggt cttgggtctt tctgttcttc ctctccgtca ccaccggtgt gcattctgcc      60
ccagagctgc ttggtggacc atccgtgttc ctgtttcctc caaagccgaa ggacaccctg     120
atgatctcaa gaactccgga agtgacttgc gtcgtcgtgg acgtgtcaca tgaggatcca     180
gaggtcaagt tcaattggta tgtggacgga gtggaagtgc ataacgccaa gaccaaaccc     240
cgcgaagaac agtacaatag cacctaccgc gtggtgagcg tccttactgt gctccaccag     300
gactggctta atgggaagga atacaagtgt aaggtgtcca acaaggccct ccccgctccc     360
atcgaaaaga ccatctcaaa ggcaaagggg caaccaaggg aacctcaagt gtacaccctg     420
cctccgagca ggaaggagat gaccaagaac caggtcagcc tgacttgtct cgtgaagggc     480
ttctatccca gcgatattgc tgtggaatgg gagtcaaatg gccagccga gaataactac     540 aaaactaccc cacccgtgct gaaatctgat ggtccttct ccttttactc caagctgacc     600
gtggacaaga gccgctggca acaaggcaat gtctttagct gctcagtgat gcatgaggct     660
ctccataatc actacactca gaagtcactg tccctgtcac ctggaggtgg cggagggcag     720
ggtggtggag tcagggagg cggaggacag ggaggaggtg acaagcacg gaacggggac     780 cattgtcccc tgggacctgg tcggtgctgc cggcttcaca ccgtcagagc ctctctggag     840
gaccttggat gggctgattg ggtgctgagc cctcggagg tgcaagtcac catgtgcatc     900
ggggcctgcc ctagccagtt ccgcgcagcc aacatgcacg ctcagatcaa aacctctctt     960
```

```
cacagactga agcccgacac cgtgccagca ccttgctgtg tgccggcctc ttataacccc   1020
atggtcctca ttcagaaaac cgacaccgga gtgtcacttc agacttacga tgacctcctg   1080
gccaaggact gccactgtat ttga                                          1104
```

<210> SEQ ID NO 82
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Met Glu Trp Ser Trp Val Phe Leu Phe Phe Leu Ser Val Thr Thr Gly
1               5                   10                  15

Val His Ser Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140

Lys Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Lys Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Gly Gly Gly Gln
225                 230                 235                 240

Gly Gly Gly Gly Gln Gly Gly Gly Gln Gly Gly Gly Gln Ala
                245                 250                 255

Arg Asn Gly Asp His Cys Pro Leu Gly Pro Gly Arg Cys Cys Arg Leu
            260                 265                 270

His Thr Val Arg Ala Ser Leu Glu Asp Leu Gly Trp Ala Asp Trp Val
        275                 280                 285

Leu Ser Pro Arg Glu Val Gln Val Thr Met Cys Ile Gly Ala Cys Pro
    290                 295                 300

Ser Gln Phe Arg Ala Ala Asn Met His Ala Gln Ile Lys Thr Ser Leu
305                 310                 315                 320

His Arg Leu Lys Pro Asp Thr Val Pro Ala Pro Cys Cys Val Pro Ala
                325                 330                 335
```

Ser Tyr Asn Pro Met Val Leu Ile Gln Lys Thr Asp Thr Gly Val Ser
                    340                 345                 350

Leu Gln Thr Tyr Asp Asp Leu Ala Lys Asp Cys His Cys Ile
            355                 360                 365

<210> SEQ ID NO 83
<211> LENGTH: 1047
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
gccccagagc tgcttggtgg accatccgtg ttcctgtttc ctccaaagcc gaaggacacc     60
ctgatgatct caagaactcc ggaagtgact tgcgtcgtcg tggacgtgtc acatgaggat    120
ccagaggtca agttcaattg gtatgtggac ggagtggaag tgcataacgc caagaccaaa    180
ccccgcgaag aacagtacaa tagcacctac cgcgtggtga cgtccttac tgtgctccac    240 caggactggc ttaatgggaa ggaatacaag tgtaaggtgt ccaacaaggc cctccccgct    300
cccatcgaaa agaccatctc aaaggcaaag gggcaaccaa gggaacctca agtgtacacc    360
ctgcctccga gcaggaagga gatgaccaag aaccaggtca gcctgacttg tctcgtgaag    420
ggcttctatc ccagcgatat tgctgtgaa tgggagtcaa atggccagcc cgagaataac    480
tacaaaacta ccccacccgt gctgaaatct gatgggtcct tcttcctttta ctccaagctg    540 accgtggaca gagccgctg gcaacaaggc aatgtctta gctgctcagt gatgcatgag    600
gctctccata atcactacac tcagaagtca ctgtccctgt cacctggagg tggcggaggg    660
cagggtggtg gaggtcaggg aggcggagga cagggaggag gtggacaagc acggaacggg    720
gaccattgtc ccctgggacc tggtcggtgc tgccggcttc acaccgtcag agcctctctg    780
gaggaccttg gatgggctga ttgggtgctg agccctcggg aggtgcaagt caccatgtgc    840 atcgggcct gccctagcca gttccgcgca gccaacatgc acgctcagat caaaacctct    900
cttcacagac tgaagcccga caccgtgcca gcaccttgct gtgtgccggc ctcttataac    960
cccatggtcc tcattcagaa aaccgacacc ggagtgtcac ttcagactta cgatgacctc   1020
ctggccaagg actgccactg tatttga                                      1047

<210> SEQ ID NO 84
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Gln Gly Gly Gly
    210                 215                 220

Gly Gln Gly Gly Gly Gln Gly Gly Gly Gln Ala Arg Asn Gly
225                 230                 235                 240

Asp His Cys Pro Leu Gly Pro Gly Arg Cys Cys Arg Leu His Thr Val
                245                 250                 255

Arg Ala Ser Leu Glu Asp Leu Gly Trp Ala Asp Trp Val Leu Ser Pro
            260                 265                 270

Arg Glu Val Gln Val Thr Met Cys Ile Gly Ala Cys Pro Ser Gln Phe
        275                 280                 285

Arg Ala Ala Asn Met His Ala Gln Ile Lys Thr Ser Leu His Arg Leu
    290                 295                 300

Lys Pro Asp Thr Val Pro Ala Pro Cys Cys Val Pro Ala Ser Tyr Asn
305                 310                 315                 320

Pro Met Val Leu Ile Gln Lys Thr Asp Thr Gly Val Ser Leu Gln Thr
                325                 330                 335

Tyr Asp Asp Leu Leu Ala Lys Asp Cys His Cys Ile
            340                 345

<210> SEQ ID NO 85
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys

```
                      85                  90                  95
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 86
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Gly Gly Gly Ser Gly Gly Gly Gly Ser Gly Gly Gly Gly Ser
1               5                   10                  15

<210> SEQ ID NO 88
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 89
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Cys Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln

Lys Ser Leu Ser Leu Ser Pro Gly Lys
    210                 215

<210> SEQ ID NO 90
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Cys Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 91
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu

| | 50 | | | 55 | | | 60 | | | | |
|---|---|---|---|---|---|---|---|---|---|---|---|

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Cys Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 92
<211> LENGTH: 1056
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 92

```
atggaatgga gctgggtctt tctgttcttc ctctccgtca ccaccggtgt gcattctgcc      60
ccagagctgc ttggtggacc atccgtgttc ctgtttcctc caaagccgaa ggacaccctg     120
atgatctcaa gaactccgga agtgacttgc gtcgtcgtgg acgtgtcaca tgaggatcca     180
gaggtcaagt tcaattggta tgtggacgga gtggaagtgc ataacgccaa gaccaaaccc     240
cgcgaagaac agtacaatag cacctaccgc gtggtgagcg tccttactgt gctccaccag     300
gactggctta tgggaagga atacaagtgt aaggtgtcca acaaggccct ccccgctccc     360
atcgaaaaga ccatctcaaa ggcaaggggg caaccaaggg aacctcaagt gtacacctgt     420
cctccgagca ggaaggagat gaccaagaac caggtcagcc tgacttgtct cgtgaagggc     480
ttctatccca gcgatattgc tgtggaatgg gagtcaaatg ccagcccga gaataactac      540
aaaactaccc cacccgtgct gaaatctgat gggtccttct ccttttactc caagctgacc     600
gtggacaaga gccgctggca acaaggcaat gtctttagct gctcagtgat gcatgaggct     660
ctccataatc actacactca gaagtcactg tccctgtcac ctggcggagg tggaggagca     720
cggaacgggg accattgtcc cctgggacct ggtcggtgct gccggcttca ccgtcaga      780
gcctctctgg aggaccttgg atgggctgat tgggtgctga ccctcgggga ggtgcaagtc     840
accatgtgca tcggggcctg ccctagccag ttccgcgcag ccaacatgca cgctcagatc     900
aaaacctctc ttcacagact gaagcccgac accgtgccag caccttgctg tgtgccggcc     960
tcttataacc ccatggtcct cattcagaaa accgacaccg gagtgtcact tcagacttac    1020
gatgacctcc tggccaagga ctgccactgc atatga                              1056
```

<210> SEQ ID NO 93
<211> LENGTH: 351
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

```
Met Glu Trp Ser Trp Val Phe Leu Phe Phe Leu Ser Val Thr Thr Gly
1               5                   10                  15

Val His Ser Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Cys Pro Pro Ser Arg
    130                 135                 140

Lys Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Lys Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Gly Gly Gly Gly Ala
225                 230                 235                 240

Arg Asn Gly Asp His Cys Pro Leu Gly Pro Gly Arg Cys Cys Arg Leu
                245                 250                 255

His Thr Val Arg Ala Ser Leu Glu Asp Leu Gly Trp Ala Asp Trp Val
            260                 265                 270

Leu Ser Pro Arg Glu Val Gln Val Thr Met Cys Ile Gly Ala Cys Pro
        275                 280                 285

Ser Gln Phe Arg Ala Ala Asn Met His Ala Gln Ile Lys Thr Ser Leu
    290                 295                 300

His Arg Leu Lys Pro Asp Thr Val Pro Ala Pro Cys Cys Val Pro Ala
305                 310                 315                 320

Ser Tyr Asn Pro Met Val Leu Ile Gln Lys Thr Asp Thr Gly Val Ser
                325                 330                 335

Leu Gln Thr Tyr Asp Asp Leu Leu Ala Lys Asp Cys His Cys Ile
            340                 345                 350
```

<210> SEQ ID NO 94

<211> LENGTH: 999
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94

| | | | | | |
|---|---|---|---|---|---|
| gccccagagc | tgcttggtgg | accatccgtg | ttcctgtttc | ctccaaagcc | gaaggacacc | 60 |
| ctgatgatct | caagaactcc | ggaagtgact | tgcgtcgtcg | tggacgtgtc | acatgaggat | 120 |
| ccagaggtca | agttcaattg | gtatgtggac | ggagtggaag | tgcataacgc | caagaccaaa | 180 |
| ccccgcgaag | aacagtacaa | tagcacctac | cgcgtggtga | cgtccttac | tgtgctccac | 240 |
| caggactggc | ttaatgggaa | ggaatacaag | tgtaaggtgt | ccaacaaggc | cctccccgct | 300 |
| cccatcgaaa | agaccatctc | aaaggcaaag | gggcaaccaa | gggaacctca | agtgtacacc | 360 |
| tgtcctccga | gcaggaagga | gatgaccaag | aaccaggtca | gcctgacttg | tctcgtgaag | 420 |
| ggcttctatc | ccagcgatat | tgctgtgaa | tgggagtcaa | atggccagcc | cgagaataac | 480 |
| tacaaaacta | ccccacccgt | gctgaaatct | gatgggtcct | tcttcctta | ctccaagctg | 540 |
| accgtggaca | agagccgctg | gcaacaaggc | aatgtctta | gctgctcagt | gatgcatgag | 600 |
| gctctccata | atcactacac | tcagaagtca | ctgtccctgt | cacctggcgg | aggtggagga | 660 |
| gcacggaacg | gggaccattg | tccccctggga | cctggtcggt | gctgccggct | tcacaccgtc | 720 |
| agagcctctc | tggaggacct | tggatgggct | gattgggtgc | tgagccctcg | ggaggtgcaa | 780 |
| gtcaccatgt | gcatcggggc | ctgccctagc | cagttccgcg | cagccaacat | gcacgctcag | 840 |
| atcaaaacct | ctcttcacag | actgaagccc | gacaccgtgc | cagcaccttg | ctgtgtgccg | 900 |
| gcctctttata | accccatggt | cctcattcag | aaaaccgaca | ccggagtgtc | acttcagact | 960 |
| tacgatgacc | tcctggccaa | ggactgccac | tgcatatga | | | 999 |

<210> SEQ ID NO 95
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Cys Pro Pro Ser Arg Lys Glu Met
        115                 120                 125

Thr Lys Asn Gln Val Ser Leu Thr Cys Leu Val Lys Gly Phe Tyr Pro

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Ala Arg Asn Gly
    210                 215                 220

Asp His Cys Pro Leu Gly Pro Gly Arg Cys Cys Arg Leu His Thr Val
225                 230                 235                 240

Arg Ala Ser Leu Glu Asp Leu Gly Trp Ala Asp Trp Val Leu Ser Pro
                245                 250                 255

Arg Glu Val Gln Val Thr Met Cys Ile Gly Ala Cys Pro Ser Gln Phe
                260                 265                 270

Arg Ala Ala Asn Met His Ala Gln Ile Lys Thr Ser Leu His Arg Leu
            275                 280                 285

Lys Pro Asp Thr Val Pro Ala Pro Cys Cys Val Pro Ala Ser Tyr Asn
        290                 295                 300

Pro Met Val Leu Ile Gln Lys Thr Asp Thr Gly Val Ser Leu Gln Thr
305                 310                 315                 320

Tyr Asp Asp Leu Leu Ala Lys Asp Cys His Cys Ile
                325                 330

<210> SEQ ID NO 96
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
atggaatgga gctgggtctt tctcttcttc ctgtcagtaa cgactggtgt ccactccgca    60
cctgaactcc tgggggggacc gtcagtcttc ctcttccccc caaaacccaa ggacaccctc   120
atgatctccc ggaccctga ggtcacatgc gtggtggtgg acgtgagcca cgaagaccct   180
gaggtcaagt tcaactggta cgtggacggc gtggaggtgc ataatgccaa gacaaagccg   240
cgggaggagc agtacaacag cacgtaccgt gtggtcagcg tcctcaccgt cctgcaccag   300
gactggctga atggcaagga gtacaagtgc aaggtctcca acaaagccct cccagccccc   360
atcgagaaaa ccatctccaa agccaaaggg cagccccgag aaccacaggt gtacaccctgt   420 cccccatccc gggaggagat gaccaagaac caggtcagcc tgacctgcct ggtcaaaggc   480
ttctatccca gcgacatcgc cgtggagtgg gagagcaatg gcagccggga gaacaactac   540
gacaccacgc ctcccgtgct ggactccgac ggctccttct tcctctatag cgacctcacc   600
gtggacaaga gcaggtggca gcaggggaac gtcttctcat gctccgtgat gcatgaggct   660
ctgcacaacc actacacgca gaagagcctc tccctgtctc cgggtaaatg a            711

<210> SEQ ID NO 97
<211> LENGTH: 236
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 97

```
Met Glu Trp Ser Trp Val Phe Leu Phe Phe Leu Ser Val Thr Thr Gly
1               5                   10                  15
Val His Ser Ala Pro Glu Leu Leu Gly Gly Pro Ser Val Phe Leu Phe
            20                  25                  30
Pro Pro Lys Pro Lys Asp Thr Leu Met Ile Ser Arg Thr Pro Glu Val
        35                  40                  45
Thr Cys Val Val Val Asp Val Ser His Glu Asp Pro Glu Val Lys Phe
    50                  55                  60
Asn Trp Tyr Val Asp Gly Val Glu Val His Asn Ala Lys Thr Lys Pro
65                  70                  75                  80
Arg Glu Glu Gln Tyr Asn Ser Thr Tyr Arg Val Val Ser Val Leu Thr
                85                  90                  95
Val Leu His Gln Asp Trp Leu Asn Gly Lys Glu Tyr Lys Cys Lys Val
            100                 105                 110
Ser Asn Lys Ala Leu Pro Ala Pro Ile Glu Lys Thr Ile Ser Lys Ala
        115                 120                 125
Lys Gly Gln Pro Arg Glu Pro Gln Val Tyr Thr Cys Pro Pro Ser Arg
    130                 135                 140
Glu Glu Met Thr Lys Asn Gln Val Ser Leu Thr Cys Leu Val Lys Gly
145                 150                 155                 160
Phe Tyr Pro Ser Asp Ile Ala Val Glu Trp Glu Ser Asn Gly Gln Pro
                165                 170                 175
Glu Asn Asn Tyr Asp Thr Thr Pro Pro Val Leu Asp Ser Asp Gly Ser
            180                 185                 190
Phe Phe Leu Tyr Ser Asp Leu Thr Val Asp Lys Ser Arg Trp Gln Gln
        195                 200                 205
Gly Asn Val Phe Ser Cys Ser Val Met His Glu Ala Leu His Asn His
    210                 215                 220
Tyr Thr Gln Lys Ser Leu Ser Leu Ser Pro Gly Lys
225                 230                 235
```

<210> SEQ ID NO 98
<211> LENGTH: 654
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 98

| gcacctgaac tcctgggggg accgtcagtc ttcctcttcc ccccaaaacc caaggacacc | 60 |
| ctcatgatct cccggacccc tgaggtcaca tgcgtggtgg tggacgtgag ccacgaagac | 120 |
| cctgaggtca agttcaactg gtacgtggac ggcgtggagg tgcataatgc caagacaaag | 180 |
| ccgcgggagg agcagtacaa cagcacgtac cgtgtggtca gcgtcctcac cgtcctgcac | 240 |
| caggactggc tgaatggcaa ggagtacaag tgcaaggtct ccaacaaagc cctcccagcc | 300 |
| cccatcgaga aaaccatctc caaagccaaa gggcagcccc gagaaccaca ggtgtacacc | 360 |
| tgtcccccat cccgggagga tgaccaagaa ccaggtca gcctgacctg cctggtcaaa | 420 |
| ggcttctatc ccagcgacat cgccgtggag tgggagagca atgggcagcc ggagaacaac | 480 |
| tacgacacca cgcctcccgt gctggactcc gacggctcct tcttcctcta tagcgacctc | 540 |

```
accgtggaca agagcaggtg gcagcagggg aacgtcttct catgctccgt gatgcatgag      600
gctctgcaca accactacac gcagaagagc ctctccctgt ctccgggtaa atga            654
```

<210> SEQ ID NO 99
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Cys Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 100
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60
```

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 101
<211> LENGTH: 1056
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
atggaatgga gctgggtctt tctgttcttc ctctccgtca ccaccggtgt gcattctgcc      60
ccagagctgc ttggtggacc atccgtgttc ctgtttcctc caaagccgaa ggacaccctg     120
atgatctcaa gaactccgga agtgacttgc gtcgtcgtgg acgtgtcaca tgaggatcca     180
gaggtcaagt tcaattggta tgtggacgga gtggaagtgc ataacgccaa gaccaaaccc     240
cgcgaagaac agtacaatag cacctaccgc gtggtgagcg tccttactgt gctccaccag     300
gactggctta tgggaagga atacaagtgt aaggtgtcca acaaggccct ccccgctccc     360
atcgaaaaga ccatctcaaa ggcaaagggg caaccaaggg aacctcaagt gtacaccctg     420
cctccgtgca ggaaggagat gaccaagaac caggtcagcc tgacttgtct cgtgaagggc     480
ttctatccca gcgatattgc tgtggaatgg gagtcaaatg gccagcccga gaataactac     540
aaaactaccc cacccgtgct gaatctgat gggtccttct cctttactc caagctgacc      600 gtggacaaga gccgctggca acaaggcaat gtctttagct gctcagtgat gcatgaggct     660
ctccataatc actacactca gaagtcactg tccctgtcac tggcggagg tggaggagca     720 cggaacgggg accattgtcc cctgggacct ggtcggtgct gccggcttca caccgtcaga     780
gcctctctgg aggaccttgg atgggctgat tgggtgctga ccctcgggga ggtgcaagtc     840
accatgtgca tcgggcctg ccctagccag ttccgcgcag ccaacatgca cgctcagatc     900
aaaacctctc ttcacagact gaagcccgac accgtgccag caccttgctg tgtgccggcc     960
tcttataacc ccatggtcct cattcagaaa accgacaccg gagtgtcact tcagacttac    1020
gatgacctcc tggccaagga ctgccactgc atatga                             1056

<210> SEQ ID NO 102
<211> LENGTH: 351
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

Met Glu Trp Ser Trp Val Phe Leu Phe Phe Leu Ser Val Thr Thr Gly
1               5                   10                  15

Val His Ser Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Cys Arg
    130                 135                 140

Lys Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Lys Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Gly Gly Gly Gly Ala
225                 230                 235                 240

Arg Asn Gly Asp His Cys Pro Leu Gly Pro Gly Arg Cys Cys Arg Leu
                245                 250                 255

His Thr Val Arg Ala Ser Leu Glu Asp Leu Gly Trp Ala Asp Trp Val
            260                 265                 270

Leu Ser Pro Arg Glu Val Gln Val Thr Met Cys Ile Gly Ala Cys Pro
        275                 280                 285

Ser Gln Phe Arg Ala Ala Asn Met His Ala Gln Ile Lys Thr Ser Leu
    290                 295                 300

His Arg Leu Lys Pro Asp Thr Val Pro Ala Pro Cys Cys Val Pro Ala
305                 310                 315                 320

Ser Tyr Asn Pro Met Val Leu Ile Gln Lys Thr Asp Thr Gly Val Ser
                325                 330                 335

Leu Gln Thr Tyr Asp Asp Leu Leu Ala Lys Asp Cys His Cys Ile
            340                 345                 350

<210> SEQ ID NO 103
<211> LENGTH: 999

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
gccccagagc tgcttggtgg accatccgtg ttcctgtttc ctccaaagcc gaaggacacc      60
ctgatgatct caagaactcc ggaagtgact tgcgtcgtcg tggacgtgtc acatgaggat     120
ccagaggtca agttcaattg gtatgtggac ggagtggaag tgcataacgc aagaccaaa     180
ccccgcgaag aacagtacaa tagcacctac cgcgtggtga cgtccttac tgtgctccac     240
caggactggc ttaatgggaa ggaatacaag tgtaaggtgt ccaacaaggc cctccccgct     300
cccatcgaaa agaccatctc aaaggcaaag gggcaaccaa gggaacctca agtgtacacc     360
ctgcctccgt gcaggaagga gatgaccaag aaccaggtca gcctgacttg tctcgtgaag     420
ggcttctatc ccagcgatat tgctgtggaa tgggagtcaa atggccagcc cgagaataac     480
tacaaaacta ccccacccgt gctgaaatct gatgggtcct tcttcctta ctccaagctg     540
accgtggaca gagccgctg gcaacaaggc aatgtcttta gctgctcagt gatgcatgag     600
gctctccata atcactacac tcagaagtca ctgtccctgt cacctggcgg aggtggagga     660
gcacggaacg gggaccattg tcccctggga cctggtcggt gctgccggct tcacaccgtc     720
agagcctctc tggaggacct tggatgggct gattgggtgc tgagccctcg ggaggtgcaa     780
gtcaccatgt gcatcggggc ctgccctagc cagttccgcg cagccaacat gcacgctcag     840
atcaaaacct ctcttcacag actgaagccc gacaccgtgc agcaccttg ctgtgtgccg     900
gcctcttata accccatggt cctcattcag aaaaccgaca ccggagtgtc acttcagact     960
tacgatgacc tcctggccaa ggactgccac tgcatatga                           999
```

<210> SEQ ID NO 104
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Cys Arg Lys Glu Met
        115                 120                 125

Thr Lys Asn Gln Val Ser Leu Thr Cys Leu Val Lys Gly Phe Tyr Pro
    130                 135                 140
```

```
Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Ala Arg Asn Gly
210                 215                 220

Asp His Cys Pro Leu Gly Pro Gly Arg Cys Cys Arg Leu His Thr Val
225                 230                 235                 240

Arg Ala Ser Leu Glu Asp Leu Gly Trp Ala Asp Trp Val Leu Ser Pro
                245                 250                 255

Arg Glu Val Gln Val Thr Met Cys Ile Gly Ala Cys Pro Ser Gln Phe
            260                 265                 270

Arg Ala Ala Asn Met His Ala Gln Ile Lys Thr Ser Leu His Arg Leu
        275                 280                 285

Lys Pro Asp Thr Val Pro Ala Pro Cys Cys Val Pro Ala Ser Tyr Asn
290                 295                 300

Pro Met Val Leu Ile Gln Lys Thr Asp Thr Gly Val Ser Leu Gln Thr
305                 310                 315                 320

Tyr Asp Asp Leu Leu Ala Lys Asp Cys His Cys Ile
                325                 330
```

<210> SEQ ID NO 105
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105

```
atggaatgga gctgggtctt tctcttcttc ctgtcagtaa cgactggtgt ccactccgca    60
cctgaactcc tgggggggacc gtcagtcttc ctcttccccc caaaacccaa ggacaccctc   120
atgatctccc ggaccectga ggtcacatgc gtggtggtgg acgtgagcca cgaagaccct   180
gaggtcaagt tcaactggta cgtggacggc gtggaggtgc ataatgccaa gacaaagccg   240
cgggaggagc agtacaacag cacgtaccgt gtggtcagcg tcctcaccgt cctgcaccag   300
gactggctga atggcaagga gtacaagtgc aaggtctcca acaaagccct cccagccccc   360
atcgagaaaa ccatctccaa agccaaaggg cagccccgag aaccacaggt gtgcaccctg   420
cccccatccc gggaggagat gaccaagaac caggtcagcc tgacctgcct ggtcaaaggc   480
ttctatccca gcgacatcgc cgtggagtgg gagagcaatg gcagccgga gaacaactac   540 gacaccacgc ctcccgtgct ggactccgac ggctccttct cctctatag cgacctcacc   600 gtggacaaga gcaggtggca gcaggggaac gtcttctcat gctccgtgat gcatgaggct   660
ctgcacaacc actacacgca gaagagcctc tccctgtctc cgggtaaatg a           711
```

<210> SEQ ID NO 106
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Met Glu Trp Ser Trp Val Phe Leu Phe Phe Leu Ser Val Thr Thr Gly
1               5                   10                  15

Val His Ser Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Cys Thr Leu Pro Pro Ser Arg
130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Asp Thr Thr Pro Pro Val Leu Asp Ser Asp Gly Ser
            180                 185                 190

Phe Phe Leu Tyr Ser Asp Leu Thr Val Asp Lys Ser Arg Trp Gln Gln
        195                 200                 205

Gly Asn Val Phe Ser Cys Ser Val Met His Glu Ala Leu His Asn His
210                 215                 220

Tyr Thr Gln Lys Ser Leu Ser Leu Ser Pro Gly Lys
225                 230                 235
```

<210> SEQ ID NO 107
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107

```
gcacctgaac tcctgggggg accgtcagtc ttcctcttcc ccccaaaacc caaggacacc    60
ctcatgatct cccggacccc tgaggtcaca tgcgtggtgg tggacgtgag ccacgaagac   120
cctgaggtca agttcaactg gtacgtggac ggcgtggagg tgcataatgc caagacaaag   180
ccgcgggagg agcagtacaa cagcacgtac cgtgtggtca gcgtcctcac cgtcctgcac   240
caggactggc tgaatggcaa ggagtacaag tgcaaggtct ccaacaaagc cctcccagcc   300
cccatcgaga aaaccatctc caaagccaaa gggcagcccc gagaaccaca ggtgtgcacc   360
ctgcccccat cccgggagga gatgaccaag aaccaggtca gcctgacctg cctggtcaaa   420
ggcttctatc ccagcgacat cgccgtggag tgggagagca atgggcagcc ggagaacaac   480
tacgacacca cgcctcccgt gctggactcc gacggctcct tcttcctcta tagcgacctc   540
accgtggaca agagcaggtg gcagcagggg aacgtcttct catgctccgt gatgcatgag   600
```
gctctgcaca accactacac gcagaagagc ctctccctgt ctccgggtaa atga             654

<210> SEQ ID NO 108
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Cys Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 109
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Cys Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 110
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

```
Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Lys Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

His Glu Ala Leu His Asn His Tyr Thr Gln Lys Ser Leu Ser Leu Ser
    210                 215                 220

Pro Gly Lys
225

<210> SEQ ID NO 111
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 112
<211> LENGTH: 1077
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
gacaaaactc acacatgccc accgtgccca gcacctgaac tcctgggggg accgtcagtc     60
ttcctcttcc ccccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240

```
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggagga gatgaccaag    420
aaccaggtca gcctgacctg cctggtcaaa ggcttctatc ccagcgacat cgccgtggag    480
tgggagagca atgggcagcc ggagaacaac tacgacacca cgcctcccgt gctggactcc    540
gacggctcct tcttcctcta tagcgacctc accgtggaca agagcaggtg gcagcagggg    600
aacgtcttct catgctccgt gatgcatgag gctctgcaca accactacac gcagaagagc    660
ctctccctgt ctccgggtgg aggtggtgga tccggaggcg gtggaagcgg aggtggtgga    720
tctggaggcg gtggaagcgc gcgcaacgga gaccactgtc cgctcgggcc cgggcgttgc    780
tgccgtctgc acacggtccg cgcgtcgctg gaagacctgg gctgggccga ttgggtgctg    840
tcgccacggg aggtgcaagt gaccatgtgc atcggcgcgt gcccgagcca gttccggcg    900 gcaaacatgc acgcgcagat caagacgagc ctgcaccgcc tgaagcccga cacggtgcca    960
gcgccctgct gcgtgcccgc cagctacaat cccatggtgc tcattcaaaa gaccgacacc   1020
ggggtgtcgc tccagaccta tgatgacttg ttagccaaag actgccactg catatga     1077
```

<210> SEQ ID NO 113  
<211> LENGTH: 358  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 113

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Asp Thr Thr Pro Pro
                165                 170                 175

Val Leu Asp Ser Asp Gly Ser Phe Phe Leu Tyr Ser Asp Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
```

```
              210                 215                 220
Pro Gly Gly Gly Gly Ser Gly Gly Gly Ser Gly Gly Gly
225                 230                 235                 240

Ser Gly Gly Gly Ser Ala Arg Asn Gly Asp His Cys Pro Leu Gly
                245                 250                 255

Pro Gly Arg Cys Cys Arg Leu His Thr Val Arg Ala Ser Leu Glu Asp
                260                 265                 270

Leu Gly Trp Ala Asp Trp Val Leu Ser Pro Arg Glu Val Gln Val Thr
            275                 280                 285

Met Cys Ile Gly Ala Cys Pro Ser Gln Phe Arg Ala Ala Asn Met His
        290                 295                 300

Ala Gln Ile Lys Thr Ser Leu His Arg Leu Lys Pro Asp Thr Val Pro
305                 310                 315                 320

Ala Pro Cys Cys Val Pro Ala Ser Tyr Asn Pro Met Val Leu Ile Gln
                325                 330                 335

Lys Thr Asp Thr Gly Val Ser Leu Gln Thr Tyr Asp Asp Leu Leu Ala
                340                 345                 350

Lys Asp Cys His Cys Ile
            355

<210> SEQ ID NO 114
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Lys Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

His Glu Ala Leu His Asn His Tyr Thr Gln Lys Ser Leu Ser Leu Ser
210                 215                 220

Pro Gly
225

<210> SEQ ID NO 115
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Asp Thr Thr Pro Pro
                165                 170                 175

Val Leu Asp Ser Asp Gly Ser Phe Phe Leu Tyr Ser Asp Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 116
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
gacaaaactc acacatgccc accgtgccca gcacctgaac tcctgggggg accgtcagtc    60
ttcctcttcc cccaaaaacc caaggacacc ctcatgatct cccggacccc tgaggtcaca   120
tgcgtggtgg tggacgtgag ccacgaagac cctgaggtca agttcaactg gtacgtggac   180

```
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaccatctc caaagccaaa     360 gggcagcccc gagaaccaca ggtgtacacc ctgcccccat cccggaagga tgaccaag      420 aaccaggtca gcctgacctg cctggtcaaa ggcttctatc ccagcgacat cgccgtggag    480
tgggagagca atgggcagcc ggagaacaac tacaagacca cgcctcccgt gctgaagtcc    540
gacggctcct tcttcctcta tagcaagctc accgtggaca agagcaggtg gcagcagggg    600
aacgtcttct catgctccgt gatgcatgag gctctgcaca accactacac gcagaagagc    660
ctctccctgt ctccgggtaa atga                                           684
```

<210> SEQ ID NO 117
<211> LENGTH: 1950
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

```
atggaatgga gctgggtctt tctcttcttc ctgtcagtaa cgactggtgt ccactccgga    60
ggtggagagc gcaaatcttc tgtcgagtgc ccaccgtgcc cagcaccacc tgtggcagga    120
ccgtcagtct tcctcttccc cccaaaaccc aaggacaccc tcatgatctc ccggacccct    180
gaggtcacgt gcgtggtggt ggacgtgagc acgaagacc ccgaggtcca gttcaactgg    240
tacgtggacg gcgtggaggt gcataatgcc aagacaaaac cacgggagga gcagttcaac    300
agcacgttcc gtgtggtcag cgtcctcacc gttgtgcacc aggactggct gaacggcaag    360
gagtacaagt gcaaggtctc caacaaaggc ctcccagccc ccatcgagaa aaccatctcc    420
aaaaccaaag ggcagcccc gagaaccacag gtgtacaccc tgcccccatc ccggaggag     480 atgaccaaga accaggtcag cctgacctgc ctggtcaaag gcttctaccc cagcgacatc    540
gccgtggagt gggagagcaa tgggcagccg gagaacaact acaagaccac acctcccatg    600
ctggactccg acggctcctt cttcctctac agcaagctca ccgtggacaa gagcaggtgg    660
cagcagggga cgtcttctc atgctccgtg atgcatgagg ctctgcacaa ccactacacg    720
cagaagagcc tctccctgtc tccgggtgga ggtggcggta gcggtggcgg aggttcaggt    780
ggtggcggtt ctggcggagg tggcagtggc ggtggcggat caggtggcgg tggcagcggt    840
ggcggcggaa gcggtggagg aggttcagag cggaaatcca gcgttgaatg tcctccgtgc    900
cctgctccac ccgtcgcggg gcctagtgtc ttccttttcc ctccaaaacc aaaggataca    960
ctgatgatca gccggacccc cgaggttacg tgcgtcgtcg tcgatgtctc ccacgaggat    1020
ccagaggtcc aattcaactg gtacgtggac ggggtcgagg tgcataatgc aaagacaaag    1080
ccacgggaag agcagtttaa ctctactttc cgcgtggttt ctgtgctgac cgtggtgcac    1140
caagattggc tcaacggcaa ggagtacaag tgcaaggtaa gcaataaggg gctccctgcc    1200
cccattgaga gactatctc caagacaaag ggacagccac gcgagccaca agtctataca    1260
ctcccccctt cccgcgaaga aatgaccaag aatcaggtta gcctgacatg cttggttaag    1320
ggtttctacc cctctgacat agccgtggag tgggagagca atggacaacc agagaacaac    1380
tacaagacca cccacccat gctggatagc gacggttcat tcttttctgta tagtaagctt    1440 accgtggaca agtcccggtg gcaacaagga aatgtctttt catgctctgt gatgcacgag    1500
```

```
gccttgcata atcactatac tcagaagagc ttgagcctca gccccggatc tggaggtggc      1560
ggatccgggg gcggtggaag cggaggtggt ggatcgggag cggtggaag cgcgcgcaac      1620 ggcgaccact gtccgctcgg gcccggacgt tgctgccgtc tgcacacggt ccgcgcgtcg      1680
ctggaagacc tgggctgggc cgattgggtg ctgtcgccac gggaggtgca agtgaccatg      1740
tgcatcggcg cgtgcccgag ccagttccgg gcggcaaaca tgcacgcgca gatcaagacg      1800
agcctgcacc gcctgaagcc cgacacggtg ccagcgccct gctgcgtgcc cgccagctac      1860
aatcccatgg tgctcattca aaagaccgac accggggtgt cgctccagac ctatgatgac      1920
ttgttagcca aagactgcca ctgcatatga                                       1950
```

<210> SEQ ID NO 118
<211> LENGTH: 649
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Met Glu Trp Ser Trp Val Phe Leu Phe Phe Leu Ser Val Thr Thr Gly
1               5                   10                  15

Val His Ser Gly Gly Gly Glu Arg Lys Ser Ser Val Glu Cys Pro Pro
            20                  25                  30

Cys Pro Ala Pro Pro Val Ala Gly Pro Ser Val Phe Leu Phe Pro Pro
        35                  40                  45

Lys Pro Lys Asp Thr Leu Met Ile Ser Arg Thr Pro Glu Val Thr Cys
    50                  55                  60

Val Val Val Asp Val Ser His Glu Asp Pro Glu Val Gln Phe Asn Trp
65                  70                  75                  80

Tyr Val Asp Gly Val Glu Val His Asn Ala Lys Thr Lys Pro Arg Glu
                85                  90                  95

Glu Gln Phe Asn Ser Thr Phe Arg Val Val Ser Val Leu Thr Val Val
            100                 105                 110

His Gln Asp Trp Leu Asn Gly Lys Glu Tyr Lys Cys Lys Val Ser Asn
        115                 120                 125

Lys Gly Leu Pro Ala Pro Ile Glu Lys Thr Ile Ser Lys Thr Lys Gly
    130                 135                 140

Gln Pro Arg Glu Pro Gln Val Tyr Thr Leu Pro Pro Ser Arg Glu Glu
145                 150                 155                 160

Met Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Met Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Gly Gly Gly Ser Gly Gly Gly
                245                 250                 255

Gly Ser Gly Gly Gly Gly Ser Gly Gly Gly Gly Ser Gly Gly Gly Gly
            260                 265                 270

Gly Ser Gly Gly Gly Gly Ser Gly Gly Gly Gly Ser Gly Gly Gly Gly
```

```
                275                 280                 285
Ser Glu Arg Lys Ser Val Glu Cys Pro Pro Cys Pro Ala Pro Pro
        290                 295                 300
Val Ala Gly Pro Ser Val Phe Leu Phe Pro Pro Lys Pro Lys Asp Thr
305                 310                 315                 320
Leu Met Ile Ser Arg Thr Pro Glu Val Thr Cys Val Val Val Asp Val
                325                 330                 335
Ser His Glu Asp Pro Glu Val Gln Phe Asn Trp Tyr Val Asp Gly Val
            340                 345                 350
Glu Val His Asn Ala Lys Thr Lys Pro Arg Glu Glu Gln Phe Asn Ser
            355                 360                 365
Thr Phe Arg Val Val Ser Val Leu Thr Val Val His Gln Asp Trp Leu
370                 375                 380
Asn Gly Lys Glu Tyr Lys Cys Lys Val Ser Asn Lys Gly Leu Pro Ala
385                 390                 395                 400
Pro Ile Glu Lys Thr Ile Ser Lys Thr Lys Gly Gln Pro Arg Glu Pro
                405                 410                 415
Gln Val Tyr Thr Leu Pro Pro Ser Arg Glu Glu Met Thr Lys Asn Gln
            420                 425                 430
Val Ser Leu Thr Cys Leu Val Lys Gly Phe Tyr Pro Ser Asp Ile Ala
            435                 440                 445
Val Glu Trp Glu Ser Asn Gly Gln Pro Glu Asn Asn Tyr Lys Thr Thr
            450                 455                 460
Pro Pro Met Leu Asp Ser Asp Gly Ser Phe Phe Leu Tyr Ser Lys Leu
465                 470                 475                 480
Thr Val Asp Lys Ser Arg Trp Gln Gln Gly Asn Val Phe Ser Cys Ser
                485                 490                 495
Val Met His Glu Ala Leu His Asn His Tyr Thr Gln Lys Ser Leu Ser
                500                 505                 510
Leu Ser Pro Gly Ser Gly Gly Gly Ser Gly Gly Gly Ser Gly
            515                 520                 525
Gly Gly Ser Gly Gly Gly Ser Ala Arg Asn Gly Asp His Cys
    530                 535                 540
Pro Leu Gly Pro Gly Arg Cys Cys Arg Leu His Thr Val Arg Ala Ser
545                 550                 555                 560
Leu Glu Asp Leu Gly Trp Ala Asp Trp Val Leu Ser Pro Arg Glu Val
                565                 570                 575
Gln Val Thr Met Cys Ile Gly Ala Cys Pro Ser Gln Phe Arg Ala Ala
            580                 585                 590
Asn Met His Ala Gln Ile Lys Thr Ser Leu His Arg Leu Lys Pro Asp
            595                 600                 605
Thr Val Pro Ala Pro Cys Cys Val Pro Ala Ser Tyr Asn Pro Met Val
            610                 615                 620
Leu Ile Gln Lys Thr Asp Thr Gly Val Ser Leu Gln Thr Tyr Asp Asp
625                 630                 635                 640
Leu Leu Ala Lys Asp Cys His Cys Ile
                645

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 119

Gly Gly Gly Gly Gly Ser Gly Gly Gly Ser Gly Gly Gly Gly Ser
1               5                   10                  15

<210> SEQ ID NO 120
<211> LENGTH: 1875
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

| | | |
|---|---|---|
| atggaatggt catgggtgtt cctttctttt ctctccgtca ctaccggtgt gcactccgga | 60 |
| ggaggcgaga ggaagagctc cgtggagtgt ccaccctgcc ctgctccgcc tgtggctgga | 120 |
| ccctctgtgt tcctgtttcc gccgaagccg aaagacaccc tcatgatcag caggactccc | 180 |
| gaggtcactt gtgtggtcgt ggatgtgagc catgaggacc cagaggtgca gttcaactgg | 240 |
| tacgtggacg gcgtggaagt ccacaacgcc aagaccaagc cacgcgagga acagttcaat | 300 |
| agcaccttcc gcgtggtcag cgtcctcacc gtggtccacc aggattggct aacggaaag | 360 |
| gaatacaaat gcaaggtgtc caacaagggg cttcctgccc cgattgaaaa gaccatctcc | 420 |
| aagaccaagg gacagccaag ggagccccaa gtgtacactc tgccacccag ccgcgaagaa | 480 |
| atgactaaga atcaagtgtc tctgacctgt cttgtcaaag gcttctaccc cagcgacatc | 540 |
| gctgtcgagt gggaatcaaa cgggcagccc gagaacaact acaagaccac tcctccaatg | 600 |
| ctcgactcag atggcagctt tttcctttac tccaagctga ccgtggacaa gtcaagatgg | 660 |
| caacagggta acgtgttctc atgctccgtg atgcacgaag ccctccataa tcactatacc | 720 |
| cagaaatctc tgtctctttc ccccggagga ggaggggggat ctggtggagg aggctctggt | 780 |
| ggtggaggta gcgaacggaa atcctcagtg gagtgcccac catgcccggc tcctccagtg | 840 |
| gctggtccat ctgtctttct ttttcctccg aaacccaagg acacccttat gatctctcgc | 900 |
| accccctgaag tgacttgcgt ggtcgtcgat gtgtcacatg aagaccctga ggtccagttc | 960 |
| aattggtatg tggacggagt cgaggtgcat aacgccaaaa ccaaacctcg cgaagaacaa | 1020 |
| ttcaactcta ccttccgggt ggtgtctgtg ctcactgtcg tccatcagga ctggctgaac | 1080 |
| gggaaggagt acaagtgtaa ggtgtctaac aaaggcctgc cggctcccat cgaaaagact | 1140 |
| atcagcaaga ctaaggggca acccagagaa ccccaagtct acaccctgcc tccgtcacgg | 1200 |
| gaggagatga ccaagaatca ggtgtccctc acctgtctgg tcaagggttt ctaccctagc | 1260 |
| gacattgctg tggagtggga gagcaatgga cagcccgaaa acaattacaa gactacccca | 1320 |
| cccatgctgg actcagacgg atcatttttc ctctactcta agctcactgt ggacaagagc | 1380 |
| cggtggcagc aagggaatgt gttcagctgt tcagtgatgc atgaggccct gcataaccac | 1440 |
| tacacccaga gagcctttc actgtcaccc gggtctggtg gcgtgggtc aggtggcgga | 1500 |
| ggatcaggag gaggtggaag cggcggagga ggatctgcca ggaacggtga tcactgccct | 1560 |
| ctgggccctg gtcgctgctg taggcttcac actgtgcggg cttccctcga agatctggga | 1620 |
| tgggccgact gggtgctgag cccaagagag gtgcaagtga ccatgtgcat cggggcatgt | 1680 |
| ccctcccaat tccgcgctgc aaacatgcat gctcagatta agacttcact gcatagactg | 1740 |
| aagccagata ccgtcccagc accctgttgt gtgcccgctt catacaaccc catggtcctg | 1800 |
| attcaaaaga ccgacaccgg ggtgtctctc cagacctatg atgatcttct tgcaaaggac | 1860 |

-continued tgccactgca tctga 1875

<210> SEQ ID NO 121
<211> LENGTH: 624
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Glu Trp Ser Trp Val Phe Leu Phe Phe Leu Ser Val Thr Thr Gly
1               5                   10                  15

Val His Ser Gly Gly Gly Glu Arg Lys Ser Ser Val Glu Cys Pro Pro
            20                  25                  30

Cys Pro Ala Pro Pro Val Ala Gly Pro Ser Val Phe Leu Phe Pro Pro
        35                  40                  45

Lys Pro Lys Asp Thr Leu Met Ile Ser Arg Thr Pro Glu Val Thr Cys
    50                  55                  60

Val Val Val Asp Val Ser His Glu Asp Pro Glu Val Gln Phe Asn Trp
65                  70                  75                  80

Tyr Val Asp Gly Val Glu Val His Asn Ala Lys Thr Lys Pro Arg Glu
                85                  90                  95

Glu Gln Phe Asn Ser Thr Phe Arg Val Val Ser Val Leu Thr Val Val
            100                 105                 110

His Gln Asp Trp Leu Asn Gly Lys Glu Tyr Lys Cys Lys Val Ser Asn
        115                 120                 125

Lys Gly Leu Pro Ala Pro Ile Glu Lys Thr Ile Ser Lys Thr Lys Gly
    130                 135                 140

Gln Pro Arg Glu Pro Gln Val Tyr Thr Leu Pro Pro Ser Arg Glu Glu
145                 150                 155                 160

Met Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Met Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Gly Gly Gly Ser Gly Gly
                245                 250                 255

Gly Gly Ser Gly Gly Gly Gly Ser Glu Arg Lys Ser Ser Val Glu Cys
            260                 265                 270

Pro Pro Cys Pro Ala Pro Pro Val Ala Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Gln Phe
305                 310                 315                 320

Asn Trp Tyr Val Asp Gly Val Glu Val His Asn Ala Lys Thr Lys Pro
                325                 330                 335

Arg Glu Glu Gln Phe Asn Ser Thr Phe Arg Val Val Ser Val Leu Thr
            340                 345                 350

```
Val Val His Gln Asp Trp Leu Asn Gly Lys Glu Tyr Lys Cys Lys Val
        355                 360                 365

Ser Asn Lys Gly Leu Pro Ala Pro Ile Glu Lys Thr Ile Ser Lys Thr
370                 375                 380

Lys Gly Gln Pro Arg Glu Pro Gln Val Tyr Thr Leu Pro Pro Ser Arg
385                 390                 395                 400

Glu Glu Met Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Met Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Ser Gly Gly Gly Gly
                485                 490                 495

Ser Gly Gly Gly Gly Ser Gly Gly Gly Ser Gly Gly Gly Gly Ser
            500                 505                 510

Ala Arg Asn Gly Asp His Cys Pro Leu Gly Pro Gly Arg Cys Cys Arg
        515                 520                 525

Leu His Thr Val Arg Ala Ser Leu Glu Asp Leu Gly Trp Ala Asp Trp
    530                 535                 540

Val Leu Ser Pro Arg Glu Val Gln Val Thr Met Cys Ile Gly Ala Cys
545                 550                 555                 560

Pro Ser Gln Phe Arg Ala Ala Asn Met His Ala Gln Ile Lys Thr Ser
                565                 570                 575

Leu His Arg Leu Lys Pro Asp Thr Val Pro Ala Pro Cys Cys Val Pro
            580                 585                 590

Ala Ser Tyr Asn Pro Met Val Leu Ile Gln Lys Thr Asp Thr Gly Val
        595                 600                 605

Ser Leu Gln Thr Tyr Asp Asp Leu Leu Ala Lys Asp Cys His Cys Ile
    610                 615                 620

<210> SEQ ID NO 122
<211> LENGTH: 1818
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
ggaggaggcg agaggaagag ctccgtggag tgtccaccct gccctgctcc gcctgtggct      60
ggaccctctg tgttcctgtt tccgccgaag ccgaaagaca ccctcatgat cagcaggact     120
cccgaggtca cttgtgtggt cgtggatgtg agccatgagg acccagaggt gcagttcaac     180
tggtacgtgg acggcgtgga agtccacaac gccaagacca gccacgcga ggaacagttc      240 aatagcacct tccgcgtggt cagcgtcctc accgtggtcc accaggattg gcttaacgga     300
aaggaataca atgcaaggt gtccaacaag gggcttcctg ccccgattga aagaccatc      360 tccaagacca agggacagcc aagggagccc caagtgtaca ctctgccacc agccgcgaa     420 gaaatgacta gaatcaagt gtctctgacc tgtcttgtca aaggcttcta ccccagcgac     480
atcgctgtcg agtgggaatc aaacgggcag ccgagaaca actacaagac cactcctcca     540
```

```
atgctcgact cagatggcag cttttteett tacteccaage tgaccgtgga caagtcaaga      600
tggcaacagg gtaacgtgtt ctcatgctcc gtgatgcacg aagccctcca taatcactat      660
acccagaaat ctctgtctct ttccccggga ggaggagggg gatctggtgg aggaggctct      720
ggtggtggag gtagcgaacg gaaatcctca gtggagtgcc caccatgccc ggctcctcca      780
gtggctggtc catctgtctt tcttttteet ccgaaaccca aggacaccct tatgatctct      840 cgcaccctg aagtgacttg cgtggtcgtc gatgtgtcac atgaagaccc tgaggtccag       900
ttcaattggt atgtggacgg agtcgaggtg cataacgcca aaaccaaacc tcgcgaagaa      960
caattcaact ctaccttccg ggtggtgtct gtgctcactg tcgtccatca ggactggctg     1020
aacgggaagg agtacaagtg taaggtgtct aacaaaggcc tgccggctcc catcgaaaag     1080
actatcagca agactaaggg gcaacccaga gaaccccaag tctacaccct gcctccgtca     1140
cgggaggaga tgaccaagaa tcaggtgtcc ctcacctgtc tggtcaaggg tttctaccct     1200
agcgacattg ctgtggagtg ggagagcaat ggacagcccg aaaacaatta caagactacc     1260
ccacccatgc tggactcaga cggatcattt ttcctctact ctaagctcac tgtggacaag     1320
agccggtggc agcaagggaa tgtgttcagc tgttcagtga tgcatgaggc cctgcataac     1380
cactacaccc agaagagcct ttcactgtca cccgggtctg gtggcggtgg gtcaggtggc     1440
ggaggatcag gaggaggtgg aagcggcgga ggaggatctg ccaggaacgg tgatcactgc     1500
cctctgggcc ctggtcgctg ctgtaggctt cacactgtgc gggcttccct cgaagatctg     1560
ggatgggccg actgggtgct gagcccaaga gaggtgcaag tgaccatgtg catcggggca     1620
tgtccctccc aattccgcgc tgcaaacatg catgctcaga ttaagacttc actgcataga     1680
ctgaagccag ataccgtccc agcacccgt tgtgtgcccg cttcatacaa ccccatggtc      1740
ctgattcaaa agaccgacac cggggtgtct ctccagacct atgatgatct tcttgcaaag     1800
gactgccact gcatctga                                                   1818
```

<210> SEQ ID NO 123
<211> LENGTH: 605
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

```
Gly Gly Gly Glu Arg Lys Ser Ser Val Glu Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125
```

Glu Pro Gln Val Tyr Thr Leu Pro Pro Ser Arg Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Gly Gly Gly Ser Gly Gly Gly Ser
225                 230                 235                 240

Gly Gly Gly Ser Glu Arg Lys Ser Ser Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Asn Ser Thr Phe Arg Val Val Ser Val Leu Thr Val Val His
                325                 330                 335

Gln Asp Trp Leu Asn Gly Lys Glu Tyr Lys Cys Lys Val Ser Asn Lys
            340                 345                 350

Gly Leu Pro Ala Pro Ile Glu Lys Thr Ile Ser Lys Thr Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Met Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Ser Gly Gly Gly Gly Ser Gly Gly
465                 470                 475                 480

Gly Gly Ser Gly Gly Gly Ser Gly Gly Gly Ser Ala Arg Asn
                485                 490                 495

Gly Asp His Cys Pro Leu Gly Pro Gly Arg Cys Cys Arg Leu His Thr
            500                 505                 510

Val Arg Ala Ser Leu Glu Asp Leu Gly Trp Ala Asp Trp Val Leu Ser
        515                 520                 525

Pro Arg Glu Val Gln Val Thr Met Cys Ile Gly Ala Cys Pro Ser Gln
    530                 535                 540

Phe Arg Ala Ala Asn Met His Ala Gln Ile Lys Thr Ser Leu His Arg
545                 550                 555                 560

Leu Lys Pro Asp Thr Val Pro Ala Pro Cys Cys Val Pro Ala Ser Tyr
                565                 570                 575

Asn Pro Met Val Leu Ile Gln Lys Thr Asp Thr Gly Val Ser Leu Gln
            580                 585                 590

Thr Tyr Asp Asp Leu Leu Ala Lys Asp Cys His Cys Ile
        595                 600                 605

<210> SEQ ID NO 124
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Gly Gly Gly Gly Ser Gly Gly Gly Gly Ser Gly Gly Gly Gly Ser
1               5                   10                  15

Gly Gly Gly Gly Gly Ser Gly Gly Gly Gly Ser
            20                  25

<210> SEQ ID NO 125
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125

| | |
|---|---|
| atggagtgga gctgggtctt ctttttcttt ctgtctgtga ctaccggagt ccattcaggc | 60 |
| ggtggagagc gcaagtcatc tgtcgagtgt ccgccctgcc ccgctccgcc ggtggctgga | 120 |
| ccctcagtgt tcctctttcc accgaagccg aaggacaccc ttatgattag ccggacccca | 180 |
| gaggtcactt gcgtcgtcgt ggacgtgtcc catgaggatc ccgaagtgca gtttaactgg | 240 |
| tatgtggacg gagtggaggt ccataacgcc aagaccaagc caagggaaga acagttcaat | 300 |
| agcaccttcc gggtggtgtc cgtgctcacc gtggtgcatc aagactggct gaatggcaaa | 360 |
| gagtacaaat gtaaggtgtc aaacaagggg ctcccagccc ctattgaaaa gaccatctca | 420 |
| aagactaagg gacagccacg cgaacctcaa gtgtataccc tcccgccttc acgcgaagaa | 480 |
| atgactaaga atcaggtcag ccttacttgt ctggtcaagg gcttctaccc gagcgacatt | 540 |
| gcagtcgaat gggagagcaa tggtcagcca gagaataact acaagaccac tcctcccatg | 600 |
| cttgatagcg atggaagctt tttcctttac agcaagctta ctgtggataa gtctcgctgg | 660 |
| caacagggaa atgtgttcag ctgttcagtg atgcatgaag cactccacaa tcattacacc | 720 |
| cagaagtcac tcagcctctc acccggagga ggaggcggtt ctggtggagg agggtctgga | 780 |
| ggtggaggga gcggcggagg cgggtctggc ggtggtgggt ctgagaggaa gtcatcagtg | 840 |
| gaatgcccac catgccctgc tcctcccgtg gccggtccga gcgtgtttct cttcccacct | 900 |
| aagcccaagg acactctgat gatctcacgg actccggaag tgacttgtgt ggtggtggac | 960 |
| gtgtctcatg aggaccctga agtgcagttc aactggtacg tggacggcgt ggaggtgcac | 1020 |
| aatgctaaga ccaagcctag agaggaacag ttcaattcca cctttcgcgt ggtgagcgtc | 1080 |
| ctgaccgtcg tgcaccagga ctggcttaac ggaaaggaat acaagtgcaa ggtgtccaac | 1140 |
| aaaggccttc cagctcccat tgagaaaacc atctctaaaa ctaagggtca accaagggaa | 1200 |

```
cccaagtct acaccctccc tccgtctaga aagagatga ccaaaaacca ggtgtccctg   1260
acctgtctgg tgaagggatt ttacccctca gacatcgccg tggagtggga aagcaacgga   1320
cagcccgaaa acaactataa gactaccct cctatgctgg actcagacgg atctttcttc   1380
ctctatagca agctcactgt ggacaaatcc agatggcaac aagggaatgt gttctcatgc   1440
agcgtgatgc acgaggctct tcacaaccac tatacccaga agagcctgtc tctttcacct   1500
ggttccggag gtggtgggag cggagggggt ggatcaggtg gtggagggtc cggaggcgga   1560
ggatccgcac ggaatggcga ccactgtcca ctgggacccg aagatgttg tcgcctccac   1620 accgtgaggg cctctctgga ggaccttggc tgggccgact gggtcctgtc acctcgggag   1680
gtccaagtca ccatgtgtat cggagcctgc cccagccaat tcagagcagc aaatatgcac   1740
gcacagatta agaccagcct gcatcggctt aaacctgata ctgtgccggc tccttgttgc   1800
gtgccagcat cttacaaccc gatggtgctg atccagaaaa ccgataccgg tgtctccctc   1860
cagacttacg acgacctcct tgcaaaggac tgccattgca tctga                   1905

<210> SEQ ID NO 126
<211> LENGTH: 634
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met Glu Trp Ser Trp Val Phe Leu Phe Phe Leu Ser Val Thr Thr Gly
1               5                   10                  15

Val His Ser Gly Gly Gly Glu Arg Lys Ser Ser Val Glu Cys Pro Pro
                20                  25                  30

Cys Pro Ala Pro Pro Val Ala Gly Pro Ser Val Phe Leu Phe Pro Pro
            35                  40                  45

Lys Pro Lys Asp Thr Leu Met Ile Ser Arg Thr Pro Glu Val Thr Cys
        50                  55                  60

Val Val Val Asp Val Ser His Glu Asp Pro Glu Val Gln Phe Asn Trp
65                  70                  75                  80

Tyr Val Asp Gly Val Glu Val His Asn Ala Lys Thr Lys Pro Arg Glu
                85                  90                  95

Glu Gln Phe Asn Ser Thr Phe Arg Val Val Ser Val Leu Thr Val Val
                100                 105                 110

His Gln Asp Trp Leu Asn Gly Lys Glu Tyr Lys Cys Lys Val Ser Asn
            115                 120                 125

Lys Gly Leu Pro Ala Pro Ile Glu Lys Thr Ile Ser Lys Thr Lys Gly
        130                 135                 140

Gln Pro Arg Glu Pro Gln Val Tyr Thr Leu Pro Pro Ser Arg Glu Glu
145                 150                 155                 160

Met Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Met Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
```

```
             225                 230                 235                 240
        Gln Lys Ser Leu Ser Leu Ser Pro Gly Gly Gly Ser Gly Gly
                        245                 250                 255

Gly Gly Ser Gly Gly Gly Ser Gly Gly Gly Ser Gly Gly Gly
                        260                 265                 270

Gly Ser Glu Arg Lys Ser Ser Val Glu Cys Pro Pro Cys Pro Ala Pro
                275                 280                 285

Pro Val Ala Gly Pro Ser Val Phe Leu Phe Pro Pro Lys Pro Lys Asp
                290                 295                 300

Thr Leu Met Ile Ser Arg Thr Pro Glu Val Thr Cys Val Val Val Asp
        305                 310                 315                 320

Val Ser His Glu Asp Pro Glu Val Gln Phe Asn Trp Tyr Val Asp Gly
                        325                 330                 335

Val Glu Val His Asn Ala Lys Thr Lys Pro Arg Glu Glu Gln Phe Asn
                        340                 345                 350

Ser Thr Phe Arg Val Val Ser Val Leu Thr Val Val His Gln Asp Trp
                        355                 360                 365

Leu Asn Gly Lys Glu Tyr Lys Cys Lys Val Ser Asn Lys Gly Leu Pro
                370                 375                 380

Ala Pro Ile Glu Lys Thr Ile Ser Lys Thr Lys Gly Gln Pro Arg Glu
        385                 390                 395                 400

Pro Gln Val Tyr Thr Leu Pro Pro Ser Arg Glu Glu Met Thr Lys Asn
                        405                 410                 415

Gln Val Ser Leu Thr Cys Leu Val Lys Gly Phe Tyr Pro Ser Asp Ile
                        420                 425                 430

Ala Val Glu Trp Glu Ser Asn Gly Gln Pro Glu Asn Asn Tyr Lys Thr
                        435                 440                 445

Thr Pro Pro Met Leu Asp Ser Asp Gly Ser Phe Phe Leu Tyr Ser Lys
                450                 455                 460

Leu Thr Val Asp Lys Ser Arg Trp Gln Gln Gly Asn Val Phe Ser Cys
        465                 470                 475                 480

Ser Val Met His Glu Ala Leu His Asn His Tyr Thr Gln Lys Ser Leu
                        485                 490                 495

Ser Leu Ser Pro Gly Ser Gly Gly Gly Ser Gly Gly Gly Gly Ser
                        500                 505                 510

Gly Gly Gly Gly Ser Gly Gly Gly Ser Ala Arg Asn Gly Asp His
                        515                 520                 525

Cys Pro Leu Gly Pro Gly Arg Cys Cys Arg Leu His Thr Val Arg Ala
                530                 535                 540

Ser Leu Glu Asp Leu Gly Trp Ala Asp Trp Val Leu Ser Pro Arg Glu
        545                 550                 555                 560

Val Gln Val Thr Met Cys Ile Gly Ala Cys Pro Ser Gln Phe Arg Ala
                        565                 570                 575

Ala Asn Met His Ala Gln Ile Lys Thr Ser Leu His Arg Leu Lys Pro
                        580                 585                 590

Asp Thr Val Pro Ala Pro Cys Cys Val Pro Ala Ser Tyr Asn Pro Met
                        595                 600                 605

Val Leu Ile Gln Lys Thr Asp Thr Gly Val Ser Leu Gln Thr Tyr Asp
                        610                 615                 620

Asp Leu Leu Ala Lys Asp Cys His Cys Ile
        625                 630

<210> SEQ ID NO 127
```

<211> LENGTH: 1848
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127

| | | | | | |
|---|---|---|---|---|---|
| ggcggtggag | agcgcaagtc | atctgtcgag | tgtccgccct | gccccgctcc | gccggtggct | 60 |
| ggaccctcag | tgttcctctt | tccaccgaag | ccgaaggaca | cccttatgat | tagccggacc | 120 |
| ccagaggtca | cttgcgtcgt | cgtggacgtg | tcccatgagg | atcccgaagt | gcagtttaac | 180 |
| tggtatgtgg | acgagtgga | ggtccataac | gccaagacca | agccaaggga | agaacagttc | 240 |
| aatagcacct | tccgggtggt | gtccgtgctc | accgtggtgc | atcaagactg | gctgaatggc | 300 |
| aaagagtaca | aatgtaaggt | gtcaaacaag | gggctcccag | cccctattga | aaagaccatc | 360 |
| tcaaagacta | agggacagcc | acgcgaacct | caagtgtata | ccctcccgcc | ttcacgcgaa | 420 |
| gaaatgacta | agaatcaggt | cagccttact | tgtctggtca | agggcttcta | cccgagcgac | 480 |
| attgcagtcg | aatgggagag | caatggtcag | ccagagaata | actacaagac | cactcctccc | 540 |
| atgcttgata | gcgatggaag | cttttccctt | tacagcaagc | ttactgtgga | taagtctcgc | 600 |
| tggcaacagg | gaaatgtgtt | cagctgttca | gtgatgcatg | aagcactcca | caatcattac | 660 |
| acccagaagt | cactcagcct | ctcacccgga | ggaggaggcg | ttctggtgg | aggagggtct | 720 |
| ggaggtggag | ggagcggcgg | aggcgggtct | ggcggtggtg | ggtctgagag | gaagtcatca | 780 |
| gtggaatgcc | caccatgccc | tgctcctccc | gtggccggtc | cgagcgtgtt | tctcttccca | 840 |
| cctaagccca | aggacactct | gatgatctca | cggactccgg | aagtgacttg | tgtggtggtg | 900 |
| gacgtgtctc | atgaggaccc | tgaagtgcag | ttcaactggt | acgtggacgg | cgtggaggtg | 960 |
| cacaatgcta | agaccaagcc | tagagaggaa | cagttcaatt | ccacctttcg | cgtggtgagc | 1020 |
| gtcctgaccg | tcgtgcacca | ggactggctt | aacggaaagg | aatacaagtg | caaggtgtcc | 1080 |
| aacaaggcc | ttccagctcc | cattgagaaa | accatctcta | aaactaaggg | tcaaccaagg | 1140 |
| gaacccaag | tctacaccct | ccctccgtct | agagaagaga | tgaccaaaaa | ccaggtgtcc | 1200 |
| ctgacctgtc | tggtgaaggg | attttacccc | tcagacatcg | ccgtggagtg | ggaaagcaac | 1260 |
| ggacagcccg | aaaacaacta | taagactacc | cctcctatgc | tggactcaga | cggatctttc | 1320 |
| ttcctctata | gcaagctcac | tgtggacaaa | tccgatggc | aacaaggaa | tgtgttctca | 1380 |
| tgcagcgtga | tgcacgaggc | tcttcacaac | cactataccc | agaagagcct | gtctctttca | 1440 |
| cctggttccg | gaggtggtgg | gagcggaggg | ggtggatcag | gtggtggagg | gtccggaggc | 1500 |
| ggaggatccg | cacggaatgg | cgaccactgt | ccactgggac | ccggaagatg | ttgtcgcctc | 1560 |
| cacaccgtga | gggcctctct | ggaggacctt | ggctgggccg | actgggtcct | gtcacctcgg | 1620 |
| gaggtccaag | tcaccatgtg | tatcggagcc | tgccccagcc | aattcagagc | agcaaatatg | 1680 |
| cacgcacaga | ttaagaccag | cctgcatcgg | cttaaacctg | atactgtgcc | ggctccttgt | 1740 |
| tgcgtgccag | catcttacaa | cccgatggtg | ctgatccaga | aaaccgatac | cggtgtctcc | 1800 |
| ctccagactt | acgacgacct | ccttgcaaag | gactgccatt | gcatctga | | 1848 |

<210> SEQ ID NO 128
<211> LENGTH: 615
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 128

```
Gly Gly Gly Glu Arg Lys Ser Ser Val Glu Cys Pro Pro Cys Pro Ala
1               5                   10                  15
Pro Pro Val Ala Gly Pro Ser Val Phe Leu Phe Pro Pro Lys Pro Lys
            20                  25                  30
Asp Thr Leu Met Ile Ser Arg Thr Pro Glu Val Thr Cys Val Val Val
        35                  40                  45
Asp Val Ser His Glu Asp Pro Glu Val Gln Phe Asn Trp Tyr Val Asp
50                  55                  60
Gly Val Glu Val His Asn Ala Lys Thr Lys Pro Arg Glu Glu Gln Phe
65                  70                  75                  80
Asn Ser Thr Phe Arg Val Val Ser Val Leu Thr Val Val His Gln Asp
                85                  90                  95
Trp Leu Asn Gly Lys Glu Tyr Lys Cys Lys Val Ser Asn Lys Gly Leu
            100                 105                 110
Pro Ala Pro Ile Glu Lys Thr Ile Ser Lys Thr Lys Gly Gln Pro Arg
        115                 120                 125
Glu Pro Gln Val Tyr Thr Leu Pro Pro Ser Arg Glu Glu Met Thr Lys
130                 135                 140
Asn Gln Val Ser Leu Thr Cys Leu Val Lys Gly Phe Tyr Pro Ser Asp
145                 150                 155                 160
Ile Ala Val Glu Trp Glu Ser Asn Gly Gln Pro Glu Asn Asn Tyr Lys
                165                 170                 175
Thr Thr Pro Pro Met Leu Asp Ser Asp Gly Ser Phe Phe Leu Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
210                 215                 220
Leu Ser Leu Ser Pro Gly Gly Gly Gly Ser Gly Gly Gly Gly Ser
225                 230                 235                 240
Gly Gly Gly Gly Ser Gly Gly Gly Gly Ser Gly Gly Gly Gly Ser Glu
                245                 250                 255
Arg Lys Ser Ser Val Glu Cys Pro Pro Cys Pro Ala Pro Pro Val Ala
            260                 265                 270
Gly Pro Ser Val Phe Leu Phe Pro Pro Lys Pro Lys Asp Thr Leu Met
        275                 280                 285
Ile Ser Arg Thr Pro Glu Val Thr Cys Val Val Val Asp Val Ser His
290                 295                 300
Glu Asp Pro Glu Val Gln Phe Asn Trp Tyr Val Asp Gly Val Glu Val
305                 310                 315                 320
His Asn Ala Lys Thr Lys Pro Arg Glu Glu Gln Phe Asn Ser Thr Phe
                325                 330                 335
Arg Val Val Ser Val Leu Thr Val Val His Gln Asp Trp Leu Asn Gly
            340                 345                 350
Lys Glu Tyr Lys Cys Lys Val Ser Asn Lys Gly Leu Pro Ala Pro Ile
        355                 360                 365
Glu Lys Thr Ile Ser Lys Thr Lys Gly Gln Pro Arg Glu Pro Gln Val
370                 375                 380
Tyr Thr Leu Pro Pro Ser Arg Glu Glu Met Thr Lys Asn Gln Val Ser
385                 390                 395                 400
Leu Thr Cys Leu Val Lys Gly Phe Tyr Pro Ser Asp Ile Ala Val Glu
```

```
            405                 410                 415
Trp Glu Ser Asn Gly Gln Pro Glu Asn Asn Tyr Lys Thr Thr Pro Pro
            420                 425                 430

Met Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
            450                 455                 460

His Glu Ala Leu His Asn His Tyr Thr Gln Lys Ser Leu Ser Leu Ser
465                 470                 475                 480

Pro Gly Ser Gly Gly Gly Gly Ser Gly Gly Gly Gly Ser Gly Gly Gly
            485                 490                 495

Gly Ser Gly Gly Gly Gly Ser Ala Arg Asn Gly Asp His Cys Pro Leu
            500                 505                 510

Gly Pro Gly Arg Cys Cys Arg Leu His Thr Val Arg Ala Ser Leu Glu
            515                 520                 525

Asp Leu Gly Trp Ala Asp Trp Val Leu Ser Pro Arg Glu Val Gln Val
            530                 535                 540

Thr Met Cys Ile Gly Ala Cys Pro Ser Gln Phe Arg Ala Ala Asn Met
545                 550                 555                 560

His Ala Gln Ile Lys Thr Ser Leu His Arg Leu Lys Pro Asp Thr Val
                565                 570                 575

Pro Ala Pro Cys Cys Val Pro Ala Ser Tyr Asn Pro Met Val Leu Ile
            580                 585                 590

Gln Lys Thr Asp Thr Gly Val Ser Leu Gln Thr Tyr Asp Asp Leu Leu
            595                 600                 605

Ala Lys Asp Cys His Cys Ile
610                 615

<210> SEQ ID NO 129
<211> LENGTH: 113
<212> TYPE: PRT
<213> ORGANISM: Homo sapiens

<400> SEQUENCE: 129

Met Ala Arg Asn Gly Asp His Cys Pro Leu Gly Pro Gly Arg Cys Cys
1               5                   10                  15

Arg Leu His Thr Val Arg Ala Ser Leu Glu Asp Leu Gly Trp Ala Asp
                20                  25                  30

Trp Val Leu Ser Pro Arg Glu Val Gln Val Thr Met Cys Ile Gly Ala
35                  40                  45

Cys Pro Ser Gln Phe Arg Ala Ala Asn Met His Ala Gln Ile Lys Thr
50                  55                  60

Ser Leu His Arg Leu Lys Pro Asp Thr Val Pro Ala Pro Cys Cys Val
65                  70                  75                  80

Pro Ala Ser Tyr Asn Pro Met Val Leu Ile Gln Lys Thr Asp Thr Gly
            85                  90                  95

Val Ser Leu Gln Thr Tyr Asp Asp Leu Leu Ala Lys Asp Cys His Cys
            100                 105                 110

Ile

<210> SEQ ID NO 130
<211> LENGTH: 342
<212> TYPE: DNA
<213> ORGANISM: Homo sapiens

<400> SEQUENCE: 130
```

```
atggcgcgca acggggacca ctgtccgctc gggcccgggc gttgctgccg tctgcacacg      60
gtccgcgcgt cgctggaaga cctgggctgg gccgattggg tgctgtcgcc acgggaggtg     120
caagtgacca tgtgcatcgg cgcgtgcccg agccagttcc gggcggcaaa catgcacgcg     180
cagatcaaga cgagcctgca ccgcctgaag cccgacacgg tgccagcgcc ctgctgcgtg     240
cccgccagct acaatcccat ggtgctcatt caaaagaccg acaccggggt gtcgctccag     300
acctatgatg acttgttagc caaagactgc cactgcatat aa                        342
```

GROWTH DIFFERENTIATION FACTOR 15 (GDF-15) POLYPEPTIDES

SEQUENCE LISTING

The instant application contains a Sequence Listing which has been submitted in ASCII format via EFS-Web and is hereby incorporated by reference in its entirety. Said ASCII copy, created on Jan. 28, 2013, is named A1682WOP.txt and is 253,155 bytes in size.

FIELD OF THE INVENTION

The instant disclosure relates to GDF15 polypeptides, polypeptides comprising GDF15, and the generation and use thereof.

BACKGROUND OF THE INVENTION

Growth differentiation factor 15 (GDF15) is a divergent member of the TGFβ superfamily. It is also called macrophage inhibitory cytokine 1 (MIC1) (Bootcov M R, 1997, *Proc Natl Acad Sci* 94:11514-9.), placental bone morphogenetic factor (PLAB) (Hromas R 1997, *Biochim Biophys Acta.* 1354:40-4), placental transforming growth factor beta (PTGFB) (Lawton L N 1997, *Gene.* 203:17-26), prostate derived factor (PDF) (Paralkar V M 1998, *J Biol. Chem.* 273:13760-7), and nonsteroidal anti-inflammatory drug-activated gene (NAG-1) (Baek S J 2001, *J Biol. Chem.* 276: 33384-92).

Human GDF15 gene is located on chromosome 19p13.2-13.1; rat GDF15 gene is located on chromosome 16; and mouse GDF15 gene is located on chromosome 8. The GDF15 open reading frames span two exons (Bottner M 1999, *Gene.* 237:105-11 and NCBI). The mature GDF15 peptide shares low homology with other family members (Katoh M 2006, *Int J Mol. Med.* 17:951-5.).

GDF15 is synthesized as a large precursor protein that is cleaved at the dibasic cleavage site to release the carboxy-terminal mature peptide. The mouse and rat GDF15 prepropeptides both contain 303 amino acids. Human full-length precursor contains 308 amino acids. The rodent mature peptides contain 115 amino acids after processing at the RGRR (SEQ ID NO:1) cleavage site. The human mature peptide contains 112 amino acids after processing at the RGRRRAR (SEQ ID NO:2) cleavage site. Human mature GDF15 peptide shares 66.1% and 68.1% sequence similarity with rat and mouse mature GDF15 peptides (Bottner M 1999, *Gene.* 237:105-11; Bauskin A R 2000, *EMBO J.* 19:2212-20; NCBI). There is no glycosylation site in the mature GDF15 peptide.

The mature GDF15 peptide contains the seven conserved cysteine residues required for the formation of the cysteine knot motif (having three intrachain disulfide bonds) and the single interchain disulfide bond that are typical for TGFβ superfamily members. The mature GDF15 peptide further contains two additional cysteine residues that form a fourth intrachain disulfide bond. Biologically active GDF15 is a 25 KD homodimer of the mature peptide covalently linked by one interchain disulfide bond.

GDF15 circulating levels have been reported to be elevated in multiple pathological and physiological conditions, most notably pregnancy (Moore A G 2000. *J Clin Endocrinol Metab* 85: 4781-4788), β-thalassemia (Tanno T 2007, Nat Med 13:1096-101) (Zimmermann M B, 2008 *Am J Clin Nutr* 88:1026-31), and congenital dyserythropoietic anemia (Tamary H 2008, *Blood.* 112:5241-4). GDF15 has also been linked to multiple biological activities in literature reports. Studies of GDF15 knockout and transgenic mice suggested that GDF15 may be protective against ischemic/reperfusion- or overload-induced heart injury (Kempf T, 2006, *Circ Res.* 98:351-60) (Xu J, 2006, *Circ Res.* 98:342-50), protective against aging-associated motor neuron and sensory neuron loss (Strelau J, 2009, *J. Neurosci.* 29:13640-8), mildly protective against metabolic acidosis in kidney, and may cause cachexia in cancer patients (Johnen H 2007 *Nat. Med.* 11:1333-40). Many groups also studied the role of GDF15 in cell apoptosis and proliferation and reported controversial results using different cell culture and xenograft models. Studies on transgenic mice showed that GDF15 is protective against carcinogen or Apc mutation induced neoplasia in intestine and lung (Baek S J 2006, *Gastroenterology.* 131:1553-60; Cekanova M 2009, *Cancer Prev Res* 2:450-8).

SUMMARY OF THE INVENTION

Provided herein is a construct comprising a GDF15 polypeptide and one or more Fc sequences. In one embodiment, the construct comprises two or more Fc sequences. In a further embodiment, the one or more of the Fc sequences independently comprise a sequence selected from the group consisting of SEQ ID NOs:18, 19, 85, 86, 89, 90, 91, 99, 100, 108, 109 and 111. In another embodiment, two or more of the Fc sequences are associated. In still a further embodiment, the GDF15 polypeptide and one or more of the Fc sequences form a contiguous sequence. In yet another embodiment, the GDF15 polypeptide and an Fc sequence are joined by a linker. In another embodiment, the construct comprises a sequence selected from the group consisting of SEQ ID NOs:44, 50, 57, 61, 65, 69, 74, 79, 84, 95 and 104. In yet a further embodiment, the construct further comprises a sequence selected from the group consisting of SEQ ID NOs:18, 19, 85, 86, 89, 90, 91, 99, 100, 108, 109 and 110. In another embodiment, a dimer comprising the constructs described herein is provided. In a particular embodiment, the construct comprises: (a) a sequence comprising SEQ ID NO:18 and a sequence comprising SEQ ID NO:44; (b) a sequence comprising SEQ ID NO:86 and a sequence comprising SEQ ID NO:50; (c) a sequence comprising SEQ ID NO:18 and a sequence comprising SEQ ID NO: 57; (d) a sequence comprising SEQ ID NO:86 and a sequence comprising SEQ ID NO:61; (e) a sequence comprising SEQ ID NO:86 and a sequence comprising SEQ ID NO:65; (f) a sequence comprising SEQ ID NO:86 and a sequence comprising SEQ ID NO:69; (g) a sequence comprising SEQ ID NO:86 and a sequence comprising SEQ ID NO:74; (h) a sequence comprising SEQ ID NO:86 and a sequence comprising SEQ ID NO:79; (i) a sequence comprising SEQ ID NO:86 and a sequence comprising SEQ ID NO:84; (j) a sequence comprising SEQ ID NO:91 and a sequence comprising SEQ ID NO:95; or (k) a sequence comprising SEQ ID NO:100 and a sequence comprising SEQ ID NO:104, as well as a dimer comprising the construct.

Also provided herein is a construct comprising a GDF15 polypeptide and two or more Fc sequences, wherein one or more Fc sequences independently comprise a sequence selected from the group consisting of SEQ ID NOs:23, 110, 114 and 115. In one embodiment, two or more Fc sequences are associated. In a further embodiment, the GDF15 polypeptide and one or more of the Fc sequences form a contiguous sequence. In yet another embodiment, the GDF15 polypeptide and an Fc sequence are joined by a linker. In still a further embodiment, the construct comprises SEQ ID NO:113. In another embodiment a dimer comprising the constructs described herein is provided. In a particular embodiment, the construct comprises: a sequence comprising SEQ ID NO:110 and a sequence comprising SEQ ID NO:113, as well as a dimer comprising the construct.

Also provided herein is a construct comprising a GDF15 polypeptide and two or more Fc sequences, wherein the Fc sequences comprise SEQ ID NO:28 and SEQ ID NO:30. In one embodiment the two Fc sequences are joined by a linker. In another embodiment the linker comprises a sequence selected from the group consisting of SEQ ID NOs: 87, 88 and 131. In still another embodiment, the C-terminus of a first Fc sequence is joined to the N-terminus of a second Fc sequence. In yet another embodiment, the GDF15 polypeptide and one or more of the Fc sequences form a contiguous sequence. In still a further embodiment, the GDF15 polypeptide and an Fc sequence are joined by a linker. In another embodiment, the linker comprises SEQ ID NO:31. In still a further embodiment, a construct comprising a dimer of the constructs described herein is provided. In a particular embodiment, the construct comprises a sequence selected from the group consisting of SEQ ID NOs:33, 123 and 128, as well as a dimer comprising the construct.

BRIEF DESCRIPTION OF THE DRAWINGS

FIG. 1 discloses "($G_4S$)$_4$" (SEQ ID NO: 20), "GS($G_4S$)$_4$" (SEQ ID NO:31) and "($G_4S$)$_8$" (SEQ ID NO: 34).

FIG. 2 is a table showing the results of a food intake assay in hyperphagic ob/ob mice in which dimers of the following GDF15 constructs were studied: DhCpmFc(−)-($G_4S$)$_4$-GDF15:DhCpmFc(+), DhCpmFc(+)-($G_4S$)$_4$-GDF15:DhCpmFc(−), DhCpmFc(−)-($G_4S$)$_4$-GDF15:DhCpmFc(+), DhCpmFc(+)-($G_4S$)$_4$-GDF15(H6D):DhCpmFc(−), DhCpmFc(+)-($G_4S$)$_4$-GDF15 (N3Q):DhCpmFc(−), DhCpmFc(+)-GDF15:DhCpmFc(−), DhCpmFc(+)-$G_4$-GDF15:DhCpmFc(−), DhCpmFc(+)-($G_4S$)$_2$-GDF15:DhCpmFc(−), DhCpmFc(+)-($G_4Q$)$_4$-GDF15:DhCpmFc(−), DhCpmFc(+)-(1K)-GDF15:DhCpmFc(−), DhCpmFc(+)(L351C)-$G_4$-GDF15:DhCpmFc(−)(L351C), DhCpmFc(+)(S354C)-$G_4$-GDF15:DhCpmFc(−)(Y349C) CpmFc(+)-($G_4S$)-4-GDF15:CpmFc(−); Fc-($G_4S$)$_8$-Fc-GS($G_4S$)$_4$-GDF15, Fc-($G_4S$)$_3$-Fc-GS($G_4S$)$_4$-GDF15, Fc-($G_4S$)$_5$-Fc-GS($G_4S$)$_4$-GDF15, GDF15 and GDF15 (H6D) variant.

GDF15:DhCpmFc(+) construct, a dimer of Fc-$(G_4S)_8$-Fc-GS$(G_4S)_4$-GDF15 construct and rosiglitizone (Rosi).

Figure 28:
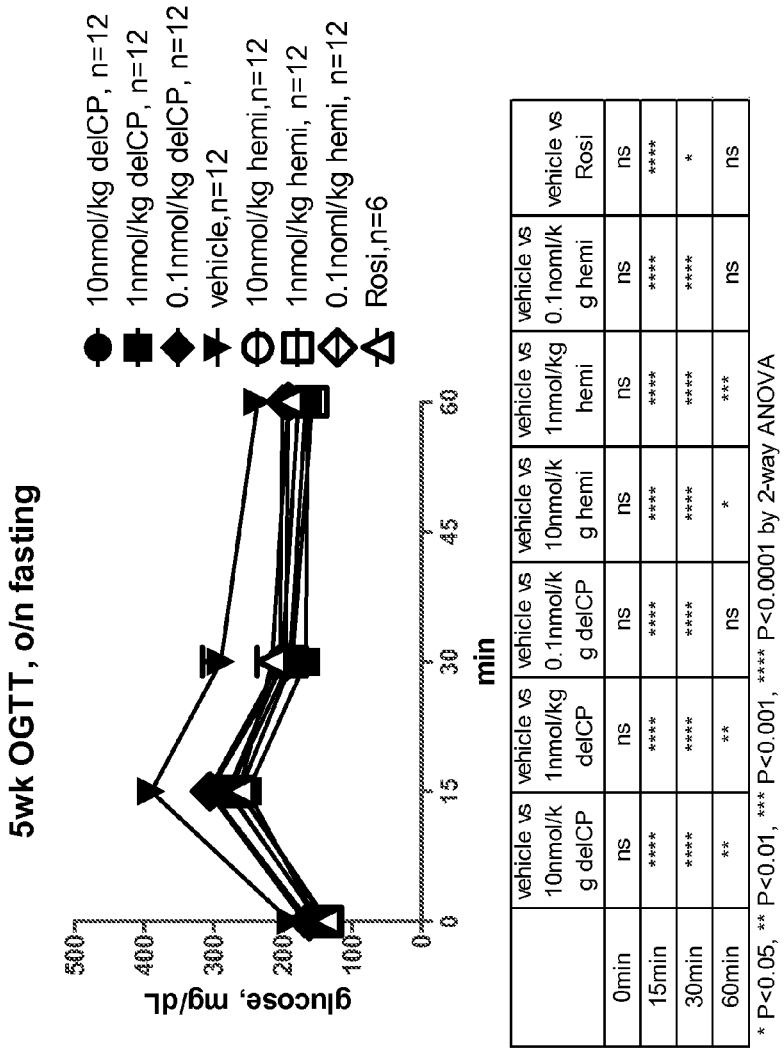
FIG. 28 is a plot showing the results of a five week OGTT performed using a dimer of the DhCpmFc(−)-($G_4S$)$_4$-
Figure 29:
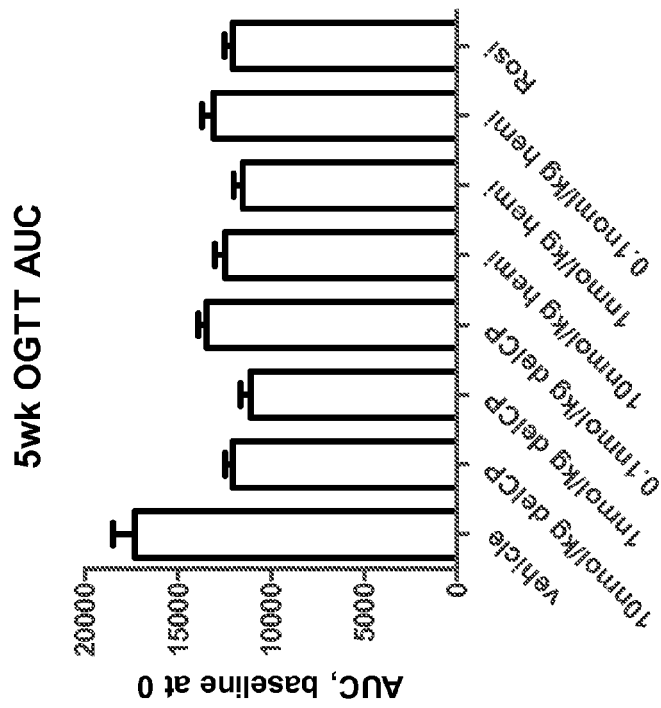

FIG. 29 is a bar graph summarizing the data of FIG. 28 in the form of AUC data.

Figure 30:
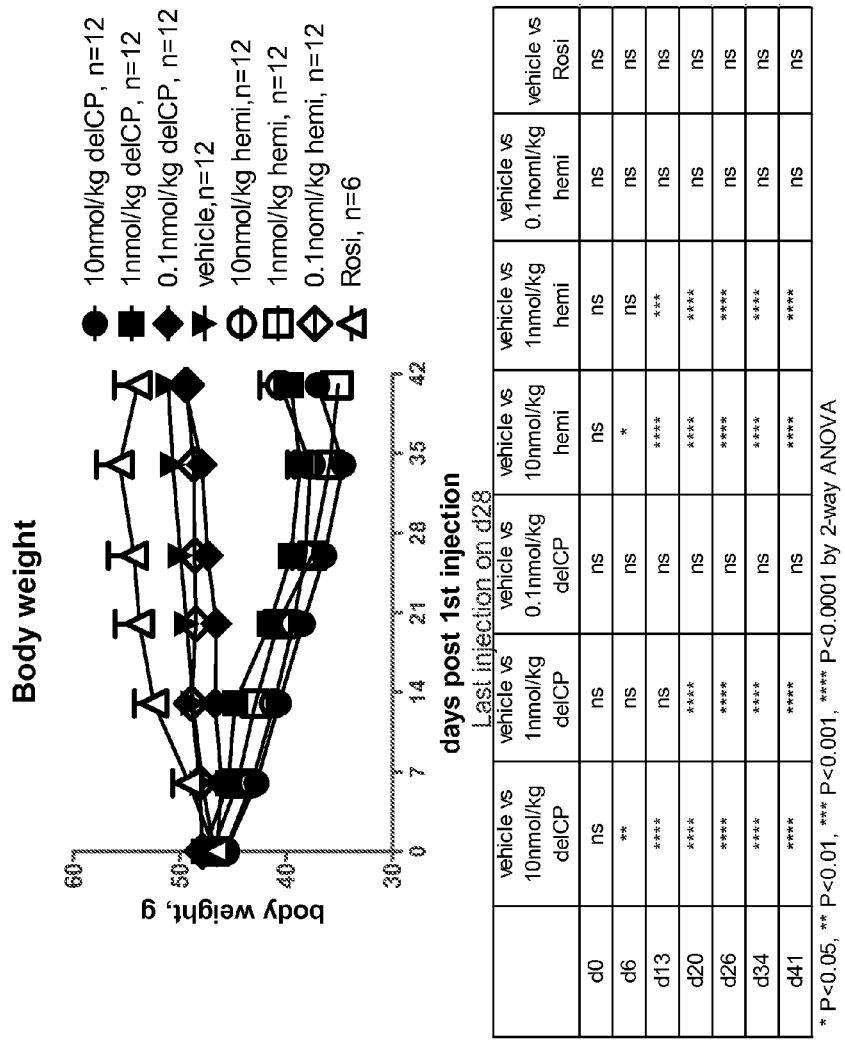

FIG. 30 is a plot showing the effect on the body weight (g) of DIO mice of a dimer of the DhCpmFc(−)-$(G_4S)_4$-GDF15:DhCpmFc(+) construct, a dimer of the Fc-$(G_4S)_8$-Fc-GS$(G_4S)_4$-GDF15 construct and rosiglitizone (Rosi).

Figure 31:
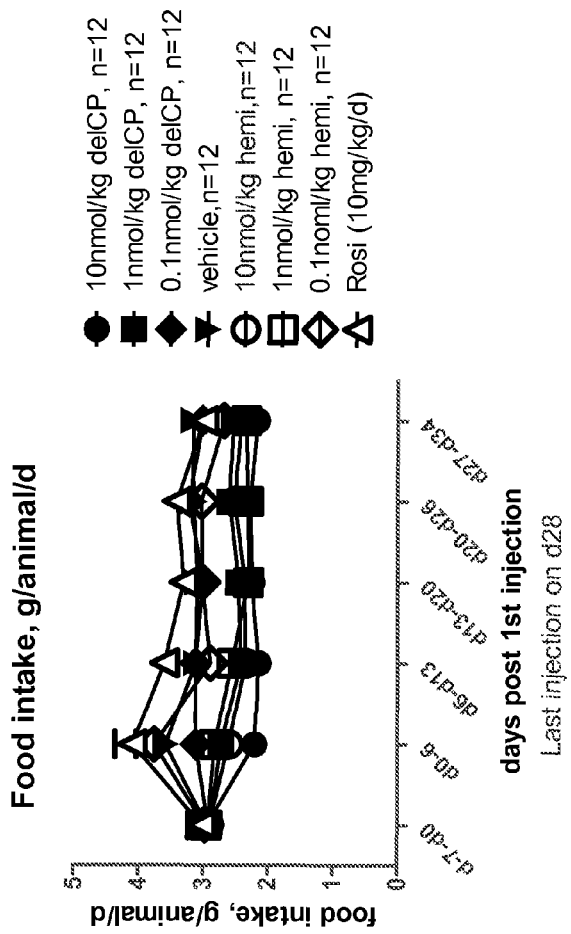

FIG. 31 is a plot showing the effect on the food intake (g food/animal/day) of DIO mice of a dimer of the DhCpmFc(−)-$(G_4S)_4$-GDF15:DhCpmFc(+) construct, a dimer of the Fc-$(G_4S)_8$-Fc-GS$(G_4S)_4$-GDF15 construct and rosiglitizone (Rosi).

Figure 32:
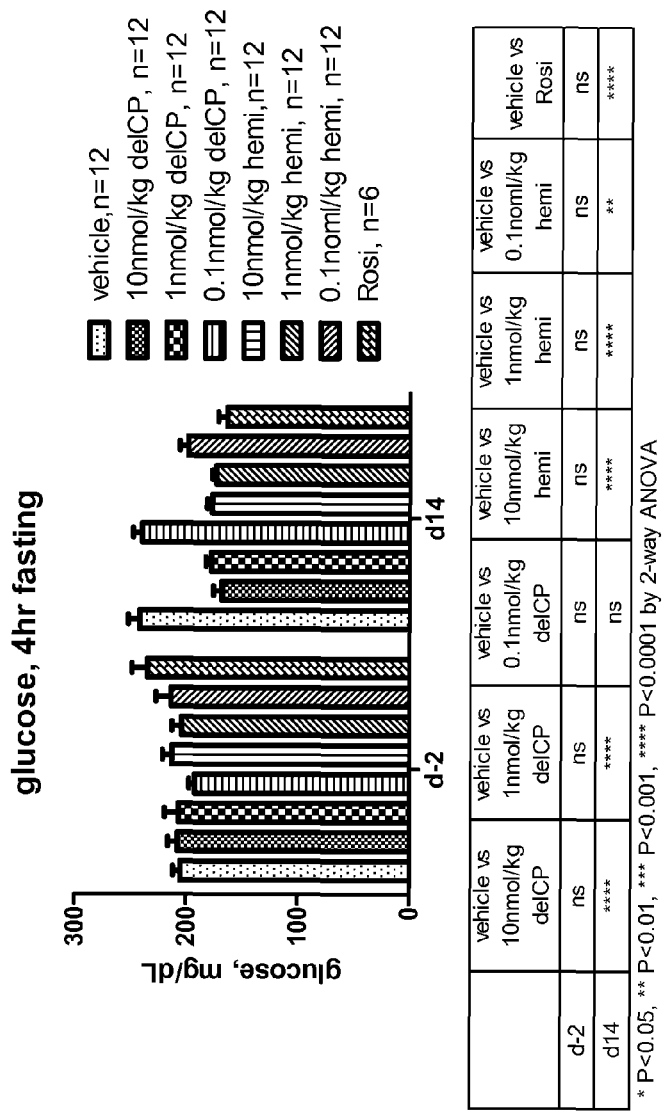

FIG. 32 is a bar graph showing the effect on the glucose levels (mg/dL) of DIO mice after 4 hour fast of a dimer of the DhCpmFc(−)-$(G_4S)_4$-GDF15:DhCpmFc(+) construct, a dimer of the Fc-$(G_4S)_8$-Fc-GS$(G_4S)_4$-GDF15 construct and rosiglitizone (Rosi).

Figure 33:
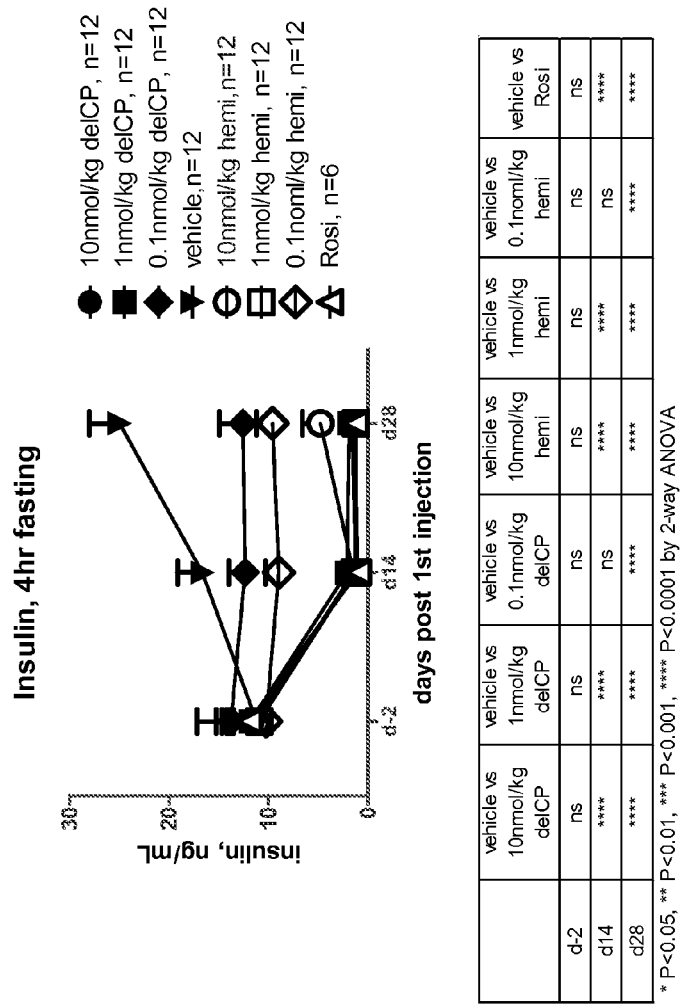

FIG. 33 is a plot showing the effect on insulin levels (ng/mL) of DIO mice after 4 hour fast of a dimer of the DhCpmFc(−)-$(G_4S)_4$-GDF15:DhCpmFc(+) construct, a dimer of the Fc-$(G_4S)_8$-Fc-GS$(G_4S)_4$-GDF15 construct and rosiglitizone (Rosi).

Figure 34:
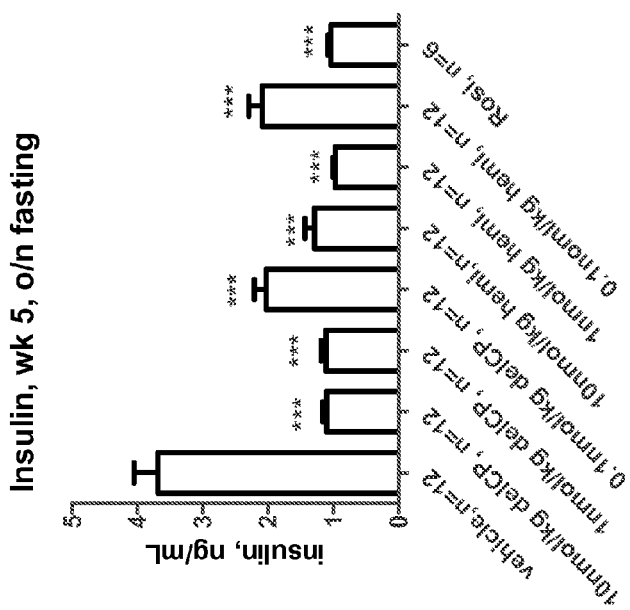

FIG. 34 is a bar graph showing the effect on insulin levels (ng/mL) of DIO mice after overnight fast dosed with a dimer of the DhCpmFc(−)-$(G_4S)_4$-GDF15:DhCpmFc(+) construct, a dimer of the Fc-$(G_4S)_8$-Fc-GS$(G_4S)_4$-GDF15 and rosiglitizone (Rosi).

Figure 35:
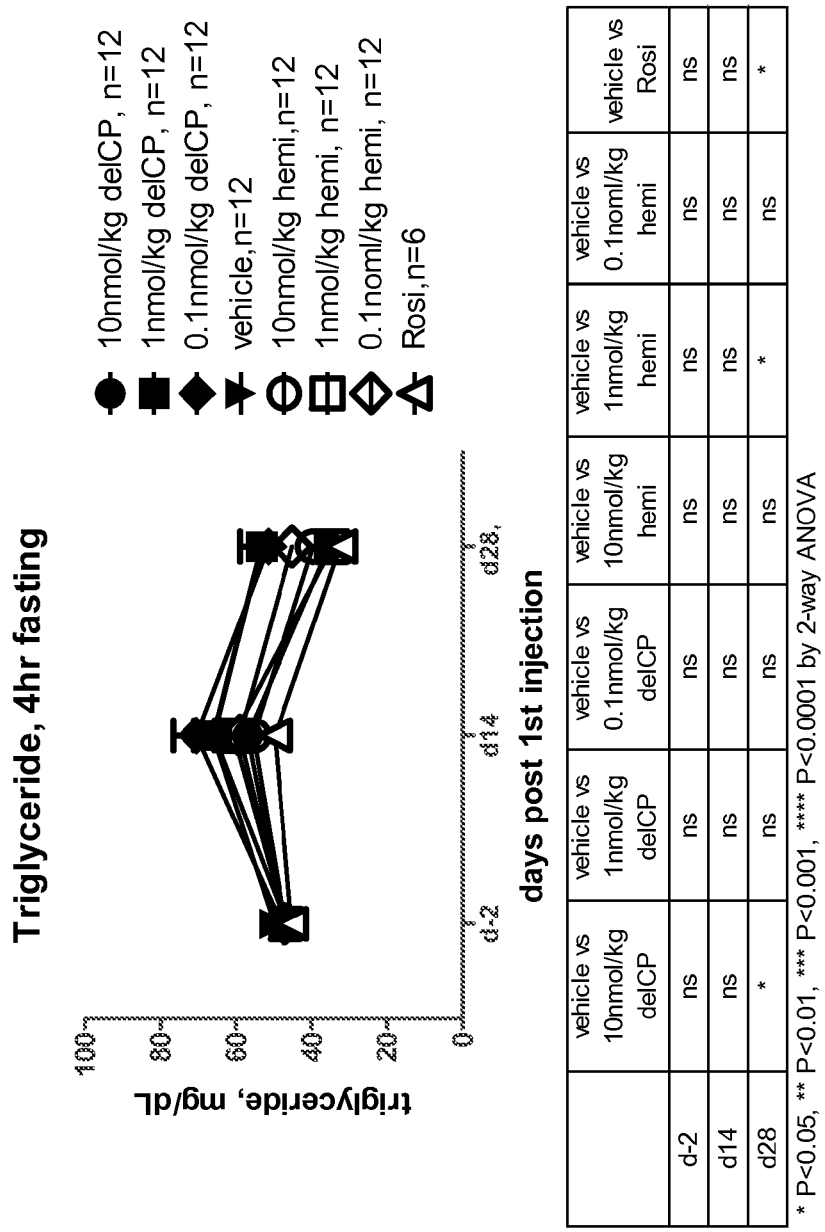

FIG. 35 is a plot showing the effect on the triglyceride levels (mg/dL) of DIO mice after 4 hour fast dosed with a dimer of the DhCpmFc(−)-$(G_4S)_4$-GDF15:DhCpmFc(+) construct, a dimer of the Fc-$(G_4S)_8$-Fc-GS$(G_4S)_4$-GDF15 construct and rosiglitizone (Rosi).

Figure 36:
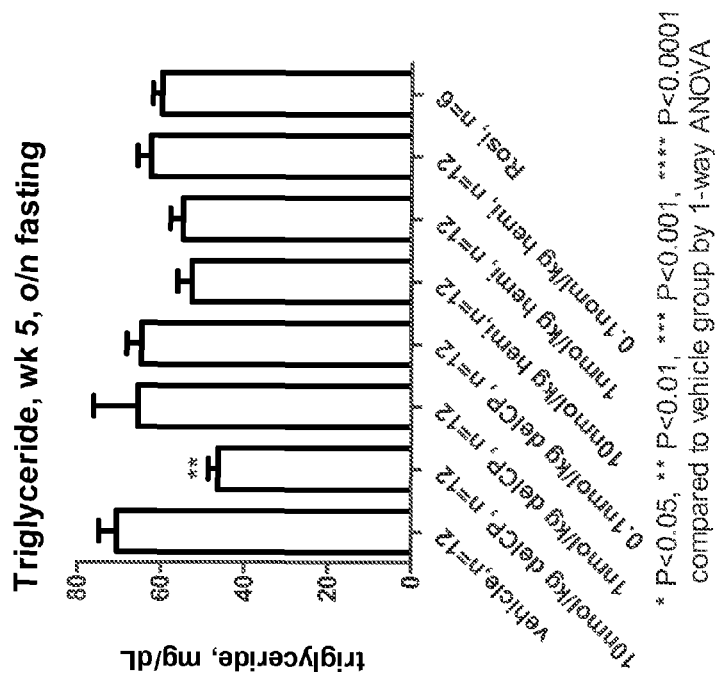

FIG. 36 is a bar graph showing the effect on the triglyceride levels (mg/dL) of DIO mice after overnight fast dosed with a dimer of the DhCpmFc(−)-$(G_4S)_4$-GDF15:DhCpmFc(+) construct, a dimer of the Fc-$(G_4S)_8$-Fc-GS$(G_4S)_4$-GDF15 construct and rosiglitizone (Rosi).

Figure 37:
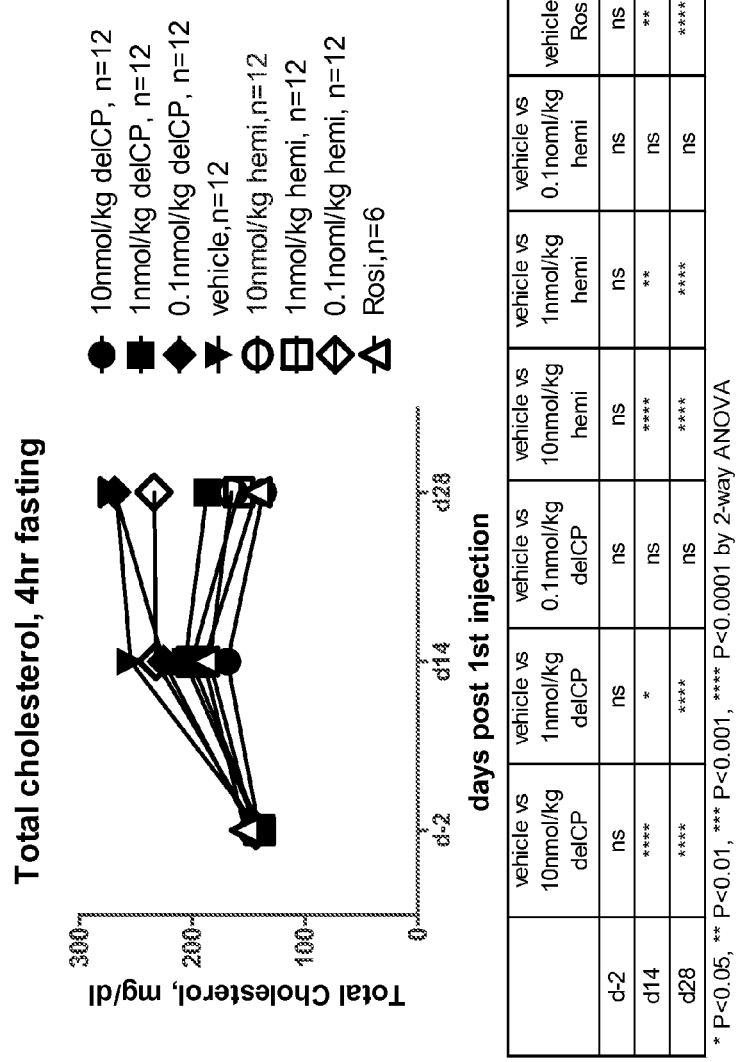

FIG. 37 is a plot showing the effect on the total cholesterol levels (mg/dL) of DIO mice after 4 hour fast dosed with a dimer of the DhCpmFc(−)-$(G_4S)_4$-GDF15:DhCpmFc(+) construct, a dimer of the Fc-$(G_4S)_8$-Fc-GS$(G_4S)_4$-GDF15 construct and rosiglitizone (Rosi).

Figure 38:
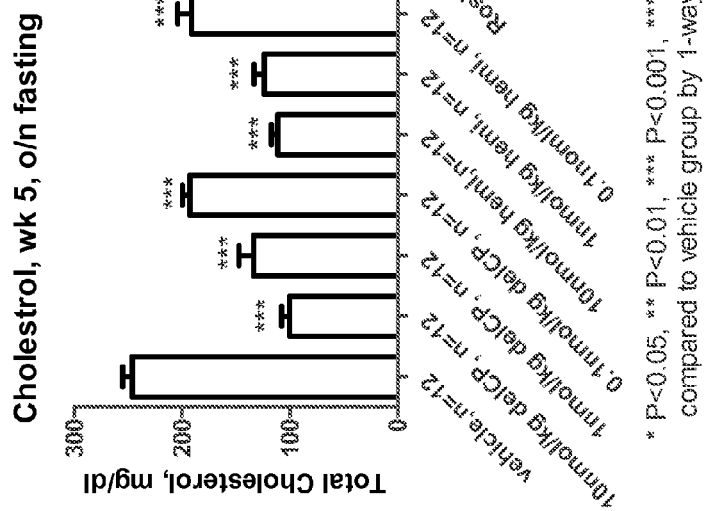

FIG. 38 is a bar graph showing the effect on the total cholesterol levels (mg/dL) of DIO mice after overnight fast dosed with a dimer of the DhCpmFc(−)-$(G_4S)_4$-GDF15:DhCpmFc(+) construct, a dimer of the Fc-$(G_4S)_8$-Fc-GS$(G_4S)_4$-GDF15 construct and rosiglitizone (Rosi).

Figure 39:
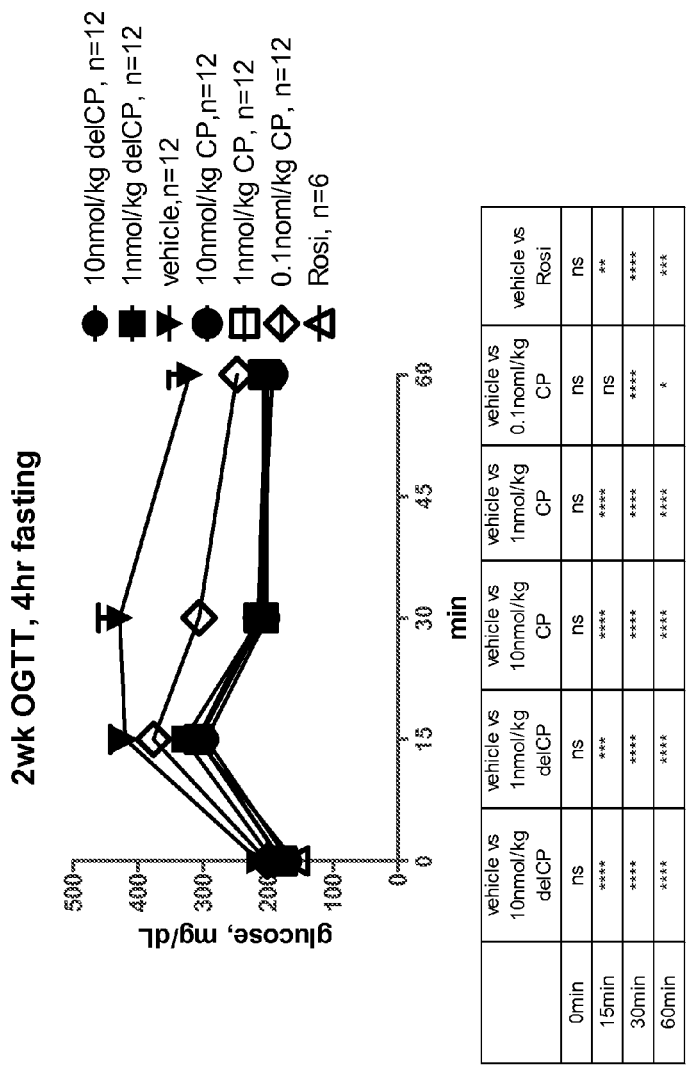

FIG. 39 is a plot showing the results of a two week OGTT after 4 hour fast performed on DIO mice dosed with a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 40:
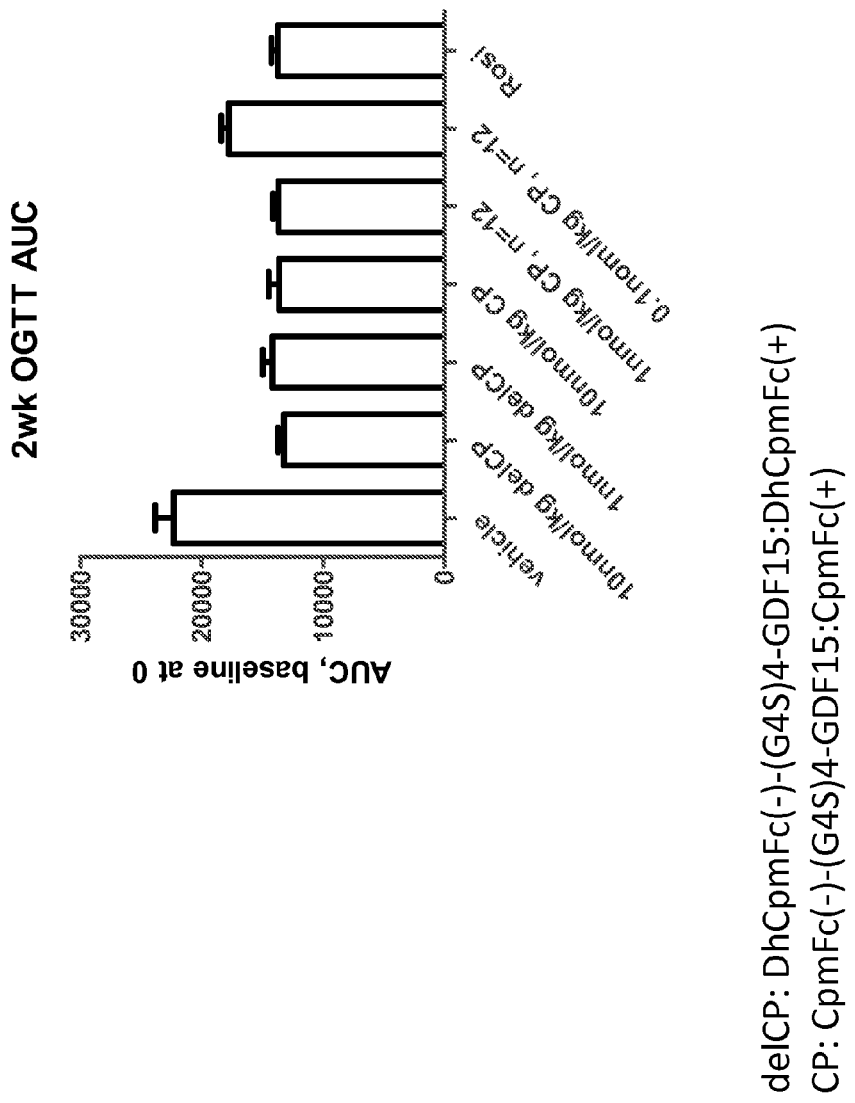

FIG. 40 is a bar graph summarizing the data of FIG. 39 in the form of AUC data.

Figure 41:
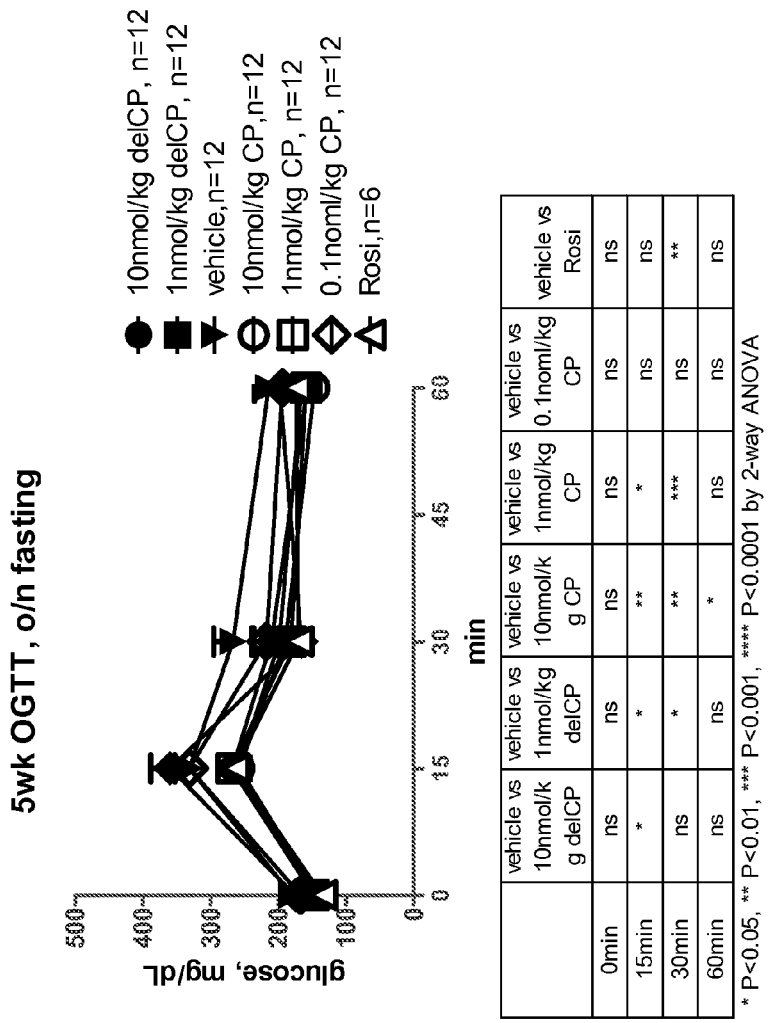

FIG. 41 is a plot showing the results of a five week OGTT after an overnight fast performed on DIO mice dosed with a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 42:
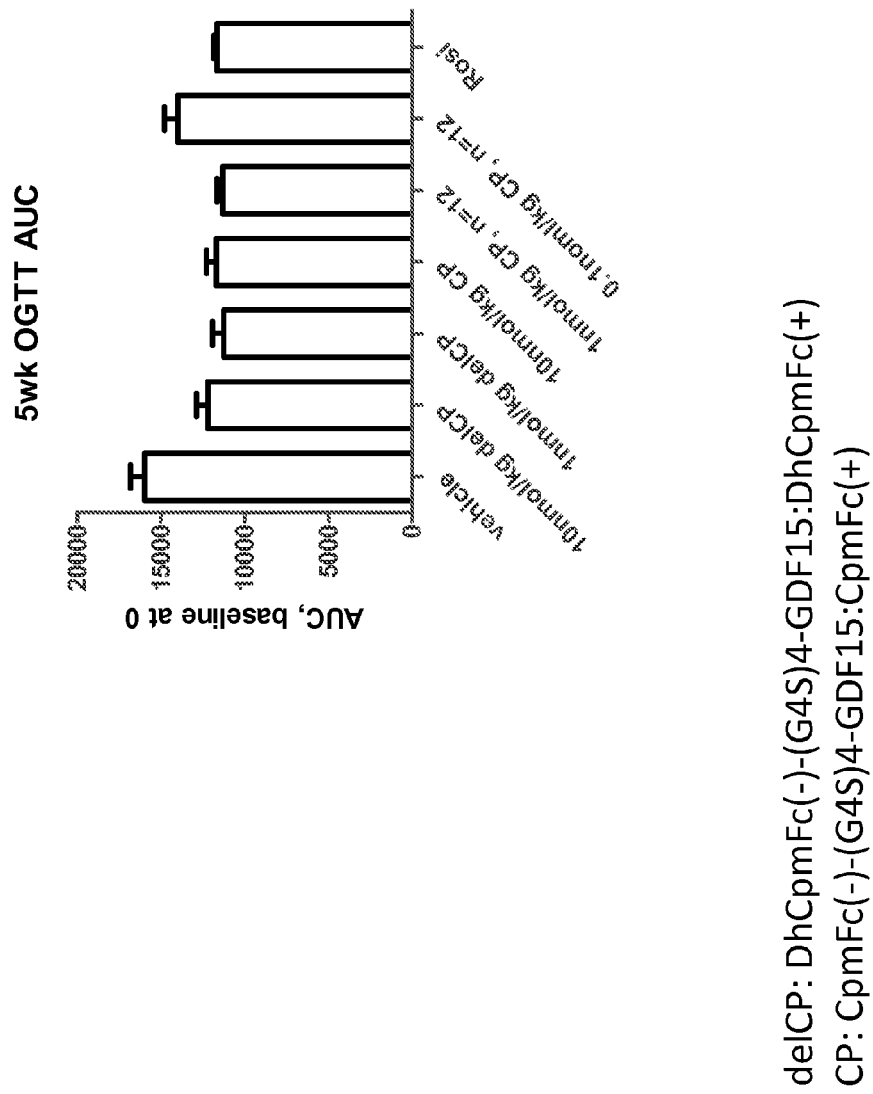

FIG. 42 is a bar graph summarizing the data of FIG. 41 in the form of AUC data.

Figure 43:
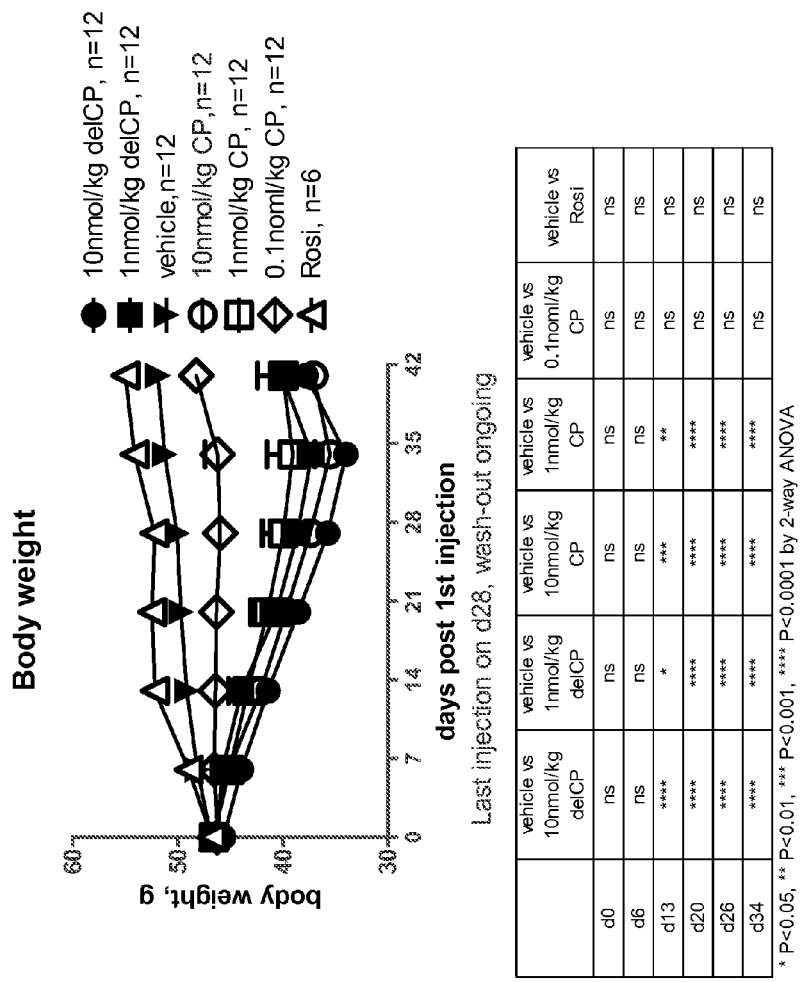

FIG. 43 is a plot showing the effect on the body weight of DIO mice dosed with a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 44:
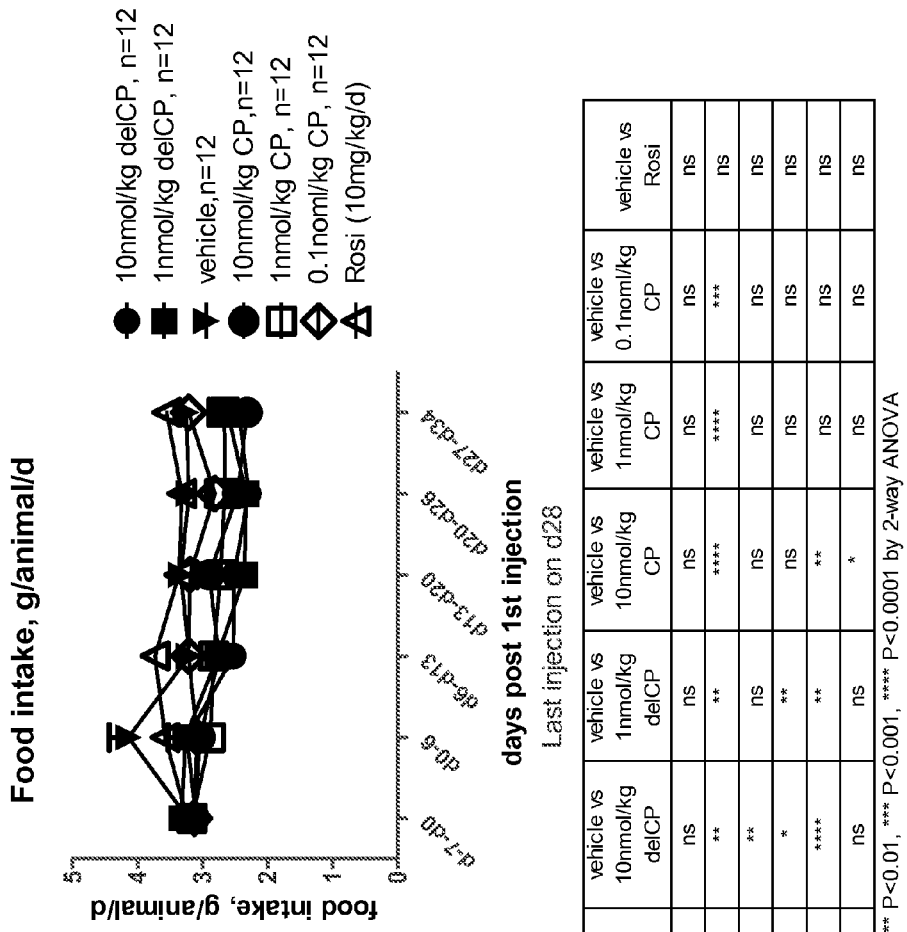

FIG. 44 is a plot showing the effect on food intake of DIO mice dosed with a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 45:
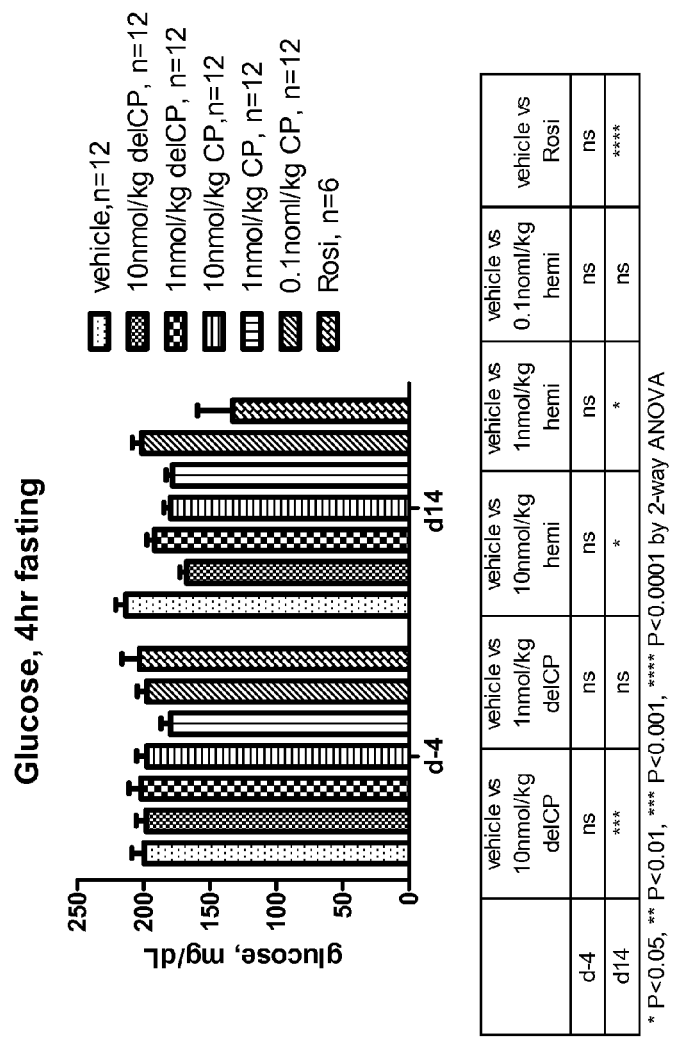

FIG. 45 is a bar graph showing the effect on glucose levels (mg/dL) of DIO mice after 4 hour fast dosed with a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 46:
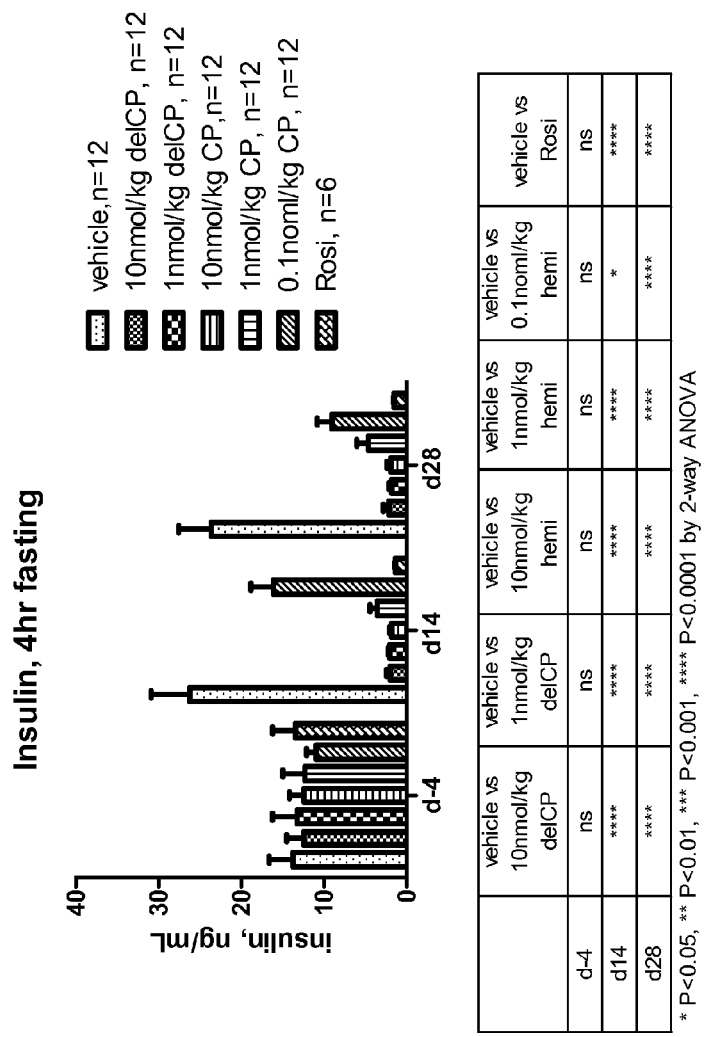

FIG. 46 is a plot showing the effect on the insulin levels (ng/mL) of DIO mice after 4 hour fast dosed with a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 47:
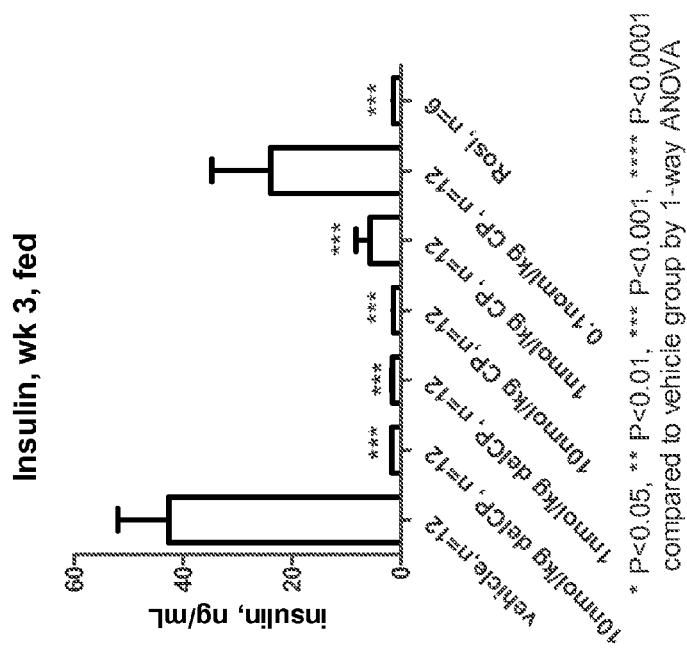

FIG. 47 is a bar graph showing the effect on the insulin levels of DIO mice fed ad libitum using a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 48:
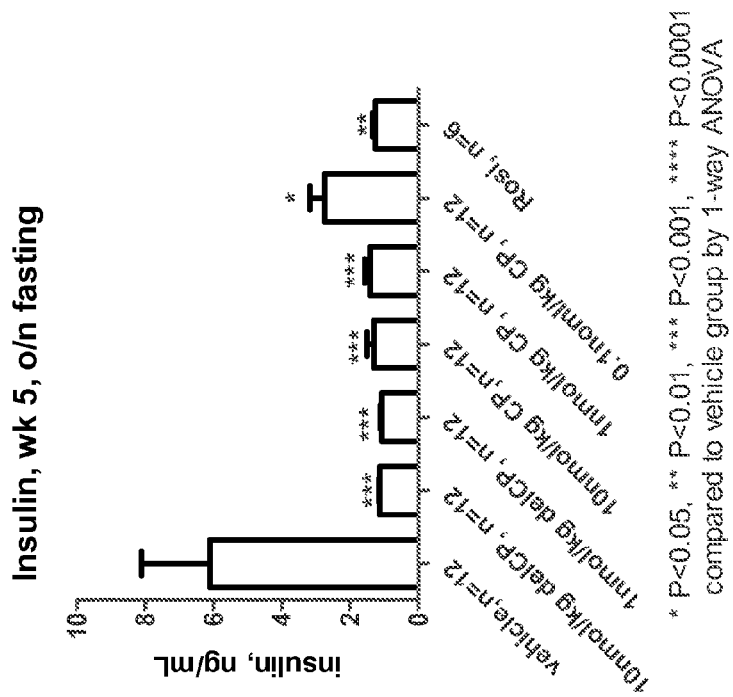

FIG. 48 is a bar graph showing the effect on the insulin levels (ng/ml) of DIO mice after overnight fast of a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 49:
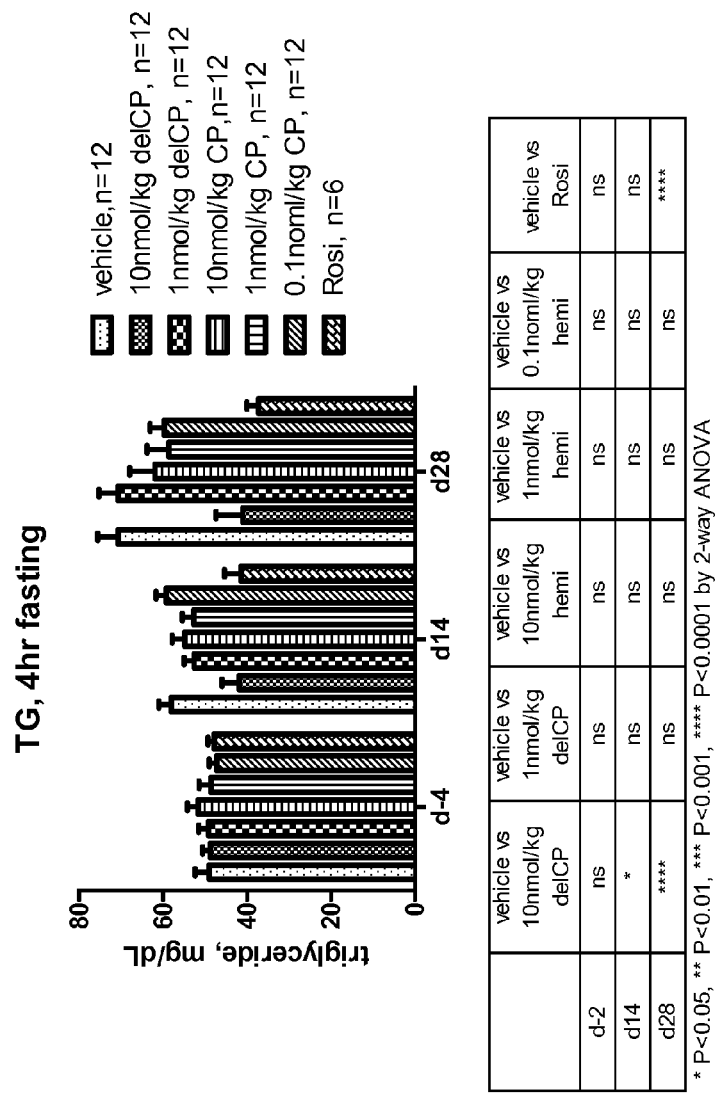

FIG. 49 is a bar graph showing the effect on the triglyceride levels (mg/dL) of DIO mice after 4 hour fast of a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 50:
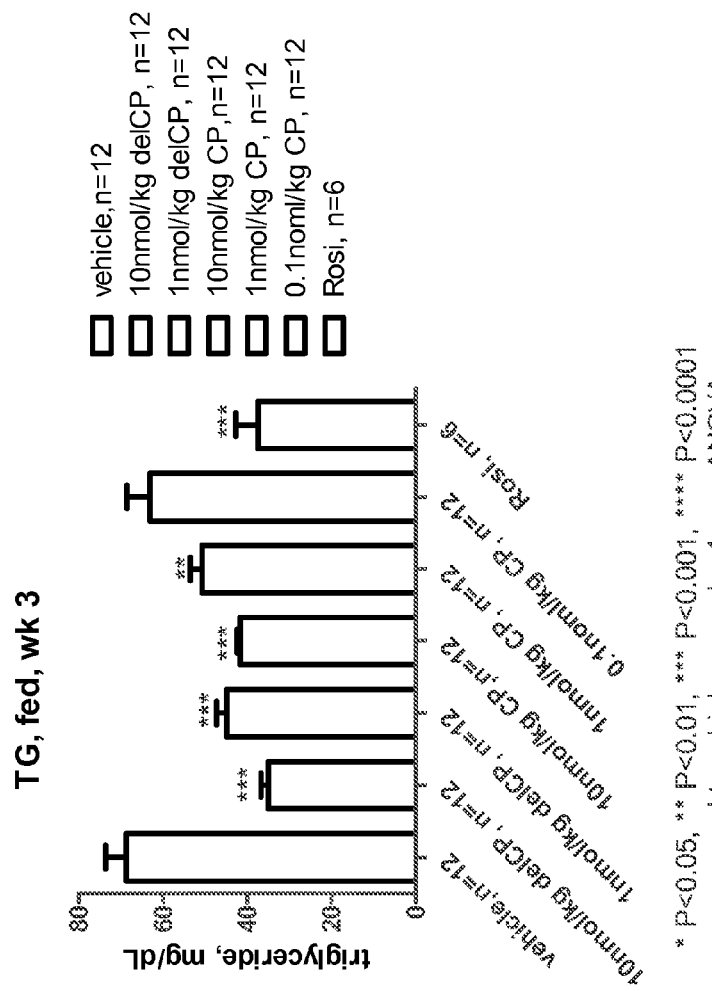

FIG. 50 is a bar graph showing the effect on the triglyceride levels (mg/dL) of DIO mice fed ad libitum of a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 51:
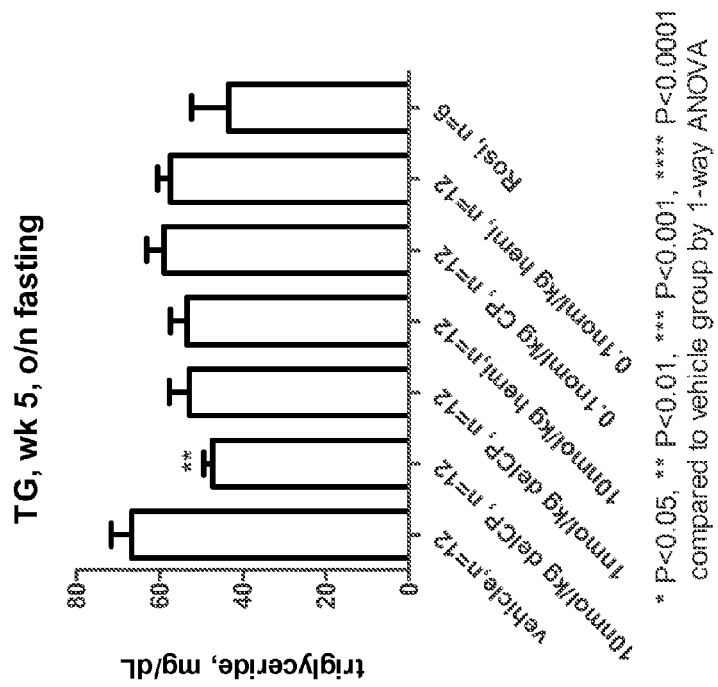

FIG. 51 is a bar graph showing the effect on the triglyceride levels (mg/dL) of DIO mice after overnight fast of a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 52:
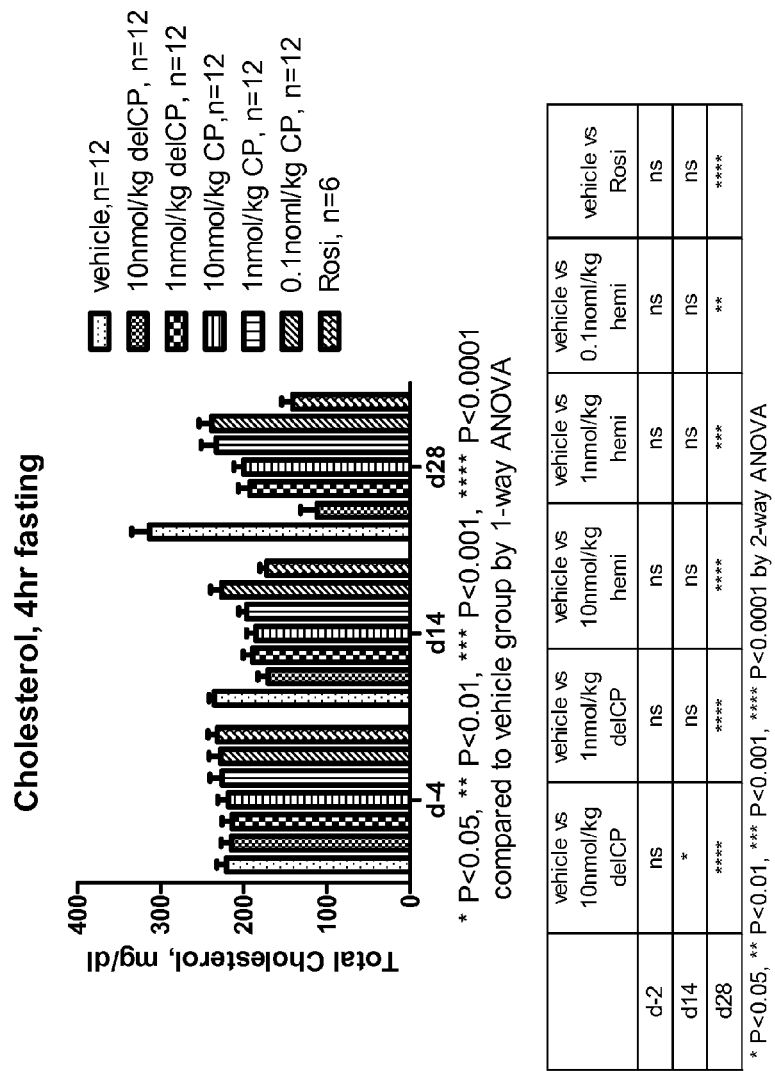

FIG. 52 is a bar graph showing the effect on the total cholesterol levels (mg/dL) of DIO mice after 4 hour fast of a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 53:
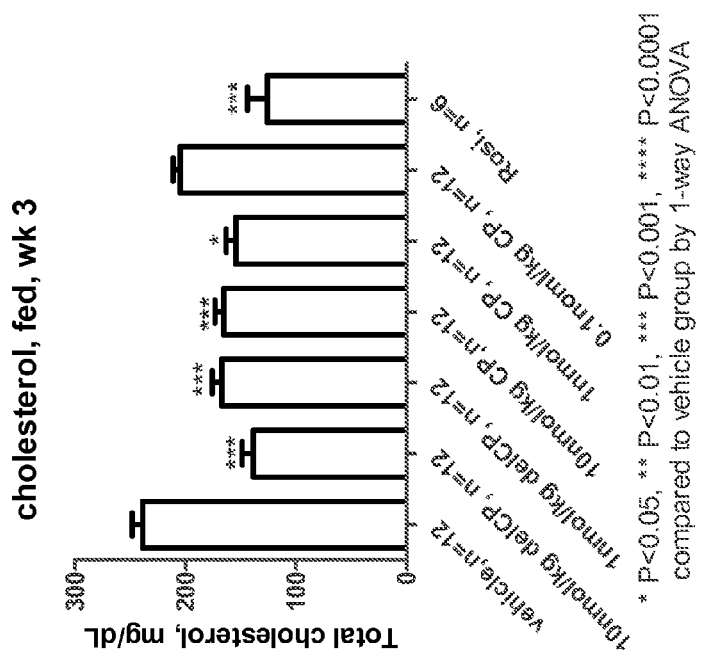

FIG. 53 is a plot showing the effect on the total cholesterol levels (mg/dL) of DIO mice fed ad libitum of a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 54:
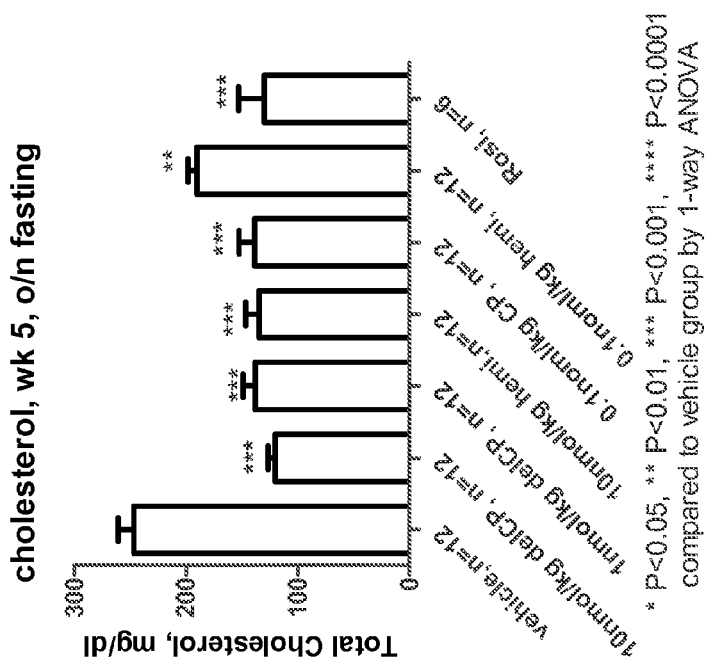

FIG. 54 is a bar graph showing the effect on the total cholesterol levels (mg/dL) of DIO mice after overnight fast of a dimer of the DhCpmFc(−)-$(G_4S)_4$-GDF15:DhCpmFc(+) construct, a dimer of the CpmFc(−)-$(G_4S)_4$-GDF15:CpmFc(+) construct and rosiglitizone (Rosi).

Figure 55:
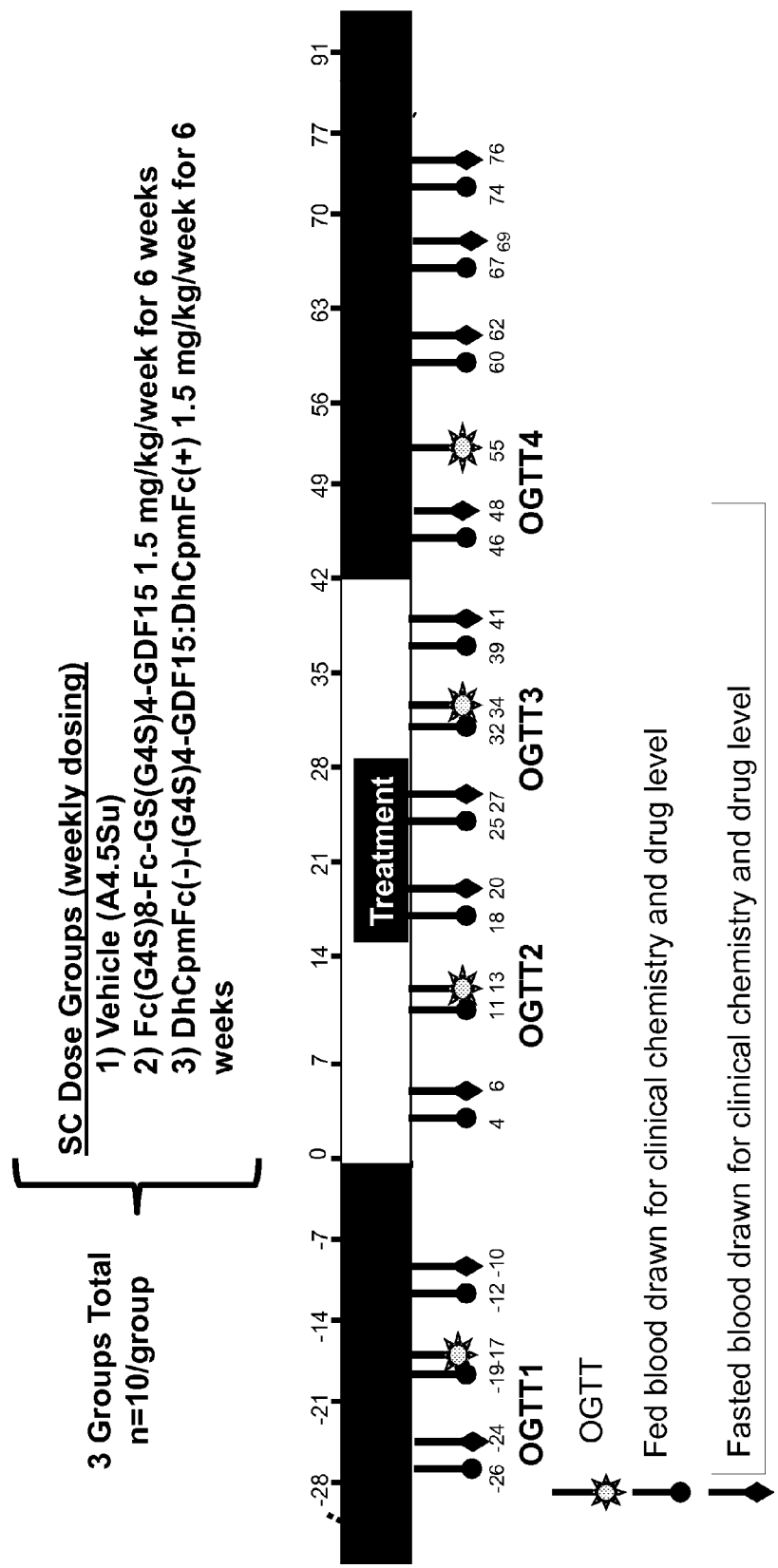

FIG. 55 is a diagram graphically depicting the study design for a five-week treatment performed in obese cynomolgous monkeys using a dimer of the Fc-$(G_4S)_8$-Fc-GS$(G_4S)_4$-GDF15 construct and a dimer of the DhCpmFc(−)-$(G_4S)_4$-GDF15:DhCpmFc(+) construct.

Figure 56:
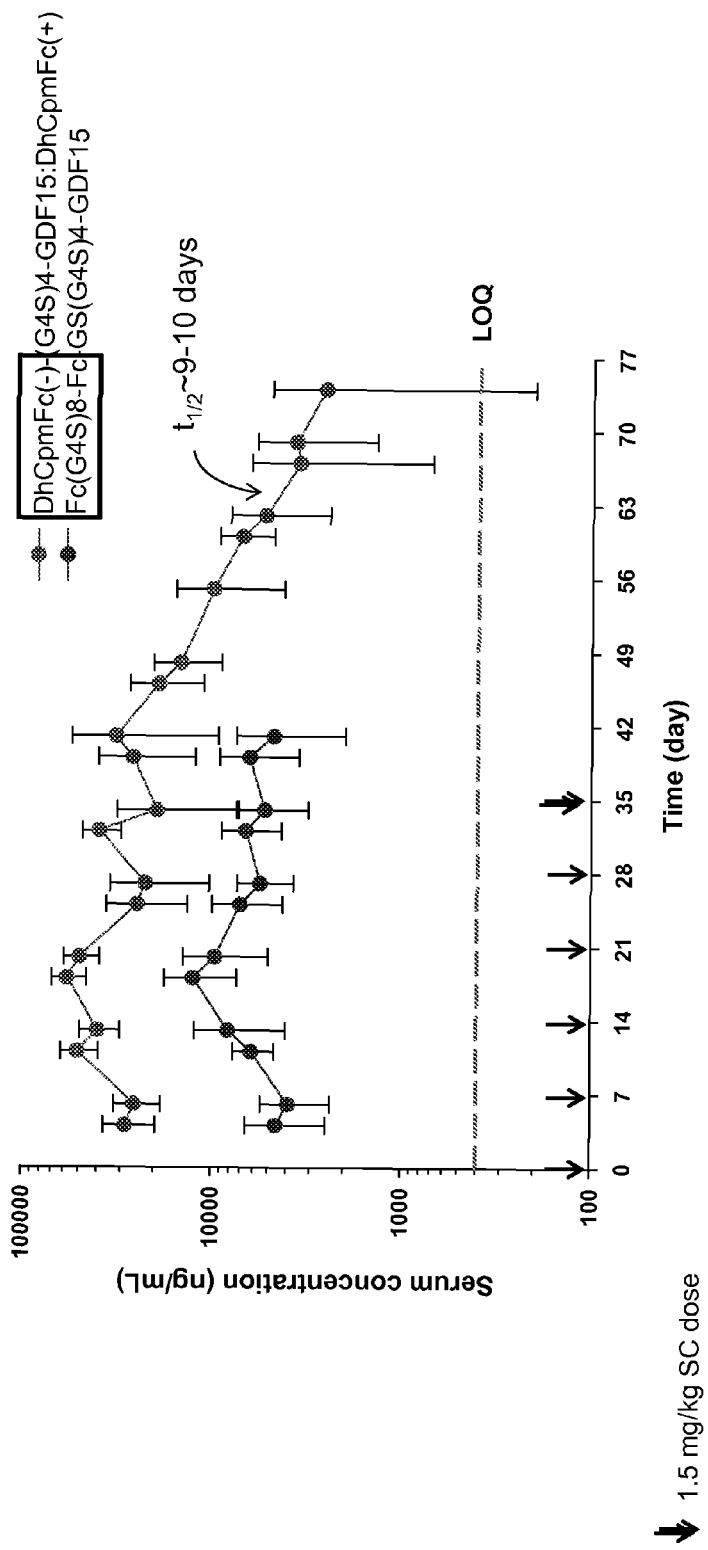

FIG. 56 is a plot showing the serum levels (ng/mL) of a dimer of the Fc-$(G_4S)_8$-Fc-GS$(G_4S)_4$-GDF15 construct and a dimer of the DhCpmFc(−)-$(G_4S)_4$-GDF15:DhCpmFc(+) construct in the cynomolgous monkeys studied.

Figure 57:
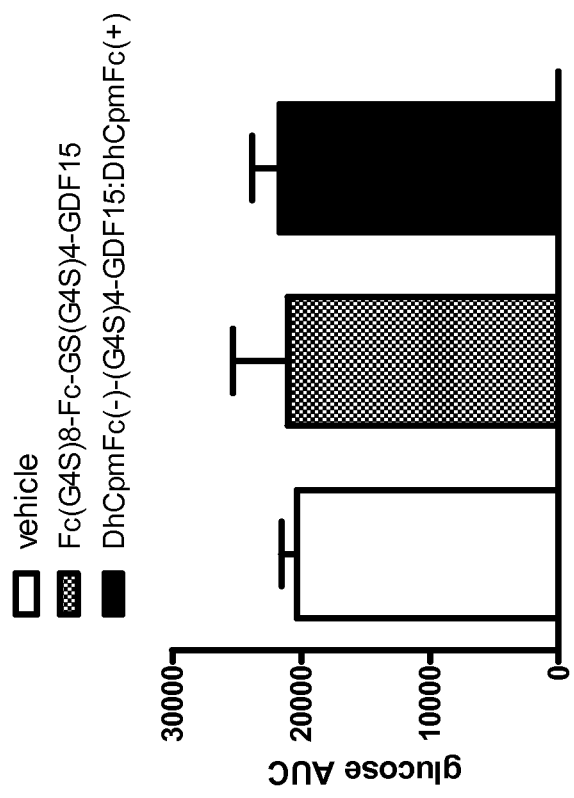

FIG. 57 is a bar graph showing the results of an acclimation OGTT following an overnight fast performed on cynomolgous monkeys using a dimer of the Fc-$(G_4S)_8$-Fc- GS(G$_4$S)$_4$-GDF15 construct, a dimer of the DhCpmFc(−)-(G$_4$S)$_4$-GDF15:DhCpmFc(+) construct and vehicle, in the form of glucose AUC data.

Figure 58:
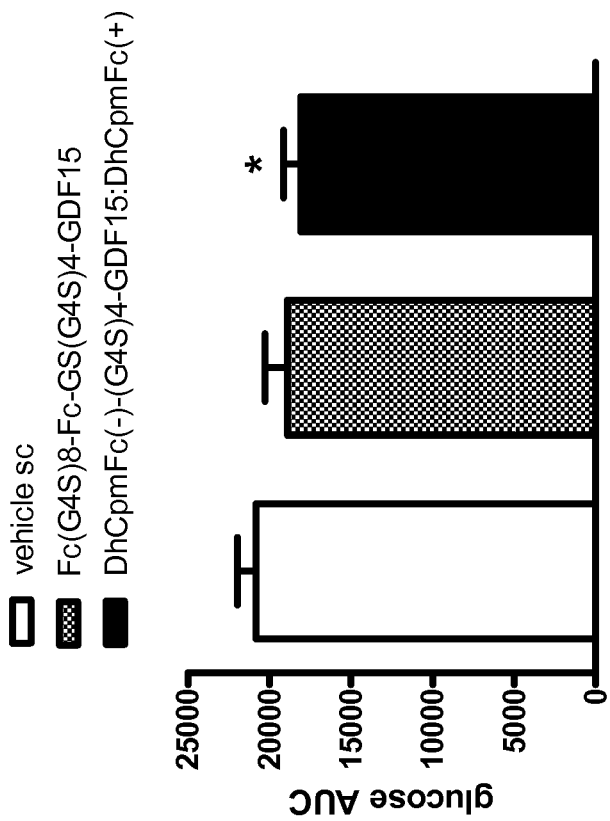

FIG. 58 is a bar graph showing the results of OGTT following an overnight fast performed on cynomolgous monkeys after 2 week administration of a dimer of the Fc-(G$_4$S)$_8$-Fc-GS(G$_4$S)$_4$-GDF15 construct, a dimer of the DhCpmFc(−)-(G$_4$S)$_4$-GDF15:DhCpmFc(+) construct and vehicle, in the form of glucose AUC data.

Figure 59:
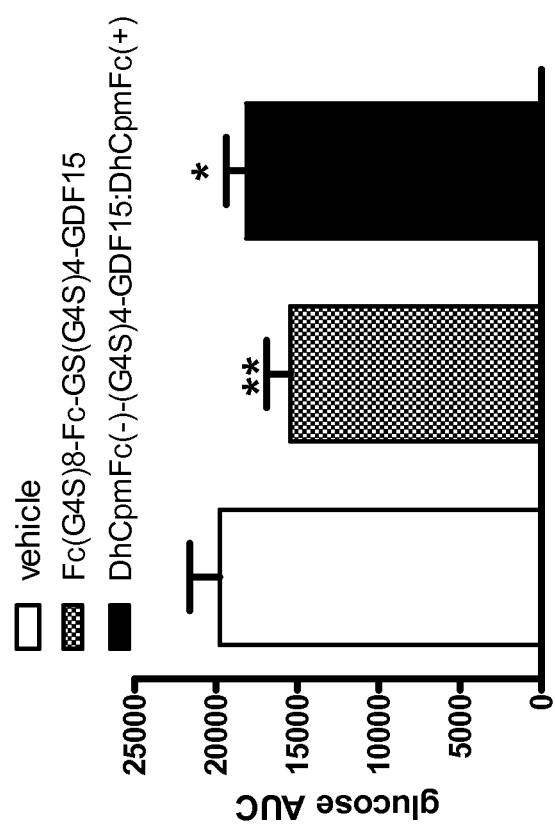

FIG. 59 is a bar graph showing the results of a OGTT following an overnight fast performed on cynomolgous monkeys after 5 week administration of a dimer of the Fc-(G$_4$S)$_8$-Fc-GS(G$_4$S)$_4$-GDF15 construct, a dimer of the DhCpmFc(−)-(G$_4$S)$_4$-GDF15:DhCpmFc(+) construct and vehicle, in the form of glucose AUC data.

Figure 60:
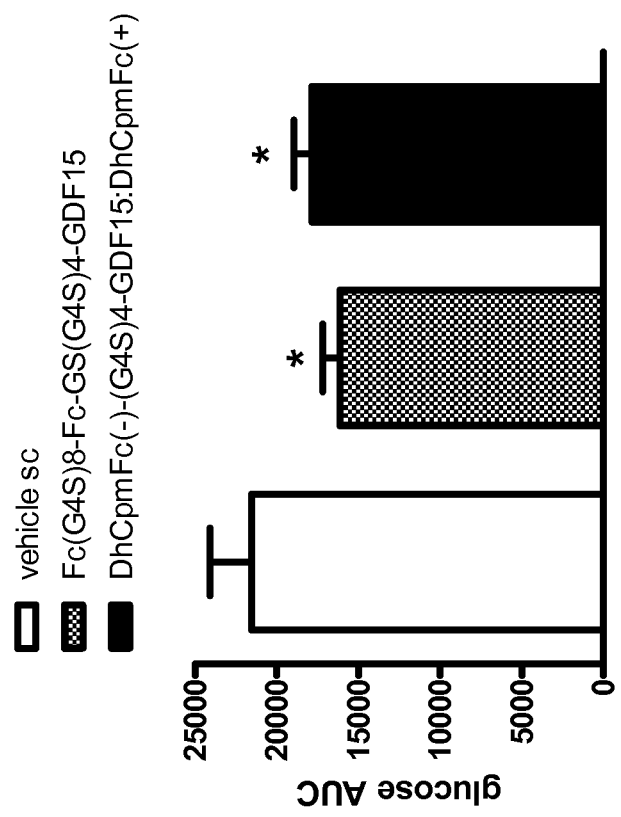

FIG. 60 is a bar graph showing the results of an OGTT following an overnight fast performed on cynomolgous monkeys after 4 week of wash out using a dimer of the Fc-(G$_4$S)$_8$-Fc-GS(G$_4$S)$_4$-GDF15 construct, a dimer of the DhCpmFc(−)-(G$_4$S)$_4$-GDF15:DhCpmFc(+) construct and vehicle in the form of glucose AUC data.

Figure 61:
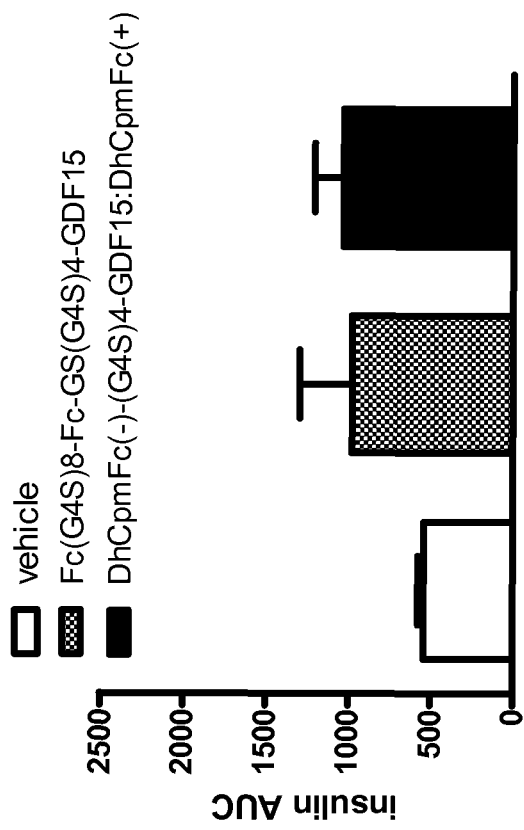

FIG. 61 is a bar graph showing the results of an acclimation OGTT following an overnight fast performed on cynomolgous monkeys using a dimer of the Fc-(G$_4$S)$_8$-Fc-GS(G$_4$S)$_4$-GDF15 construct, a dimer of the DhCpmFc(−)-(G$_4$S)$_4$-GDF15:DhCpmFc(+) construct and vehicle, in the form of insulin AUC data.

Figure 62:
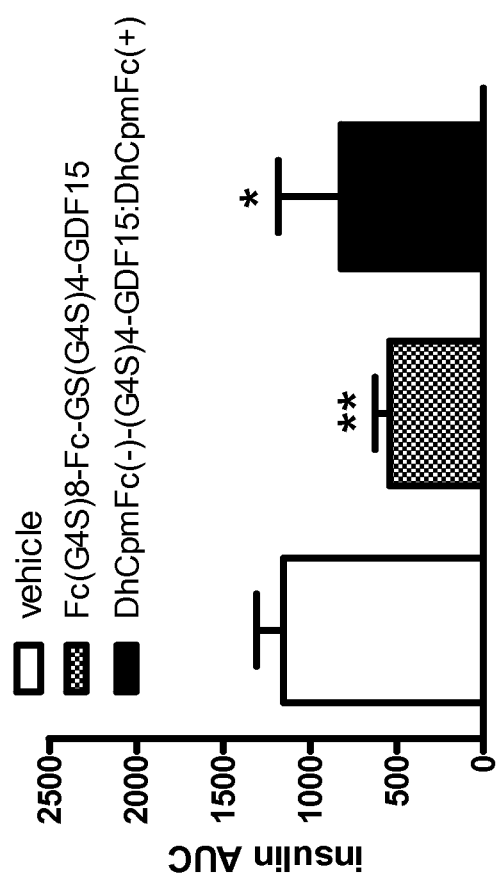

FIG. 62 is a bar graph showing the results of OGTT following an overnight fast performed on cynomolgous monkeys after 2 week administration of a dimer of the Fc-(G$_4$S)$_8$-Fc-GS(G$_4$S)$_4$-GDF15 construct, a dimer of the DhCpmFc(−)-(G$_4$S)$_4$-GDF15:DhCpmFc(+) construct and vehicle, in the form of insulin AUC data.

Figure 63:
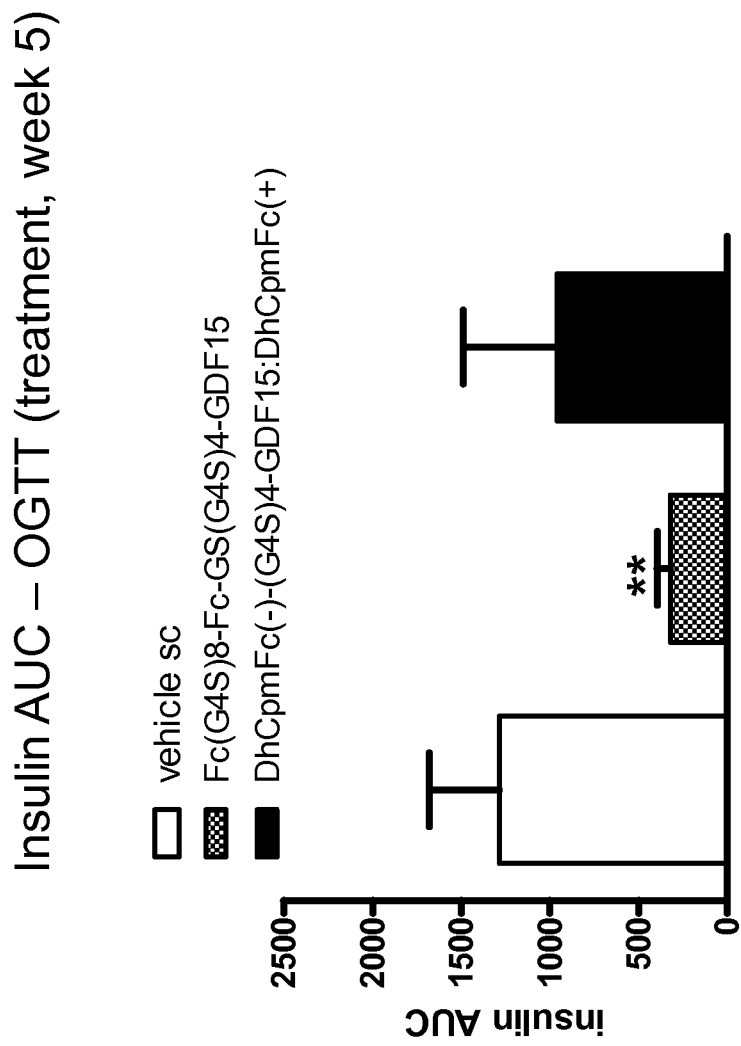

FIG. 63 is a bar graph showing the results of a OGTT following an overnight fast performed on cynomolgous monkeys after 5 week administration of a dimer of the Fc-(G$_4$S)$_8$-Fc-GS(G$_4$S)$_4$-GDF15 construct, a dimer of the DhCpmFc(−)-(G$_4$S)$_4$-GDF15:DhCpmFc(+) construct and vehicle, in the form of insulin AUC data.

Figure 64:
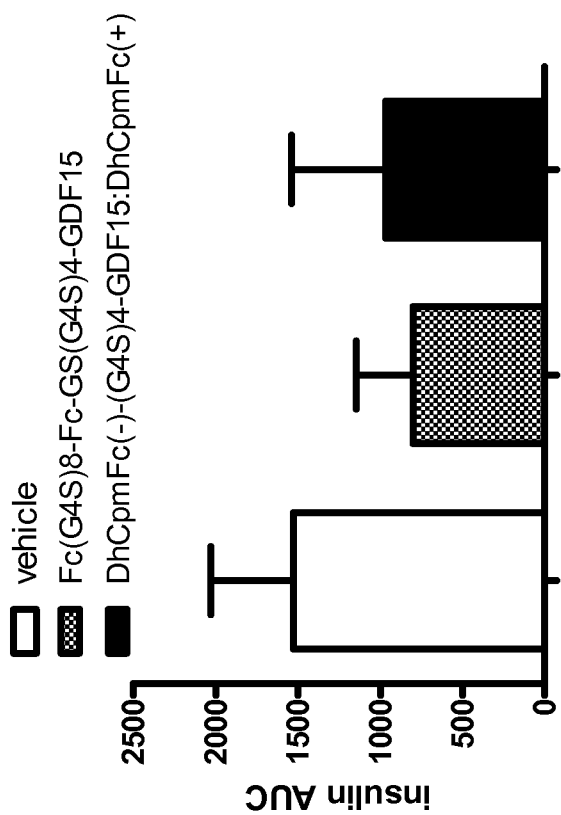

FIG. 64 is a bar graph showing the results of a OGTT following an overnight fast performed on cynomolgous monkeys 4 week of wash out of a dimer of the Fc-(G$_4$S)$_8$-Fc-GS(G$_4$S)$_4$-GDF15 construct, a dimer of the DhCpmFc(−)-(G$_4$S)$_4$-GDF15:DhFc(+) construct and vehicle in the form of insulin AUC data.

Figure 65:
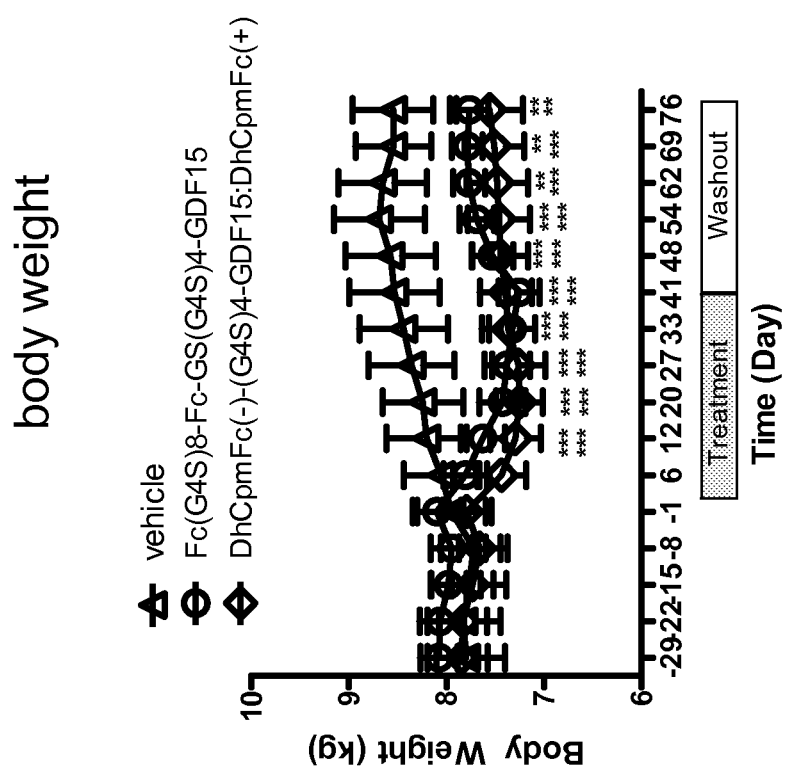

FIG. 65 is a plot of body weight (kg) as a function of time (days) collected in the month preceding, during a 30 day treatment and subsequent washout period performed on cynomolgous monkeys using a dimer of the Fc-(G$_4$S)$_8$-Fc-GS(G$_4$S)$_4$-GDF15 construct, a dimer of the DhCpmFc(−)-(G$_4$S)$_4$-GDF15:DhCpmFc(+) construct and vehicle.

Figure 66:
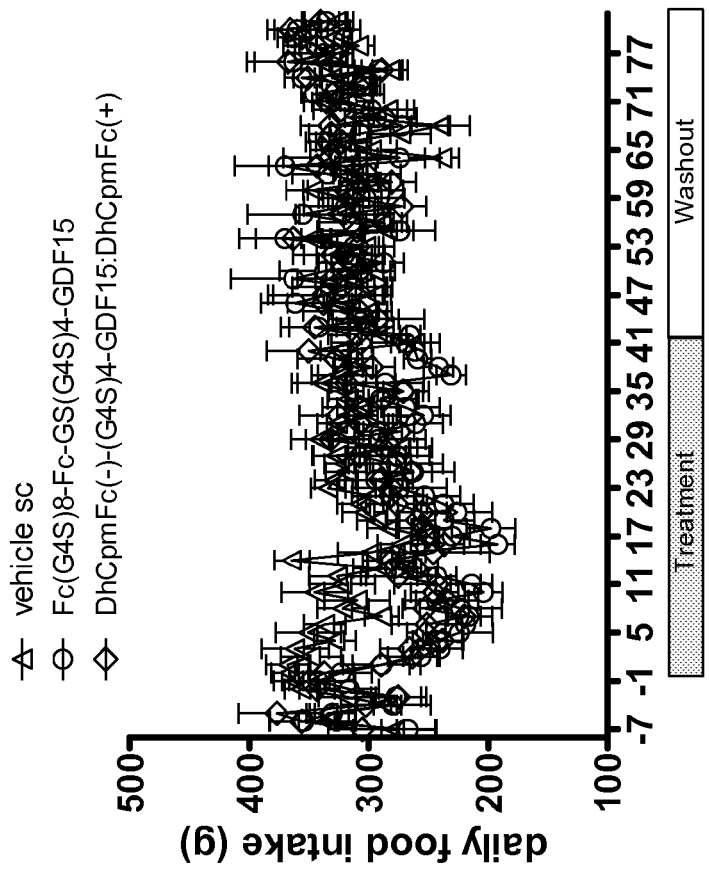

FIG. 66 is a plot of daily food intake (g) as a function of time (days) collected in the week preceding, during a 5 week treatment and subsequent 4 week washout period performed on cynomolgous monkeys using a dimer of the Fc-(G$_4$S)$_8$-Fc-GS(G$_4$S)$_4$-GDF15 construct, a dimer of the DhCpmFc(−)-(G$_4$S)$_4$-GDF15:DhCpmFc(+) construct and vehicle.

Figure 67:
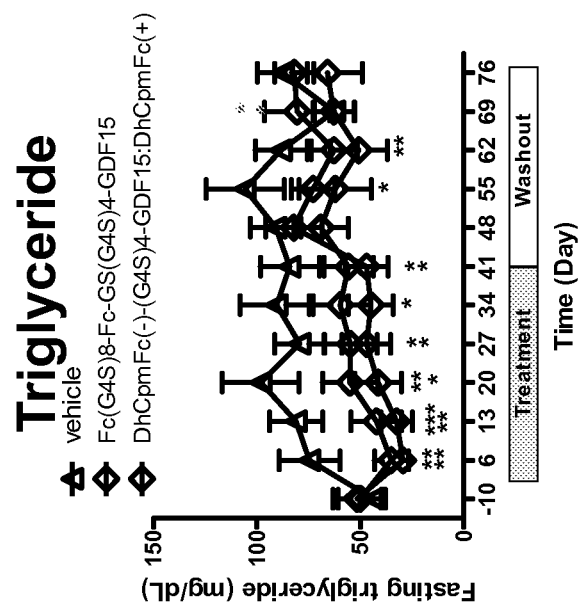

FIG. 67 is a plot of fasting triglyceride (mg/dL) as a function of time (days) collected in the week preceding, during a 5 week treatment and subsequent 4 week washout period performed on cynomolgous monkeys using a dimer of the Fc-(G$_4$S)$_8$-Fc-GS(G$_4$S)$_4$-GDF15 construct, a dimer of the DhCpmFc(−)-(G$_4$S)$_4$-GDF15:DhCpmFc(+) construct and vehicle.

Figure 68:
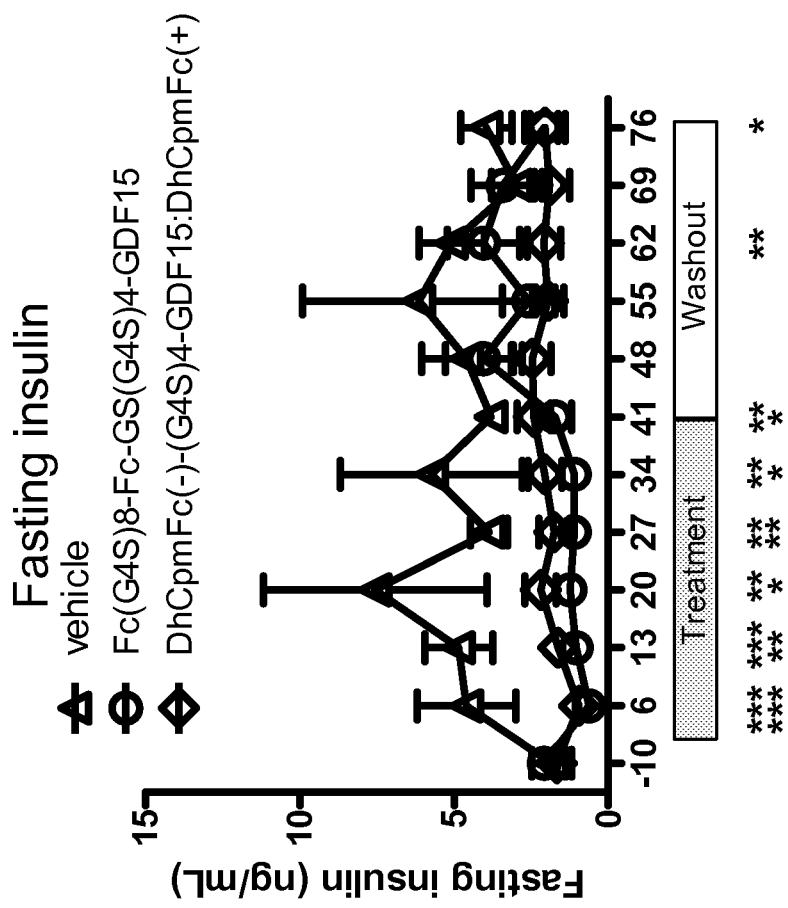

FIG. 68 is a plot of fasting insulin (ng/dL) as a function of time (days) collected in the week preceding, during a 5 week treatment and subsequent 4 week washout period performed on cynomolgous monkeys using a dimer of the Fc-(G$_4$S)$_8$-Fc-GS(G$_4$S)$_4$-GDF15 construct, a dimer of the DhCpmFc(−)-(G$_4$S)$_4$-GDF15:DhCpmFc(+) construct and vehicle.

DETAILED DESCRIPTION OF THE INVENTION

The instant disclosure provides GDF15 polypeptides and constructs comprising GDF15 polypeptides. Also provided is the generation and uses of the disclosed molecules, for example in treating a metabolic disorder, such as Type 2 diabetes, elevated glucose levels, elevated insulin levels, dyslipidemia or obesity.

Recombinant polypeptide and nucleic acid methods used herein, including in the Examples, are generally those set forth in Sambrook et al., Molecular Cloning: A Laboratory Manual (Cold Spring Harbor Laboratory Press, 1989) or Current Protocols in Molecular Biology (Ausubel et al., eds., Green Publishers Inc. and Wiley and Sons 1994), both of which are incorporated herein by reference for any purpose.

I. GENERAL DEFINITIONS

Following convention, as used herein "a" and "an" mean "one or more" unless specifically indicated otherwise.

As used herein, the terms "amino acid" and "residue" are interchangeable and, when used in the context of a peptide or polypeptide, refer to both naturally occurring and synthetic amino acids, as well as amino acid analogs, amino acid mimetics and non-naturally occurring amino acids that are chemically similar to the naturally occurring amino acids.

The terms "naturally occurring amino acid" and "naturally encoded amino acid" are used interchangeably and refer to an amino acid that is encoded by the genetic code, as well as those amino acids that are encoded by the genetic code that are modified after synthesis, e.g., hydroxyproline, γ-carboxyglutamate, and O-phosphoserine.

An "amino acid analog" is a compound that has the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but will retain the same basic chemical structure as a naturally occurring amino acid.

An "amino acid mimetic" is a chemical compound that has a structure that is different from the general chemical structure of an amino acid, but that functions in a manner similar to a naturally occurring amino acid. Examples include a methacryloyl or acryloyl derivative of an amide, β-, γ-, δ-imino acids (such as piperidine-4-carboxylic acid) and the like.

The terms "non-naturally occurring amino acid" and "non-naturally encoded amino acid" are used interchangeably and refer to a compound that has the same basic chemical structure as a naturally occurring amino acid, but is not incorporated into a growing polypeptide chain by the translation complex. "Non-naturally occurring amino acid" also includes, but is not limited to, amino acids that occur by modification (e.g., posttranslational modifications) of a naturally encoded amino acid (including but not limited to, the 20 common amino acids) but are not themselves naturally incorporated into a growing polypeptide chain by the translation complex. A non-limiting lists of examples of non-naturally occurring amino acids that can be inserted into a polypeptide sequence or substituted for a wild-type residue in polypeptide sequence include β-amino acids, homoamino acids, cyclic amino acids and amino acids with derivatized side chains. Examples include (in the L-form or D-form; abbreviated as in parentheses): citrulline (Cit), homocitrulline (hCit), Nα-methylcitrulline (NMeCit), Nα-methylhomocitrulline (Nα-MeHoCit), ornithine (Orn), Nα-Methylornithine (Nα-MeOrn or NMeOrn), sarcosine (Sar), homolysine (hLys or hK), homoarginine (hArg or hR), homoglutamine (hQ), Nα-methylarginine (NMeR), Nα-methylleucine (Nα-MeL or NMeL), N-methylhomolysine (NMeHoK), Nα-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl) alanine (1-Nal), 3-(2-naphthyl)alanine (2-Nal), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), glycyllysine (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α,β-diaminopropionoic acid (Dpr), α,γ-diaminobutyric acid (Dab), diaminopropionic acid (Dap), cyclohexylalanine (Cha), 4-methyl-phenylalanine (MePhe), β,β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, 4-Amino-O-Phthalic Acid (4APA), N-acetylglucosaminyl-L-serine, N-acetylglucosylaminyl-L-threonine, O-phosphotyrosine and other similar amino acids, and derivatized forms of any of those specifically listed.

Also included in the definition of "non-naturally occurring amino acid" is any amino acid comprising the structure

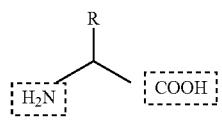

wherein the R group is any substituent other than the one used in the twenty natural amino acids.

In some embodiments, the non-naturally encoded amino acid comprises a carbonyl group. In some embodiments, the non-naturally encoded amino acid has the structure:

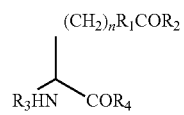

wherein n is 0-10; $R_1$ is an alkyl, aryl, substituted alkyl, or substituted aryl; $R_2$ is H, an alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group.

In some embodiments, the non-naturally encoded amino acid comprises an aminooxy group. In some embodiments, the non-naturally encoded amino acid comprises a hydrazide group. In some embodiments, the non-naturally encoded amino acid comprises a hydrazine group. In some embodiments, the non-naturally encoded amino acid residue comprises a semicarbazide group.

In some embodiments, the non-naturally encoded amino acid residue comprises an azide group. In some embodiments, the non-naturally encoded amino acid has the structure:

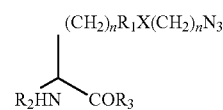

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group.

In some embodiments, the non-naturally encoded amino acid comprises an alkyne group. In some embodiments, the non-naturally encoded amino acid has the structure:

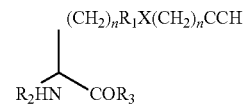

wherein n is 0-10; $R_1$ is an alkyl, aryl, substituted alkyl, or substituted aryl; X is O, N, S or not present; m is 0-10, $R_2$ is H, an amino acid, a polypeptide, or an amino terminus modification group, and $R_3$ is H, an amino acid, a polypeptide, or a carboxy terminus modification group.

The term "substituted" means that a hydrogen atom on a molecule or group is replaced with a group or atom, which is referred to as a substituent. Typical substitutents include: halogen, $C_{1-8}$alkyl, hydroxyl, $C_{1-8}$alkoxy, $-NR^xR^x$, nitro, cyano, halo or perhalo$C_{1-8}$alkyl, $C_{2-8}$alkenyl, $C_{2-8}$alkynyl, $-SR^x$, $-S(=O)_2R^x$, $-C(=O)OR^x$, $-C(=O)R^x$, wherein each $R^x$ is independently hydrogen or $C_1$-$C_8$ alkyl. It is noted that when the substituent is $-NR^xR^x$, the $R^x$ groups may be joined together with the nitrogen atom to form a ring.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "perfluoroalkyl" means an alkyl group in which all of the hydrogen atoms have been replaced with fluorine atoms. Common perfluoroalkyl groups are $C_{1-8}$ perfluoroalkyl. An example of a common perfluoroalkyl group is —$CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heterotaoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heterotaoms are particularly common.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b) pyridinyl, pyrano(3,4-b)pyrrolyl, benzofuryl, isobenzofuryl, benzo[b]thienyl, benzo[c]thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "isolated nucleic acid molecule" refers to a single or double-stranded polymer of deoxyribonucleotide or ribonucleotide bases read from the 5' to the 3' end (e.g., a GDF15 nucleic acid sequence provided herein), or an analog thereof, that has been separated from at least about 50 percent of polypeptides, peptides, lipids, carbohydrates, polynucleotides or other materials with which the nucleic acid is naturally found when total nucleic acid is isolated from the source cells. Preferably, an isolated nucleic acid molecule is substantially free from any other contaminating nucleic acid molecules or other molecules that are found in the natural environment of the nucleic acid that would interfere with its use in polypeptide production or its therapeutic, diagnostic, prophylactic or research use.

The term "isolated polypeptide" refers to a polypeptide (e.g., a GDF15 polypeptide sequence provided herein) that has been separated from at least about 50 percent of polypeptides, peptides, lipids, carbohydrates, polynucleotides, or other materials with which the polypeptide is naturally found when isolated from a source cell. Preferably, the isolated polypeptide is substantially free from any other contaminating polypeptides or other contaminants that are found in its natural environment that would interfere with its therapeutic, diagnostic, prophylactic or research use.

The term "encoding" refers to a polynucleotide sequence encoding one or more amino acids. The term does not require a start or stop codon. An amino acid sequence can be encoded in any one of the different reading frames provided by a polynucleotide sequence.

The terms "identical" and percent "identity," in the context of two or more nucleic acids or polypeptide sequences, refer to two or more sequences or subsequences that are the same. "Percent identity" means the percent of identical residues between the amino acids or nucleotides in the compared molecules and is calculated based on the size of the smallest of the molecules being compared. For these calculations, gaps in alignments (if any) can be addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), (1988) New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., (1987) Sequence Analysis in Molecular Biology, New York: Academic Press; Sequence Analysis Primer, (Gribskov, M. and Devereux, J., eds.), 1991, New York: M. Stockton Press; and Carillo et al., (1988) *SIAM J. Applied Math.* 48:1073.

In calculating percent identity, the sequences being compared are aligned in a way that gives the largest match between the sequences. The computer program used to determine percent identity is the GCG program package, which includes GAP (Devereux et al., (1984) *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually ⅒ times the gap opening penalty), as well as a comparison matrix such as PAM 250 or BLOSUM 62 are used in conjunction with the algorithm. In certain embodiments, a standard comparison matrix (see, Dayhoff et al., (1978) *Atlas of Protein Sequence and Structure* 5:345-352 for the PAM 250 comparison matrix; Henikoff et al., (1992) *Proc. Natl. Acad. Sci. U.S.A.* 89:10915-10919 for the BLOSUM 62 comparison matrix) is also used by the algorithm.

Recommended parameters for determining percent identity for polypeptides or nucleotide sequences using the GAP program are the following:

Algorithm: Needleman et al., 1970, *J. Mol. Biol.* 48:443-453;

Comparison matrix: BLOSUM 62 from Henikoff et al., 1992, supra;

Gap Penalty: 12 (but with no penalty for end gaps)
Gap Length Penalty: 4
Threshold of Similarity: 0

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans at least 50 contiguous amino acids of the target polypeptide.

The terms "GDF15 polypeptide" and "GDF15 protein" are used interchangeably and mean a naturally-occurring wild-type polypeptide expressed in a mammal, such as a human or a mouse. For purposes of this disclosure, the term "GDF15 polypeptide" can be used interchangeably to refer to any full-length GDF15 polypeptide, e.g., SEQ ID NO:4, which consists of 308 amino acid residues and which is encoded by the nucleotide sequence SEQ ID NO:3; any form comprising the active and prodomains of the polypeptide, e.g., SEQ ID NO:8, which consists of 279 amino acid residues and which is encoded by the nucleotide sequence SEQ ID NO:7, and in which the 29 amino acid residues at the amino-terminal end of the full-length GDF15 polypeptide (i.e., which constitute the signal peptide) have been removed; and any form of the polypeptide comprising the active domain from which the prodomain and signal sequence have been removed, e.g., SEQ ID NO:12, which consists of 112 amino acid residues and which is encoded by the nucleotide sequence SEQ ID NO:11, in which the signal sequence and the prodomain have been removed. GDF15 polypeptides can but need not comprise an amino-terminal methionine, which may be introduced by engineering or as a result of a bacterial expression process.

The term "GDF15 mutant polypeptide" encompasses a GDF15 polypeptide in which a naturally occurring GDF15 polypeptide sequence (e.g., SEQ ID NOs:4, 8 or 12) has been modified. Such modifications include, but are not limited to, one or more amino acid substitutions, including substitutions with non-naturally occurring amino acids non-naturally-occurring amino acid analogs and amino acid mimetics.

In one aspect, the term "GDF15 mutant polypeptide" refers to a GDF15 polypeptide sequence (e.g., SEQ ID NOs:4, 8 or 12) in which at least one residue normally found at a given position of a native GDF15 polypeptide is deleted or is replaced by a residue not normally found at that position in the native GDF15 sequence. In some cases it will be desirable to replace a single residue normally found at a given position of a native GDF15 polypeptide with more than one residue that is not normally found at the position; in still other cases it may be desirable to maintain the native GDF15 polypeptide sequence and insert one or more residues at a given position in the protein; in still other cases it may be desirable to delete a given residue entirely; all of these constructs are encompassed by the term "GDF15 mutant polypeptide."

In various embodiments, a GDF15 mutant polypeptide comprises an amino acid sequence that is at least about 85 percent identical to a naturally-occurring GDF15 polypeptide (e.g., SEQ ID NOs:4, 8 or 12). In other embodiments, a GDF15 polypeptide comprises an amino acid sequence that is at least about 90 percent, or about 95, 96, 97, 98, or 99 percent identical to a naturally-occurring GDF15 polypeptide amino acid sequence (e.g., SEQ ID NOs:4, 8 or 12). Such GDF15 mutant polypeptides preferably, but need not, possess at least one activity of a wild-type GDF15 mutant polypeptide, such as the ability to lower blood glucose, insulin, triglyceride, or cholesterol levels; the ability to reduce body weight; or the ability to improve glucose tolerance, energy expenditure, or insulin sensitivity. The present invention also encompasses nucleic acid molecules encoding such GDF15 mutant polypeptide sequences.

As stated herein, a GDF15 mutant polypeptide can comprise a signal sequence (residues 1-29 of SEQ ID NO:4) or it can have the signal sequence removed (providing SEQ ID NO:8). In other embodiments, a GDF15 mutant polypeptide can have the signal sequence removed and can also be cleaved at residue 196, separating the primary sequence of the prodomain (residues 30-196 of SEQ ID NO:4) from the primary sequence of the active domain. The naturally-occurring biologically active form of a GDF15 mutant polypeptide is a homodimer comprising the processed mature peptide (SEQ ID NO:12; residues 197-308 of SEQ ID NO:4). Although the GDF15 polypeptides and GDF15 mutant polypeptides, and the constructs comprising such polypeptides are primarily disclosed in terms of human GDF15, the invention is not so limited and extends to GDF15 polypeptides and GDF15 mutant polypeptides and the constructs comprising such polypeptides where the GDF15 polypeptides and GDF15 mutant polypeptides are derived from other species (e.g., cynomolgous monkeys, mice and rats). In some instances, a GDF15 polypeptide or a GDF15 mutant polypeptide can be used to treat or ameliorate a metabolic disorder in a subject is a mature form of a GDF15 mutant polypeptide that is derived from the same species as the subject.

A GDF15 mutant polypeptide is preferably biologically active. In various respective embodiments, a GDF15 polypeptide or a GDF15 mutant polypeptide has a biological activity that is equivalent to, greater to or less than that of the naturally occurring form of the mature GDF15 protein or GDF15 mutant polypeptide from which the signal peptide has been removed from the N-terminus of a full length GDF15 mutant polypeptide sequence and in which the prodomain has been cleaved (but not necessarily removed from) the active domain. Examples of biological activities include the ability to lower blood glucose, insulin, triglyceride, or cholesterol levels; the ability to reduce body weight; or the ability to improve glucose tolerance, lipid tolerance, or insulin sensitivity; the ability to lower urine glucose and protein excretion.

The terms "therapeutically effective dose" and "therapeutically effective amount," as used herein, means an amount of GDF15 or GDF15 mutant polypeptide that elicits a biological or medicinal response in a tissue system, animal, or human being sought by a researcher, physician, or other clinician, which includes alleviation or amelioration of the symptoms of the disease or disorder being treated, i.e., an amount of GDF15 or GDF15 mutant polypeptide that supports an observable level of one or more desired biological or medicinal response, for example lowering blood glucose, insulin, triglyceride, or cholesterol levels; reducing body weight; or improving glucose tolerance, energy expenditure, or insulin sensitivity.

II. GDF15 POLYPEPTIDES AND CONSTRUCTS COMPRISING GDF15, INCLUDING MUTANT FORMS THEREOF, AND POLYNUCLEOTIDES

A range of GDF15 polypeptides and constructs comprising a GDF15 polypeptide are provided herein. Some of these molecules were studied in a variety of assays, as described in the Examples presented herein below. Some of the GDF15 polypeptides and constructs comprising a GDF15 polypeptide provided herein include those described below.

II.A. Native Mature GDF15 and Variants

II.A.1 Native Mature GDF15

Bearing in mind that the biologically active form of GDF15 comprises a homodimer, the construct designated "native mature GDF15 dimer" in the instant disclosure refers to a homodimer comprising two mature GDF15 monomers, each of which comprises SEQ ID NO:12. The monomer that homodimerizes to form the native mature GDF15 dimer is encoded by the nucleic acid sequence:

(SEQ ID NO: 11)
gcgcgcaacggggaccactgtccgctcgggcccgggcgttgct gccgtctgcacacggtccgcgcgtcgctggaagacctgggctgggccgat tgggtgctgtcgccacgggaggtgcaagtgaccatgtgcatcggcgcgtg cccgagccagttccgggcggcaaacatgcacgcgcagatcaagacgagcc tgcaccgcctgaagcccgacacggtgccagcgccctgctgcgtgcccgcc agctacaatcccatggtgctcattcaaaagaccgacaccggggtgtcgct ccagacctatgatgacttgttagccaaagactgccactgcatatga and comprises the amino acid sequence:

(SEQ ID NO: 12)
ARNGDHCPLGPGRCCRLHTVRASLEDLGWAD

WVLSPREVQVTMCIGACPSQFRAANMHAQIKTSLHRLKPDTVPAPCCVPA

SYNPMVLIQKTDTGVSLQTYDDLLAKDCHCI.

Thus, the "native mature GDF15 dimer" comprises two covalently associated monomers comprising SEQ ID NO:12.

In some embodiments, a leader, or signal, sequence may be used to direct secretion of a polypeptide. A signal sequence may be positioned within or directly at the 5' end of a polypeptide coding region. Many signal sequences have been identified and may be selected based upon the host cell used for expression, e.g., the cleaved VH21 signal sequence (see EP2330197 for discussion of the VH21 signal sequence).

In an embodiment employing the VH21 signal sequence, the monomer that homodimerizes to form the native mature GDF15 dimer is encoded by the nucleic acid sequence (VH21 signal sequence underlined):

(SEQ ID NO: 15)
<u>atggaatggagctgggtctttctcttcttcctgtcagtaacgaccggtgt</u>

<u>ccactcc</u>gcgcgcaacggggaccactgtccgctcgggcccgggcgttgct gccgtctgcacacggtccgcgcgtcgctggaagacctgggctgggccgat tgggtgctgtcgccacgggaggtgcaagtgaccatgtgcatcggcgcgtg cccgagccagttccgggcggcaaacatgcacgcgcagatcaagacgagcc tgcaccgcctgaagcccgacacggtgccagcgccctgctgcgtgcccgcc agctacaatcccatggtgctcattcaaaagaccgacaccggggtgtcgct ccagacctatgatgacttgttagccaaagactgccactgcatatga and comprises the amino acid sequence (cleaved VH21 signal sequence underlined):

(SEQ ID NO: 16)
MEWSWVFLFFLSVTTGVHSARNGDHCPLGPGRCCRLHTVRASLEDLGWAD

WVLSPREVQVTMCIGACPSQFRAANMHAQIKTSLHRLKPDTVPAPCCVPA

SYNPMVLIQKTDTGVSLQTYDDLLAKDCHCI

II.A.2 Mature GDF15(H6D) Variant

The GDF15(H6D) variant is a naturally occurring human GDF15 variant due to a C→G polymorphism, resulting in the His to Asp change at residue 202 in full-length peptide (SEQ ID NO:4); residue 6 in mature peptide (SEQ ID NO:12).

The construct designated "mature GDF15(H6D) dimer" in the instant disclosure refers to a homodimer comprising two mature GDF15(H6D) monomers, each of which comprises SEQ ID NO:38. The monomer that homodimerizes to form the mature GDF15(H6D) dimer is encoded by the nucleic acid sequence:

(SEQ ID NO: 37)
gcgcgcaacggggacgattgtccgctcgggcccgggcgttgct gccgtctgcacacggtccgcgcgtcgctggaagacctgggctgggccgat tgggtgctgtcgccacgggaggtgcaagtgaccatgtgcatcggcgcgtg cccgagccagttccgggcggcaaacatgcacgcgcagatcaagacgagcc tgcaccgcctgaagcccgacacggtgccagcgcctgctgcgtgcccgcc agctacaatcccatggtgctcattcaaaagaccgacaccggggtgtcgct ccagacctatgatgacttgttagccaaagactgccactgcatatga and comprises the amino acid sequence:

(SEQ ID NO: 38)
ARNGDDCPLGPGRCCRLHTVRASLEDLGWADWVLSPREVQ

VTMCIGACPSQFRAANMHAQIKTSLHRLKPDTVPAPCCVP

ASYNPMVLIQKTDTGVSLQTYDDLLAKDCHCI

Thus, the "mature GDF15(H6D) dimer" comprises two covalently associated monomers comprising SEQ ID NO:38.

In an embodiment employing the VH21 signal sequence, the monomer that homodimerizes to form the mature GDF15(H6D) dimer is encoded by the nucleic acid sequence (signal sequence underlined):

(SEQ ID NO: 35)
atggaatggagctgggtctttctcttcttcctgtcagtaacgaccggtgt ccactccgcgcgcaacggggacgattgtccgctcgggcccgggcgttgct gccgtctgcacacggtccgcgcgtcgctggaagacctgggctgggccgat tgggtgctgtcgccacgggaggtgcaagtgaccatgtgcatcggcgcgtg cccgagccagttccgggcggcaaacatgcacgcgcagatcaagacgagcc tgcaccgcctgaagcccgacacggtgccagcgcctgctgcgtgcccgcc agctacaatcccatggtgctcattcaaaagaccgacaccggggtgtcgct ccagacctatgatgacttgttagccaaagactgccactgcatatga and comprises the amino acid sequence (signal sequence underlined):

(SEQ ID NO: 36)
MEWSWVFLFFLSVTTGVHSARNGDDCPLGPGRCCRLHTVRASLEDLGWAD

WVLSPREVQVTMCIGACPSQFRAANMHAQIKTSLHRLKPDTVPAPCCVPA

SYNPMVLIQKTDTGVSLQTYDDLLAKDCHCI

II.A.3 Mature GDF15(N3Q) Variant

The GDF15(N3Q) variant is a human GDF15 mutant with Asn at residue 3 of the mature peptide (SEQ ID NO:12) replaced by Gln to avoid potential N deamidation.

The construct designated "mature GDF15(N3Q) dimer" in the instant disclosure refers to a homodimer comprising two mature GDF15(N3Q) monomers, each of which comprises SEQ ID NO:42. The monomer that homodimerizes to form the mature GDF15(N3Q) dimer is encoded by the nucleic acid sequence:

(SEQ ID NO: 41)
gcgcgccagggagaccactgtccgctcgggcccgggcgttgct gccgtctgcacacggtccgcgcgtcgctggaagacctgggctgggccgat tgggtgctgtcgccacgggaggtgcaagtgaccatgtgcatcggcgcgtg cccgagccagttccgggcggcaaacatgcacgcgcagatcaagacgagcc tgcaccgcctgaagcccgacacggtgccagcgcctgctgcgtgcccgcc agctacaatcccatggtgctcattcaaaagaccgacaccggggtgtcgct ccagacctatgatgacttgttagccaaagactgccactgcata and comprises the amino acid sequence:

SEQ ID NO: 42)
ARQGDHCPLGPGRCCRLHTVRASLEDLGWADWVLSPREVQ

VTMCIGACPSQFRAANMHAQIKTSLHRLKPDTVPAPCCVPA

SYNPMVLIQKTDTGVSLQTYDDLLAKDCHCI

In an embodiment employing the VH21 signal sequence, the monomer that homodimerizes to form the native mature GDF15 dimer is encoded by the nucleic acid sequence (including the cleaved VH21 signal sequence, which is underlined):

(SEQ ID NO: 39)
atggaatggagctgggtctttctcttcttcctgtcagtaacgaccggtgt ccactccgcgcgccagggagaccactgtccgctcgggcccgggcgttgct gccgtctgcacacggtccgcgcgtcgctggaagacctgggctgggccgat tgggtgctgtcgccacgggaggtgcaagtgaccatgtgcatcggcgcgtg cccgagccagttccgggcggcaaacatgcacgcgcagatcaagacgagcc tgcaccgcctgaagcccgacacggtgccagcgcctgctgcgtgcccgcc agctacaatcccatggtgctcattcaaaagaccgacaccggggtgtcgct ccagacctatgatgacttgttagccaaagactgccactgcata and comprises the amino acid sequence (cleaved VH21 signal sequence underlined):

(SEQ ID NO: 40)
MEWSWVFLFFLSVTTGVHSARQGDHCPLGPGRCCRLHTVRASLEDLGWAD

WVLSPREVQVTMCIGACPSQFRAANMHAQIKTSLHRLKPDTVPAPCCVPA

SYNPMVLIQKTDTGVSLQTYDDLLAKDCHCI.

Thus, the "mature GDF15(N3Q) dimer" comprises two covalently associated monomers comprising SEQ ID NO:42.

II.B. Charged Pair (delHinge) Constructs

Constructs designated "charged pair (delHinge)" or "charged pair (delHinge) Fc" in the instant disclosure refer to a construct comprising (i) a "negatively charged" Fc sequence lacking the hinge region and comprising a charged pair mutation and (ii) a "positively charged" Fc sequence lacking the hinge region and comprising a charged pair mutation. Note that use of the terms "positively charged" and "negatively charged" is for ease of reference (i.e., to describe the nature of the charge pair mutations in the Fc sequences) and not to indicate that the overall sequence or construct necessary has a positive or negative charge.

The introduction of an aspartatic acid-to-lysine mutation (E356K) and a glutamic acid-to-lysine mutation (D399K) into the unmodified Fc sequence lacking the hinge region provides the positively charged Fc sequence lacking the hinge region (referred to herein as "DhCpmFc(+)"). The introduction of two lysine-to-aspartate mutations (K392D, K409D) into the unmodified Fc sequence lacking the hinge region provides the negatively charged Fc sequence lacking the hinge region (referred to herein as "DhCpmFc(-)"). The C-terminal lysine (K477) optionally also may be deleted in the negatively charged DhCpmFc(-) sequence, the positively charged DhCpmFc(+) sequence, or both. See, e.g., SEQ ID NOs: 18, 19, 85, 86, 89, 90, 91, 99, 100, 108, 109 and 111 (DhCpmFc sequences).

When incubated together, the aspartate residues associate with the lysine residues through electrostatic force, facilitating formation of Fc heterodimers between the DhCpmFc(+) and DhCpmFc(-) sequences, and reducing or preventing formation of Fc homodimers between the DhCpmFc(+) sequences or between DhCpmFc(-) sequences.

Figure 1:
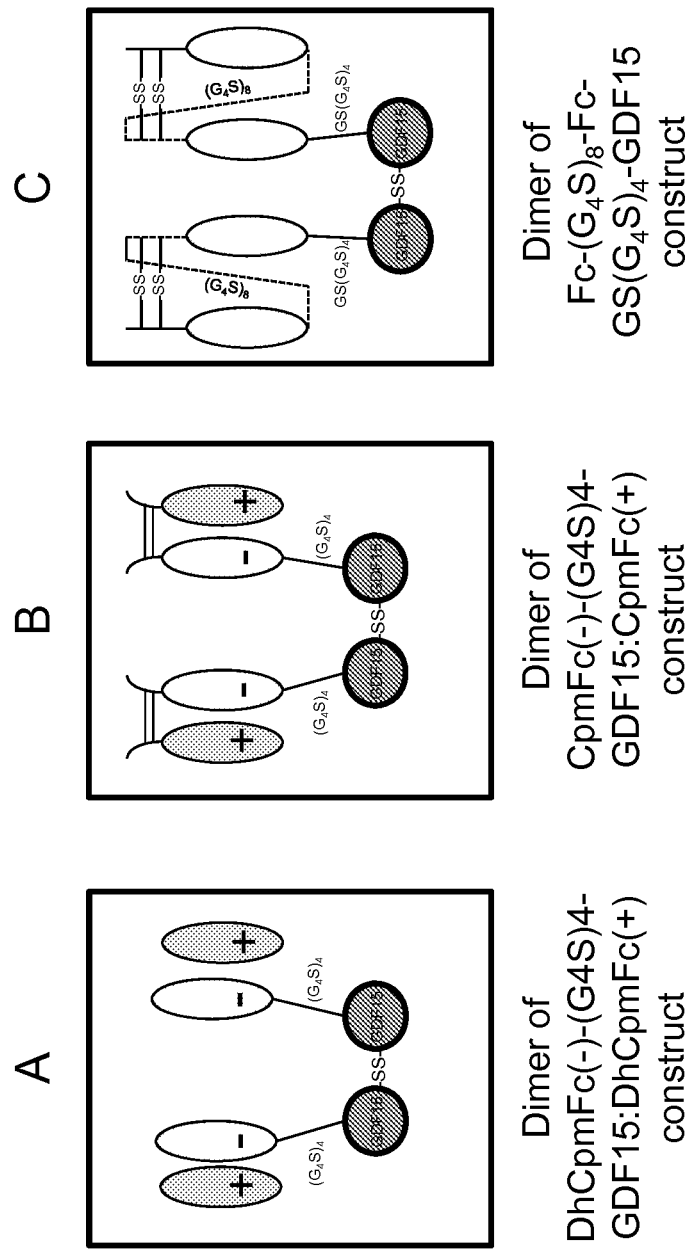
FIG. 1 is a series of graphics depicting the arrangement of the charged pair (delHinge) construct DhCpmFc(−)-($G_4S$)$_4$-GDF15:DhCpmFc(+) (FIG. 1A); the charged pair construct CpmFc(−)-($G_4S$)$_4$-GDF15:CpmFc(+) (FIG. 1B); and the hemi construct Fc-($G_4S$)$_8$-Fc-GS($G_4S$)$_4$-GDF15 (FIG. 1C).
Figure 3:
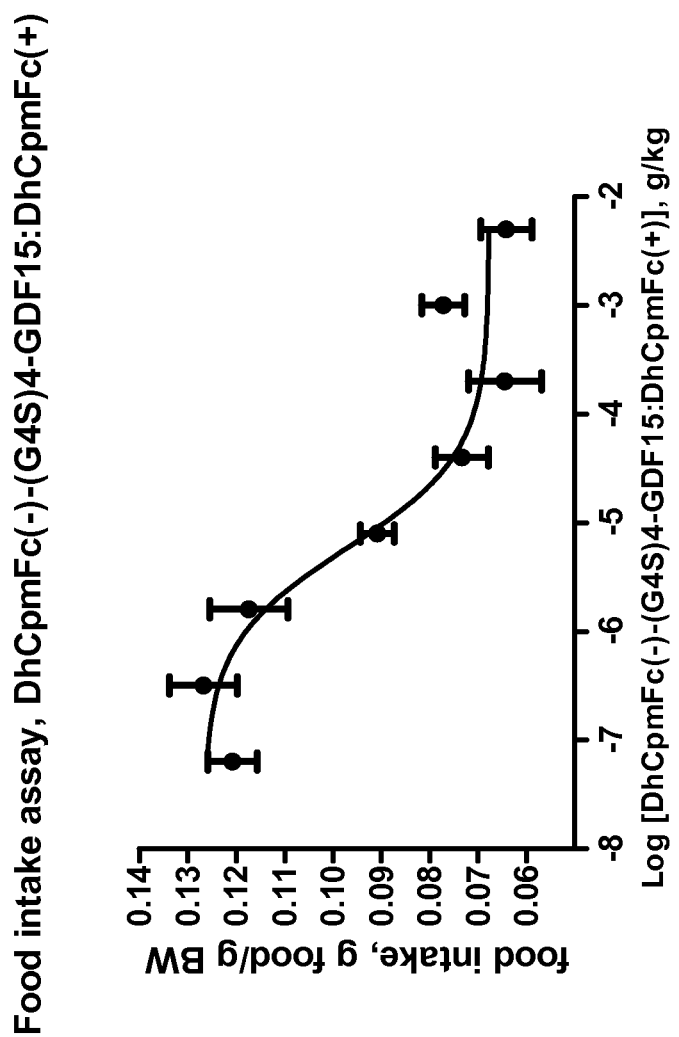
FIG. 3 is a plot showing the effect on food intake (g food/g body weight (BW)) of ob/ob mice as a function of dose (log [g protein/kg BW]) using a dimer of the DhCpmFc(−)-($G_4S$)$_4$-GDF15:DhCpmFc(+) construct.
Figure 4:
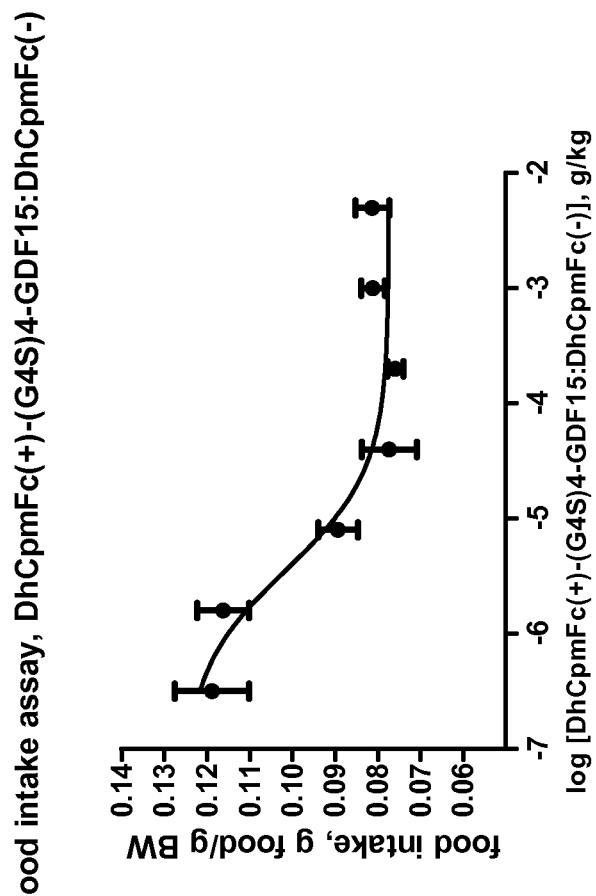
FIG. 4 is a plot showing the effect on food intake of ob/ob mice as a function of dose using a dimer of the DhCpmFc(+)-($G_4S$)$_4$-GDF15:DhCpmFc(−) construct.
Figure 5:
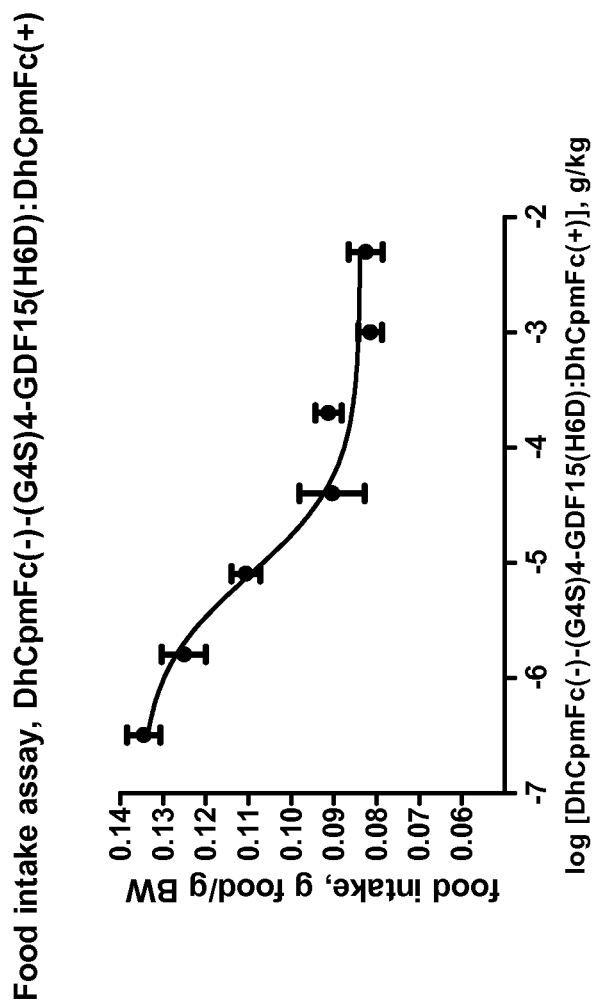
FIG. 5 is a plot showing the effect on food intake of ob/ob mice as a function of dose using a dimer of the DhCpmFc(−)-($G_4S$)$_4$-GDF15:DhCpmFc(+) construct.
Figure 6:
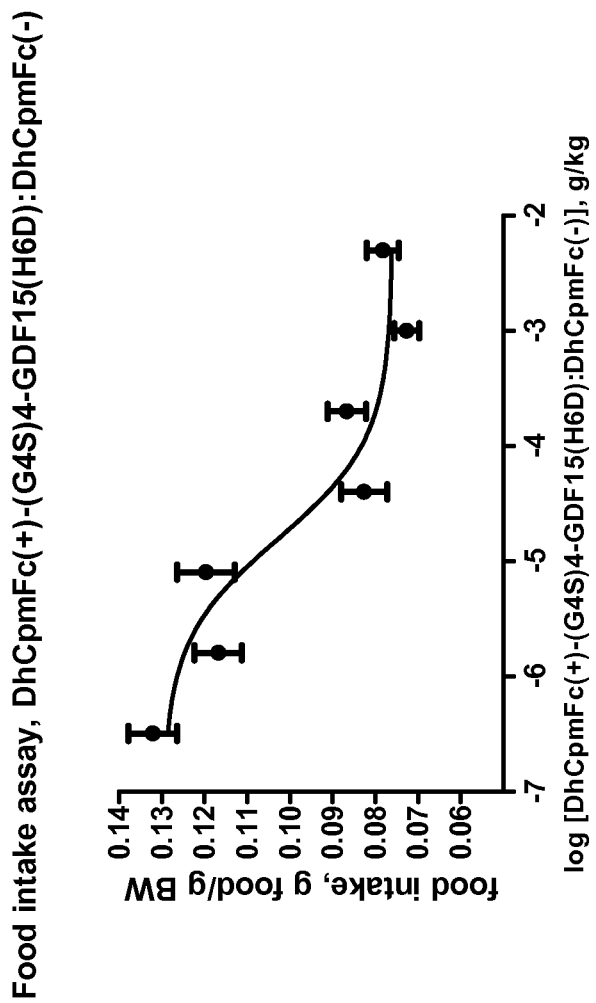
FIG. 6 is a plot showing the effect on food intake of ob/ob mice as a function of dose using a dimer of the DhCpmFc(+)-($G_4S$)$_4$-GDF15(H6D):DhCpmFc(−) construct.
Figure 7:
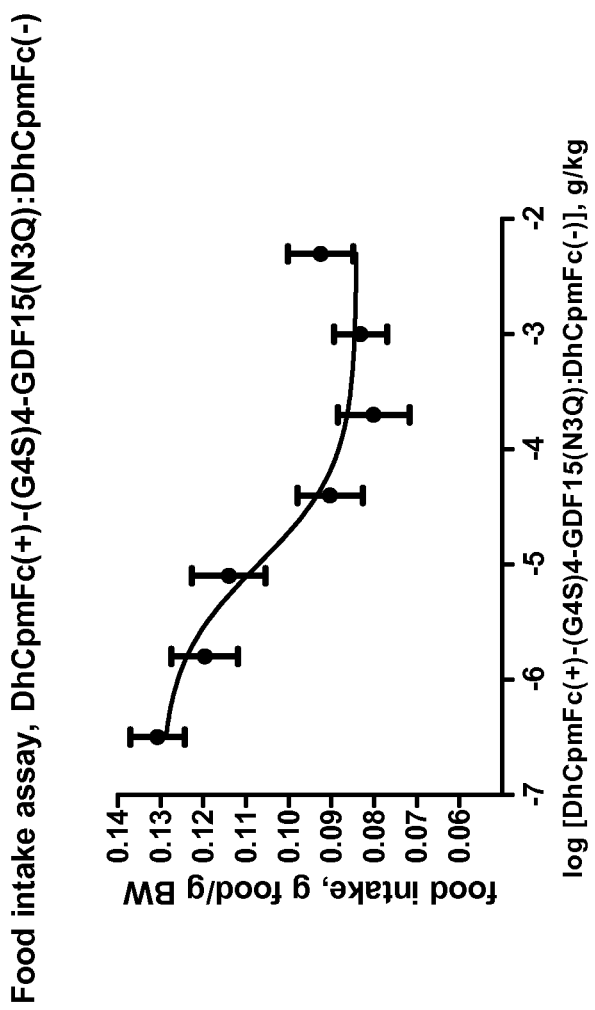
FIG. 7 is a plot showing the effect on food intake of ob/ob mice as a function of dose using a dimer of the DhCpmFc(+)-($G_4S$)$_4$-GDF15(N3Q):DhCpmFc(−) construct.
Figure 8:
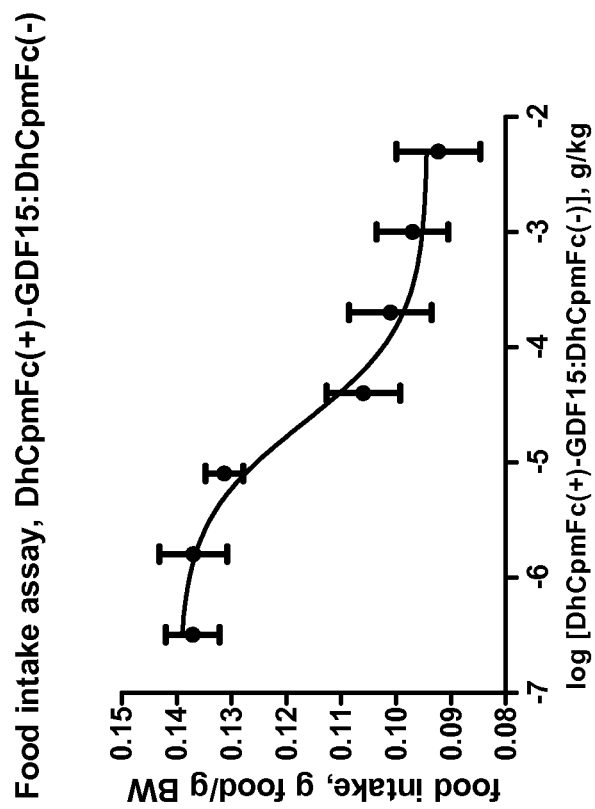
FIG. 8 is a plot showing the effect on food intake of ob/ob mice as a function of dose using a dimer of the DhCpmFc(+)-GDF15:DhCpmFc(−) construct.
Figure 9:
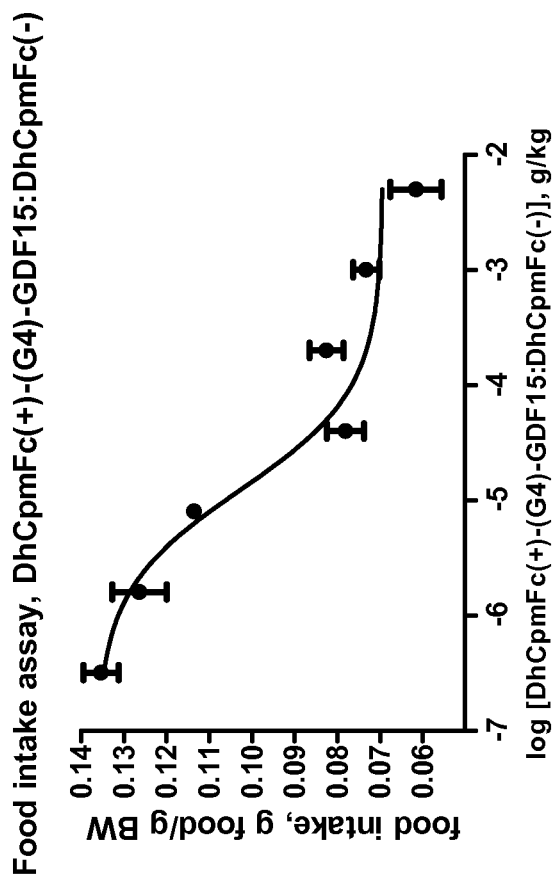
FIG. 9 is a plot showing the effect on food intake of ob/ob mice as a function of dose using a dimer of the DhCpmFc(+)-$G_4$-GDF15:DhCpmFc(−) construct.
Figure 10:
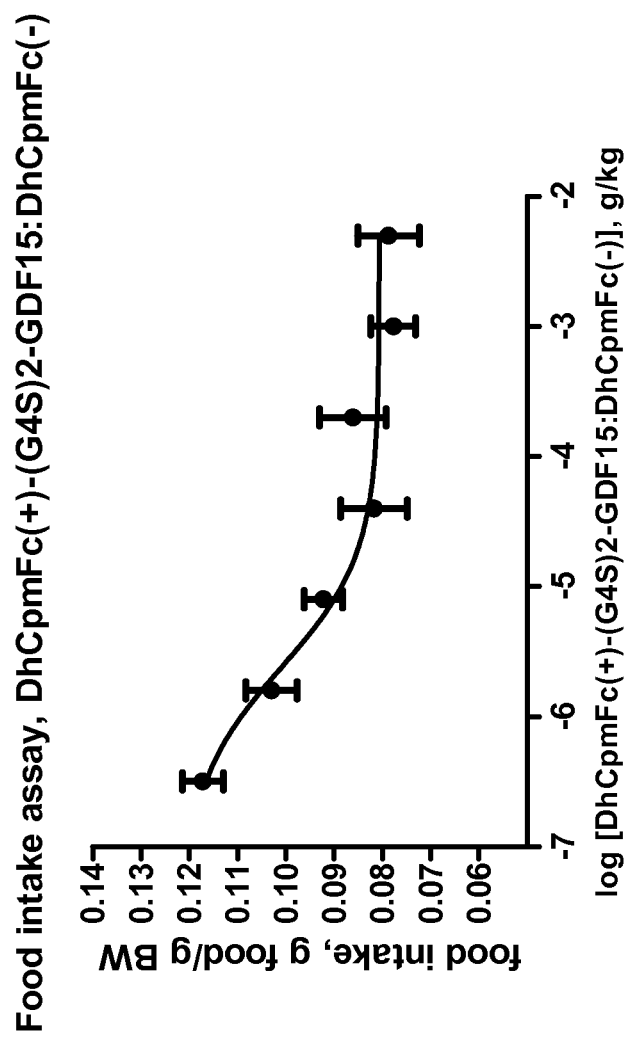
FIG. 10 is a plot showing the effect on food intake of ob/ob mice as a function of dose using a dimer of the DhCpmFc(+)-($G_4S$)$_2$-GDF15:DhCpmFc(−) construct.
Figure 11:
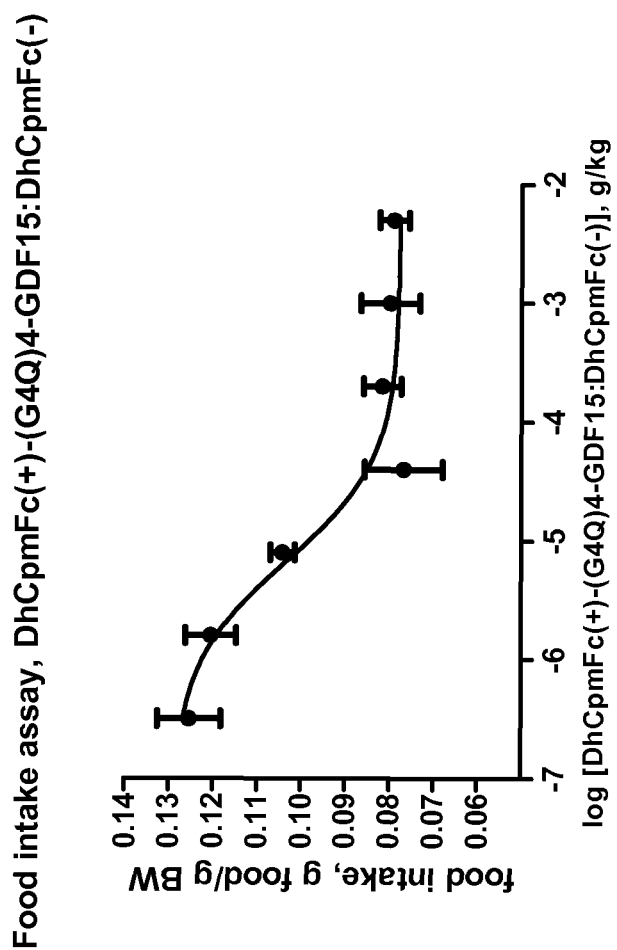
FIG. 11 is a plot showing the effect on food intake of ob/ob mice as a function of dose using a dimer of the DhCpmFc(+)-($G_4Q$)$_4$-GDF15:DhCpmFc(−) construct.
Figure 12:
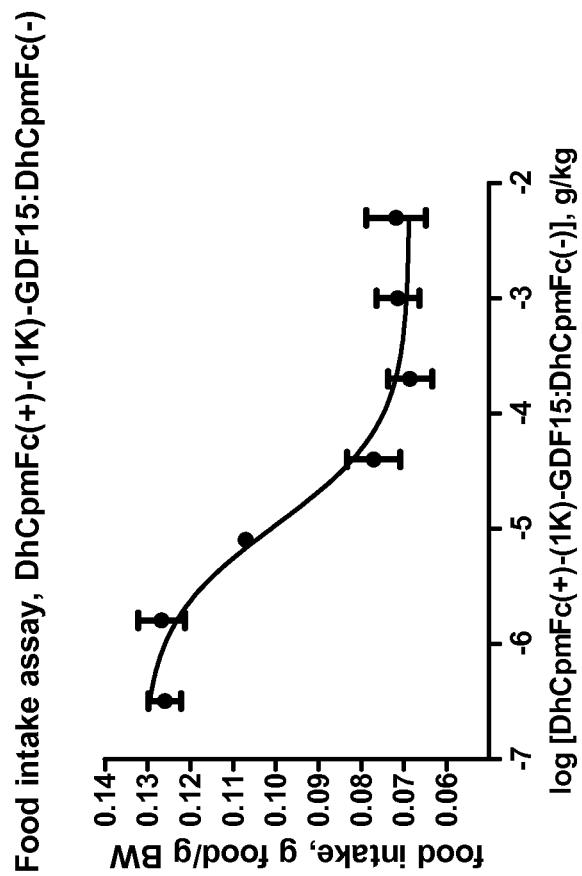
FIG. 12 is a plot showing the effect on food intake of ob/ob mice as a function of dose using a dimer of the DhCpmFc(+)-(1K)-GDF15:DhCpmFc(−) construct.
Figure 13:
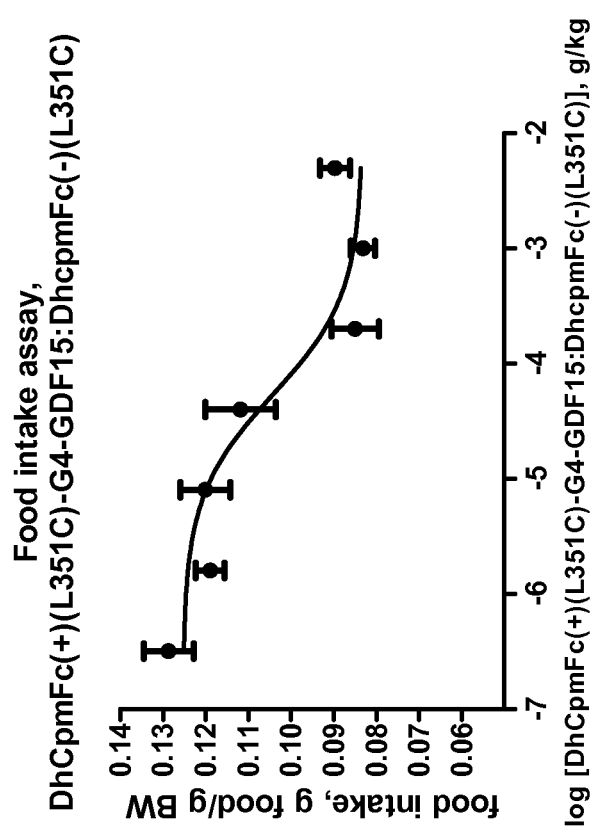
FIG. 13 is a plot showing the effect on food intake of ob/ob mice as a function of dose using a dimer of the DhCpmFc(+)(L351C)-$G_4$-GDF15:DhCpmFc(−)(L351C) construct.
Figure 14:
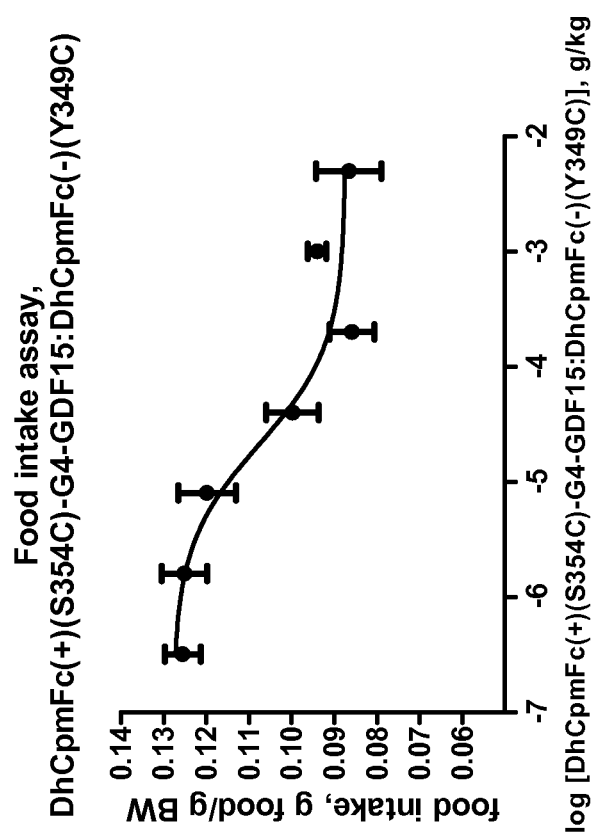
FIG. 14 is a plot showing the effect on food intake of ob/ob mice as a function of dose using a dimer of the DhCpmFc(+)(S354C)-$G_4$-GDF15:DhCpmFc(−)(Y349C) construct.
Figure 15:
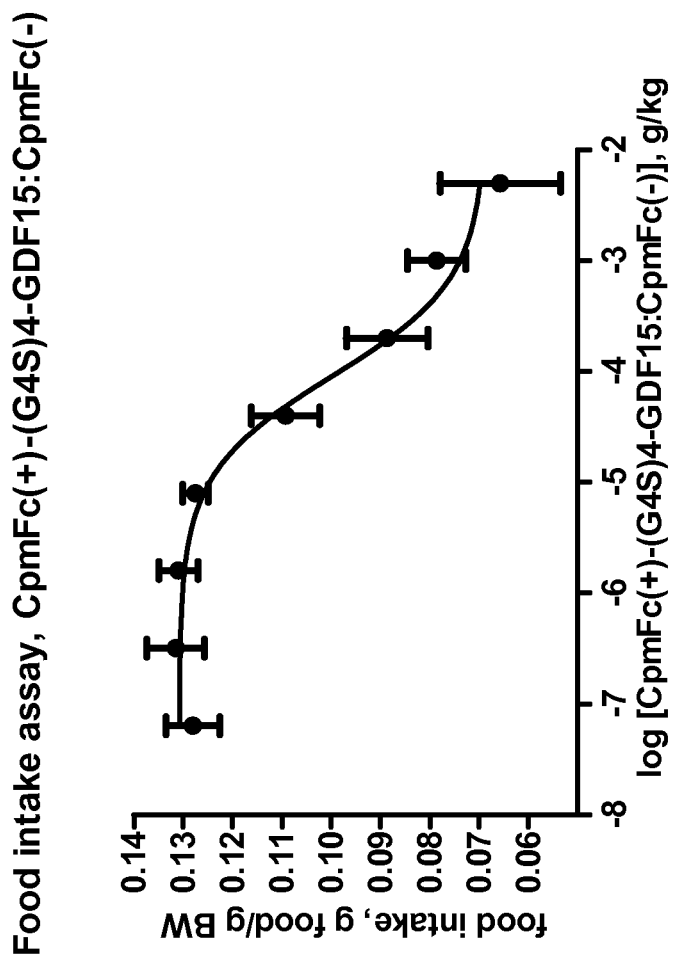
FIG. 15 is a plot showing the effect on food intake of ob/ob mice as a function of dose using a dimer of the CpmFc(+)-($G_4S$)$_4$-GDF15:CpmFc(−) construct.
Figure 16:
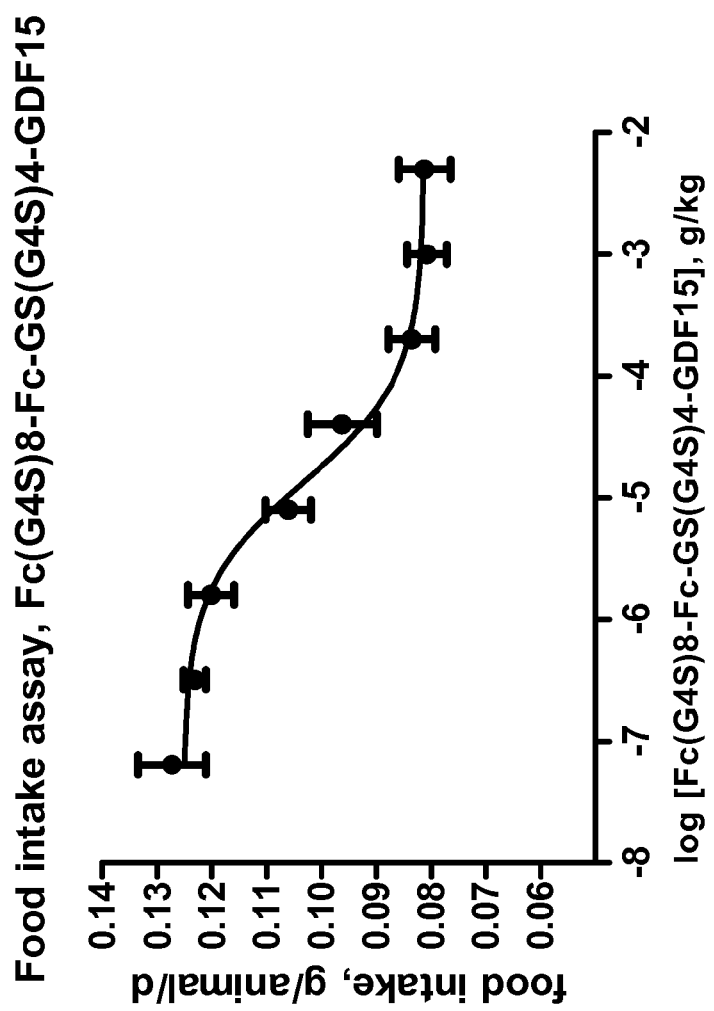
FIG. 16 is a plot showing the effect on food intake of ob/ob mice as a function of dose using a dimer of the Fc-G($G_4S$)-8-Fc-GS($G_4S$)$_4$-GDF15 construct.
Figure 17:
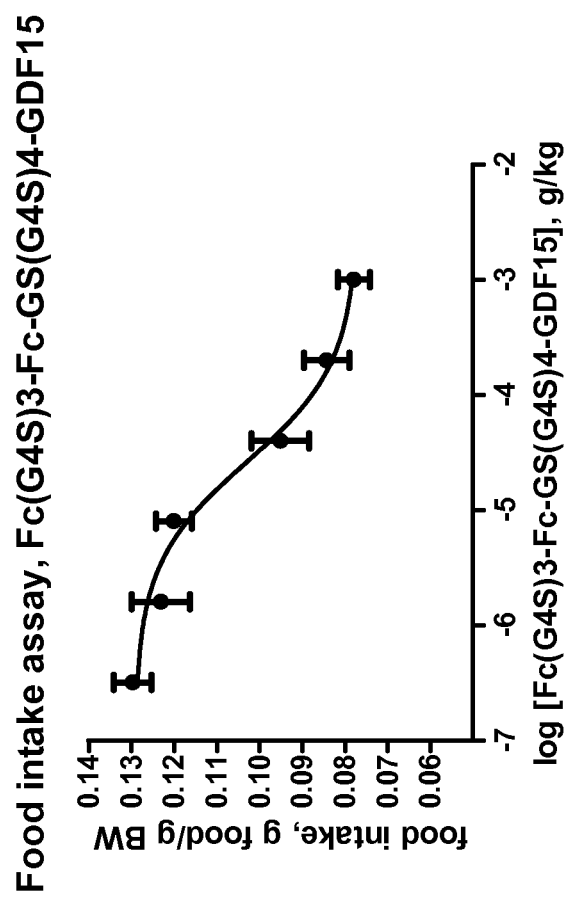
FIG. 17 is a plot showing the effect on food intake of ob/ob mice as a function of dose using a dimer of the Fc-G($G_4S$)$_3$-Fc-GS($G_4S$)$_4$-GDF15 construct.
Figure 18:
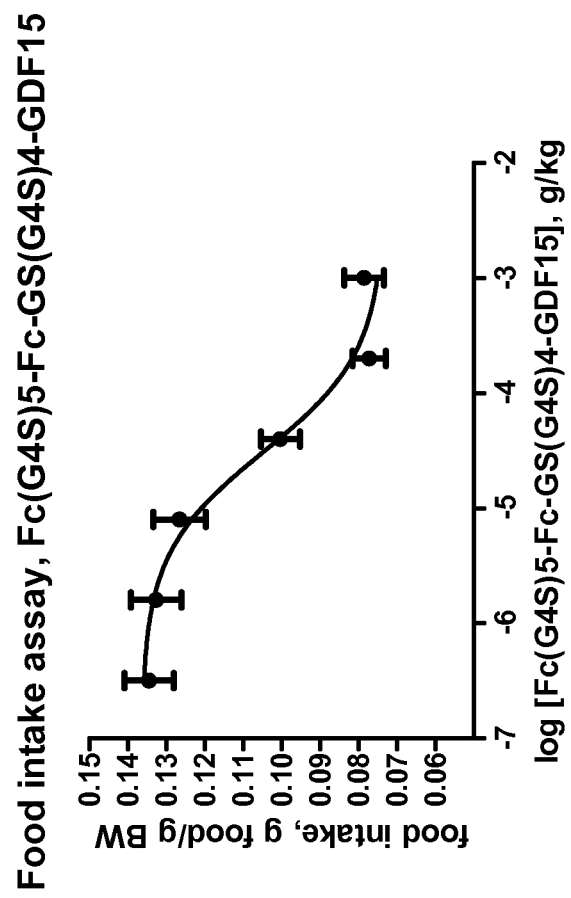
FIG. 18 is a plot showing the effect on food intake of ob/ob mice as a function of dose using a dimer of the Fc-G($G_4S$)$_5$-Fc-GS($G_4S$)$_4$-GDF15 construct.
Figure 19:
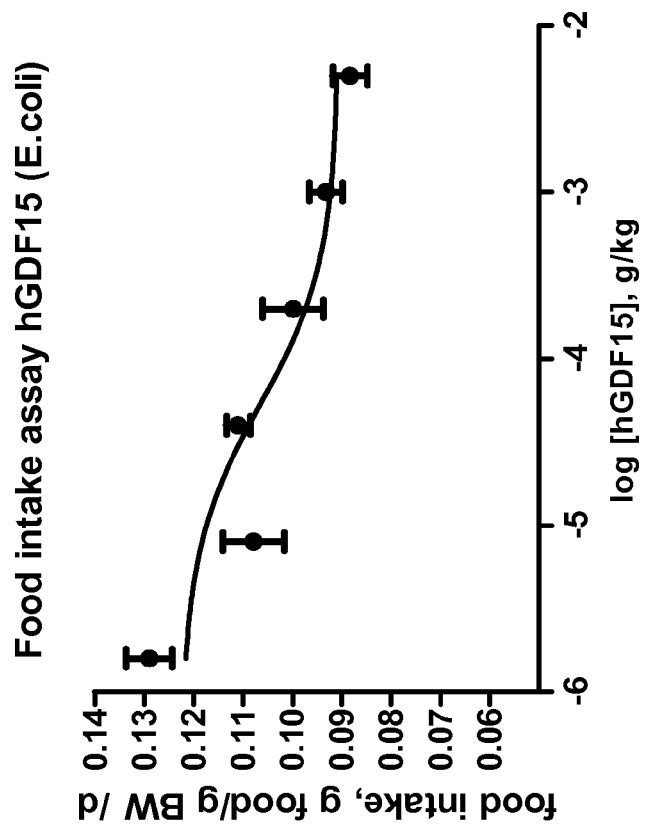
FIG. 19 is a plot showing the effect on food intake of ob/ob mice as a function of dose using native mature GDF15 dimer.
Figure 20:
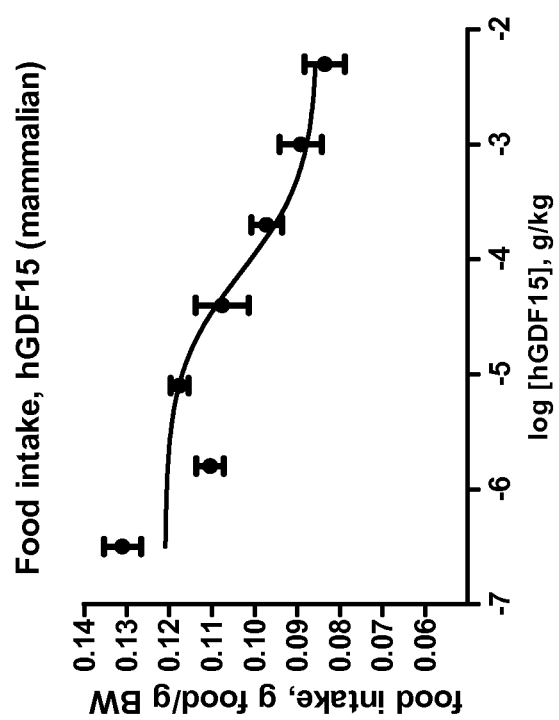
FIG. 20 is a plot showing the effect on food intake of ob/ob mice as a function of dose using native mature hGDF15 dimer.
Figure 21:
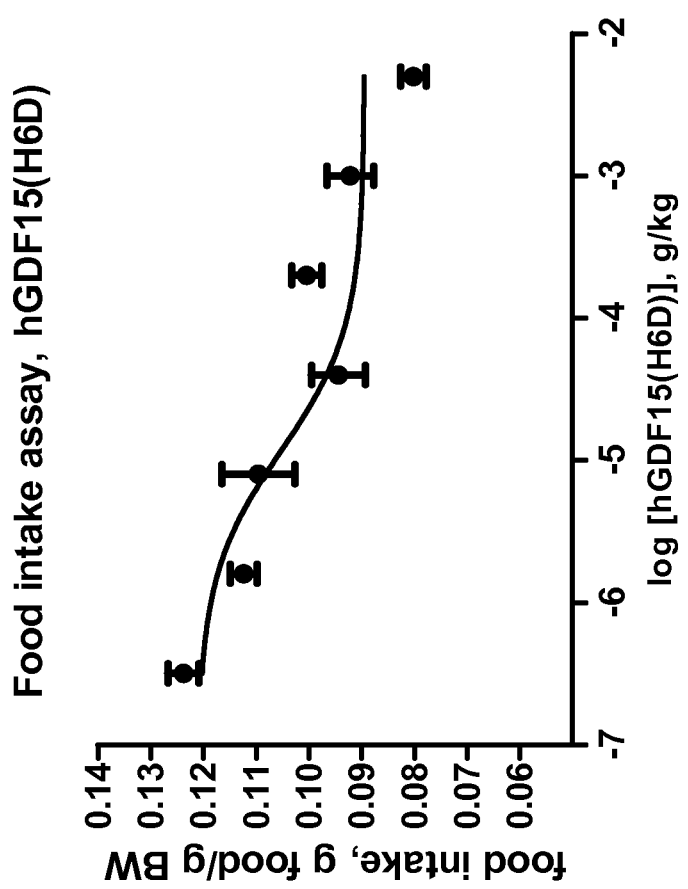
FIG. 21 is a plot showing the effect on food intake of ob/ob mice as a function of dose using mature hGDF15 (H6D) variant dimer

In some embodiments a heterodimer comprises (i) a mature GDF15 sequence linked directly or via a linker to the C-terminus of a DhCpmFc(-) and (ii) a DhCpmFc(+). In other embodiments the heterodimer comprises (i) a mature GDF15 sequence linked directly or via a linker to the C-terminus of a DhCpmFc(+) and (ii) a DhCpmFc(-). In either event, two such heterodimers associate to form tetramer in which the heterodimers are linked via an interchain disulfide bond between the two GDF15 sequences. See FIG. 1 for a graphic depiction of a tetramer comprising two heterodimers linked via an interchain disulfide bond between the two human GDF15 sequences, in which each heterodimer is the charged pair (delHinge) construct designated "DhCpmFc(-)-(G$_4$S)$_4$-GDF15:DhCpmFc(-)" in the instant disclosure (i.e., where each heterodimer comprises (i) a first monomer comprising a mature GDF15 polypeptide linked via a (G$_4$S)$_4$ (SEQ ID NO:20) linker to the C-terminus of a DhCpmFc(-) sequence and (ii) a second monomer comprising a DhCpmFc(+) sequence).

II.B.1 DhCpmFc(-)-(G$_4$S)$_4$-GDF15:DhCpmFc(+)

The charged pair (delHinge) construct designated "DhCpmFc(-)-(G$_4$S)$_4$-GDF15:DhCpmFc(+)" in the instant disclosure refers to a construct comprising a heterodimer, which comprises (i) a first monomer comprising a mature human GDF15 polypeptide linked via a (G$_4$S)$_4$ (SEQ ID NO:20) linker to the C-terminus of a DhCpmFc(-) sequence and (ii) a second monomer comprising a DhCpmFc(+) sequence. The negatively charged DhCpmFc(-)-(G$_4$S)$_4$-hGDF15 chain associates with the negatively charged DhCpmFc(-) chain to form the heterodimer. Two such heterodimers associate to form a tetramer in which the heterodimers are linked via an interchain disulfide bond between the two human GDF15 sequences.

More particularly, in a specific embodiment, the DhCpmFc(-)-(G$_4$S)$_4$-GDF15:DhCpmFc(+) construct comprises:

(a) two chains (one each heterodimer) of an engineered positively charged Fc sequence comprising the sequence:

(SEQ ID NO: 18)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRKEMTKNQVSLTCLVKGFYPSDIAVE

WESNGQPENNYKTTPPVLKSDGSFFLYSKLTVDKSRWQQGNVFSCSVMHE

ALHNHYTQKSLSLSPGK, (b) two chains (one each heterodimer) of an engineered negatively charged Fc sequence comprising the sequence:

(SEQ ID NO: 19)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVE

WESNGQPENNYDTTPPVLDSDGSFFLYSDLTVDKSRWQQGNVFSCSVMHE

ALHNHYTQKSLSLSPG, and (c) two chains (one each heterodimer) of a native mature human GDF15 polypeptide comprising SEQ ID NO:12.

The GDF15 polypeptide is fused via a linker comprising the sequence:

(SEQ ID NO: 20)
GGGGSGGGGSGGGGSGGGGS at the N-terminus of the GDF15 polypeptide via peptide bond to the negatively charged Fc sequence.

In its final form, the first monomer comprising the heterodimer, that with another such heterodimer forms the tetramer, is encoded by the nucleic acid sequence:

(SEQ ID NO: 43)
gcacctgaactcctgggggaccgtcagtcttcctcttccccc caaaacccaaggacaccctcatgatctcccggaccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagcccccatcgagaaaaccatctccaaagccaaagggcagccccgag -continued

```
aaccacaggtgtacaccctgcccccatcccgggaggagatgaccaagaac caggtcagcctgacctgcctggtcaaaggcttctatcccagcgacatcgc cgtggagtgggagagcaatgggcagccggagaacaactacgacaccacgc ctcccgtgctggactccgacggctccttcttcctctatagcgacctcacc gtggacaagagcaggtggcagcaggggaacgtcttctcatgctccgtgat gcatgaggctctgcacaaccactacacgcagaagagcctctccctgtctc cgggtggaggtggtggatccggaggcggtggaagcggaggtggtggatct ggaggcggtggaagcgcgcgcaacggagaccactgtccgctcgggcccgg gcgttgctgccgtctgcacacggtccgcgcgtcgctggaagacctgggct gggccgattgggtgctgtcgccacgggaggtgcaagtgaccatgtgcatc ggcgcgtgcccgagccagttccgggcggcaaacatgcacgcgcagatcaa gacgagcctgcaccgcctgaagcccgacacggtgccagcgccctgctgcg tgcccgccagctacaatcccatggtgctcattcaaaagaccgacaccggg gtgtcgctccagacctatgatgacttgttagccaaagactgccactgcat atga
``` and comprises the amino acid sequence (linker double underlined):

(SEQ ID NO: 44)
APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMTKN

QVSLTCLVKGFYPSDIAVEWESNGQPENNYDTTPPVLDSDGSFFLYSDLT

VDKSRWQQGNVFSCSVMHEALHNHYTQKSLSLSPG<u>GGGGSGGGGSGGGGS</u>

<u>GGGGS</u>ARNGDHCPLGPGRCCRLHTVRASLEDLGWADWVLSPREVQVTMCI

GACPSQFRAANMHAQIKTSLHRLKPDTVPAPCCVPASYNPMVLIQKTDTG

VSLQTYDDLLAKDCHCI.

In an embodiment employing the VH21 signal sequence, in its final form, the first monomer comprising the heterodimer is encoded by the nucleic acid sequence (signal sequence underlined):

(SEQ ID NO: 21)
<u>atggaatggagctgggtctttctcttcttcctgtcagtaacgactggtgt</u>

<u>ccactccg</u>cacctgaactcctgggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagccccatcgagaaaccatctccaaagccaaagggcagccccgag aaccacaggtgtacaccctgcccccatcccgggaggagatgaccaagaac caggtcagcctgacctgcctggtcaaaggcttctatcccagcgacatcgc cgtggagtgggagagcaatgggcagccggagaacaactacgacaccacgc ctcccgtgctggactccgacggctccttcttcctctatagcgacctcacc gtggacaagagcaggtggcagcaggggaacgtcttctcatgctccgtgat gcatgaggctctgcacaaccactacacgcagaagagcctctccctgtctc cgggtggaggtggtggatccggaggcggtggaagcggaggtggtggatct ggaggcggtggaagcgcgcgcaacggagaccactgtccgctcgggcccgg gcgttgctgccgtctgcacacggtccgcgcgtcgctggaagacctgggct gggccgattgggtgctgtcgccacgggaggtgcaagtgaccatgtgcatc ggcgcgtgcccgagccagttccgggcggcaaacatgcacgcgcagatcaa gacgagcctgcaccgcctgaagcccgacacggtgccagcgccctgctgcg tgcccgccagctacaatcccatggtgctcattcaaaagaccgacaccggg gtgtcgctccagacctatgatgacttgttagccaaagactgccactgcat atga
``` and comprises the amino acid sequence (signal sequence single underlined, linker sequence double underlined):

(SEQ ID NO: 22)
<u>MEWSWVFLFFLSVTTGVHS</u>APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMTKN

QVSLTCLVKGFYPSDIAVEWESNGQPENNYDTTPPVLDSDGSFFLYSDLT

VDKSRWQQGNVFSCSVMHEALHNHYTQKSLSLSPG<u>GGGGSGGGGSGGGGS</u>

<u>GGGGS</u>ARNGDHCPLGPGRCCRLHTVRASLEDLGWADWVLSPREVQVTMCI

GACPSQFRAANMHAQIKTSLHRLKPDTVPAPCCVPASYNPMVLIQKTDTG

VSLQTYDDLLAKDCHCI.

The second monomer comprising the heterodimer is encoded by the nucleic acid sequence:

(SEQ ID NO: 46)
```
gcacctgaactcctgggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagccccatcgagaaaccatctccaaagccaaagggcagccccgag aaccacaggtgtacaccctgcccccatcccggaaggagatgaccaagaac caggtcagcctgacctgcctggtcaaaggcttctatcccagcgacatcgc cgtggagtgggagagcaatgggcagccggagaacaactacaagaccacgc ctcccgtgctgaagtccgacggctccttcttcctctatagcaagctcacc gtggacaagagcaggtggcagcaggggaacgtcttctcatgctccgtgat gcatgaggctctgcacaaccactacacgcagaagagcctctccctgtctc cgggtaaatga
``` and comprises the amino acid sequence of SEQ ID NO:18.

In an embodiment employing the VH21 signal sequence, the second monomer comprising the heterodimer is encoded by the nucleic acid sequence (signal sequence underlined):

(SEQ ID NO: 17)
<u>atggaatggagctgggtctttctcttcttcctgtcagtaacgactggtgt</u>
<u>ccactccg</u>cacctgaactcctggggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagccccatcgagaaaaccatctccaaagccaaagggcagccccgag aaccacaggtgtacaccctgcccccatcccggaaggagatgaccaagaac caggtcagcctgacctgcctggtcaaaggcttctatcccagcgacatcgc cgtggagtgggagagcaatgggcagccggagaacaactacaagaccacgc ctcccgtgctgaagtccgacggctccttcttcctctatagcaagctcacc gtggacaagagcaggtggcagcaggggaacgtcttctcatgctccgtgat gcatgaggctctgcacaaccactacacgcagaagagcctctccctgtctc cgggtaaatga and comprises the amino acid sequence (signal sequence underlined):

(SEQ ID NO: 45)
<u>MEWSWVFLFFLSVTTGVHS</u>APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPGK.

The first and second monomers associate to form the heterodimer. Two such heterodimers associate to form the final tetramer. Accordingly, the resulting tetramer (a dimer of the DhCpmFc(−)-(G₄S)₄-GDF15:DhCpmFc(+) construct) comprises two monomers comprising SEQ ID NO:18 and two monomers comprising SEQ ID NO:44.

II.B.2 DhCpmFc (+)-(G₄S)₄-GDF15:DhCpmFc(−)

The charged pair (delHinge) construct designated "DhCpmFc(+)-(G₄S)₄-GDF15:DhCpmFc(−)" in the instant disclosure refers to a construct comprising a heterodimer, which comprises (i) a first monomer comprising a mature human GDF15 polypeptide linked via a (G₄S)₄ (SEQ ID NO:20) linker to the C-terminus of a DhCpmFc(+) sequence and (ii) a second monomer comprising a DhCpmFc(−) sequence. The positively charged DhCpmFc(+)-(G₄S)₄-hGDF15 chain associates with the negatively charged DhCpmFc(−) chain to form the heterodimer. Two such heterodimers associate to form tetramer in which the heterodimers are linked via an interchain disulfide bond between the two human GDF15 sequences.

More particularly, in a specific embodiment, the DhCpmFc(+)-(G₄S)₄-GDF15:DhCpmFc(−) tetramer comprises:

(a) two chains (one each heterodimer) of an engineered positively charged Fc sequence comprising the sequence:

(SEQ ID NO: 85)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRKEMTKNQVSLTCLVKGFYPSDIAVE

WESNGQPENNYKTTPPVLKSDGSFFLYSKLTVDKSRWQQGNVFSCSVMHE

ALHNHYTQKSLSLSPG (b) two chains (one each heterodimer) of an engineered negatively charged Fc sequence comprising the sequence (SEQ ID NO: 86)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVE

WESNGQPENNYDTTPPVLDSDGSFFLYSDLTVDKSRWQQGNVFSCSVMHE

ALHNHYTQKSLSLSPGK, and (c) two chains (one each heterodimer) of a native mature human GDF15 polypeptide comprising SEQ ID NO:12.

The GDF15 polypeptide is fused via a linker comprising SEQ ID NO:20 at the N-terminus of the GDF15 polypeptide via peptide bond to the positively charged Fc sequence.

In its final form, the first monomer comprising the heterodimer, that with another such heterodimer forms the tetramer, is encoded by the nucleic acid sequence:

(SEQ ID NO: 49)
gcacctgaactcctggggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagccccatcgagaaaaccatctccaaagccaaagggcagccccgag aaccacaggtgtacaccctgcccccatcccggaaggagatgaccaagaac caggtcagcctgacctgcctggtcaaaggcttctatcccagcgacatcgc cgtggagtgggagagcaatgggcagccggagaacaactacaagaccacgc ctcccgtgctgaagtccgacggctccttcttcctctatagcaagctcacc gtggacaagagcaggtggcagcaggggaacgtcttctcatgctccgtgat gcatgaggctctgcacaaccactacacgcagaagagcctctccctgtctc cgggtggaggtggtggatccggaggcggtggaagcggaggtggtggatct ggaggcggtggaagcgcgcgcaacggagaccactgtccgctcgggcccgg gcgttgctgccgtctgcacacggtccgcgcgtcgctggaagacctgggct gggccgattgggtgctgtcgccacgggaggtgcaagtgaccatgtgcatc ggcgcgtgcccgagccagttccgggcggcaaacatgcacgcgcagatcaa gacgagcctgcaccgcctgaagcccgacacggtgccagcgccctgctgcg tgcccgccagctacaatcccatggtgctcattcaaaagaccgacaccggg -continued
```
gtgtcgctccagacctatgatgacttgttagccaaagactgccactgcat
atga
``` and comprises the amino acid sequence (linker double underlined):

(SEQ ID NO: 50)
```
APELLGGPSVFLFPPKPKDTLMISRTPEVTC
VVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRKEMTKN
QVSLTCLVKGFYPSDIAVEWESNGQPENNYKTTPPVLKSDGSFFLYSKLT
VDKSRWQQGNVFSCSVMHEALHNHYTQKSLSLSPGGGGSGGGGSGGGGS
GGGGSARNGDHCPLGPGRCCRLHTVRASLEDLGWADWVLSPREVQVTMCI
GACPSQFRAANMHAQIKTSLHRLKPDTVPAPCCVPASYNPMVLIQKTDTG
VSLQTYDDLLAKDCHCI.
```

In an embodiment employing the VH21 signal sequence, in its final form, the first monomer comprising the heterodimer is encoded by the nucleic acid sequence (signal sequence underlined):

(SEQ ID NO: 47)
```
atggaatggagctgggtctttctcttcttcctgtcagtaacgactggtgt
ccactccgcacctgaactcctggggggaccgtcagtcttcctcttccccc
caaaacccaaggacaccctcatgatctcccggacccctgaggtcacatgc
gtggtggtggacgtgagccacgaagaccctgaggtcaagttcaactggta
cgtggacggcgtggaggtgcataatgccaagacaaagccgcgggaggagc
agtacaacagcacgtaccgtgtggtcagcgtcctcaccgtcctgcaccag
gactggctgaatggcaaggagtacaagtgcaaggtctccaacaaagccct
cccagcccccatcgagaaaaccatctccaaagccaaagggcagccccgag
aaccacaggtgtacaccctgcccccatcccgggaggagatgaccaagaac
caggtcagcctgacctgcctggtcaaaggcttctatcccagcgacatcgc
cgtggagtgggagagcaatgggcagccggagaacaactacaagaccacgc
ctcccgtgctgaagtccgacggctccttcttcctctatagcaagctcacc
gtggacaagagcaggtggcagcaggggaacgtcttctcatgctccgtgat
gcatgaggctctgcacaaccactacacgcagaagagcctctccctgtctc
cgggtggaggtggtggatccggaggcggtggaagcggaggtggtggatct
ggaggcggtggaagcgcgcgcaacggagaccactgtccgctcgggcccgg
gcgttgctgccgtctgcacacggtccgcgcgtcgctggaagacctgggct
gggccgattgggtgctgtcgccacgggaggtgcaagtgaccatgtgcatc
ggcgcgtgcccgagccagttccgggcggcaaacatgcacgcgcagatcaa
gacgagcctgcaccgcctgaagcccgacacggtgccagcgccctgctgcg
tgcccgccagctacaatcccatggtgctcattcaaaagaccgacaccggg
gtgtcgctccagacctatgatgacttgttagccaaagactgccactgcat
atga
``` and comprises the amino acid sequence (signal sequence single underlined, linker sequence double underlined):

(SEQ ID NO: 48)
```
MEWSWVFLFFLSVTTGVHSAPELLGGPSVFLFPPKPKDTLMISRTPEVTC
VVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRKEMTKN
QVSLTCLVKGFYPSDIAVEWESNGQPENNYKTTPPVLKSDGSFFLYSKLT
VDKSRWQQGNVFSCSVMHEALHNHYTQKSLSLSPGGGGSGGGGSGGGGS
GGGGSARNGDHCPLGPGRCCRLHTVRASLEDLGWADWVLSPREVQVTMCI
GACPSQFRAANMHAQIKTSLHRLKPDTVPAPCCVPASYNPMVLIQKTDTG
VSLQTYDDLLAKDCHCI.
```

The second monomer comprising the heterodimer is encoded by the nucleic acid sequence:

(SEQ ID NO: 53)
```
gcacctgaactcctggggggaccgtcagtcttcctcttccccc
caaaacccaaggacaccctcatgatctcccggacccctgaggtcacatgc
gtggtggtggacgtgagccacgaagaccctgaggtcaagttcaactggta
cgtggacggcgtggaggtgcataatgccaagacaaagccgcgggaggagc
agtacaacagcacgtaccgtgtggtcagcgtcctcaccgtcctgcaccag
gactggctgaatggcaaggagtacaagtgcaaggtctccaacaaagccct
cccagcccccatcgagaaaaccatctccaaagccaaagggcagccccgag
aaccacaggtgtacaccctgcccccatcccgggaggagatgaccaagaac
caggtcagcctgacctgcctggtcaaaggcttctatcccagcgacatcgc
cgtggagtgggagagcaatgggcagccggagaacaactacgacaccacgc
ctcccgtgctggactccgacggctccttcttcctctatagcgacctcacc
gtggacaagagcaggtggcagcaggggaacgtcttctcatgctccgtgat
gcatgaggctctgcacaaccactacacgcagaagagcctctccctgtctc
cgggtaaatga
``` and comprises the amino acid sequence of SEQ ID NO:86.

In an embodiment employing the VH21 signal sequence, the second monomer comprising the heterodimer is encoded by the nucleic acid sequence (signal sequence underlined):

(SEQ ID NO: 51)
```
atggaatggagctgggtctttctcttcttcctgtcagtaacgactggtgt
ccactccgcacctgaactcctggggggaccgtcagtcttcctcttccccc
caaaacccaaggacaccctcatgatctcccggacccctgaggtcacatgc
gtggtggtggacgtgagccacgaagaccctgaggtcaagttcaactggta
cgtggacggcgtggaggtgcataatgccaagacaaagccgcgggaggagc
agtacaacagcacgtaccgtgtggtcagcgtcctcaccgtcctgcaccag
gactggctgaatggcaaggagtacaagtgcaaggtctccaacaaagccct
cccagcccccatcgagaaaaccatctccaaagccaaagggcagccccgag
aaccacaggtgtacaccctgcccccatcccgggaggagatgaccaagaac
caggtcagcctgacctgcctggtcaaaggcttctatcccagcgacatcgc
cgtggagtgggagagcaatgggcagccggagaacaactacgacaccacgc
```

-continued
```
ctcccgtgctggactccgacggctccttcttcctctatagcgacctcacc gtggacaagagcaggtggcagcaggggaacgtcttctcatgctccgtgat gcatgaggctctgcacaaccactacacgcagaagagcctctccctgtctc cgggtaaatga
``` and comprises the amino acid sequence (signal sequence underlined):

(SEQ ID NO: 52)
MEWSWVFLFFLSVTTGVHSAPELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMTKN

QVSLTCLVKGFYPSDIAVEWESNGQPENNYDTTPPVLDSDGSFFLYSDLT

VDKSRWQQGNVFSCSVMHEALHNHYTQKSLSLSPGK.

The first and second monomers associate to form the heterodimer. Two such heterodimers associate to form the final tetramer. Accordingly, the resulting tetramer (a dimer of the DhCpmFc(+)-(G4S)4-GDF15:DhCpmFc(−) construct) comprises two monomers comprising SEQ ID NO:86 and two monomers comprising SEQ ID NO:50.

II.B.3. DhCpmFc(−)-(G4S)4-GDF15(H6D):DhCpmFc(+)

The charged pair (delHinge) construct designated "DhCpmFc(−)-(G4S)4-GDF15(H6D):DhCpmFc(+)" in the instant disclosure refers to a construct comprising a heterodimer, which comprises (i) a first monomer comprising a mature human GDF15(H6D) polypeptide linked via a (G4S)4 (SEQ ID NO:20) linker to the C-terminus of a DhCpmFc(−) sequence and (ii) a second monomer comprising a DhCpmFc(+) sequence. The negatively charged DhCpmFc(−)-(G4S)4-GDF15(H6D) chain associates with the positively charged DhCpmFc(+) chain. Two such heterodimers associate to form a tetramer in which the heterodimers linked via an interchain disulfide bond between the two human GDF15 (H6D) sequences.

More particularly, in a specific embodiment, the DhCpmFc(−)-(G4S)4-GDF15(H6D):DhCpmFc(+) tetramer comprises:

(a) two chains (one each heterodimer) of an engineered positively charged Fc sequence comprising SEQ ID NO:18, (b) two chains (one each heterodimer) of an engineered negatively charged Fc sequence comprising SEQ ID NO:19, and (c) two chains (one each heterodimer) of a mature human GDF15(H6D) polypeptide comprising SEQ ID NO:38.

The GDF15(H6D) polypeptide is fused via a linker comprising SEQ ID NO:20 at the N-terminus of the GDF15 (H6D) polypeptide via peptide bond to the negatively charged Fc sequence.

In its final form, the first monomer comprising the heterodimer, that with another such heterodimer forms the tetramer, is encoded by the nucleic acid sequence:

(SEQ ID NO: 56)
```
gcacctgaactcctgggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagcccccatcgagaaaaccatctccaaagccaaagggcagccccgag aaccacaggtgtacaccctgcccccatcccgggaggagatgaccaagaac caggtcagcctgacctgcctggtcaaaggcttctatcccagcgacatcgc cgtggagtgggagagcaatgggcagccggagaacaactacgacaccacgc ctcccgtgctggactccgacggctccttcttcctctatagcgacctcacc gtggacaagagcaggtggcagcaggggaacgtcttctcatgctccgtgat gcatgaggctctgcacaaccactacacgcagaagagcctctccctgtctc cgggtggaggtggtggatccgaggcggtggaagcggaggtggtggatct ggaggcggtggaagcgcgcgcaacggagacgactgtccgctcgggcccgg gcgttgctgccgtctgcacacggtccgcgcgtcgctggaagacctgggct gggccgattgggtgctgtcgccacgggaggtgcaagtgaccatgtgcatc ggcgcgtgcccgagccagttccgggcggcaaacatgcacgcgcagatcaa gacgagcctgcaccgcctgaagcccgacacggtgccagcgccctgctgcg tgcccgccagctacaatcccatggtgctcattcaaaagaccgacaccggg gtgtcgctccagacctatgatgacttgttagccaaagactgccactgcat atga
``` and comprises the amino acid sequence (linker double underlined):

(SEQ ID NO: 57)
APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMTKN

QVSLTCLVKGFYPSDIAVEWESNGQPENNYDTTPPVLDSDGSFFLYSDLT

VDKSRWQQGNVFSCSVMHEALHNHYTQKSLSLSPG̲G̲G̲G̲G̲S̲G̲G̲G̲G̲S̲G̲G̲G̲G̲S̲

G̲G̲G̲G̲S̲ARNGDDCPLGPGRCCRLHTVRASLEDLGWADWVLSPREVQVTMCI

GACPSQFRAANMHAQIKTSLHRLKPDTVPAPCCVPASYNPMVLIQKTDTG

VSLQTYDDLLAKDCHCI

In an embodiment employing the VH21 signal sequence, in its final form, the first monomer comprising the heterodimer is encoded by the nucleic acid sequence (signal sequence underlined):

(SEQ ID NO: 54)
a̲t̲g̲g̲a̲a̲t̲g̲g̲a̲g̲c̲t̲g̲g̲g̲t̲c̲t̲t̲t̲c̲t̲c̲t̲t̲c̲t̲t̲c̲c̲t̲g̲t̲c̲a̲g̲t̲a̲a̲c̲g̲a̲c̲t̲g̲g̲t̲g̲t̲ c̲c̲a̲c̲t̲c̲c̲g̲cacctgaactcctgggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct -continued
```
cccagccccatcgagaaaaccatctccaaagccaaagggcagccccgag aaccacaggtgtacaccctgcccccatcccgggaggagatgaccaagaac caggtcagcctgacctgcctggtcaaaggcttctatcccagcgacatcgc cgtggagtgggagagcaatgggcagccggagaacaactacgacaccacgc ctcccgtgctggactccgacggctccttcttcctctatagcgacctcacc gtggacaagagcaggtggcagcaggggaacgtcttctcatgctccgtgat gcatgaggctctgcacaaccactacacgcagaagagcctctccctgtctc cggggtggaggtggtggatccggaggcggtggaagcggaggtggtggatct ggaggcggtggaagcgcgcgcaacggagacgactgtccgctcgggccgg gcgttgctgccgtctgcacacggtccgcgcgtcgctggaagacctgggct gggccgattgggtgctgtcgccacgggaggtgcaagtgaccatgtgcatc ggcgcgtgcccgagccagttccgggcggcaaacatgcacgcgcagatcaa gacgagcctgcaccgcctgaagcccgacacggtgccagcgccctgctgcg tgcccgccagctacaatcccatggtgctcattcaaaagaccgacaccggg gtgtcgctccagacctatgatgacttgttagccaaagactgccactgcat atga
``` and comprises the amino acid sequence (signal sequence underlined, linker double underlined):

```
                                       (SEQ ID NO: 55)
MEWSWVFLFFLSVTTGVHSAPELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMTKN

QVSLTCLVKGFYPSDIAVEWESNGQPENNYDTTPPVLDSGSFFLYSDLT

VDKSRWQQGNVFSCSVMHEALHNHYTQKSLSLSPGGGGSGGGGSGGGGS

GGGGSARNGDDCPLGPGRCCRLHTVRASLEDLGWADWVLSPREVQVTMCI

GACPSQFRAANMHAQIKTSLHRLKPDTVPAPCCVPASYNPMVLIQKTDTG

VSLQTYDDLLAKDCHCI
```

The second monomer comprising the heterodimer is encoded by the nucleic acid sequence of SEQ ID NO:46 and comprises the amino acid sequence of SEQ ID NO:18.

In an embodiment employing the VH21 signal sequence, the second monomer comprising the heterodimer is encoded by the nucleic acid sequence of SEQ ID NO:17 and comprises the amino acid sequence of SEQ ID NO: 45.

The first and second monomers associate to form the heterodimer. Two such heterodimers associate to form the final tetramer. Accordingly, the resulting tetramer (a dimer of the DhCpmFc(-)-(G$_4$S)$_4$-GDF15(H6D):DhCpmFc(+) construct) comprises two monomers comprising SEQ ID NO:18 and two monomers comprising SEQ ID NO:57.

II.B.4. DhCpmFc(+)-(G$_4$S)$_4$-GDF15(H6D):DhCpmFc(-)

The charged pair (delHinge) construct designated "DhCpmFc(+)-(G$_4$S)$_4$-GDF15(H6D):DhCpmFc(-)" in the instant disclosure refers to a construct comprising a heterodimer, which comprises (i) a first monomer comprising a mature human GDF15(H6D) polypeptide linked via a (G$_4$S)$_4$ (SEQ ID NO:20) linker to the C-terminus of a DhCpmFc(+) sequence and (ii) a second monomer comprising a DhCpmFc(-) sequence. The positively charged DhCpmFc(+)-(G$_4$S)$_4$-GDF15(H6D) chain associates with the negatively charged DhCpmFc(-) chain. Two such heterodimers associate to form a tetramer in which the heterodimers are linked via an interchain disulfide bond between the two human GDF15(H6D) sequences.

More particularly, in a specific embodiment, the DhCpmFc(+)-(G$_4$S)$_4$-GDF15(H6D):DhCpmFc(-) tetramer comprises:

(a) two chains (one each heterodimer) of an engineered positively charged Fc sequence comprising SEQ ID NO:85, (b) two chains (one each heterodimer) of an engineered negatively charged Fc sequence comprising SEQ ID NO:86, and (c) two chains (one each heterodimer) of a mature human GDF15(H6D) polypeptide comprising SEQ ID NO:38.

The GDF15(H6D) polypeptide is fused via a linker comprising SEQ ID NO:20 at the N-terminus of the GDF15(H6D) polypeptide via peptide bond to the positively charged Fc sequence.

In its final form, the first monomer comprising the heterodimer, that with another such heterodimer forms the tetramer, is encoded by the nucleic acid sequence:

```
                                       (SEQ ID NO: 60)
gcacctgaactcctgggggggaccgtcagtcttcctcttccccc caaaacccaaggacaccctcatgatctcccgggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagccccatcgagaaaaccatctccaaagccaaagggcagccccgag aaccacaggtgtacaccctgcccccatcccgaaggagatgaccaagaac caggtcagcctgacctgcctggtcaaaggcttctatcccagcgacatcgc cgtggagtgggagagcaatgggcagccggagaacaactacaagaccacgc ctcccgtgctgaagtccgacggctccttcttcctctatagcaagctcacc gtggacaagagcaggtggcagcaggggaacgtcttctcatgctccgtgat gcatgaggctctgcacaaccactacacgcagaagagcctctccctgtctc cgggtggaggtggtggatccggaggcggtggaagcggaggtggtggatct ggaggcggtggaagcgcgcgcaacggagacgactgtccgctcgggccgg gcgttgctgccgtctgcacacggtccgcgcgtcgctggaagacctgggct gggccgattgggtgctgtcgccacgggaggtgcaagtgaccatgtgcatc ggcgcgtgcccgagccagttccgggcggcaaacatgcacgcgcagatcaa gacgagcctgcaccgcctgaagcccgacacggtgccagcgccctgctgcg tgcccgccagctacaatcccatggtgctcattcaaaagaccgacaccggg gtgtcgctccagacctatgatgacttgttagccaaagactgccactgcat atga
``` and comprises the amino acid sequence (linker double underlined):

```
                                       (SEQ ID NO: 61)
APELLGGPSVFLFPPKPKDTLMISRTPEVTC

VVVDVSHEDPEVKFNWYVDGVEVHNAKTKPREEQYNSTYRVVSVLTVLHQ
```

-continued

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPG<u>GGGGSGGGGSGGGGS</u>

<u>GGGGS</u>ARNGDDCPLGPGRCCRLHTVRASLEDLGWADWVLSPREVQVTMCI

GACPSQFRAANMHAQIKTSLHRLKPDTVPAPCCVPASYNPMVLIQKTDTG

VSLQTYDDLLAKDCHCI.

In an embodiment employing the VH21 signal sequence, in its final form, the first monomer comprising the heterodimer is encoded by the nucleic acid sequence (signal sequence underlined):

(SEQ ID NO: 58)
<u>atggaatggagctgggtctttctcttcttcctgtcagtaacgactggtgt</u>

<u>ccactccg</u>cacctgaactcctgggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagcccccatcgagaaaaccatctccaaagccaaagggcagccccgag aaccacaggtgtacaccctgcccccatcccggaaggagatgaccaagaac caggtcagcctgacctgcctggtcaaaggcttctatcccagcgacatcgc cgtggagtgggagagcaatgggcagccggagaacaactacaagaccacg ctcccgtgctgaagtccgacggctccttcttcctctatagcaagctcacc gtggacaagagcaggtggcagcaggggaacgtcttctcatgctccgtgat gcatgaggctctgcacaaccactacacgcagaagagcctctccctgtctc cggggtggaggtggtggatccggaggcggtggaagcggaggtggtggatct ggaggcggtggaagcgcgcgcaacggagacgactgtccgctcgggccgg gcgttgctgccgtctgcacacggtccgcgcgtcgctggaagacctgggct gggccgattgggtgctgtcgccacgggaggtgcaagtgaccatgtgcatc ggcgcgtgcccgagccagttccggcggcaaacatgcacgcgcagatcaa gacgagcctgcaccgcctgaagcccgacacggtgccagcgccctgctgcg tgcccgccagctacaatcccatggtgctcattcaaaagaccgacaccggg gtgtcgctccagacctatgatgacttgttagccaaagactgccactgcat atga and comprises the amino acid sequence (signal sequence single underlined, linker double underlined):

(SEQ ID NO: 59)
<u>MEWSWVFLFFLSVTTGVHS</u>APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

-continued
VDKSRWQQGNVFSCSVMHEALHNHYTQKSLSLSPG<u>GGGGSGGGGSGGGGS</u>

<u>GGGGS</u>ARNGDDCPLGPGRCCRLHTVRASLEDLGWADWVLSPREVQVTMCI

GACPSQFRAANMHAQIKTSLHRLKPDTVPAPCCVPASYNPMVLIQKTDTG

VSLQTYDDLLAKDCHCI.

The second monomer comprising the heterodimer is encoded by the nucleic acid of SEQ ID NO:53 and comprises the amino acid sequence of SEQ ID NO:86.

In an embodiment employing the VH21 signal sequence, the second monomer comprising the heterodimer is encoded by the nucleic acid sequence of SEQ ID NO:51 and comprises the amino acid sequence of SEQ ID NO:52.

The first and second monomers associate to form the heterodimer. Two such heterodimers associate to form the final tetramer. Accordingly, the resulting tetramer (a dimer of the DhCpmFc(+)-(G$_4$S)$_4$-GDF15(H6D):DhCpmFc(−) construct) comprises two monomers comprising SEQ ID NO:86 and two monomers comprising SEQ ID NO:61.

II.B.5. DhCpmFc (+)-(G$_4$S)$_4$-GDF15(N3Q):DhCpmFc(−)

The charged pair (delHinge) construct designated "DhCpmFc(+)-(G$_4$S)$_4$-GDF15(N3Q):DhCpmFc(−)" in the instant disclosure refers to a construct comprising a heterodimer, which comprises (i) a first monomer comprising a mature human GDF15(N3Q) polypeptide linked via a (G$_4$S)$_4$ (SEQ ID NO:20) linker to the C-terminus of a DhCpmFc(+)") sequence and (ii) a second monomer comprising a DhCpmFc(−) sequence. The positively charged DhCpmFc(+)-(G$_4$S)$_4$-GDF15(N3Q) chain then associates with the negatively charged DhCpmFc(−) chain. Two such heterodimers associate to form a tetramer in which the heterodimers are linked via an interchain disulfide bond between the two human GDF15(N3Q) sequences.

More particularly, in a specific embodiment, the DhCpmFc(+)-(G$_4$S)$_4$-GDF15(N3Q):DhCpmFc(−) tetramer comprises:

(a) two chains (one each heterodimer) of an engineered positively charged Fc sequence comprising SEQ ID NO:85

(b) two chains (one each heterodimer) of an engineered negatively charged Fc sequence comprising SEQ ID NO:86, and (c) two chains (one each heterodimer) of a mature human GDF15(N3Q) polypeptide comprising SEQ ID NO:42.

The GDF15(N3Q) polypeptide is fused via a linker comprising SEQ ID NO:20 at the N-terminus of the GDF15(N3Q) polypeptide via peptide bond to the positively charged Fc sequence.

In its final form, the first monomer comprising the heterodimer, that with another such heterodimer forms the tetramer, is encoded by the nucleic acid sequence:

(SEQ ID NO: 64)
gcacctgaactcctgggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagcccccatcgagaaaaccatctccaaagccaaagggcagccccgag -continued
```
aaccacaggtgtacaccctgccccatcccggaaggagatgaccaagaac caggtcagcctgacctgcctggtcaaaggcttctatcccagcgacatcgc cgtggagtgggagagcaatgggcagccggagaacaactacaagaccacgc ctcccgtgctgaagtccgacggctccttcttcctctatagcaagctcacc gtggacaagagcaggtggcagcaggggaacgtcttctcatgctccgtgat gcatgaggctctgcacaaccactacacgcagaagagcctctccctgtctc cgggtggaggtggtggatccggaggcggtggaagcggaggtggtggatct ggaggcggtggaagcgcgcgccagggagaccactgtccgctcgggcccgg gcgttgctgccgtctgcacacggtccgcgcgtcgctggaagacctgggct gggccgattgggtgctgtcgccacgggaggtgcaagtgaccatgtgcatc ggcgcgtgcccgagccagttccgggcggcaaacatgcacgcgcagatcaa gacgagcctgcaccgcctgaagcccgacacggtgccagcgcctgctgcg tgcccgccagctacaatcccatggtgctcattcaaaagaccgacaccggg gtgtcgctccagacctatgatgacttgttagccaaagactgccactgcat atga
``` and comprises the amino acid sequence (linker sequence double underlined):

(SEQ ID NO: 65)
APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPG<u>GGGGSGGGGSGGGGS

GGGGS</u>ARQGDHCPLGPGRCCRLHTVRASLEDLGWADWVLSPREVQVTMCI

GACPSQFRAANMHAQIKTSLHRLKPDTVPAPCCVPASYNPMVLIQKTDTG

VSLQTYDDLLAKDCHCI

In an embodiment employing the VH21 signal sequence, in its final form, the first monomer comprising the heterodimer is encoded by the nucleic acid sequence (signal sequence underlined):

(SEQ ID NO: 62)
<u>atggaatggagctgggtctttctcttcttcctgtcagtaacgactggtgt ccactcc</u>gcacctgaactcctgggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagcccccatcgagaaaaccatctccaaagccaaagggcagcccgag aaccacaggtgtacaccctgccccatcccggaaggagatgaccaagaac caggtcagcctgacctgcctggtcaaaggcttctatcccagcgacatcgc cgtggagtgggagagcaatgggcagccggagaacaactacaagaccacgc -continued
```
ctcccgtgctgaagtccgacggctccttcttcctctatagcaagctcacc gtggacaagagcaggtggcagcaggggaacgtcttctcatgctccgtgat gcatgaggctctgcacaaccactacacgcagaagagcctctccctgtctc cgggtggaggtggtggatccggaggcggtggaagcggaggtggtggatct ggaggcggtggaagcgcgcgccagggagaccactgtccgctcgggcccgg gcgttgctgccgtctgcacacggtccgcgcgtcgctggaagacctgggct gggccgattgggtgctgtcgccacgggaggtgcaagtgaccatgtgcatc ggcgcgtgcccgagccagttccgggcggcaaacatgcacgcgcagatcaa gacgagcctgcaccgcctgaagcccgacacggtgccagcgcctgctgcg tgcccgccagctacaatcccatggtgctcattcaaaagaccgacaccggg gtgtcgctccagacctatgatgacttgttagccaaagactgccactgcat atga
``` and comprises the amino acid sequence (signal sequence single underlined, linker sequence double underlined):

(SEQ ID NO: 63)
<u>MEWSWVFLFFLSVTTGVHS</u>APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPG<u>GGGGSGGGGSGGGGS

GGGGS</u>ARQGDHCPLGPGRCCRLHTVRASLEDLGWADWVLSPREVQVTMCI

GACPSQFRAANMHAQIKTSLHRLKPDTVPAPCCVPASYNPMVLIQKTDTG

VSLQTYDDLLAKDCHCI

The second monomer comprising the heterodimer is encoded by the nucleic acid of SEQ ID NO: 53 and comprises the amino acid sequence of SEQ ID NO:86.

In an embodiment employing the VH21 signal sequence, the second monomer comprising the heterodimer is encoded by the nucleic acid sequence of SEQ ID NO:51 and comprises the amino acid sequence of SEQ ID NO:52.

The first and second monomers associate to form the heterodimer. Two such heterodimers associate to form the final tetramer. Accordingly, the resulting tetramer (a dimer of the DhCpmFc(+)-(G4S)4-GDF15(N3Q):DhCpmFc(−) construct) comprises two monomers comprising SEQ ID NO:86 and two monomers comprising SEQ ID NO:65.

II.B.6. DhCpmFc(+)-GDF15:DhCpmFc(−)

The charged pair (delHinge) construct designated "DhCpmFc(+)-GDF15:DhCpmFc(−)" in the instant disclosure refers to a construct comprising a heterodimer, which comprises (i) a first monomer comprising a one mature human GDF15 polypeptide linked to the C-terminus of a DhCpmFc(+) sequence and (ii) a second monomer comprising a DhCpmFc(−) sequence. The positively charged DhCpmFc(+)-GDF15 chain associates with the negatively charged DhCpmFc(−) chain to form the heterodimer. Two such heterodimers associate to form a tetramer in which the heterodimers are linked via an interchain disulfide bond between the two human GDF15 sequences.

More particularly, in a specific embodiment, the DhCpmFc(+)-GDF15:DhCpmFc(−) tetramer comprises:

(a) two chains (one each heterodimer) of an engineered positively charged Fc sequence comprising SEQ ID NO:85

(b) two chains (one each heterodimer) of an engineered negatively charged Fc sequence comprising SEQ ID NO:86, and (c) two chains (one each heterodimer) of a native mature human GDF15 polypeptide comprising SEQ ID NO:12.

The GDF15 polypeptide is fused at the N-terminus of the GDF15 polypeptide via peptide bond to the positively charged Fc sequence.

In its final form, the first monomer comprising the heterodimer, that with another such heterodimer forms the tetramer, is encoded by the nucleic acid sequence:

(SEQ ID NO: 68)
gccccagagctgcttggtggaccatccgtgttcctgtttcctc caaagccgaaggacaccctgatgatctcaagaactccggaagtgacttgc gtcgtcgtggacgtgtcacatgaggatccagaggtcaagttcaattggta tgtggacggagtggaagtgcataacgccaagaccaaacccgcgaagaac agtacaatagcacctaccgcgtggtgagcgtccttactgtgctccaccag gactggcttaatgggaaggaatacaagtgtaaggtgtccaacaaggccct ccccgctcccatcgaaaagaccatctcaaaggcaaaggggcaaccaaggg aacctcaagtgtacaccctgcctccgagcaggaaggagatgaccaagaac caggtcagcctgacttgtctcgtgaagggcttctatcccagcgatattgc tgtggaatgggagtcaaatggccagcccgagaataactacaaaactaccc cacccgtgctgaaatctgatgggtccttcttcctttactccaagctgacc gtggacaagagccgctggcaacaaggcaatgtctttagctgctcagtgat gcatgaggctctccataatcactacactcagaagtcactgtccctgtcac ctggagcacggaacggggaccattgtccctgggacctggtcggtgctgc cggcttcacaccgtcagagcctctctggaggaccttggatgggctgattg ggtgctgagccctcgggaggtgcaagtcaccatgtgcatcggggcctgcc ctagccagttccgcgcagccaacatgcacgctcagatcaaaacctctctt cacagactgaagcccgacaccgtgccagcaccttgctgtgtgccggcctc ttataaccccatggtcctcattcagaaaaccgacaccggagtgtcacttc agacttacgatgacctcctggccaaggactgccactgtatttga and comprises the amino acid sequence:

(SEQ ID NO: 69)
APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPGARNGDHCPLGPGRCC

RLHTVRASLEDLGWADVVLSPREVQVTMCIGACPSQFRAANMHAQIKTSL

HRLKPDTVPAPCCVPASYNPMVLIQKTDTGVSLQTYDDLLAKDCHCI.

In an embodiment employing the VH21 signal sequence, in its final form, the first monomer comprising the heterodimer is encoded by the nucleic acid sequence (signal sequence underlined):

(SEQ ID NO: 66)
atggagtggtcttgggtctttctgttcttcctctccgtcaccaccggtgt gcattctgccccagagctgcttggtggaccatccgtgttcctgtttcctc caaagccgaaggacaccctgatgatctcaagaactccggaagtgacttgc gtcgtcgtggacgtgtcacatgaggatccagaggtcaagttcaattggta tgtggacggagtggaagtgcataacgccaagaccaaacccgcgaagaac agtacaatagcacctaccgcgtggtgagcgtccttactgtgctccaccag gactggcttaatgggaaggaatacaagtgtaaggtgtccaacaaggccct ccccgctcccatcgaaaagaccatctcaaaggcaaaggggcaaccaaggg aacctcaagtgtacaccctgcctccgagcaggaaggagatgaccaagaac caggtcagcctgacttgtctcgtgaagggcttctatcccagcgatattgc tgtggaatgggagtcaaatggccagcccgagaataactacaaaactaccc cacccgtgctgaaatctgatgggtccttcttcctttactccaagctgacc gtggacaagagccgctggcaacaaggcaatgtctttagctgctcagtgat gcatgaggctctccataatcactacactcagaagtcactgtccctgtcac ctggagcacggaacggggaccattgtccctgggacctggtcggtgctgc cggcttcacaccgtcagagcctctctggaggaccttggatgggctgattg ggtgctgagccctcgggaggtgcaagtcaccatgtgcatcggggcctgcc ctagccagttccgcgcagccaacatgcacgctcagatcaaaacctctctt cacagactgaagcccgacaccgtgccagcaccttgctgtgtgccggcctc ttataaccccatggtcctcattcagaaaaccgacaccggagtgtcacttc agacttacgatgacctcctggccaaggactgccactgtatttga and comprises the amino acid sequence (signal sequence underlined,):

(SEQ ID NO: 67)
<u>MEWSWVFLFFLSVTTGVHS</u>APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPGARNGDHCPLGPGRCC

RLHTVRASLEDLGWADVVLSPREVQVTMCIGACPSQFRAANMHAQIKTSL

HRLKPDTVPAPCCVPASYNPMVLIQKTDTGVSLQTYDDLLAKDCHCI.

The second monomer comprising the heterodimer is encoded by the nucleic acid of SEQ ID NO:53 and comprises the amino acid sequence of SEQ ID NO:86.

In an embodiment employing the VH21 signal sequence, the second monomer comprising the heterodimer is encoded by the nucleic acid sequence of SEQ ID NO:51 and comprises the amino acid sequence of SEQ ID NO:52. The first and second monomers associate to form the heterodimer. Two such heterodimers associate to form the final tetramer. Accordingly, the resulting tetramer (a dimer of the DhCpmFc(+)-GDF15:DhCpmFc(−) construct) comprises two monomers comprising SEQ ID NO:19 and two monomers comprising SEQ ID NO:69.

II.B.7. DhCpmFc(+)-G₄-GDF15:DhCpmFc(−)

The charged pair (delHinge) construct designated "DhCpmFc(+)-G₄-GDF15:DhCpmFc(−)" in the instant disclosure refers to a construct comprising a heterodimer, which comprises (i) a first monomer comprising a mature human GDF15 polypeptide linked via $G_4$ (SEQ ID NO:70) linker to the C-terminus of a DhCpmFc(+) sequence and (ii) a second monomer comprising aDhCpmFc(−) sequence. The positively charged DhCpmFc(+)-$G_4$-GDF15 chain associates with the negatively charged DhCpmFc(−) chain. Two such heterodimers associate to form a tetramer in which the heterodimers linked via an interchain disulfide bond between the two human GDF15 sequences.

More particularly, in a specific embodiment, the DhCpmFc(+)-$G_4$-GDF15:DhCpmFc(−) tetramer comprises:

(a) two chains (one each heterodimer) of an engineered positively charged Fc sequence comprising SEQ ID NO:85, (b) two chains (one each heterodimer) of an engineered negatively charged Fc sequence comprising SEQ ID NO:86, and (c) two chains (one each heterodimer) of a native mature human GDF15 polypeptide comprising SEQ ID NO:12.

The GDF15 polypeptide is fused via a linker comprising the sequence (SEQ ID NO: 70)
GGGG at the N-terminus of the GDF15 polypeptide via peptide bond to the positively charged Fc sequence.

In its final form, the first monomer comprising the heterodimer, that with another such heterodimer forms the tetramer, is encoded by the nucleic acid sequence:

(SEQ ID NO: 73)
gcccagagctgcttggtggaccatccgtgttcctgtttcctc caaagccgaaggacaccctgatgatctcaagaactccggaagtgacttgc gtcgtcgtggacgtgtcacatgaggatccagaggtcaagttcaattggta tgtggacggagtggaagtgcataacgccaagaccaaaccccgcgaagaac agtacaatagcacctaccgcgtggtgagcgtccttactgtgctccaccag gactggcttaatgggaaggaatacaagtgtaaggtgtccaacaaggccct ccccgctcccatcgaaaagaccatctcaaaggcaaaggggcaaccaaggg aacctcaagtgtacaccctgcctccgagcaggaaggagatgaccaagaac caggtcagcctgacttgtctcgtgaagggcttctatcccagcgatattgc tgtggaatgggagtcaaatggccagcccgagaataactacaaaactaccc cacccgtgctgaaatctgatgggtccttcttcctttactccaagctgacc gtggacaagagccgctggcaacaaggcaatgtctttagctgctcagtgat gcatgaggctctccataatcactacactcagaagtcactgtccctgtcac ctggcggaggtggaggagcacggaacggggaccattgtcccctgggacct ggtcggtgctgccggcttcacaccgtcagagcctctctggaggaccttgg atgggctgattgggtgctgagccctcgggaggtgcaagtcaccatgtgca tcggggcctgccctagccagttccgcgcagccaacatgcacgctcagatc aaaacctctcttcacagactgaagcccgacaccgtgccagcaccttgctg tgtgccggcctcttataacccatggtcctcattcagaaaaccgacaccg gagtgtcacttcagacttacgatgacctcctggccaaggactgccactgt atttga and comprises the amino acid sequence (linker sequence double underlined):

(SEQ ID NO: 74)
APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPG<u>GGGG</u>ARNGDHCPLGP

GRCCRLHTVRASLEDLGWADWVLSPREVQVTMCIGACPSQFRAANMHAQI

KTSLHRLKPDTVPAPCCVPASYNPMVLIQKTDTGVSLQTYDDLLAKDCHC

I.

In an embodiment employing the VH21 signal sequence, in its final form, the first monomer comprising the heterodimer is encoded by the nucleic acid sequence (cleaved signal sequence underlined):

(SEQ ID NO: 71)
<u>atggagtggtcttgggtctttctgttcttcctctccgtcaccaccggtgt</u>

<u>gcattct</u>gccccagagctgcttggtggaccatccgtgttcctgtttcctc caaagccgaaggacaccctgatgatctcaagaactccggaagtgacttgc gtcgtcgtggacgtgtcacatgaggatccagaggtcaagttcaattggta tgtggacggagtggaagtgcataacgccaagaccaaaccccgcgaagaac agtacaatagcacctaccgcgtggtgagcgtccttactgtgctccaccag gactggcttaatgggaaggaatacaagtgtaaggtgtccaacaaggccct ccccgctcccatcgaaaagaccatctcaaaggcaaaggggcaaccaaggg aacctcaagtgtacaccctgcctccgagcaggaaggagatgaccaagaac caggtcagcctgacttgtctcgtgaagggcttctatcccagcgatattgc tgtggaatgggagtcaaatggccagcccgagaataactacaaaactaccc cacccgtgctgaaatctgatgggtccttcttcctttactccaagctgacc gtggacaagagccgctggcaacaaggcaatgtctttagctgctcagtgat gcatgaggctctccataatcactacactcagaagtcactgtccctgtcac ctggcggaggtggaggagcacggaacggggaccattgtcccctgggacct ggtcggtgctgccggcttcacaccgtcagagcctctctggaggaccttgg atgggctgattgggtgctgagccctcgggaggtgcaagtcaccatgtgca tcggggcctgccctagccagttccgcgcagccaacatgcacgctcagatc aaaacctctcttcacagactgaagcccgacaccgtgccagcaccttgctg tgtgccggcctcttataacccatggtcctcattcagaaaaccgacaccg gagtgtcacttcagacttacgatgacctcctggccaaggactgccactgt atttga and comprises the amino acid sequence (signal sequence single underlined, linker sequence double underlined):

(SEQ ID NO: 72)
MEWSWVFLFFLSVTTGVHSAPELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPG<u>GGGG</u>ARNGDHCPLGP

GRCCRLHTVRASLEDLGWADWVLSPREVQVTMCIGACPSQFRAANMHAQI

KTSLHRLKPDTVPAPCCVPASYNPMVLIQKTDTGVSLQTYDDLLAKDCHC

I.

The second monomer comprising the heterodimer is encoded by the nucleic acid of SEQ ID NO:53 and comprises the amino acid sequence of SEQ ID NO:86.

In an embodiment employing the VH21 signal sequence, the second monomer comprising the heterodimer is encoded by the nucleic acid sequence of SEQ ID NO:51 and comprises the amino acid sequence of SEQ ID NO:52.

The first and second monomers associate to form the heterodimer. Two such heterodimers associate to form the final tetramer. Accordingly, the resulting tetramer (a dimer of the DhCpmFc(+)-G$_4$-GDF15:DhCpmFc(−) construct) comprises two monomers comprising SEQ ID NO:86 and two monomers comprising SEQ ID NO:74.

II.B.8. DhCpmFc (+)-(G$_4$S)$_2$-GDF15:DhCpmFc(−)

The charged pair (delHinge) construct designated "DhCpmFc(+)-(G$_4$S)$_2$-GDF15:DhCpmFc(−)" in the instant disclosure refers to a construct comprising heterodimer, which comprises (i) a first monomer comprising a mature human GDF15 polypeptide linked via a (G$_4$S)$_2$ (SEQ ID NO:75) linker to the C-terminus of a DhCpmFc(+) sequence and (ii) a second monomer comprising aDhCpmFc(−) sequence. The positively charged DhCpmFc(+)-(G$_4$S)$_2$-GDF15 chain associates with the negatively charged DhCpmFc(−) chain. Two such heterodimers associate to form a tetramer in which the heterodimers are linked via an interchain disulfide bond between the two human GDF15 sequences.

More particularly, in a specific embodiment, the DhCpmFc(+)-(G$_4$S)$_2$-GDF15:DhCpmFc(−) tetramer comprises:

(a) two chains (one each heterodimer) of an engineered positively charged Fc sequence comprising SEQ ID NO:85, (b) two chains (one each heterodimer) of an engineered negatively charged Fc sequence comprising SEQ ID NO:86 and (c) two chains (one each heterodimer) of a native mature human GDF15 polypeptide comprising SEQ ID NO:12.

The GDF15 polypeptide is fused via a linker comprising the sequence (SEQ ID NO: 75)
GGGGSGGGGS at the N-terminus of the GDF15 polypeptide via peptide bond to the positively charged Fc.

In its final form, the first monomer comprising the heterodimer, that with another such heterodimer forms the tetramer, is encoded by the nucleic acid sequence:

(SEQ ID NO: 78)
gcgccggaactgctgggcggcccgagcgtgtttctgtttccgc cgaaaccgaaagataccctgatgattagccgcaccccggaagtgacctgc gtggtggtggatgtgagccatgaagatccggaagtgaaatttaactggta tgtggatggcgtggaagtgcataacgcgaaaaccaaaccgcgcgaagaac agtataacagcacctatcgcgtggtgagcgtgctgaccgtgctgcatcag gattggctgaacggcaaagaatataaatgcaaagtgagcaacaaagcgct gccggcgccgattgaaaaaaccattagcaaagcgaaaggccagccgcgcg aaccgcaggtgtataccctgccgccgagccgcaaagaaatgaccaaaaac caggtgagcctgacctgcctggtgaaaggcttttatccgagcgatattgc ggtggaatgggaaagcaacggccagccggaaaacaactataaaaccaccc cgccggtgctgaaaagcgatggcagcttttttctgtatagcaaactgacc gtggataaaagccgctggcagcagggcaacgtgtttagctgcagcgtgat gcatgaagcgctgcataaccattatacccagaaaagcctgagcctgagcc cgggcggcggcggcggcagcggcggcggcggcagcgcgcgcaacggcgat cattgcccgctgggcccgggccgctgctgccgcctgcataccgtgcgcgc gagcctggaagatctgggctgggcggattgggtgctgagcccgcgcgaag tgcaggtgaccatgtgcattggcgcgtgcccgagccagtttcgcgcggcg aacatgcatgcgcagattaaaaccagcctgcatcgcctgaaaccggatac cgtgccggcgccgtgctgcgtgccggcgagctataacccgatggtgctga ttcagaaaaccgataccggcgtgagcctgcagacctatgatgatctgctg gcgaaagattgccattgcatttga and comprises the amino acid sequence (linker sequence double underlined):

(SEQ ID NO: 79)
APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPG<u><u>GGGGSGGGGS</u></u>ARNGD

HCPLGPGRCCRLHTVRASLEDLGWADWVLSPREVQVTMCIGACPSQFRAA

NMHAQIKTSLHRLKPDTVPAPCCVPASYNPMVLIQKTDTGVSLQTYDDLL

AKDCHCI.

In an embodiment employing the VH21 signal sequence, in its final form, the first monomer comprising the heterodimer is encoded by the nucleic acid sequence (signal sequence underlined):

(SEQ ID NO: 76)
<u>atggaatggagctgggtctttctcttcttcctgtcagtaacgactggtgt</u>

<u>ccactccg</u>cgccggaactgctgggcggcccgagcgtgtttctgtttccgc cgaaaccgaaagataccctgatgattagccgcaccccggaagtgacctgc gtggtggtggatgtgagccatgaagatccggaagtgaaatttaactggta tgtggatggcgtggaagtgcataacgcgaaaaccaaaccgcgcgaagaac agtataacagcacctatcgcgtggtgagcgtgctgaccgtgctgcatcag -continued
```
gattggctgaacggcaaagaatataaatgcaaagtgagcaacaaagcgct gccggcgccgattgaaaaaaccattagcaaagcgaaaggccagccgcgcg aaccgcaggtgtataccctgccgccgagccgcaaagaaatgaccaaaaac caggtgagcctgacctgcctggtgaaaggcttttatccgagcgatattgc ggtggaatgggaaagcaacggccagccggaaaacaactataaaaccaccc cgccggtgctgaaaagcgatggcagcttttttctgtatagcaaactgacc gtggataaaagccgctggcagcagggcaacgtgtttagctgcagcgtgat gcatgaagcgctgcataaccattatacccagaaaagcctgagcctgagcc cgggcggcggcggcggcagcggcggcggcggcagcgcgcgcaacggcgat cattgcccgctgggcccggccgctgctgccgcctgcataccgtgcgcgc gagcctggaagatctgggctgggcggattgggtgctgagcccgcgcgaag tgcaggtgaccatgtgcattggcgcgtgcccgagccagtttcgcgcggcg aacatgcatgcgcagattaaaaccagcctgcatcgcctgaaaccggatac cgtgccggcgccgtgctgcgtgccggcgagctataacccgatggtgctga ttcagaaaaccgataccggcgtgagcctgcagacctatgatgatctgctg gcgaaagattgccattgcatttga
``` and comprises the amino acid sequence (signal sequence single underlined, linker sequence double underlined):

(SEQ ID NO: 77)
<u>MEWSWVFLFFLSVTTGVHS</u>APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPG<u>GGGGSGGGGS</u>ARNGD

HCPLGPGRCCRLHTVRASLEDLGWADWVLSPREVQVTMCIGACPSQFRAA

NMHAQIKTSLHRLKPDTVPAPCCVPASYNPMVLIQKTDTGVSLQTYDDLL

AKDCHCI.

The second monomer comprising the heterodimer is encoded by the nucleic acid of SEQ ID NO:53 and comprises the amino acid sequence of SEQ ID NO:86.

In an embodiment employing the VH21 signal sequence, the second monomer comprising the heterodimer is encoded by the nucleic acid sequence of SEQ ID NO:51 and comprises the amino acid sequence of SEQ ID NO:52.

The first and second monomers associate to form the heterodimer. Two such heterodimers associate to form the final tetramer. Accordingly, the resulting tetramer (a dimer of the DhCpmFc(+)-(G$_4$S)$_2$-GDF15:DhCpmFc(−) construct) comprises two monomers comprising SEQ ID NO:86 and two monomers comprising SEQ ID NO:79.

II.B.9. DhCpmFc(+)-(G$_4$Q)$_2$-GDF15:DhCpmFc(−)

The charged pair (delHinge) construct designated "DhCpmFc(+)-(G$_4$Q)$_4$-GDF15:DhCpmFc(−)" in the instant disclosure refers to a construct comprising a heterodimer, which comprises (i) a first monomer comprising a mature human GDF15 polypeptide linked via a (G$_4$Q)$_4$ (SEQ ID NO:80) linker to the C-terminus of a DhCpmFc(+) sequence and (ii) a second monomer comprising a DhCpmFc(−) sequence. The positively charged DhCpmFc(+)-(G$_4$Q)$_4$-GDF15 chain associates with the negatively charged DhCpmFc(−) chain. Two such heterodimers associate to form a tetramer in which the heterodimers are linked via an interchain disulfide bond between the two human GDF15 sequences.

More particularly, in a specific embodiment, the DhCpmFc(+)-(G$_4$Q)$_4$-GDF15:DhCpmFc(−) tetramer comprises:

(a) two chains (one each heterodimer) of an engineered positively charged Fc sequence comprising SEQ ID NO:85, (b) two chains (one each heterodimer) of an engineered negatively charged Fc sequence comprising SEQ ID NO:86, and (c) two chains (one each heterodimer) of a native mature human GDF15 polypeptide comprising SEQ ID NO:12.

The GDF15 polypeptide is fused via a linker comprising the sequence (SEQ ID NO: 80)
GGGGQGGGGQGGGGQGGGGQ at the N-terminus of the GDF15 polypeptide via peptide bond to the positively charged Fc.

In its final form, the first monomer comprising the heterodimer, that with another such heterodimer forms the tetramer is encoded by the nucleic acid sequence:

(SEQ ID NO: 83)
```
gccccagagctgcttggtggaccatccgtgttcctgtttcctc caaagccgaaggacaccctgatgatctcaagaactccggaagtgacttgc gtcgtcgtggacgtgtcacatgaggatccagaggtcaagttcaattggta tgtggacggagtggaagtgcataacgccaagaccaaacccgcgaagaac agtacaatagcacctaccgcgtggtgagcgtccttactgtgctccaccag gactggcttaatgggaaggaatacaagtgtaaggtgtccaacaaggccct ccccgctcccatcgaaaagaccatctcaaaggcaaaggggcaaccaaggg aacctcaagtgtacaccctgcctccgagcaggaaggagatgaccaagaac caggtcagcctgacttgtctcgtgaagggcttctatcccagcgatattgc tgtggaatgggagtcaaatggccagcccgagaataactacaaaactaccc cacccgtgctgaaatctgatgggtccttcttcctttactccaagctgacc gtggacaagagccgctggcaacaaggcaatgtctttagctgctcagtgat gcatgaggctctccataatcactacactcagaagtcactgtccctgtcac ctggaggtggcggagggcagggtggtggaggtcagggaggcggaggacag ggaggaggtggacaagcacggaacggggaccattgtccctgggacctgg tcggtgctgccggcttcacaccgtcagagcctctctggaggaccttggat gggctgattgggtgctgagccctcgggaggtgcaagtcaccatgtgcatc ggggcctgccctagccagttccgcgcagccaacatgcacgctcagatcaa aacctctcttcacagactgaagcccgacaccgtgccagcaccttgctgtg tgccggcctcttataacccatggtcctcattcagaaaaccgacaccgga gtgtcacttcagacttacgatgacctcctggccaaggactgccactgtat ttga
``` and comprises the amino acid sequence (linker sequence double underlined):

(SEQ ID NO: 84)
APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPG<u>GGGGQGGGGQGGGGQ</u>

<u>GGGGQ</u>ARNGDHCPLGPGRCCRLHTVRASLEDLGWADWVLSPREVQVTMCI

GACPSQFRAANMHAQIKTSLHRLKPDTVPAPCCVPASYNPMVLIQKTDTG

VSLQTYDDLLAKDCHCI.

In an embodiment employing the VH21 signal sequence, in its final form, the first monomer comprising the heterodimer is encoded by the nucleic acid sequence (signal sequence underlined):

(SEQ ID NO: 81)
<u>atggagtggtcttgggtctttctgttcttcctctccgtcaccaccgtgt</u>

<u>gcattct</u>gcccagagctgcttggtggaccatccgtgttcctgtttcctc caaagccgaaggacaccctgatgatctcaagaactccggaagtgacttgc gtcgtcgtggacgtgtcacatgaggatccagaggtcaagttcaattggta tgtggacggagtggaagtgcataacgccaagaccaaacccgcgaagaac agtacaatagcacctaccgcgtggtgagcgtccttactgtgctccaccag gactggcttaatgggaaggaatacaagtgtaaggtgtccaacaaggccct ccccgctcccatcgaaaagaccatctcaaaggcaaaggggcaaccaaggg aacctcaagtgtacaccctgcctccgagcaggaaggagatgaccaagaac caggtcagcctgacttgtctcgtgaagggcttctatcccagcgatattgc tgtggaatgggagtcaaatggccagcccgagaataactacaaaactaccc cacccgtgctgaaatctgatgggtccttcttcctttactccaagctgacc gtggacaagagccgctggcaacaaggcaatgtctttagctgctcagtgat gcatgaggctctccataatcactacactcagaagtcactgtccctgtcac ctggaggtggcggagggcagggtggtggaggtcagggaggcggaggacag ggaggaggtggacaagcacggaacggggaccattgtccctgggacctgg tcggtgctgccggcttcacaccgtcagagcctctctggaggaccttggat gggctgattgggtgctgagccctcgggaggtgcaagtcaccatgtgcatc ggggcctgccctagccagttccgcgcagccaacatgcacgctcagatcaa aacctctcttcacagactgaagcccgacaccgtgccagcaccttgctgtg tgccggcctcttataacccatggtcctcattcagaaaaccgacaccgga gtgtcacttcagacttacgatgacctcctggccaaggactgccactgtat ttga and comprises the amino acid sequence (signal sequence single underlined, linker sequence double underlined):

(SEQ ID NO: 82)
<u>MEWSWVFLFFLSVTTGVHS</u>APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPG<u>GGGGQGGGGQGGGGQ</u>

<u>GGGGQ</u>ARNGDHCPLGPGRCCRLHTVRASLEDLGWADWVLSPREVQVTMCI

GACPSQFRAANMHAQIKTSLHRLKPDTVPAPCCVPASYNPMVLIQKTDTG

VSLQTYDDLLAKDCHCI.

The second monomer comprising the heterodimer is encoded by the nucleic acid of SEQ ID NO:53 and comprises the amino acid sequence of SEQ ID NO:86.

In an embodiment employing the VH21 signal sequence, the second monomer comprising the heterodimer is encoded by the nucleic acid sequence of SEQ ID NO:51 and comprises the amino acid sequence of SEQ ID NO:52.

The first and second monomers associate to form the heterodimer. Two such heterodimers associate to form the final tetramer. Accordingly, the resulting tetramer (a dimer of the DhCpmFc(+)-(G$_4$Q)$_4$-GDF15:DhCpmFc(−) construct) comprises two monomers comprising SEQ ID NO:86 and two monomers comprising SEQ ID NO:84.

II.B.10. DhCpmFc(+)(L351C)-G$_4$-GDF15:DhCpmFc(−)(L351C)

The charged pair (delHinge) construct designated "DhCpmFc(+)(L351C)-G$_4$-GDF15:DhCpmFc(−)(L351C)" in the instant disclosure refers to a construct comprising a heterodimer, which comprises (i) a first monomer comprising a mature human GDF15 polypeptide linked via a G$_4$ (SEQ ID ID:70) linker to the C-terminus of a positively charged Fc monomer lacking the hinge region (referred to herein as "DhCpmFc(+)(L351C)") and one negatively charged Fc monomer lacking the hinge region (referred to herein as "DhCpmFc(−)(L351C)").

As discussed above, the introduction of an aspartatic acid-to-lysine mutation (E356K) and a glutamic acid-to-lysine mutation (D399K) in the unmodified Fc sequence lacking the hinge region provides the positively charged DhCpmFc(+) sequence. The introduction of two lysine-to-aspartate mutations (K392D, K409D) provides the negatively charged DhCpmFc(−) sequence. The C-terminal lysine (K477) optionally may also deleted in the negatively charged DhCpmFc(−) sequence, the positively charged DhCpmFc(+) sequence, or both. When incubated together, the aspartate residues associate with the lysine residues through electrostatic force, facilitating formation of Fc heterodimers between the DhCpmFc(+) and DhCpmFc(−) sequences, and reducing or preventing formation of Fc homodimers between DhCpmFc(+) sequences or between DhCpmFc(−) sequences.

Introduction of a leucine-to-cysteine mutation (L351C) in the positively charged DhCpmFc(+) sequence (referred to herein as "DhCpmFc(+)(L351C)") and a leucine-to-cysteine mutation (L351C) in the negatively charged DhCpmFc(−) sequence (referred to herein as "DhCpmFc(−)(L351C)") further enhances the formation of Fc heterodimers between the DhCpmFc(+)(L351C) and DhCpmFc(−) (L351C) sequences by the formation of a disulfide bond (or "cysteine clamp") between them. The positively charged DhCpmFc(+)(L351C)-G$_4$-GDF15 chain associates with the negatively charged DhCpmFc(−)(L351C) chain. Two such heterodimers associate to form a tetramer in which the heterodimers are linked via an interchain disulfide bond between the two human GDF15 sequences.

More particularly, in a specific embodiment, the DhCpmFc(+)(L351C)-G₄-GDF15:DhCpmFc(−)(L351C) tetramer comprises:

(a) two chains (one each heterodimer) of an engineered positively charged Fc(L351) sequence comprising:

(SEQ ID NO: 90)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTCPPSRKEMTKNQVSLTCLVKGFYPSDIAVE

WESNGQPENNYKTTPPVLKSDGSFFLYSKLTVDKSRWQQGNVFSCSVMHE

ALHNHYTQKSLSLSPG (b) two chains (one each heterodimer) of an engineered negatively charged Fc(L351) sequence:

(SEQ ID NO: 91)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTCPPSREEMTKNQVSLTCLVKGFYPSDIAVE

WESNGQPENNYDTTPPVLDSDGSFFLYSDLTVDKSRWQQGNVFSCSVMHE

ALHNHYTQKSLSLSPGK and.

(c) two chains (one each heterodimer) of a native mature human GDF15 polypeptide comprising SEQ ID NO:12.

The GDF15 polypeptide is fused via a linker comprising SEQ ID NO:70 at the N-terminus of the GDF15 polypeptide via peptide bond to the positively charged Fc(L351C) sequence.

In its final form, the first monomer comprising the heterodimer, that with another such heterodimer forms the tetramer is encoded by the nucleic acid sequence:

(SEQ ID NO: 94)
gccccagagctgcttggtggaccatccgtgttcctgtttcctc caaagccgaaggacaccctgatgatctcaagaactccggaagtgacttgc gtcgtcgtggacgtgtcacatgaggatccagaggtcaagttcaattggta tgtggacggagtggaagtgcataacgccaagaccaaaccccgcgaagaac agtacaatagcacctaccgcgtggtgagcgtccttactgtgctccaccag gactggcttaatgggaaggaatacaagtgtaaggtgtccaacaaggccct ccccgctcccatcgaaaagaccatctcaaaggcaaaggggcaaccaaggg aacctcaagtgtacacctgtcctccgagcaggaaggagatgaccaagaac caggtcagcctgacttgtctcgtgaagggcttctatcccagcgatattgc tgtggaatgggagtcaaatggccagcccgagaataactacaaaactaccc cacccgtgctgaaatctgatgggtccttcttcctttactccaagctgacc gtggacaagagccgctggcaacaaggcaatgtctttagctgctcagtgat gcatgaggctctccataatcactacactcagaagtcactgtccctgtcac ctggcggaggtggaggagcacggaacggggaccattgtcccctgggacct ggtcggtgctgccggcttcacaccgtcagagcctctctggaggaccttgg atgggctgattgggtgctgagccctcgggaggtgcaagtcaccatgtgca tcggggcctgccctagccagttccgcgcagccaacatgcacgctcagatc aaaacctctcttcacagactgaagcccgacaccgtgccagcaccttgctg tgtgccggcctcttataaccccatggtcctcattcagaaaaccgacaccg gagtgtcacttcagacttacgatgacctcctggccaaggactgccactgc atatga and comprises the amino acid sequence (linker sequence double underlined):

(SEQ ID NO: 95)
APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTCPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPG<u><u>GGGG</u></u>ARNGDHCPLGP

GRCCRLHTVRASLEDLGWADWVLSPREVQVTMCIGACPSQFRAANMHAQI

KTSLHRLKPDTVPAPCCVPASYNPMVLIQKTDTGVSLQTYDDLLAKDCHC

I.

In an embodiment employing the VH21 signal sequence, in its final form, the first monomer comprising the heterodimer is encoded by the nucleic acid sequence (signal sequence underlined):

(SEQ ID NO: 92)
<u>atggaatggagctgggtctttctgttcttcctctccgtcaccaccggtgt</u>

<u>gcattctg</u>ccccagagctgcttggtggaccatccgtgttcctgtttcctc caaagccgaaggacaccctgatgatctcaagaactccggaagtgacttgc gtcgtcgtggacgtgtcacatgaggatccagaggtcaagttcaattggta tgtggacggagtggaagtgcataacgccaagaccaaaccccgcgaagaac agtacaatagcacctaccgcgtggtgagcgtccttactgtgctccaccag gactggcttaatgggaaggaatacaagtgtaaggtgtccaacaaggccct ccccgctcccatcgaaaagaccatctcaaaggcaaaggggcaaccaaggg aacctcaagtgtacacctgtcctccgagcaggaaggagatgaccaagaac caggtcagcctgacttgtctcgtgaagggcttctatcccagcgatattgc tgtggaatgggagtcaaatggccagcccgagaataactacaaaactaccc cacccgtgctgaaatctgatgggtccttcttcctttactccaagctgacc gtggacaagagccgctggcaacaaggcaatgtctttagctgctcagtgat gcatgaggctctccataatcactacactcagaagtcactgtccctgtcac ctggcggaggtggaggagcacggaacggggaccattgtcccctgggacct ggtcggtgctgccggcttcacaccgtcagagcctctctggaggaccttgg atgggctgattgggtgctgagccctcgggaggtgcaagtcaccatgtgca tcggggcctgccctagccagttccgcgcagccaacatgcacgctcagatc aaaacctctcttcacagactgaagcccgacaccgtgccagcaccttgctg tgtgccggcctcttataaccccatggtcctcattcagaaaaccgacaccg -continued gagtgtcacttcagacttacgatgacctcctggccaaggactgccactgc atatga and comprises the amino acid sequence (signal sequence single underlined, linker sequence double underlined):

(SEQ ID NO: 93)
<u>MEWSWVFLFFLSVTTGVHS</u>APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTCPPSRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPG<u>GGGG</u>ARNGDHCPLGP

GRCCRLHTVRASLEDLGWADWVLSPREVQVTMCIGACPSQFRAANMHAQI

KTSLHRLKPDTVPAPCCVPASYNPMVLIQKTDTGVSLQTYDDLLAKDCHC

I.

The second monomer comprising the heterodimer is encoded by the nucleic acid sequence:

(SEQ ID NO: 98)
gcacctgaactcctgggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagcccccatcgagaaaaccatctccaaagccaaagggcagccccgag aaccacaggtgtacacctgtcccccatcccggaggagatgaccaagaac caggtcagcctgacctgcctggtcaaaggcttctatcccagcgacatcgc cgtggagtgggagagcaatgggcagccggagaacaactacgacaccacgc ctcccgtgctggactccgacggctccttcttcctctatagcgacctcacc gtggacaagagcaggtggcagcaggggaacgtcttctcatgctccgtgat gcatgaggctctgcacaaccactacacgcagaagagcctctccctgtctc cgggtaaatga and comprises the amino acid sequence of SEQ ID NO:91.

In an embodiment employing the VH21 signal sequence, the second monomer comprising the heterodimer is encoded by the nucleic acid sequence (signal sequence underlined):

(SEQ ID NO: 96)
<u>atggaatggagctgggtctttctcttcttcctgtcagtaacgactggtgt</u>

<u>ccactccg</u>cacctgaactcctgggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagcccccatcgagaaaaccatctccaaagccaaagggcagccccgag aaccacaggtgtacacctgtcccccatcccggaggagatgaccaagaac caggtcagcctgacctgcctggtcaaaggcttctatcccagcgacatcgc cgtggagtgggagagcaatgggcagccggagaacaactacgacaccacgc ctcccgtgctggactccgacggctccttcttcctctatagcgacctcacc gtggacaagagcaggtggcagcaggggaacgtcttctcatgctccgtgat gcatgaggctctgcacaaccactacacgcagaagagcctctccctgtctc cgggtaaatga and comprises the amino acid sequence (signal sequence underlined):

(SEQ ID NO: 97)
<u>MEWSWVFLFFLSVTTGVHS</u>APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTCPPSREEMTKN

QVSLTCLVKGFYPSDIAVEWESNGQPENNYDTTPPVLDSDGSFFLYSDLT

VDKSRWQQGNVFSCSVMHEALHNHYTQKSLSLSPGK

The first and second monomers associate to form the heterodimer. Two such heterodimers associate to form the final tetramer. Accordingly, the resulting tetramer (a dimer of the DhCpmFc(+)(L351C)-G$_4$-GDF15:DhCpmFc(−) (L351C) construct comprises two monomers comprising SEQ ID NO:91 and two monomers comprising SEQ ID NO:95.

II.B.11.    DhCpmFc(+)(S354C)-G$_4$-GDF15:DhCpmFc(−) (Y349C)

The charged pair (delHinge) construct designated "DhCpmFc(+)(S354C)-G$_4$-GDF15:DhCpmFc(−)(Y349C)" in the instant disclosure refers to a construct comprising a heterodimer, which comprises (i) a first monomer comprising a mature human GDF15 polypeptide linked via a G$_4$ (SEQ ID NO:70) linker to the C-terminus of a positively charged Fc monomer lacking the hinge region (referred to herein as "DhCpmFc(+)(S354C)") and one negatively charged Fc monomer lacking the hinge region (referred to herein as "DhCpmFc(−)(Y349C)").

As discussed above, the introduction of an aspartatic acid-to-lysine mutation (E356K) and a glutamic acid-to-lysine mutation (D399K) in the unmodified Fc sequence lacking the hinge region provides the positively charged DhCpmFc(+) sequence. The introduction of two lysine-to-aspartate mutations (K392D, K409D) provides the negatively charged DhCpmFc(−) sequence. The C-terminal lysine (K477) optionally may also deleted in the negatively charged DhCpmFc(−) sequence, the positively charged DhCpmFc(+) sequence, or both. When incubated together, the aspartate residues associate with the lysine residues through electrostatic force, facilitating formation of Fc heterodimers between the DhCpmFc(+) and DhCpmFc(−) sequences, and reducing or preventing formation of Fc homodimers between DhCpmFc(+) sequences or between DhCpmFc(−) sequences.

Introduction of a leucine-to-cysteine mutation (S354C) in the positively charged DhCpmFc(+) sequence (referred to herein as "DhCpmFc(+)(S354C)") and a leucine-to-cysteine mutation (Y349C) in the negatively charged DhCpmFc(−)

sequence (referred to herein as "DhCpmFc(−)(L351C)") further enhances the formation of Fc heterodimers between the two DhCpmFc(+)(S354C) and DhCpmFc(−) (Y349C) sequences by the formation of a disulfide bond (or "cysteine clamp") between them. The positively charged DhCpmFc (+)(S354C)-G₄-GDF15 chain associates with the negatively charged DhCpmFc(−)(Y349C) chain. Two such heterodimers associate to form a tetramer in which the heterodimers are linked via an interchain disulfide bond between the two human GDF15 sequences.

More particularly, in a specific embodiment, the DhCpmFc(+)(S354C)-G₄-GDF15:DhCpmFc(−)(Y349C) tetramer comprises (a) two chains (one each heterodimer) of an engineered positively charged Fc(S354C) comprising the sequence:

(SEQ ID NO: 99)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPCRKEMTKNQVSLTCLVKGFYPSDIAVE

WESNGQPENNYKTTPPVLKSDGSFFLYSKLTVDKSRWQQGNVFSCSVMHE

ALHNHYTQKSLSLSPG, (b) two chains (one each heterodimer) of an engineered negatively charged Fc(Y349C) comprising the sequence:

(SEQ ID NO: 100)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVCTLPPSREEMTKNQVSLTCLVKGFYPSDIAVE

WESNGQPENNYDTTPPVLDSDGSFFLYSDLTVDKSRWQQGNVFSCSVMHE

ALHNHYTQKSLSLSPGK and (c) two chains (one each) of a native mature human GDF15 polypeptide comprising SEQ ID NO:12.

The GDF15 polypeptide is fused via a linker comprising SEQ ID NO:70 at the N-terminus of the GDF15 polypeptide via peptide bond to the positively charged Fc(S354C) sequence.

In its final form, the first monomer comprising the heterodimer, that with another such heterodimer forms the tetramer is encoded by the nucleic acid sequence:

(SEQ ID NO: 103)
gccccagagctgcttggtggaccatccgtgttcctgtttcctc caaagccgaaggacaccctgatgatctcaagaactccggaagtgacttgc gtcgtcgtggacgtgtcacatgaggatccagaggtcaagttcaattggta tgtggacggagtggaagtgcataacgccaagaccaaacccgcgaagaac agtacaatagcacctaccgcgtggtgagcgtccttactgtgctccaccag gactggcttaatgggaaggaatacaagtgtaaggtgtccaacaaggccct ccccgctcccatcgaaagaccatctcaaaggcaaggggcaaccaaggg aacctcaagtgtacaccctgcctccgtgcaggaaggagatgaccaagaac caggtcagcctgacttgtctcgtgaagggcttctatcccagcgatattgc tgtggaatgggagtcaaatggccagcccgagaataactacaaaactaccc cacccgtgctgaaatctgatgggtccttcttcctttactccaagctgacc gtggacaagagccgctggcaacaaggcaatgtctttagctgctcagtgat gcatgaggctctccataatcactacactcagaagtcactgtccctgtcac ctggcgaggtggaggagcacggaacggggaccattgtccctgggacct ggtcggtgctgccggcttcacaccgtcagagcctctctggaggaccttgg atgggctgattgggtgctgagccctcgggaggtgcaagtcaccatgtgca tcggggcctgccctagccagttccgcgcagccaacatgcacgctcagatc aaaacctctcttcacagactgaagcccgacaccgtgccagcaccttgctg tgtgccggcctcttataacccatggtcctcattcagaaaaccgacaccg gagtgtcacttcagacttacgatgacctcctggccaaggactgccactgc atatga and comprises the amino acid sequence (linker sequence double underlined):

(SEQ ID NO: 104)
APELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPCRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPG<u><u>GGGG</u></u>ARNGDHCPLGP

GRCCRLHTVRASLEDLGWADWVLSPREVQVTMCIGACPSQFRAANMHAQI

KTSLHRLKPDTVPAPCCVPASYNPMVLIQKTDTGVSLQTYDDLLAKDCHC

I

In an embodiment employing the VH21 signal sequence, in its final form, the first monomer comprising the heterodimer is encoded by the nucleic acid sequence (signal sequence underlined):

(SEQ ID NO: 101)
<u>atggaatggagctgggtctttctgttcttcctctccgtcaccaccggtgt</u>

<u>gcattct</u>gccccagagctgcttggtggaccatccgtgttcctgtttcctc caaagccgaaggacaccctgatgatctcaagaactccggaagtgacttgc gtcgtcgtggacgtgtcacatgaggatccagaggtcaagttcaattggta tgtggacggagtggaagtgcataacgccaagaccaaacccgcgaagaac agtacaatagcacctaccgcgtggtgagcgtccttactgtgctccaccag gactggcttaatgggaaggaatacaagtgtaaggtgtccaacaaggccct ccccgctcccatcgaaagaccatctcaaaggcaaggggcaaccaaggg aacctcaagtgtacaccctgcctccgtgcaggaaggagatgaccaagaac caggtcagcctgacttgtctcgtgaagggcttctatcccagcgatattgc tgtggaatgggagtcaaatggccagcccgagaataactacaaaactaccc cacccgtgctgaaatctgatgggtccttcttcctttactccaagctgacc gtggacaagagccgctggcaacaaggcaatgtctttagctgctcagtgat gcatgaggctctccataatcactacactcagaagtcactgtccctgtcac

```
ctggcggaggtggaggagcacggaacggggaccattgtccctgggacct ggtcggtgctgccggcttcacaccgtcagagcctctctggaggaccttgg atgggctgattgggtgctgagccctcgggaggtgcaagtcaccatgtgca tcggggcctgccctagccagttccgcgcagccaacatgcacgctcagatc aaaacctctcttcacagactgaagcccgacaccgtgccagcaccttgctg tgtgccggcctcttataacccatggtcctcattcagaaaaccgacaccg gagtgtcacttcagacttacgatgacctcctggccaaggactgccactgc atatga
``` and comprises the amino acid sequence (signal sequence single underlined, linker sequence double underlined):

```
                                    (SEQ ID NO: 102)
MEWSWVFLFFLSVTTGVHSAPELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPCRKEMTKN

QVSLTCLVKGFYPSDIAVEWESNGQPENNYKTTPPVLKSDGSFFLYSKLT

VDKSRWQQGNVFSCSVMHEALHNHYTQKSLSLSPGGGGGARNGDHCPLGP

GRCCRLHTVRASLEDLGWADWVLSPREVQVTMCIGACPSQFRAANMHAQI

KTSLHRLKPDTVPAPCCVPASYNPMVLIQKTDTGVSLQTYDDLLAKDCHC

I
```

The second monomer comprising the heterodimer is encoded by the nucleic acid sequence:

```
                                    (SEQ ID NO: 107)
gcacctgaactcctgggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagcccccatcgagaaaaccatctccaaagccaaagggcagccccgag aaccacaggtgtgcaccctgcccccatcccgggaggagatgaccaagaac caggtcagcctgacctgcctggtcaaaggcttctatcccagcgacatcgc cgtggagtgggagagcaatgggcagccggagaacaactacgacaccacgc ctcccgtgctggactccgacggctccttcttcctctatagcgacctcacc gtggacaagagcaggtggcagcaggggaacgtcttctcatgctccgtgat gcatgaggctctgcacaaccactacacgcagaagagcctctccctgtctc cgggtaaatga
``` and comprises the amino acid sequence of SEQ ID NO:100.

In an embodiment employing the VH21 signal sequence, the second monomer comprising the heterodimer is encoded by the nucleic acid sequence (signal sequence underlined):

```
                                    (SEQ ID NO: 105)
atggaatggagctgggtctttctcttcttcctgtcagtaacgactggtgt ccactccgcacctgaactcctgggggaccgtcagtcttcctcttccccc caaaacccaaggacaccctcatgatctcccggacccctgaggtcacatgc gtggtggtggacgtgagccacgaagaccctgaggtcaagttcaactggta cgtggacggcgtggaggtgcataatgccaagacaaagccgcgggaggagc agtacaacagcacgtaccgtgtggtcagcgtcctcaccgtcctgcaccag gactggctgaatggcaaggagtacaagtgcaaggtctccaacaaagccct cccagcccccatcgagaaaaccatctccaaagccaaagggcagccccgag aaccacaggtgtgcaccctgcccccatcccgggaggagatgaccaagaac caggtcagcctgacctgcctggtcaaaggcttctatcccagcgacatcgc cgtggagtgggagagcaatgggcagccggagaacaactacgacaccacgc ctcccgtgctggactccgacggctccttcttcctctatagcgacctcacc gtggacaagagcaggtggcagcaggggaacgtcttctcatgctccgtgat gcatgaggctctgcacaaccactacacgcagaagagcctctccctgtctc cgggtaaatga
``` and comprises the amino acid sequence (signal sequence underlined):

```
                                    (SEQ ID NO: 106)
MEWSWVFLFFLSVTTGVHSAPELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVCTLPPSREEMTKN

QVSLTCLVKGFYPSDIAVEWESNGQPENNYDTTPPVLDSDGSFFLYSDLT

VDKSRWQQGNVFSCSVMHEALHNHYTQKSLSLSPGK
```

The first and second monomers associate to form the heterodimer. Two such heterodimers associate to form the final tetramer. Accordingly, the resulting tetramer (a dimer of the DhCpmFc(+)(S354C)-G$_4$-GDF15:DhCpmFc(−)(Y349C) construct) comprises two monomers comprising SEQ ID NO:100 and two monomers comprising SEQ ID NO:104.

II.C. Charged Pair Construct

Constructs designated "charged pair" or "charged pair Fc" in the instant disclosure refer to a construct comprising a "negatively charged" Fc sequence comprising a charge pair mutation and (ii) a positively charged Fc sequence comprising a charged pair mutation. Note that use of the terms "positively charged" and "negatively charged" is for ease of reference (i.e., to describe the nature of the charge pair mutations in the Fc sequences) and not to indicate that the overall sequence or construct necessarily has a positive or negative charge.

The introduction of an aspartatic acid-to-lysine mutation (E356K) and a glutamic acid-to-lysine mutation (D399K) in the unmodified Fc sequence provides the positively charged Fc sequence (referred to herein as "CpmFc(+)"). The introduction of two lysine-to-aspartate mutations (K392D, K409D) into the unmodified Fc sequence provides the negatively charged Fc sequence (referred to herein as "CpmFc(−)"). The C-terminal lysine (K477) optionally also may be deleted in the negatively charged CpmFc(−) sequence, the positively charged CpmFc(+) sequence, or both. See, e.g., SEQ ID NOs: 23, 110, 114 and 115 (CpmFc sequences). When incubated together, the aspartate residues associate with the lysine residues, facilitating forming of Fc heterodimers between the CpmFc(+) and CpmFc(−) sequences, and reducing or preventing forming of Fc homodimers between the CpmFc(+) and CpmFc(−) sequences.

In some embodiments a heterodimer comprises (i) a mature GDF15 sequence linked directly or via a linker to the C-terminus of a CpmFc(−) and (ii) a CpmFc(+). In other embodiments the heterodimer comprises (i) a mature GDF15 sequence linked directly or via a linker to the C-terminus of a CpmFc(+) and (ii) a CpmFc(−). In either event, two such heterodimers associate to form tetramer in which the heterodimers are linked via an interchain disulfide bond between the two GDF15 sequences. See FIG. 1 for a graphic depiction of a tetramer comprising two heterodimers linked via an interchain disulfide bond between two human GDF15 sequences, in which each heterodimer is the charged pair construct designated "CpmFc(−)-(G$_4$S)$_4$-GDF15 CpmFc(−)" in the instant disclosure (i.e., where each heterodimer comprises (i) a first monomer comprising a mature GDF15 polypeptide linked via a (G$_4$S)$_4$ (SEQ ID NO:20) linker to the C-terminus of a CpmFc(−) sequence and (ii) a second monomer comprising a CpmFc(+) sequence).

CpmFc(−)-(G$_4$S)$_4$-GDF15:CpmFc(+)

The charged pair construct designated "CpmFc(−)-(G$_4$S)$_4$-GDF15:CpmFc(+)" in the instant disclosure refers to a construct comprising a heterodimer, which comprises (i) a first monomer comprising a mature human GDF15 polypeptide linked via a (G$_4$S)$_4$ (SEQ ID NO:20) linker to the C-terminus of a CpmFc(−) sequence and (ii) a second monomer comprising a CpmFc(+) sequence. Although the hinge region is present, the negatively charged CpmFc(−)-(G$_4$S)$_4$-hGDF15 chain associates with the negatively charged CpmFc(−) chain to form the heterodimer. Two such heterodimers associate to form a tetramer in which the heterodimers are linked via an interchain disulfide bond between the two human GDF15 sequences.

More particularly, in a specific embodiment, the CpmFc (−)-(G$_4$S)$_4$-GDF15:CpmFc(+) construct comprises:

(a) two chains (one each heterodimer) of an engineered positively charge Fc sequence comprising the sequence (with the hinge region indicated by parentheses):

(SEQ ID NO: 110)
(DKTHTCPPCP)APELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRKEMTKNQVSLTCL

VKGFYPSDIAVEWESNGQPENNYKTTPPVLKSDGSFFLYSKLTVDKSRWQ

QGNVFSCSVMHEALHNHYTQKSLSLSPGK, (b) two chains (one each) of an engineered negatively charged Fc sequence comprising the sequence (with the hinge region indicated by parentheses):

(SEQ ID NO: 23)
(DKTHTCPPCP)APELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYDTTPPVLDSDGSFFLYSDLTVDKSRWQ

QGNVFSCSVMHEALHNHYTQKSLSLSPG, and (c) two chains of a native mature human GDF15 polypeptide comprising SEQ ID NO:12.

The GDF15 polypeptide is fused via a linker comprising SEQ ID NO:20 at the N-terminus of the GDF15 polypeptide via peptide bond to the negatively charged Fc monomer.

In its final form, the first monomer comprising the heterodimer, that with another such heterodimer forms the tetramer, is encoded by the nucleic acid sequence:

(SEQ ID NO: 112)
gacaaaactcacacatgcccaccgtgcccagcacctgaactcc tggggggaccgtcagtcttcctcttccccccaaaacccaaggacaccctc atgatctcccggacccctgaggtcacatgcgtggtggtggacgtgagcca cgaagaccctgaggtcaagttcaactggtacgtggacggcgtggaggtgc ataatgccaagacaaagccgcgggaggagcagtacaacagcacgtaccgt gtggtcagcgtcctcaccgtcctgcaccaggactggctgaatggcaagga gtacaagtgcaaggtctccaacaaagcccteccageccccatcgagaaaa ccatctccaaagccaaagggcagccccgagaaccacaggtgtacaccctg cccccatcccgggaggagatgaccaagaaccaggtcagcctgacctgcct ggtcaaaggcttctatcccagcgacatcgccgtggagtgggagagcaatg ggcagccggagaacaactacgacaccacgcctcccgtgctggactccgac ggctccttcttcctctatagcgacctcaccgtggacaagagcaggtggca gcaggggaacgtcttctcatgctccgtgatgcatgaggctctgcacaacc actacacgcagaagagcctctccctgtctccgggtggaggtggtggatcc ggaggcggtggaagcggaggtggtggatctggaggcggtggaagcgcgcg caacggagaccactgtccgctcgggcccgggcgttgctgccgtctgcaca cggtccgcgcgtcgctggaagacctgggctgggccgattgggtgctgtcg ccacgggaggtgcaagtgaccatgtgcatcggcgcgtgcccgagccagtt ccgggcggcaaacatgcacgcgcagatcaagacgagcctgcaccgcctga agcccgacacggtgccagcgccctgctgcgtgcccgccagctacaatccc atggtgctcattcaaaagaccgacaccgggatgtcgctccagacctatga tgacttgttagccaaagactgccactgcatatga and comprises the amino acid sequence (hinge region indicated by parentheses and linker sequence double underlined):

(SEQ ID NO: 113)
(DKTHTCPPCP)APELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYDTTPPVLD

SDGSFFLYSDLTVDKSRWQQGNVFSCSVMHEALHNHYTQKSLSLSPG<u>GGG</u>

-continued

GSGGGGSGGGGSGGGGSARNGDHCPLGPGRCCRLHTVRASLEDLGWADWV

LSPREVQVTMCIGACPSQFRAANMHAQIKTSLHRLKPDTVPAPCCVPASY

NPMVLIQKTDTGVSLQTYDDLLAKDCHCI

In an embodiment employing the VH21 signal sequence, in its final form, the first monomer comprising the heterodimer is encoded by the nucleic acid sequence (signal sequence underlined):

(SEQ ID NO: 24)
<u>atggaatggagctgggtctttctcttcttcctgtcagtaacgactggtgt</u>

<u>ccactcc</u>gacaaaactcacacatgcccaccgtgcccagcacctgaactcc tgggggaccgtcagtcttcctcttccccccaaaacccaaggacaccctc atgatctcccggacccctgaggtcacatgcgtggtggtggacgtgagcca cgaagaccctgaggtcaagttcaactggtacgtggacggcgtggaggtgc ataatgccaagacaaagccgcgggaggagcagtacaacagcacgtaccgt gtggtcagcgtcctcaccgtcctgcaccaggactggctgaatggcaagga gtacaagtgcaaggtctccaacaaagcccteccagcccccatcgagaaaa ccatctccaaagccaaagggcagccccgagaaccacaggtgtacaccctg cccccatcccgggaggagatgaccaagaaccaggtcagcctgacctgcct ggtcaaaggcttctatcccagcgacatcgccgtggagtgggagagcaatg ggcagccggagaacaactacgacaccacgcctcccgtgctggactccgac ggctccttcttcctctatagcgacctcaccgtggacaagagcaggtggca gcaggggaacgtcttctcatgctccgtgatgcatgaggctctgcacaacc actacacgcagaagagcctctccctgtctccgggtggaggtggtggatcc ggaggcggtggaagcggaggtggtggatctggaggcggtggaagcgcgcg caacggagaccactgtccgctcgggcccgggcgttgctgccgtctgcaca cggtccgcgcgtcgctggaagacctgggctgggccgattgggtgctgtcg ccacgggaggtgcaagtgaccatgtgcatcggcgcgtgcccgagccagtt ccgggcggcaaacatgcacgcgcagatcaagacgagcctgcaccgcctga agcccgacacggtgccagcgcctgctgcgtgcccgccagctacaatccc atggtgctcattcaaaagaccgacaccggggtgtcgctccagacctatga tgacttgttagccaaagactgccactgcatatga and comprises the amino acid sequence (signal sequence single underlined, hinge region in parentheses and linker sequence double underlined):

(SEQ ID NO: 25)
<u>MEWSWVFLFFLSVTTGVHS</u>(DKTHTCPPCP)APELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYDTTPPVLD

SDGSFFLYSDLTVDKSRWQQGNVFSCSVMHEALHNHYTQKSLSLSPG<u>GGG</u>

<u>GSGGGGSGGGGSGGGGS</u>ARNGDHCPLGPGRCCRLHTVRASLEDLGWADWV

-continued

LSPREVQVTMCIGACPSQFRAANMHAQIKTSLHRLKPDTVPAPCCVPASY

NPMVLIQKTDTGVSLQTYDDLLAKDCHCI.

The second monomer comprising the heterodimer is encoded by the nucleic acid sequence:

(SEQ ID NO: 116)
gacaaaactcacacatgcccaccgtgcccagcacctgaactcc tgggggaccgtcagtcttcctcttccccccaaaacccaaggacaccctc atgatctcccggacccctgaggtcacatgcgtggtggtggacgtgagcca cgaagaccctgaggtcaagttcaactggtacgtggacggcgtggaggtgc ataatgccaagacaaagccgcgggaggagcagtacaacagcacgtaccgt gtggtcagcgtcctcaccgtcctgcaccaggactggctgaatggcaagga gtacaagtgcaaggtctccaacaaagcccteccagcccccatcgagaaaa ccatctccaaagccaaagggcagccccgagaaccacaggtgtacaccctg cccccatcccgggaggagatgaccaagaaccaggtcagcctgacctgcct ggtcaaaggcttctatcccagcgacatcgccgtggagtgggagagcaatg ggcagccggagaacaactacaagaccacgcctcccgtgctgaagtccgac ggctccttcttcctctatagcaagctcaccgtggacaagagcaggtggca gcaggggaacgtcttctcatgctccgtgatgcatgaggctctgcacaacc actacacgcagaagagcctctccctgtctccgggtaaatga and comprises the amino acid sequence of SEQ ID NO:110.

In an embodiment employing the VH21 signal sequence, the second monomer comprising the heterodimer is encoded by the nucleic acid sequence (signal sequence underlined):

(SEQ ID NO: 26)
<u>atggaatggagctgggtctttctcttcttcctgtcagtaacgactggtgt</u>

<u>ccactcc</u>gacaaaactcacacatgcccaccgtgcccagcacctgaactcc tgggggaccgtcagtcttcctcttccccccaaaacccaaggacaccctc atgatctcccggacccctgaggtcacatgcgtggtggtggacgtgagcca cgaagaccctgaggtcaagttcaactggtacgtggacggcgtggaggtgc ataatgccaagacaaagccgcgggaggagcagtacaacagcacgtaccgt gtggtcagcgtcctcaccgtcctgcaccaggactggctgaatggcaagga gtacaagtgcaaggtctccaacaaagcccteccagcccccatcgagaaaa ccatctccaaagccaaagggcagccccgagaaccacaggtgtacaccctg cccccatcccgggaggagatgaccaagaaccaggtcagcctgacctgcct ggtcaaaggcttctatcccagcgacatcgccgtggagtgggagagcaatg ggcagccggagaacaactacaagaccacgcctcccgtgctgaagtccgac ggctccttcttcctctatagcaagctcaccgtggacaagagcaggtggca gcaggggaacgtcttctcatgctccgtgatgcatgaggctctgcacaacc actacacgcagaagagcctctccctgtctccgggtaaatga and comprises the amino acid sequence (signal sequence underlined, hinge region in parentheses):

(SEQ ID NO: 27)
MEWSWVFLFFLSVTTGVHS(DKTHTCPPCP)APELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRKEMTKNQVSLTCLVKGFYPSDIAVEWESNGQPENNYKTTPPVLK

SDGSFFLYSKLTVDKSRWQQGNVFSCSVMHEALHNHYTQKSLSLSPGK.

The first and second monomers associate to form the heterodimer. Two such heterodimers associate to form the final tetramer. Accordingly, the resulting tetramer (a dimer of the CpmFc(−)-(G$_4$S)$_4$-GDF15:CpmFc(+) construct) comprises two monomers comprising SEQ ID NO:110 and two monomers comprising SEQ ID NO:113.

II.D. HemiFc Constructs

Constructs designated "hemi" or "hemiFc" in the instant disclosure refer to a construct comprising two Fc sequences joined in tandem by a linker that connects the N-terminus of a first Fc sequence (e.g., SEQ ID NOs: 28 or 30) to the C-terminus of a second Fc sequence (e.g., SEQ ID NOs: 28 or 30). In some embodiments, a monomer comprises a mature GDF15 sequence linked to the first Fc sequence by a first linker that connects the N-terminus of the GDF15 sequence to the C-terminus of the first Fc sequence, wherein the first Fc sequence is linked to the second Fc sequence by a second linker that connects the N-terminus of the first Fc sequence to the C-terminus of the second Fc sequence. The first and second Fc sequences also are associated by the Fc hinge regions. Two such monomers associate to form a dimer in which the monomers are linked via an interchain disulfide bond between the two GDF15 sequences. See FIG. 1 for a graphic depiction of a hemi construct "Fc-(G$_4$S)$_8$-Fc-GS(G$_4$S)$_4$-GDF15" (i.e., two monomers, each comprising a mature GDF15 polypeptide linked via a GS(G$_4$S)$_4$ linker to the C-terminus of a first Fc sequence, the N-terminus of which is linked via a (G$_4$S)$_8$ linker to the C-terminus of a second Fc sequence; and where the two mature GDF15 sequences are linked via an interchain disulfide bond).

II.D.1 Fc-(G$_4$S)$_8$-Fc-GS(G$_4$S)$_4$-GDF15

The hemiFc construct designated "Fc-(G$_4$S)$_8$-Fc-GS (G$_4$S)$_4$-GDF15" in the instant disclosure refers to a construct comprising a monomer, which comprises a mature human GDF15 sequence linked to a first Fc sequence via a first linker comprising SEQ ID NO:31 that connects the N-terminus of the human GDF15 sequence to the C-terminus of the first Fc sequence and a second linker comprising the amino acid sequence:

(SEQ ID NO: 34)
GGGGSGGGGSGGGGSGGGGSGGGGSGGGGSGGGGSGGGGS.

that connects the N-terminus of the first Fc sequence to the C-terminus of the second Fc sequence. The first and second Fc sequences also are associated by the Fc hinge regions. Two such monomers associate to form a homodimer in which the monomers are linked via an interchain disulfide bond between the two GDF15 sequences.

More particularly, in a specific embodiment, the hemi construct Fc-(G$_4$S)$_8$-Fc-GS(G$_4$S)$_4$-GDF15 comprises a monomer comprising a second Fc chain comprising the sequence (hinge region in parentheses):

(SEQ ID NO: 28)
GGG(ERKSSVECPPCP)APPVAGPSVFLFPPKPKDTLMISRTPEVTCVVV

DVSHEDPEVQFNWYVDGVEVHNAKTKPREEQFNSTFRVVSVLTVVHQDWL

NGKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVDK

SRWQQGNVFSCSVMHEALHNHYTQKSLSLSP

Joined by the linker:

(SEQ ID NO: 29)
GGGGGSGGGGSGGGGSGGGGSGGGGSGGGGSGGGGSGGGGS to a first Fc chain comprising the sequence (hinge region in parentheses):

(SEQ ID NO: 30)
(ERKSSVECPPCP)APPVAGPSVFLFPPKPKDTLMISRTPEVTCVVVDVS

HEDPEVQFNWYVDGVEVHNAKTKPREEQFNSTFRVVSVLTVVHQDWLNGK

EYKCKVSNKGLPAPIEKTISKTKGQPREPQVYTLPPSREEMTKNQVSLTC

LVKGFYPSDIAVEWESNGQPENNYKTTPPMLDSDGSFFLYSKLTVDKSRW

QQGNVFSCSVMHEALHNHYTQKSLSLSP to the C-terminus of which, the GDF15 polypeptide comprising SEQ ID NO:12 is joined by a linker having the sequence:

(SEQ ID NO: 31)
GSGGGGSGGGGSGGGGSGGGGS

In its final form, the monomer is encoded by the nucleic acid sequence:

(SEQ ID NO: 32)
ggaggtggagagcgcaaatcttctgtcgagtgcccaccgtgcccagcacc acctgtggcaggaccgtcagtcttcctcttccccccaaaacccaaggaca ccctcatgatctcccggacccctgaggtcacgtgcgtggtggtggacgtg agccacgaagacccgaggtccagttcaactggtacgtggacggcgtgga ggtgcataatgccaagacaaaaccacgggaggagcagttcaacagcacgt tccgtgtggtcagcgtcctcaccgttgtgcaccaggactggctgaacggc aaggagtacaagtgcaaggtctccaacaaaggcctcccagcccccatcga gaaaaccatctccaaaaccaaagggcagccccgagaaccacaggtgtaca ccctgccccatcccgggaggagatgaccaagaaccaggtcagcctgacc tgcctggtcaaaggcttctaccccagcgacatcgccgtggagtgggagag caatgggcagccggagaacaactacaagaccacacctcccatgctggact ccgacggctccttcttcctctacagcaagctcaccgtggacaagagcagg tggcagcaggggaacgtcttctcatgctccgtgatgcatgaggctctgca caaccactacacgcagaagagcctctccctgtctccgggtggaggtggcg gtagcggtggcggaggttcaggtggtggcggttctggcggaggtggcagt ggcggtggcggatcaggtggcggtggcagcggtggcggcggaagcggtgg aggaggttcagagcggaaatccagcgttgaatgtcctccgtgccctgctc -continued

```
cacccgtcgcggggcctagtgtcttccttttccctccaaaaccaaaggat
acactgatgatcagccggaccccgaggttacgtgcgtcgtcgtcgatgt
ctcccacgaggatccagaggtccaattcaactggtacgtggacgggtcg
aggtgcataatgcaaagacaaagccacgggaagagcagtttaactctact
ttccgcgtggtttctgtgctgaccgtggtgcaccaagattggctcaacgg
caaggagtacaagtgcaaggtaagcaataaggggctccctgcccccattg
agaagactatctccaagacaaagggacagccacgcgagccacaagtctat
acactccccccttcccgcgaagaaatgaccaagaatcaggttagcctgac
atgcttggttaagggtttctaccccctctgacatagccgtggagtgggaga
gcaatggacaaccagagaacaactacaagaccaccccacccatgctggat
agcgacggttcattctttctgtatagtaagcttaccgtggacaagtcccg
gtggcaacaaggaaatgtcttttcatgctctgtgatgcacgaggccttgc
ataatcactatactcagaagagcttgagcctcagccccggatctggaggt
ggcggatccgggggcggtggaagcggaggtggtggatcgggaggcggtgg
aagcgcgcgcaacggcgaccactgtccgctcgggcccggacgttgctgcc
gtctgcacacggtccgcgcgtcgctggaagacctgggctgggccgattgg
gtgctgtcgccacgggaggtgcaagtgaccatgtgcatcggcgcgtgccc
gagccagttccggcggcaaacatgcacgcgcagatcaagacgagcctgc
accgcctgaagcccgacacggtgccagcgcctgctgcgtgcccgccagc
tacaatcccatggtgctcattcaaaagaccgacaccggggtgtcgctcca
gacctatgatgacttgttagccaaagactgccactgcatatga
``` and comprises the amino acid sequence (hinge regions in parentheses, linkers sequences double underlined):

(SEQ ID NO: 33)
GGG(ERKSSVECPPCP)APPVAGPSVFLFPPKPKDTLMISRTPEVT
CVVVDVSHEDPEVQFNWYVDGVEVHNAKTKPREEQFNSTFRVVSVL
TVVHQDWLNGKEYKCKVSNKGLPAPIEKTISKTKGQPREPQVYTLP
PSREEMTKNQVSLTCLVKGFYPSDIAVEWESNGQPENNYKTTPPML
DSDGSFFLYSKLTVDKSRWQQGNVFSCSVMHEALHNHYTQKSLSLS
P<u>GGGGGSGGGGSGGGGSGGGGSGGGGSGGGGSGGGGSGGGGS</u>(ERK
SSVECPPCP)APPVAGPSVFLFPPKPKDTLMISRTPEVTCVVVDVS
HEDPEVQFNWYVDGVEVHNAKTKPREEQFNSTFRVVSVLTVVHQDW
LNGKEYKCKVSNKGLPAPIEKTISKTKGQPREPQVYTLPPSREEMT
KNQVSLTCLVKGFYPSDIAVEWESNGQPENNYKTTPPMLDSDGSFF
LYSKLTVDKSRWQQGNVFSCSVMHEALHNHYTQKSLSLSP<u>GSGGGG
SGGGGSGGGGSGGGGS</u>ARNGDHCPLGPGRCCRLHTVRASLEDLGWA
DWVLSPREVQVTMCIGACPSQFRAANMHAQIKTSLHRLKPDTVPAP
CCVPASYNPMVLIQKTDTGVSLQTYDDLLAKDCHCI

In an embodiment employing the VH21 signal sequence, in its final form, the monomer is encoded by the nucleic acid (signal sequence underlined):

(SEQ ID NO: 117)
<u>atggaatggagctgggtctttctcttcttcctgtcagtaacgactg
gtgtccactcc</u>ggaggtggagagcgcaaatcttctgtcgagtgccc
accgtgcccagcaccacctgtggcaggaccgtcagtcttcctcttc
cccccaaaacccaaggacaccctcatgatctcccggacccctgagg
tcacgtgcgtggtggtggacgtgagccacgaagaccccgaggtcca
gttcaactggtacgtggacggcgtggaggtgcataatgccaagaca
aaaccacgggaggagcagttcaacagcacgttccgtgtggtcagcg
tcctcaccgttgtgcaccaggactggctgaacggcaaggagtacaa
gtgcaaggtctccaacaaaggcctcccagcccccatcgagaaaacc
atctccaaaaccaaagggcagccccgagaaccacaggtgtacaccc
tgcccccatcccgggaggagatgaccaagaaccaggtcagcctgac
ctgcctggtcaaaggcttctaccccagcgacatcgccgtggagtgg
gagagcaatgggcagccggagaacaactacaagaccacacctccca
tgctggactccgacggctccttcttcctctacagcaagctcaccgt
ggacaagagcaggtggcagcaggggaacgtcttctcatgctccgtg
atgcatgaggctctgcacaaccactacacgcagaagagcctctccc
tgtctccgggtggaggtggcggtagcggtggcggaggttcaggtgg
tggcggttctggcggaggtggcagtggcggtggcggatcaggtggc
ggtggcagcggtggcggcggaagcggtggaggaggttcagagcgga
aatccagcgttgaatgtcctccgtgccctgctccacccgtcgcggg
gcctagtgtcttccttttccctccaaaaccaaaggatacactgatg
atcagccggaccccgaggttacgtgcgtcgtcgtcgatgtctccc
acgaggatccagaggtccaattcaactggtacgtggacggggtcga
ggtgcataatgcaaagacaaagccacgggaagagcagtttaactct
actttccgcgtggtttctgtgctgaccgtggtgcaccaagattggc
tcaacggcaaggagtacaagtgcaaggtaagcaataaggggctccc
tgccccattgagaagactatctccaagacaaagggacagccacgc
gagccacaagtctatacactccccccttcccgcgaagaaatgacca
agaatcaggttagcctgacatgcttggttaagggtttctaccccctc
tgacatagccgtggagtgggagagcaatggacaaccagagaacaac
tacaagaccaccccacccatgctggatagcgacggttcattctttc
tgtatagtaagcttaccgtggacaagtcccggtggcaacaaggaaa
tgtcttttcatgctctgtgatgcacgaggccttgcataatcactat
actcagaagagcttgagcctcagccccggatctggaggtggcggat
ccggggcggtggaagcggaggtggtggatcgggaggcggtggaag
cgcgcgcaacggcgaccactgtccgctcgggcccggacgttgctgc
cgtctgcacacggtccgcgcgtcgctggaagacctgggctgggccg
attgggtgctgtcgccacgggaggtgcaagtgaccatgtgcatcgg
cgcgtgcccgagccagttccggcggcaaacatgcacgcgcagatc
aagacgagcctgcaccgcctgaagcccgacacggtgccagcgccct
```

-continued
```
gctgcgtgcccgccagctacaatcccatggtgctcattcaaaagac cgacaccggggtgtcgctccagacctatgatgacttgttagccaaa gactgccactgcatatga
``` and comprises the amino acid sequence (signal sequence underlined, hinge region in parentheses and linker sequences double underlined):

(SEQ ID NO: 118)
MEWSWVFLFFLSVTTGVHSGGG(ERKSSVECPPCP)APPVAGPSVF

LFPPKPKDTLMISRTPEVTCVVVDVSHEDPEVQFNWYVDGVEVHNA

KTKPREEQFNSTFRVVSVLTVVHQDWLNGKEYKCKVSNKGLPAPIE

KTISKTKGQPREPQVYTLPPSREEMTKNQVSLTCLVKGFYPSDIAV

EWESNGQPENNYKTTPPMLDSDGSFFLYSKLTVDKSRWQQGNVFSC

SVMHEALHNHYTQKSLSLSPGGGGSGGGGSGGGGSGGGGSGGGGS

GGGGSGGGGSGGGGS(ERKSSVECPPCP)APPVAGPSVFLFPPKPK

DTLMISRTPEVTCVVVDVSHEDPEVQFNWYVDGVEVHNAKTKPREE

QFNSTFRVVSVLTVVHQDWLNGKEYKCKVSNKGLPAPIEKTISKTK

GQPREPQVYTLPPSREEMTKNQVSLTCLVKGFYPSDIAVEWESNGQ

PENNYKTTPPMLDSDGSFFLYSKLTVDKSRWQQGNVFSCSVMHEAL

HNHYTQKSLSLSPGSGGGSGGGGSGGGGSGGGGSARNGDHCPLGP

GRCCRLHTVRASLEDLGWADWVLSPREVQVTMCIGACPSQFRAANM

HAQIKTSLHRLKPDTVPAPCCVPASYNPMVLIQKTDTGVSLQTYDD

LLAKDCHCI

Two such monomers associate to form the dimer in which the two hGDF15 polypeptides are linked via a disulfide bond between two naturally occurring (i.e., not engineered) cysteine residues. Accordingly, the specific hemiFc dimeric construct Fc-(G$_4$S)$_8$-Fc-GS(G$_4$S)$_4$-GDF15 comprises two monomers comprising SEQ ID NO:33.

II.D.2 Fc-(G$_4$S)$_3$-Fc-GS(G$_4$S)$_4$-GDF15

The hemiFc construct designated "Fc(G$_4$S)$_3$-Fc-GS(G$_4$S)$_4$-GDF15" in the instant disclosure refers to a construct comprising a monomer, which comprises a mature human GDF15 sequence linked to a first Fc sequence via a first linker comprising SEQ ID NO:31 that connects the N-terminus of the human GDF15 sequence to the C-terminus of the first Fc sequence and a second linker comprising the amino acid sequence:

(SEQ ID NO: 87)
GGGGSGGGGSGGGGS.

that connects the N-terminus of the first Fc sequence to the C-terminus of the second Fc sequence. The first and second Fc sequences are also associated by the Fc hinge regions. Two such monomers associate to form a homodimer in which the monomers are linked via an interchain disulfide bond between the two GDF15 sequences.

More particularly, in a specific embodiment, the hemiFc construct Fc(G$_4$S)$_3$-Fc-GS(G$_4$S)$_4$-GDF15 comprises a monomer comprising a second Fc chain comprising the sequence of SEQ ID NO:28 joined by the linker:

(SEQ ID NO: 119)
GGGGGSGGGSGGGGS to a first Fc chain comprising the sequence of SEQ ID NO:30 to the C-terminus of which, the GDF15 polypeptide comprising SEQ ID NO:12 is joined by a linker having the sequence of SEQ ID NO:31.

In its final form, the monomer is encoded by the nucleic acid sequence:

(SEQ ID NO: 122)
```
ggaggaggcgagaggaagagctccgtggagtgtccaccctgccctgc tccgcctgtggctggaccctctgtgttcctgtttccgccgaagccga aagacaccctcatgatcagcaggactcccgaggtcacttgtgtggtc gtggatgtgagccatgaggacccagaggtgcagttcaactggtacgt ggacggcgtggaagtccacaacgccaagaccaagccacgcgaggaac agttcaatagcaccttccgcgtggtcagcgtcctcaccgtggtccac caggattggcttaacggaaaggaatacaaatgcaaggtgtccaacaa ggggcttcctgccccgattgaaaagaccatctccaagaccaagggac agccaagggagccccaagtgtacactctgccacccagccgcgaagaa atgactaagaatcaagtgtctctgacctgtcttgtcaaaggcttcta ccccagcgacatcgctgtcgagtgggaatcaaacgggcagcccgaga acaactacaagaccactcctccaatgctcgactcagatggcagcttt ttccttactccaagctgaccgtggacaagtcaagatggcaacaggg taacgtgttctcatgctccgtgatgcacgaagccctccataatcact atacccagaaatctctgtctctttccccgggaggaggaggggggatct ggtggaggaggctctggtggtggaggtagcgaacggaaatcctcagt ggagtgccccaccatgcccggctcctccagtggctggtccatctgtct ttcttttttcctccgaaacccaaggacaccttatgatctctcgcacc cctgaagtgacttgcgtggtcgtcgatgtgtcacatgaagaccctga ggtccagttcaattggtatgtggacggagtcgaggtgcataacgcca aaaccaaacctcgcgaagaacaattcaactctaccttccgggtggtg tctgtgctcactgtcgtccatcaggactggctgaacgggaaggagta caagtgtaaggtgtctaacaaaggcctgccggctcccatcgaaaaga ctatcagcaagactaaggggcaacccagagaaccccaagtctacacc ctgcctccgtcacgggaggagatgaccaagaatcaggtgtccctcac ctgtctggtcaagggtttctaccctagcgacattgctgtggagtggg agagcaatggacagcccgaaaacaattacaagactacccaccatg ctggactcagacggatcatttttcctctactctaagctcactgtgga caagagccggtggcagcaagggaatgtgttcagctgttcagtgatgc atgaggccctgcataaccactacacccagaagagcctttcactgtca cccgggtctggtggcggtgggtcaggtggcggaggatcaggaggagg
```

-continued

```
tggaagcggcggaggaggatctgccaggaacggtgatcactgccctc
tgggccctggtcgctgctgtaggcttcacactgtgcgggcttccctc
gaagatctgggatgggccgactgggtgctgagcccaagagaggtgca
agtgaccatgtgcatcgggcatgtccctcccaattccgcgctgcaa
acatgcatgctcagattaagacttcactgcatagactgaagccagat
accgtcccagcaccctgttgtgtgcccgcttcatacaacccatggt
cctgattcaaaagaccgacaccggggtgtctctccagacctatgatg
atcttcttgcaaaggactgccactgcatctga
``` and comprises the amino acid sequence (hinge regions in parentheses, linker sequences double underlined):

(SEQ ID NO: 123)
GGG(ERKSSVECPPCP)APPVAGPSVFLFPPKPKDTLMISRTPEVT
CVVVDVSHEDPEVQFNWYVDGVEVHNAKTKPREEQFNSTFRVVSVL
TVVHQDWLNGKEYKCKVSNKGLPAPIEKTISKTKGQPREPQVYTLP
PSREEMTKNQVSLTCLVKGFYPSDIAVEWESNGQPENNYKTTPPML
DSDGSFFLYSKLTVDKSRWQQGNVFSCSVMHEALHNHYTQKSLSLS
PG<u>GGGGSGGGGSGGGGS</u>(ERKSSVECPPCP)APPVAGPSVFLFPPK
PKDTLMISRTPEVTCVVVDVSHEDPEVQFNWYVDGVEVHNAKTKPR
EEQFNSTFRVVSVLTVVHQDWLNGKEYKCKVSNKGLPAPIEKTISK
TKGQPREPQVYTLPPSREEMTKNQVSLTCLVKGFYPSDIAVEWESN
GQPENNYKTTPPMLDSDGSFFLYSKLTVDKSRWQQGNVFSCSVMHE
ALHNHYTQKSLSLSP<u>GSGGGGSGGGGSGGGGSGGGGS</u>ARNGDHCPL
GPGRCCRLHTVRASLEDLGWADWVLSPREVQVTMCIGACPSQFRAA
NMHAQIKTSLHRLKPDTVPAPCCVPASYNPMVLIQKTDTGVSLQTY
DDLLAKDCHCI.

In an embodiment employing the VH21 signal sequence, in its final form, the monomer is encoded by the nucleic acid (signal sequence underlined):

(SEQ ID NO: 120)
<u>atggaatggtcatgggtgttccttttctttctctccgtcactaccggtgt
gcactcc</u>ggaggaggcgagaggaagagctccgtggagtgtccaccctgcc
ctgctccgcctgtggctggaccctctgtgttcctgtttccgccgaagcc
aaagacaccctcatgatcagcaggactcccgaggtcacttgtgtggtcgt
ggatgtgagccatgaggacccagaggtgcagttcaactggtacgtggacg
gcgtggaagtccacaacgccaagaccaagccacgcgaggaacagttcaat
agcaccttccgcgtggtcagcgtcctcaccgtggtccaccaggattggct
taacggaaaggaatacaaatgcaaggtgtccaacaaggggcttcctgccc
cgattgaaaagaccatctccaagaccaagggacagccaagggagcccaa
gtgtacactctgccacccagccgcgaagaaatgactaagaatcaagtgtc
tctgacctgtcttgtcaaaggcttctaccccagcgacatcgctgtcgagt
gggaatcaaacgggcagcccgagaacaactacaagaccactcctccaatg ctcgactcagatggcagcttttttcctttactccaagctgaccgtggacaa
gtcaagatggcaacagggtaacgtgttctcatgctccgtgatgcacgaag
ccctccataatcactatacccagaaatctctgtctcttcccgggagga
ggaggggatctggtggaggaggctctggtggtggaggtagcgaacggaa
atcctcagtggagtgcccaccatgcccggctcctccagtggctggtccat
ctgtctttcttttcctccgaaacccaaggacacccttatgatctctcgc
accctgaagtgacttgcgtggtcgtcgatgtgtcacatgaagaccctga
ggtccagttcaattggtatgtggacggagtcgaggtgcataacgccaaaa
ccaaacctcgcgaagaacaattcaactctaccttccgggtggtgtctgtg
ctcactgtcgtccatcaggactggctgaacgggaaggagtacaagtgtaa
ggtgtctaacaaaggcctgccggctcccatcgaaaagactatcagcaaga
ctaaggggcaacccagagaaccccaagtctacaccctgcctccgtcacgg
gaggagatgaccaagaatcaggtgtccctcacctgtctggtcaagggttt
ctaccctagcgacattgctgtggagtgggagagcaatggacagcccgaaa
acaattacaagactaccccacccatgctggactcagacggatcatttttc
ctctactctaagctcactgtggacaagagccggtggcagcaagggaatgt
gttcagctgttcagtgatgcatgaggccctgcataaccactacacccaga
agagcctttcactgtcacccgggtctggtggcggtgggtcaggtggcgga
ggatcaggaggaggtggaagcggcggaggaggatctgccaggaacggtga
tcactgccctctgggccctggtcgctgctgtaggcttcacactgtgcggg
cttccctcgaagatctgggatgggccgactgggtgctgagcccaagagag
gtgcaagtgaccatgtgcatcggggcatgtccctcccaattccgcgctgc
aaacatgcatgctcagattaagacttcactgcatagactgaagccagata
ccgtcccagcaccctgttgtgtgcccgcttcatacaacccatggtcctg
attcaaaagaccgacaccggggtgtctctccagacctatgatgatcttct
tgcaaaggactgccactgcatctga
``` and comprises the amino acid sequence (signal sequence single underlined, hinge regions in parentheses and linker sequences double underlined):

(SEQ ID NO: 121)
<u>MEWSWVFLFFLSVTTGVHS</u>GGG(ERKSSVECPPCP)APPVAGPSVFLF
PPKPKDTLMISRTPEVTCVVVDVSHEDPEVQFNWYVDGVEVHNAKTK
PREEQFNSTFRVVSVLTVVHQDWLNGKEYKCKVSNKGLPAPIEKTISK
TKGQPREPQVYTLPPSREEMTKNQVSLTCLVKGFYPSDIAVEWESNGQ
PENNYKTTPPMLDSDGSFFLYSKLTVDKSRWQQGNVFSCSVMHEALHN
HYTQKSLSLSPG<u>GGGGSGGGGSGGGGS</u>(ERKSSVECPPCP)APPVAGP
SVFLFPPKPKDTLMISRTPEVTCVVVDVSHEDPEVQFNWYVDGVEVHN
AKTKPREEQFNSTFRVVSVLTVVHQDWLNGKEYKCKVSNKGLPAPIEK
TISKTKGQPREPQVYTLPPSREEMTKNQVSLTCLVKGFYPSDIAVEWE
SNGQPENNYKTTPPMLDSDGSFFLYSKLTVDKSRWQQGNVFSCSVMHE
ALHNHYTQKSLSLSP<u>GSGGGGSGGGGSGGGGSGGGGS</u>ARNGDHCPLGP

GRCCRLHTVRASLEDLGWADWVLSPREVQVTMCIGACPSQFRAANMHA

QIKTSLHRLKPDTVPAPCCVPASYNPMVLIQKTDTGVSLQTYDDLLAK

DCHCI.

Two such monomers associate to form the dimer in which the two hGDF15 polypeptides are linked via a disulfide bond between two naturally occurring (i.e., not engineered) cysteine residues. Accordingly, the specific hemiFc dimeric construct Fc-(G$_4$S)$_3$-Fc-GS(G$_4$S)$_4$-GDF15 comprises two monomers comprising SEQ ID NO:123.

II.D.3 Fc-(G$_4$S)$_5$-Fc-GS(G$_4$S)$_4$-GDF15

The hemiFc construct designated "Fc-(G$_4$S)$_5$-Fc-GS(G$_4$S)$_4$-GDF15" in the instant disclosure refers to a construct comprising a monomer, which comprises a mature human GDF15 sequence linked to a first Fc sequence via a first linker comprising SEQ ID NO:31 that connects the N-terminus of the human GDF15 sequence to the C-terminus of the first Fc sequence and a second linker comprising the amino acid sequence:

(SEQ ID NO: 88)
GGGGSGGGGSGGGGSGGGGSGGGGS.

That connects the N-terminus of the first Fc sequence to the C-terminus of the second Fc sequence. The first and second Fc sequences are also associated by the Fc hinge regions. Two such monomers associate to form a homodimer in which the monomers are linked via an interchain disulfide bond between the two GDF15 sequences.

More particularly, in a specific embodiment, the hemiFc construct Fc-(G$_4$S)$_5$-Fc-GS(G$_4$S)$_4$-GDF15 comprises a monomer comprising a second Fc chain comprising the sequence of SEQ ID NO:28 joined by the linker:

(SEQ ID NO: 124)
GGGGGSGGGGSGGGGSGGGGGSGGGGGS to a first Fc chain comprising the sequence of SEQ ID NO:30 to the C-terminus of which, the GDF15 polypeptide comprising SEQ ID NO:12 is joined by a linker having the sequence of SEQ ID NO:31.

In its final form, the monomer is encoded by the nucleic acid sequence:

(SEQ ID NO: 127)
ggcggtggagagcgcaagtcatctgtcgagtgtccgccctgccccgctc cgccggtggctggaccctcagtgttcctctttccaccgaagccgaagga caccccttatgattagccggaccccagaggtcacttgcgtcgtcgtggac gtgtcccatgaggatcccgaagtgcagtttaactggtatgtggacggag tggaggtccataacgccaagaccaagccaagggaagaacagttcaatag caccttccgggtggtgtccgtgctcaccgtggtgcatcaagactggctg aatggcaaagagtacaaatgtaaggtgtcaaacaaggggctcccagccc ctattgaaaagaccatctcaaagactaagggacagccacgcgaacctca agtgtataccctcccgccttcacgcgaagaaatgactaagaatcaggtc agccttacttgtctggtcaagggcttctaccgagcgacattgcagtcg aatgggagagcaatggtcagccagagaataactacaagaccactcctcc catgcttgatagcgatggaagcttttcctttacagcaagcttactgtg gataagtctcgctggcaacagggaaatgtgttcagctgttcagtgatgc atgaagcactccacaatcattacacccagaagtcactcagcctctcacc cggaggaggaggcggttctggtggaggagggtctggaggtggagggagc ggcggaggcgggtctggcggtggtgggtctgagaggaagtcatcagtgg aatgcccaccatgccctgctcctcccgtggccggtccgagcgtgtttct cttcccacctaagcccaaggacactctgatgatctcacggactccggaa gtgacttgtgtggtggtggacgtgtctcatgaggaccctgaagtgcagt tcaactggtacgtggacggcgtggaggtgcacaatgctaagaccaagcc tagagaggaacagttcaattccaccttcgcgtggtgagcgtcctgacc gtcgtgcaccaggactggcttaacggaaaggaatacaagtgcaaggtgt ccaacaaggccttccagctcccattgagaaaaccatctctaaaactaa gggtcaaccaagggaaccccaagtctacaccctccctccgtctagaaa gagatgaccaaaaaccaggtgtccctgacctgtctggtgaagggattt acccctcagacatcgccgtggagtgggaaagcaacggacagcccgaaaa caactataagactacccctcctatgctggactcagacggatctttcttc ctctatagcaagctcactgtggacaaatccagatggcaacaagggaatg tgttctcatgcagcgtgatgcacgaggctcttcacaaccactatcccca gaagagcctgtctctttcacctggttccggaggtggtgggagcggaggg ggtggatcaggtggtggagggtccggaggcggaggatccgcacggaatg gcgaccactgtccactgggacccggaagatgttgtcgcctccacaccgt gagggcctctctggaggaccttggctgggccgactgggtcctgtcacct cgggaggtccaagtcaccatgtgtatcggagcctgccccagccaattca gagcagcaaatatgcacgcacagattaagaccagcctgcatcggcttaa acctgatactgtgccggctccttgttgcgtgccagcatcttacaacccg atggtgctgatccagaaaaccgataccggtgtctccctccagacttacg acgacctccttgcaaaggactgccattgcatctga and comprises the amino acid sequence (hinge regions in parentheses, linker sequences double underlined):

(SEQ ID NO: 128)
GGG(ERKSSVECPPCP)APPVAGPSVFLFPPKPKDTLMISRTPEVTC

VVVDVSHEDPEVQFNWYVDGVEVHNAKTKPREEQFNSTFRVVSVLTV

VHQDWLNGKEYKCKVSNKGLPAPIEKTISKTKGQPREPQVYTLPPSR

EEMTKNQVSLTCLVKGFYPSDIAVEWESNGQPENNYKTTPPMLDSDG

SFFLYSKLTVDKSRWQQGNVFSCSVMHEALHNHYTQKSLSLSPG<u>GGG</u>

<u>GSGGGGSGGGGSGGGGSGGGGS</u>(ERKSSVECPP)CPAPPVAGPSVFL

FPPKPKDTLMISRTPEVTCVVVDVSHEDPEVQFNWYVDGVEVHNAKT

KPREEQFNSTFRVVSVLTVVHQDWLNGKEYKCKVSNKGLPAPIEKTI

SKTKGQPREPQVYTLPPSREEMTKNQVSLTCLVKGFYPSDIAVEWES

NGQPENNYKTTPPMLDSDGSFFLYSKLTVDKSRWQQGNVFSCSVMHE

-continued
ALHNHYTQKSLSLSPGSGGGGSGGGGSGGGGSGGGGSARNGDHCPLG

PGRCCRLHTVRASLEDLGWADWVLSPREVQVTMCIGACPSQFRAANM

HAQIKTSLHRLKPDTVPAPCCVPASYNPMVLIQKTDTGVSLQTYDDL

LAKDCHCI

In an embodiment employing the VH21 signal sequence, in its final form, the monomer is encoded by the nucleic acid (signal sequence underlined):

(SEQ ID NO: 125)
atggagtggagctgggtctttcttttctttctgtctgtgactaccggagt ccattcaggcggtggagagcgcaagtcatctgtcgagtgtccgcctgcc ccgctccgccggtggctggaccctcagtgttcctcttcccaccgaagccg aaggacacccttatgattagccggaccccagaggtcacttgcgtcgtcgt ggacgtgtcccatgaggatcccgaagtgcagtttaactggtatgtggacg gagtggaggtccataacgccaagaccaagccaagggaagaacagttcaat agcaccttccgggtggtgtccgtgctcaccgtggtgcatcaagactggct gaatggcaaagagtacaaatgtaaggtgtcaaacaaggggctcccagccc ctattgaaaagaccatctcaaagactaagggacagccacgcgaacctcaa gtgtatacccctcccgccttcacgcgaagaaatgactaagaatcaggtcag ccttacttgtctggtcaagggcttctacccgagcgacattgcagtcgaat gggagagcaatggtcagccagaataactacaagaccactcctcccatg cttgatagcgatggaagcttttccttacagcaagcttactgtggataa gtctcgctggcaacagggaaatgtgttcagctgttcagtgatgcatgaag cactccacaatcattacacccagaagtcactcagcctctcaccggagga ggaggcggttctggtggaggagggtctggaggtggagggagcggcggagg cgggtctggcggtggtgggtctgagaggaagtcatcagtggaatgccac catgccctgctcctcccgtggccggtccgagcgtgtttctcttcccacct aagcccaaggacactctgatgatctcacggactccggaagtgacttgtgt ggtggtggacgtgtctcatgaggaccctgaagtgcagttcaactggtacg tggacggcgtggaggtgcacaatgctaagaccaagcctagagaggaacag ttcaattccacctttcgcgtggtgagcgtcctgaccgtcgtgcaccagga ctggcttaacggaaaggaatacaagtgcaaggtgtccaacaaaggccttc cagctcccattgagaaaaccatctctaaaactaagggtcaaccaagggaa ccccaagtctacaccctccctccgtctagagaagagatgaccaaaaacca ggtgtccctgacctgtctggtgaagggatttttaccctcagacatcgccg tggagtgggaaagcaacggacagcccgaaaacaactataagactacccct cctatgctggactcagacggatctttcttcctctatagcaagctcactgt ggacaaatccagatggcaacaagggaatgtgttctcatgcagcgtgatgc acgaggctcttcacaaccactatacccagaagagcctgtctctttcacct ggttccggaggtggtgggagcggaggggtggatcaggtggtggagggtc cggaggcggaggatccgcacggaatggcgaccactgtccactgggacccg gaagatgttgtcgcctccacaccgtgagggcctctctggaggaccttggc -continued
tgggccgactgggtcctgtcacctcgggaggtccaagtcaccatgtgtat cggagcctgccccagccaattcagagcagcaaatatgcacgcacagatta agaccagcctgcatcggcttaaacctgatactgtgccggctccttgttgc gtgccagcatcttacaacccgatggtgctgatccagaaaaccgataccgg tgtctccctccagacttacgacgacctccttgcaaaggactgccattgca tctga and comprises the amino acid sequence (signal sequence single underlined, hinge regions in parentheses and linker sequences double underlined):

(SEQ ID NO: 126)
MEWSWVFLFFLSVTTGVHS

GGG(ERKSSVECPPCP)APPVAGPSVFLFPPKPKDTLMISRTPEVTCVVV

DVSHEDPEVQFNWYVDGVEVHNAKTKPREEQFNSTFRVVSVLTVVHQDWL

NGKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVDK

SRWQQGNVFSCSVMHEALHNHYTQKSLSLSPGGGGSGGGGSGGGGSGGG

GSGGGGS(ERKSSVECPPCP)APPVAGPSVFLFPPKPKDTLMISRTPEVT

CVVVDVSHEDPEVQFNWYVDGVEVHNAKTKPREEQFNSTFRVVSVLTVVH

QDWLNGKEYKCKVSNKGLPAPIEKTISKTKGQPREPQVYTLPPSREEMTK

NQVSLTCLVKGFYPSDIAVEWESNGQPENNYKTTPPMLDSDGSFFLYSKL

TVDKSRWQQGNVFSCSVMHEALHNHYTQKSLSLSPGSGGGSGGGSGGG

GSGGGGSARNGDHCPLGPGRCCRLHTVRASLEDLGWADWVLSPREVQVTM

CIGACPSQFRAANMHAQIKTSLHRLKPDTVPAPCCVPASYNPMVLIQKTD

TGVSLQTYDDLLAKDCHCI

Two such monomers associate to form the dimer in which the two hGDF15 polypeptides are linked via a disulfide bond between two naturally occurring (i.e., not engineered) cysteine residues. Accordingly, the specific hemiFc dimeric construct Fc-(G$_4$S)$_5$-Fc-GS(G$_4$S)$_4$-GDF15 comprises two monomers comprising SEQ ID NO:128.

III. GDF15 POLYPEPTIDES AND CONSTRUCTS COMPRISING GDF15, INCLUDING MUTANT FORMS THEREOF

As disclosed herein, the GDF15 polypeptides (including the full length and mature forms of human GDF15) and the constructs comprising GDF15 described in the instant disclosure can be engineered and/or produced using standard molecular biology methodology to form a mutant form of the GDF15 polypeptides and constructs provided herein. In various examples, a nucleic acid sequence encoding a mutant form of the GDF15 polypeptides and constructs provided herein, which can comprise all or a portion of SEQ ID NOs:4, 8 or 12 can be isolated and/or amplified from genomic DNA, or cDNA using appropriate oligonucleotide primers. Primers can be designed based on the nucleic and amino acid sequences provided herein according to standard (RT)-PCR amplification techniques. The amplified GDF15 mutant polypeptide nucleic acid can then be cloned into a suitable vector and characterized by DNA sequence analysis.

Oligonucleotides for use as probes in isolating or amplifying all or a portion of a mutant form of the GDF15 polypeptides and constructs provided herein can be designed and generated using standard synthetic techniques, e.g., automated DNA synthesis apparatus, or can be isolated from a longer sequence of DNA.

III.A. GDF15 Polypeptide and Polynucleotide Sequences

In vivo, GDF15 is expressed as a contiguous amino acid sequence comprising a signal sequence, a pro domain and an active domain.

The 308 amino acid sequence of full length human GDF15 is:

(SEQ ID NO: 4)
MPGQELRTVNGSQMLLVLLVLSWLPHGGALSLAEASRASFPGPSELHSED

SRFRELRKRYEDLLTRLRANQSWEDSNTDLVPAPAVRILTPEVRLGSGGH

LHLRISRAALPEGLPEASRLHRALFRLSPTASRSWDVTRPLRRQLSLARP

QAPALHLRLSPPPSQSDQLLAESSSARPQLELHLRPQAARGRRRARARNG

DHCPLGPGRCCRLHTVRASLEDLGWADWVLSPREVQVTMCIGACPSQFRA

ANMHAQIKTSLHRLKPDTVPAPCCVPASYNPMVLIQKTDTGVSLQTYDDL

LAKDCHCI and is encoded by the DNA sequence:

(SEQ ID NO: 3)
atgcccgggcaagaactcaggacggtgaatggctctcagatgctcctggt gttgctggtgctctcgtggctgccgcatgggggcgccctgtctctggccg aggcgagccgcgcaagtttcccgggacccTcagagttgcactccgaagac tccagattccgagagttgcggaaacgctacgaggacctgctaaccaggct gcgggccaaccagagctgggaagattcgaacaccgacctcgtcccggccc ctgcagtccggatactcacgccagaagtgcggctgggatccggcggccac ctgcacctgcgtatctctcgggccgcccttcccgaggggctccccgaggc ctcccgcctTcaccgggctctgttccggctgtccccgacggcgtcaaggt cgtgggacgtgacacgaccgctgcggcgtcagctcagccttgcaagacc caggcgcccgcgctgcacctgcgactgtcgccgccgccgtcgcagtcgga ccaactgctggcagaatcttcgtccgcacggcccccagctggagttgcact tgcggccgcaagccgccaggggggccgcagagcgcgtgcgcgcaacggg gaccactgtccgctcgggcccgggcgttgctgccgtctgcacacggtccg cgcgtcgctggaagacctgggctgggccgattgggtgctgtcgccacggg aggtgcaagtgaccatgtgcatcggcgcgtgcccgagccagttccgggcg gcaaacatgcacgcgcagatcaagacgagcctgcaccgcctgaagcccga cacggtgccagcgcctgctgcgtgccgccagctacaatcccatggtgc tcattcaaaagaccgacaccggggtgtcgctccagacctatgatgacttg ttagccaaagactgccactgcatatga.

The 303 amino acid sequence of full length murine GDF15 is:

(SEQ ID NO: 6)
MAPPALQAQPPGGSQLRFLLFLLLLLLLLSWPSQGDALAMPEQRPSGPES

QLNADELRGRFQDLLSRLHANQSREDSNSEPSPDPAVRILSPEVRLGSHG

QLLLRVNRASLSQGLPEAYRVHRALLLLTPTARPWDITRPLKRALSLRGP

RAPALRLRLTPPPDLAMLPSGGTQLELRLRVAAGRGRRSAHAHPRDSCPL

GPGRCCHLETVQATLEDLGWSDWVLSPRQLQLSMCVGECPHLYRSANTHA

QIKARLHGLQPDKVPAPCCVPSSYTPVVLMHRTDSGVSLQTYDDLVARGC

HCA and is encoded by the DNA sequence:

(SEQ ID NO: 5)
atggccccgcccgcgctccaggcccagcctccaggcggctctcaactgag gttcctgctgttcctgctgctgttgctgctgctgtcatggccatcgc aggggacgccctggcaatgcctgaacagcgaccctccggccctgagtcc caactcaacgccgacgagctacggggtcgcttccaggacctgctgagccg gctgcatgccaaccagagccgagaggactcgaactcagaaccaagtcctg acccagctgtccggatactcagtccagaggtgagattggggtcccacggc cagctgctactccgcgtcaaccgggcgtcgctgagtcagggtctccccga agcctaccgcgtgcaccgagcgctgctcctgctgacgccgacggcccgcc cctgggacatcactaggccctgaagcgtgcgctcagctccggggaccc cgtgctcccgcattacgcctgcgcctgacgccgcctccggacctggctat gctgccctctggcggcacgcagctggaactgcgcttacgggtagccgccg gcaggggcgccgaagcgcgcatgcgcacccaagagactcgtgcccactg ggtccggggcgctgctgtcacttggagactgtgcaggcaactcttgaaga cttgggctggagcgactgggtgctgtccccgcgccagctgcagctgagca tgtgcgtgggcgagtgtccccacctgtatcgctccgcgaacacgcatgcg cagatcaaagcacgcctgcatggcctgcagcctgacaaggtgcctgcccc gtgctgtgtcccctccagctacacccggtggttcttatgcacaggacag acagtggtgtgtcactgcagacttatgatgacctggtggcccggggctgc cactgcgcttga.

The amino acid sequence of human GDF15 following cleavage of the 29 residue signal sequence is:

(SEQ ID NO: 8)
LSLAEASRASFPGPSELHSEDSRFRELRKRYEDLLTRLRANQSWEDSNTD

LVPAPAVRILTPEVRLGSGGHLHLRISRAALPEGLPEASRLHRALFRLSP

TASRSWDVTRPLRRQLSLARPQAPALHLRLSPPPSQSDQLLAESSSARPQ

LELHLRPQAARGRRRARARNGDHCPLGPGRCCRLHTVRASLEDLGWADWV

LSPREVQVTMCIGACPSQFRAANMHAQIKTSLHRLKPDTVPAPCCVPASY

NPMVLIQKTDTGVSLQTYDDLLAKDCHCI and is encoded by the DNA sequence:

(SEQ ID NO: 7)
ctgtctctggccgaggcgagccgcgcaagtttcccgggaccctcagagtt gcactccgaagactccagattccgagagttgcggaaacgctacgaggacc tgctaaccaggctgcgggccaaccagagctgggaagattcgaacaccgac ctcgtcccggccctgcagtccggatactcacgccagaagtgcggctggg atccggcggccacctgcacctgctatctctcgggccgcccttcccgagg ggctccccgaggcctcccgccttcaccgggctctgttccggctgtcccg acggcgtcaaggtcgtgggacgtgacacgaccgctgcggcgtcagctcag ccttgcaagaccccaggcgcccgcgctgcacctgcgactgtcgccgccgc cgtcgcagtcggaccaactgctggcagaatcttcgtccgcacggccccag ctggagttgcacttgccggccgcaagccgccaggggggcgccgcagagcgcg tgcgcgcaacggggaccactgtccgctcgggcccgggcgttgctgccgtc tgcacacggtccgcgcgtcgctggaagacctgggctgggccgattgggtg ctgtcgccacgggaggtgcaagtgaccatgtgcatcggcgcgtgcccgag ccagttccgggcggcaaacatgcacgcgcagatcaagacgagcctgcacc gcctgaagcccgacacggtgccagcgccctgctgcgtgcccgccagctac aatcccatggtgctcattcaaaagaccgacaccggggtgtcgctccagac ctatgatgacttgttagccaaagactgccactgcatatga The amino acid sequence of murine GDF15 following cleavage of the 32 residue signal sequence is:

(SEQ ID NO: 10)
SQGDALAMPEQRPSGPESQLNADELRGRFQDLLSRLHANQSREDSNSEPS

PDPAVRILSPEVRLGSHGQLLLRVNRASLSQGLPEAYRVHRALLLLTPTA

RPWDITRPLKRALSLRGPRAPALRLRLTPPPDLAMLPSGGTQLELRLRVA

AGRGRRSAHAHPRDSCPLGPGRCCHLETVQATLEDLGWSDWVLSPRQLQL

SMCVGECPHLYRSANTHAQIKARLHGLQPDKVPAPCCVPSSYTPVVLMHR

TDSGVSLQTYDDLVARGCHCA and is encoded by the DNA sequence:

(SEQ ID NO: 9)
tcgcaggggacgccctggcaatgcctgaacagcgaccctccggccctga gtcccaactcaacgccgacgagctacgggtcgcttccaggacctgctga gccggctgcatgccaaccagagccgagaggactcgaactcagaaccaagt cctgacccagctgtccggatactcagtccagaggtgagattggggtccca cggccagctgctactccgcgtcaaccgggcgtcgctgagtcagggtctcc ccgaagcctaccgcgtgcaccgagcgctgctcctgctgacgccgacggcc cgcccctgggacatcactaggcccctgaagcgtgcgctcagcctccgggg acccgtgctccgcattacgcctgcgcctgacgccgcctccggacctgg ctatgctgccctctggcggcacgcagctggaactgcgcttacgggtagcc gccggcagggggcgccgaagcgcgcatgcgcacccaagagactcgtgccc actgggtccggggcgctgctgtcacttggagactgtgcaggcaactcttg aagacttgggctggagcgactgggtgctgtccccgcgccagctgcagctg agcatgtgcgtgggcgagtgtccccacctgtatcgctccgcgaacacgca tgcgcagatcaaagcacgcctgcatggcctgcagcctgacaaggtgcctg ccccgtgctgtgtccctccagctacaccccggtggttcttatgcacagg acagacagtggtgtgtcactgcagacttatgatgacctggtggcccgggg ctgccactgcgcttga The amino acid sequence of the recombinant active form of the human GDF15, which comprises a homodimer comprising nine cysteines in each monomer to form one interchain disulfide bond and four intrachain disulfide bonds (shown with an optional N-terminal methionine residue in parentheses), is:

(SEQ ID NO: 129)
(M)ARNGDHCPLGPGRCCRLHTVRASLEDLGWADWVLSPREVQVTMCIGA

CPSQFRAANMHAQIKTSLHRLKPDTVPAPCCVPASYNPMVLIQKTDTGVS

LQTYDDLLAKDCHCI and is encoded by the DNA sequence (shown with an optional N-terminal methionine codon in parentheses):

(SEQ ID NO: 130)
(atg)gcgcgcaacggggaccactgtccgctcgggcccgggcgttgctgc cgtctgcacacggtccgcgcgtcgctggaagacctgggctgggccgattg ggtgctgtcgccacgggaggtgcaagtgaccatgtgcatcggcgcgtgcc cgagccagttccgggcggcaaacatgcacgcgcagatcaagacgagcctg caccgcctgaagcccgacacggtgccagcgccctgctgcgtgcccgccag ctacaatcccatggtgctcattcaaaagaccgacaccggggtgtcgctcc agacctatgatgacttgttagccaaagactgccactgcatataa.

The amino acid sequence of the recombinant active form of the murine GDF15, which comprises a homodimer comprising nine cysteines in each monomer to form one interchain disulfide bond and four intrachain disulfide bonds, is:

(SEQ ID NO: 14)
(M)SAHAHPRDSCPLGPGRCCHLETVQATLEDLGWSDWVLSPRQLQLSMC

VGECPHLYRSANTHAQIKARLHGLQPDKVPAPCCVPSSYTPVVLMHRTDS

GVSLQTYDDLVARGCHCA and is encoded by the DNA sequence:

(SEQ ID NO: 13)
(atg)agcgcgcatgcgcacccaagagactcgtgccactgggtccgggg cgctgctgtcacctggagactgtgcaggcaactcttgaagacttggctg gagcgactgggtgttgtccccgcgccagctgcagctgagcatgtgcgtgg gcgagtgtccccacctgtatcgctccgcgaacacgcatgcgcagatcaaa gcacgcctgcatggcctgcagcctgacaaggtgcctgccccgtgctgtgt -continued

```
cccctccagctacaccccggtggttcttatgcacaggacagacagtggtg tgtcactgcagacttatgatgacctggtggcccggggctgccactgcgct tga.
```

As stated herein, the term "GDF15 polypeptide" refers to a GDF polypeptide comprising the human amino acid sequences SEQ ID NOs:4, 8 and 12. The term "GDF15 mutant polypeptide," however, encompasses polypeptides comprising an amino acid sequence that differs from the amino acid sequence of a naturally occurring GDF polypeptide sequence, e.g., SEQ ID NOs: 4, 8 and 12, by one or more amino acids, such that the sequence is at least 85% identical to SEQ ID NOs: 4, 8 and 12. GDF15 polypeptides can be generated by introducing one or more amino acid substitutions, either conservative or non-conservative and using naturally or non-naturally occurring amino acids, at particular positions of the GDF15 polypeptide, or by deleting particular residues or stretches of residues.

A "conservative amino acid substitution" can involve a substitution of a native amino acid residue (i.e., a residue found in a given position of the wild-type GDF15 polypeptide sequence) with a non-native residue (i.e., a residue that is not found in a given position of the wild-type GDF15 polypeptide sequence) such that there is little or no effect on the polarity or charge of the amino acid residue at that position. Conservative amino acid substitutions also encompass non-naturally occurring amino acid residues (as defined herein) that are typically incorporated by chemical peptide synthesis rather than by synthesis in biological systems. These include peptidomimetics, and other reversed or inverted forms of amino acid moieties.

Naturally occurring residues can be divided into classes based on common side chain properties:
(1) hydrophobic: norleucine, Met, Ala, Val, Leu, Ile;
(2) neutral hydrophilic: Cys, Ser, Thr;
(3) acidic: Asp, Glu;
(4) basic: Asn, Gln, H is, Lys, Arg;
(5) residues that influence chain orientation: Gly, Pro; and
(6) aromatic: Trp, Tyr, Phe.

Additional groups of amino acids can also be formulated using the principles described in, e.g., Creighton (1984) PROTEINS: STRUCTURE AND MOLECULAR PROPERTIES (2d Ed. 1993), W.H. Freeman and Company. In some instances it can be useful to further characterize substitutions based on two or more of such features (e.g., substitution with a "small polar" residue, such as a Thr residue, can represent a highly conservative substitution in an appropriate context).

Conservative substitutions can involve the exchange of a member of one of these classes for another member of the same class. Non-conservative substitutions can involve the exchange of a member of one of these classes for a member from another class.

Synthetic, rare, or modified amino acid residues having known similar physiochemical properties to those of an above-described grouping can be used as a "conservative" substitute for a particular amino acid residue in a sequence. For example, a D-Arg residue may serve as a substitute for a typical L-Arg residue. It also can be the case that a particular substitution can be described in terms of two or more of the above described classes (e.g., a substitution with a small and hydrophobic residue means substituting one amino acid with a residue(s) that is found in both of the above-described classes or other synthetic, rare, or modified residues that are known in the art to have similar physiochemical properties to such residues meeting both definitions).

Nucleic acid sequences encoding a GDF15 mutant polypeptide provided herein, including those degenerate to SEQ ID NOs: 3, 7, 11 and 15, and those encoding polypeptide variants of SEQ ID NOs:4, 8 and 12, form other aspects of the instant disclosure.

III.B. Vectors Useful for Expressing GDF15 Polypeptides and Constructs Comprising GDF15, Including Mutant Forms Thereof In order to express the nucleic acid sequences encoding the GDF15 polypeptides and construct comprising GDF15 provided herein, the appropriate coding sequences, e.g., SEQ ID NOs:3, 7, 11, 15, 17, 21, 24, 26 and 32, can be cloned into a suitable vector and after introduction in a suitable host, the sequence can be expressed to produce the encoded polypeptide according to standard cloning and expression techniques, which are known in the art (e.g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989). The invention also relates to such vectors comprising a nucleic acid sequence according to the invention.

A "vector" refers to a delivery vehicle that (a) promotes the expression of a polypeptide-encoding nucleic acid sequence; (b) promotes the production of the polypeptide therefrom; (c) promotes the transfection/transformation of target cells therewith; (d) promotes the replication of the nucleic acid sequence; (e) promotes stability of the nucleic acid; (f) promotes detection of the nucleic acid and/or transformed/transfected cells; and/or (g) otherwise imparts advantageous biological and/or physiochemical function to the polypeptide-encoding nucleic acid. A vector can be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors.

A recombinant expression vector can be designed for expression of a GDF15 mutant polypeptide in prokaryotic (e.g., E. coli) or eukaryotic cells (e.g., insect cells, using baculovirus expression vectors, yeast cells, or mammalian cells). Representative host cells include those hosts typically used for cloning and expression, including Escherichia coli strains TOP10F', TOP10, DH10B, DH5a, HB101, W3110, BL21(DE3) and BL21 (DE3)pLysS, BLUESCRIPT (Stratagene), mammalian cell lines CHO, CHO-K1, HEK293, 293-EBNA pIN vectors (Van Heeke & Schuster, *J. Biol. Chem.* 264: 5503-5509 (1989); pET vectors (Novagen, Madison Wis.). Alternatively, the recombinant expression vector can be transcribed and translated in vitro, for example using T7 promoter regulatory sequences and T7 polymerase and an in vitro translation system. Preferably, the vector contains a promoter upstream of the cloning site containing the nucleic acid sequence encoding the polypeptide. Examples of promoters, which can be switched on and off, include the lac promoter, the T7 promoter, the trc promoter, the tac promoter and the trp promoter.

Thus, provided herein are vectors comprising a nucleic acid sequence encoding a GDF15 polypeptide or construct comprising a GDF15 polypeptide, including mutant forms thereof, that facilitate the expression of the polypeptide or construct of interest. In various embodiments, the vectors comprise an operably linked nucleotide sequence which regulates the expression of a GDF15 polypeptide construct comprising a GDF15 polypeptide or a mutant form thereof. A vector can comprise or be associated with any suitable promoter, enhancer, and other expression-facilitating elements. Examples of such elements include strong expression promoters (e.g., a human CMV IE promoter/enhancer, an RSV promoter, SV40 promoter, SL3-3 promoter, MMTV promoter, or HIV LTR promoter, EF1alpha promoter, CAG promoter), effective poly (A) termination sequences, an origin of replication for plasmid product in E. coli, an antibiotic resistance gene as a selectable marker, and/or a convenient cloning site (e.g., a polylinker). Vectors also can comprise an inducible promoter as opposed to a constitutive promoter such as CMV IE. In one aspect, a nucleic acid comprising a sequence encoding a GDF15 polypeptide, construct comprising a GDF15 polypeptide or a mutant form thereof, which is operatively linked to a tissue specific promoter which promotes expression of the sequence in a metabolically-relevant tissue, such as liver or pancreatic tissue is provided.

III.C. Host Cells

In another aspect of the instant disclosure, host cells comprising the nucleic acids and vectors disclosed herein are provided. In various embodiments, the vector or nucleic acid is integrated into the host cell genome, which in other embodiments the vector or nucleic acid is extra-chromosomal.

Recombinant cells, such as yeast, bacterial (e.g., E. coli), and mammalian cells (e.g., immortalized mammalian cells) comprising such a nucleic acid, vector, or combinations of either or both thereof are provided. In various embodiments, cells comprising a non-integrated nucleic acid, such as a plasmid, cosmid, phagemid, or linear expression element, which comprises a sequence coding for expression of a GDF15 polypeptide, construct comprising a GDF15 polypeptide or a mutant form thereof, are provided.

A vector comprising a nucleic acid sequence encoding a GDF15 mutant polypeptide provided herein can be introduced into a host cell by transformation or by transfection. Methods of transforming a cell with an expression vector are well known.

A nucleic acid encoding a GDF15 polypeptide-, construct comprising a GDF15 polypeptide or a mutant form thereof can be positioned in and/or delivered to a host cell or host animal via a viral vector. Any suitable viral vector can be used in this capacity. A viral vector can comprise any number of viral polynucleotides, alone or in combination with one or more viral proteins, which facilitate delivery, replication, and/or expression of the nucleic acid of the invention in a desired host cell. The viral vector can be a polynucleotide comprising all or part of a viral genome, a viral protein/nucleic acid conjugate, a virus-like particle (VLP), or an intact virus particle comprising viral nucleic acids and a GDF15 mutant polypeptide-encoding nucleic acid. A viral particle viral vector can comprise a wild-type viral particle or a modified viral particle. The viral vector can be a vector which requires the presence of another vector or wild-type virus for replication and/or expression (e.g., a viral vector can be a helper-dependent virus), such as an adenoviral vector amplicon. Typically, such viral vectors consist of a wild-type viral particle, or a viral particle modified in its protein and/or nucleic acid content to increase transgene capacity or aid in transfection and/or expression of the nucleic acid (examples of such vectors include the herpes virus/AAV amplicons). Typically, a viral vector is similar to and/or derived from a virus that normally infects humans. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, flaviviral vectors, alphaviral vectors, herpes viral vectors, pox virus vectors, retroviral vectors, including lentiviral vectors.

III.D. Isolation of a GDF15 Polypeptide, Construct Comprising a GDF15 Polypeptide or a Mutant Form Thereof A GDF15 polypeptide, construct comprising a GDF15 polypeptide or a mutant form thereof expressed as described herein can be isolated using standard protein purification methods. A GDF15 polypeptide, construct comprising a GDF15 polypeptide or a mutant form thereof can be isolated from a cell that has been engineered to express a GDF15 polypeptide, construct comprising a GDF15 polypeptide or a mutant form thereof, for example a cell that does not naturally express native GDF15.

Protein purification methods that can be employed to isolate a GDF15 mutant polypeptide, as well as associated materials and reagents, are known in the art. Exemplary methods of purifying a GDF15 polypeptide, construct comprising a GDF15 polypeptide or a mutant form thereof are provided in the Examples herein below. Additional purification methods that may be useful for isolating a GDF15 polypeptide, construct comprising a GDF15 polypeptide or a mutant form thereof can be found in references such as Bootcov M R, 1997, *Proc. Natl. Acad. Sci. USA* 94:11514-9, Fairlie W D, 2000, *Gene* 254: 67-76.

IV. PHARMACEUTICAL COMPOSITIONS COMPRISING A GDF15 POLYPEPTIDE, CONSTRUCT COMPRISING A GDF15 POLYPEPTIDE OR A MUTANT FORM THEREOF

Pharmaceutical compositions comprising a GDF15 polypeptide, construct comprising a GDF15 polypeptide or a mutant form thereof are provided. Such polypeptide pharmaceutical compositions can comprise a therapeutically effective amount of a GDF15 polypeptide, construct comprising a GDF15 polypeptide or a mutant form thereof in admixture with a pharmaceutically or physiologically acceptable formulation agent selected for suitability with the mode of administration. The term "pharmaceutically acceptable carrier" or "physiologically acceptable carrier" as used herein refers to one or more formulation agents suitable for accomplishing or enhancing the delivery of a GDF15 polypeptide, construct comprising a GDF15 polypeptide or a mutant form thereof into the body of a human or non-human subject. The term includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In some cases it will be preferable to include isotonic agents, for example, sugars, polyalcohols such as mannitol, sorbitol, or sodium chloride in a pharmaceutical composition. Pharmaceutically acceptable substances such as wetting or minor amounts of auxiliary substances such as wetting or emulsifying agents, preservatives or buffers, which enhance the shelf life or effectiveness of the GDF15 polypeptide, construct comprising a GDF15 polypeptide or a mutant form thereof polypeptide can also act as, or form a component of, a carrier.

Acceptable pharmaceutically acceptable carriers are preferably nontoxic to recipients at the dosages and concentrations employed.

A pharmaceutical composition can contain formulation agent(s) for modifying, maintaining, or preserving, for example, the pH, osmolarity, viscosity, clarity, color, isotonicity, odor, sterility, stability, rate of dissolution or release, adsorption, or penetration of the composition. Suitable formulation agents include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as free serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as Polysorbate 20 or Polysorbate 80; Triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON: THE SCIENCE AND PRACTICE OF PHARMACY, 19th edition, (1995); Berge et al., J. Pharm. Sci., 6661), 1-19 (1977). Additional relevant principles, methods, and agents are described in, e.g., Lieberman et al., PHARMACEUTICAL DOSAGE FORMS-DISPERSE SYSTEMS (2nd ed., vol. 3, 1998); Ansel et al., PHARMACEUTICAL DOSAGE FORMS & DRUG DELIVERY SYSTEMS (7th ed. 2000); Martindale, THE EXTRA PHARMACOPEIA (31st edition), Remington's PHARMACEUTICAL SCIENCES (16th-20$^{th}$ and subsequent editions); The Pharmacological Basis Of Therapeutics, Goodman and Gilman, Eds. (9th ed.—1996); Wilson and Gisvolds' TEXTBOOK OF ORGANIC MEDICINAL AND PHARMACEUTICAL CHEMISTRY, Delgado and Remers, Eds. (10th ed., 1998). Principles of formulating pharmaceutically acceptable compositions also are described in, e.g., Aulton, PHARMACEUTICS: THE SCIENCE OF DOSAGE FORM DESIGN, Churchill Livingstone (New York) (1988), EXTEMPORANEOUS ORAL LIQUID DOSAGE PREPARATIONS, CSHP (1998), incorporated herein by reference for any purpose).

The optimal pharmaceutical composition will be determined by a skilled artisan depending upon, for example, the intended route of administration, delivery format, and desired dosage (see, e.g., Remington's PHARMACEUTICAL SCIENCES, supra). Such compositions can influence the physical state, stability, rate of in vivo release, and rate of in vivo clearance of a GDF15 polypeptide, construct comprising a GDF15 polypeptide or a mutant form thereof.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with free serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the present invention, compositions comprising a GDF15 polypeptide, construct comprising a GDF15 polypeptide or a mutant form thereof can be prepared for storage by mixing the selected composition having the desired degree of purity with optional formulation agents (Remington's PHARMACEUTICAL SCIENCES, supra) in the form of a lyophilized cake or an aqueous solution. Furthermore, a product comprising a GDF15 polypeptide, construct comprising a GDF15 polypeptide or a mutant form thereof can be formulated as a lyophilizate using appropriate excipients such as sucrose.

The polypeptide pharmaceutical compositions can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention can be in the form of a pyrogen-free, parenterally acceptable, aqueous solution comprising a desired GDF15 polypeptide, construct comprising a GDF15 polypeptide or a mutant form thereof, in a pharmaceutically acceptable vehicle. A particularly suitable vehicle for parenteral injection is sterile distilled water in which a GDF15 polypeptide, construct comprising a GDF15 polypeptide or a mutant form thereof, is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a GDF15 mutant polypeptide can be formulated as a dry powder for inhalation. GDF15 polypeptide inhalation solutions can also be formulated with a propellant for aerosol delivery. In yet another embodiment, solutions can be nebulized. Pulmonary administration is further described in International Publication No. WO 94/20069, which describes the pulmonary delivery of chemically modified proteins.

It is also contemplated that certain formulations can be administered orally. In one embodiment of the present invention, a GDF15 polypeptide, construct comprising a GDF15 polypeptide or a mutant form thereof that is administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of a GDF15 polypeptide, construct comprising a GDF15 polypeptide or a mutant form thereof. Diluents, flavorings, low melting point waxes, vegetable oils, lubricants, suspending agents, tablet disintegrating agents, and binders can also be employed.

Another pharmaceutical composition can involve an effective quantity of a GDF15 polypeptide, construct comprising a GDF15 polypeptide or a mutant form thereof in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions comprising a GDF15 polypeptide, construct comprising a GDF15 polypeptide or a mutant form thereof will be evident to those skilled in the art, including formulations comprising a GDF15 polypeptide, construct comprising a GDF15 polypeptide or a mutant form thereof, in sustained- or controlled-delivery formulations. Techniques for formulating a variety of other sustained- or controlled-delivery means, such as liposome carriers, bio-erodible microparticles or porous beads and depot injections, are also known to those skilled in the art (see, e.g., International Publication No. WO 93/15722, which describes the controlled release of porous polymeric microparticles for the delivery of pharmaceutical compositions, and Wischke & Schwendeman, 2008, Int. J. Pharm. 364: 298-327, and Freiberg & Zhu, 2004, Int. J. Pharm. 282: 1-18, which discuss microsphere/microparticle preparation and use). As described herein, a hydrogel is an example of a sustained- or controlled-delivery formulation.

Additional examples of sustained-release preparations include semipermeable polymer matrices in the form of shaped articles, e.g. films, or microcapsules. Sustained release matrices can include polyesters, hydrogels, polylactides (U.S. Pat. No. 3,773,919 and European Patent No. 0 058 481), copolymers of L-glutamic acid and gamma ethyl-L-glutamate (Sidman et al., 1983, Biopolymers 22: 547-56), poly(2-hydroxyethyl-methacrylate) (Langer et al., 1981, J. Biomed. Mater. Res. 15: 167-277 and Langer, 1982, Chem. Tech. 12: 98-105), ethylene vinyl acetate (Langer et al., supra) or poly-D(-)-3-hydroxybutyric acid (European Patent No. 0 133 988). Sustained-release compositions can also include liposomes, which can be prepared by any of several methods known in the art. See, e.g., Epstein et al., 1985, Proc. Natl. Acad. Sci. U.S.A. 82: 3688-92; and European Patent Nos. 0 036 676, 0 088 046, and 0 143 949.

A pharmaceutical composition comprising a GDF15 polypeptide, construct comprising a GDF15 polypeptide or a mutant form thereof, which is to be used for in vivo administration typically should be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

In a specific embodiment, the present invention is directed to kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

The effective amount of pharmaceutical composition comprising a GDF15 polypeptide, construct comprising a GDF15 polypeptide or a mutant form thereof, which is to be employed therapeutically will depend, for example, upon the therapeutic context and objectives. One skilled in the art will appreciate that the appropriate dosage levels for treatment will thus vary depending, in part, upon the molecule delivered, the indication for which a GDF15 polypeptide, construct comprising a GDF15 polypeptide or a mutant form thereof, is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg; or 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 100 µg/kg, 200 µg/kg or up to about 10 mg/kg.

The frequency of dosing will depend upon the pharmacokinetic parameters of the GDF15 polypeptide, construct comprising a GDF15 polypeptide or a mutant form thereof, in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems (which may also be injected); or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

In order to deliver drug, e.g., a GDF15 polypeptide, construct comprising a GDF15 polypeptide or a mutant form thereof, at a predetermined rate such that the drug concentration can be maintained at a desired therapeutically effective level over an extended period, a variety of different approaches can be employed. In one example, a hydrogel comprising a polymer such as a gelatin (e.g., bovine gelatin, human gelatin, or gelatin from another source) or a naturally-occurring or a synthetically generated polymer can be employed. Any percentage of polymer (e.g., gelatin) can be employed in a hydrogel, such as 5, 10, 15 or 20%. The selection of an appropriate concentration can depend on a variety of factors, such as the therapeutic profile desired and the pharmacokinetic profile of the therapeutic molecule.

Examples of polymers that can be incorporated into a hydrogel include polyethylene glycol ("PEG"), polyethylene oxide, polyethylene oxide-co-polypropylene oxide, co-polyethylene oxide block or random copolymers, polyvinyl alcohol, poly(vinyl pyrrolidinone), poly(amino acids), dextran, heparin, polysaccharides, polyethers and the like.

Another factor that can be considered when generating a hydrogel formulation is the degree of crosslinking in the hydrogel and the crosslinking agent. In one embodiment, cross-linking can be achieved via a methacrylation reaction involving methacrylic anhydride. In some situations, a high degree of cross-linking may be desirable while in other situations a lower degree of crosslinking is preferred. In some cases a higher degree of crosslinking provides a longer sustained release. A higher degree of crosslinking may provide a firmer hydrogel and a longer period over which drug is delivered.

Any ratio of polymer to crosslinking agent (e.g., methacrylic anhydride) can be employed to generate a hydrogel with desired properties. For example, the ratio of polymer to crosslinker can be, e.g., 8:1, 16:1, 24:1, or 32:1. For example, when the hydrogel polymer is gelatin and the crosslinker is methacrylate, ratios of 8:1, 16:1, 24:1, or 32:1 methyacrylic anhydride:gelatin can be employed.

V. THERAPEUTIC USES OF A GDF15 POLYPEPTIDE, CONSTRUCT COMPRISING A GDF15 POLYPEPTIDE OR A MUTANT FORM THEREOF

A GDF15 polypeptide, construct comprising a GDF15 polypeptide or a mutant form thereof, can be used to treat, diagnose or ameliorate, a metabolic condition or disorder. In one embodiment, the metabolic disorder to be treated is diabetes, e.g., type 2 diabetes. In another embodiment, the metabolic condition or disorder is obesity. In other embodiments the metabolic condition or disorder is dyslipidemia, elevated glucose levels, elevated insulin levels or diabetic nephropathy. For example, a metabolic condition or disorder that can be treated or ameliorated using a GDF15 polypeptide, construct comprising a GDF15 polypeptide or a mutant form thereof, includes a state in which a human subject has a fasting blood glucose level of 125 mg/dL or greater, for example 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL. Conditions that can be treated using a pharmaceutical composition comprising a GDF15 mutant polypeptide can also be found in the American Diabetes Association Standards of Medical Care in Diabetes Care-2011, American Diabetes Association, Diabetes Care Vol. 34, No. Supplement 1, S11-S61, 2010, incorporated herein by reference.

In application, a metabolic disorder or condition, such as Type 2 diabetes, elevated glucose levels, elevated insulin levels, dyslipidemia, obesity or diabetic nephropathy, can be treated by administering a therapeutically effective dose of a GDF15 polypeptide, construct comprising a GDF15 polypeptide or a mutant form thereof, to a patient in need thereof. The administration can be performed as described herein, such as by IV injection, intraperitoneal (IP) injection, subcutaneous injection, intramuscular injection, or orally in the form of a tablet or liquid formation. In some situations, a therapeutically effective or preferred dose of a GDF15 polypeptide, construct comprising a GDF15 polypeptide or a mutant form thereof, can be determined by a clinician. A therapeutically effective dose of a GDF15 polypeptide, construct comprising a GDF15 polypeptide or a mutant form thereof, will depend, inter alia, upon the administration schedule, the unit dose of agent administered, whether the GDF15 polypeptide, construct comprising a GDF15 polypeptide or a mutant form thereof is administered in combination with other therapeutic agents, the immune status and the health of the recipient. The term "therapeutically effective dose," as used herein, means an amount of a GDF15 polypeptide, construct comprising a GDF15 polypeptide or a mutant form thereof, that elicits a biological or medicinal response in a tissue system, animal, or human being sought by a researcher, medical doctor, or other clinician, which includes alleviation or amelioration of the symptoms of the disease or disorder being treated, i.e., an amount of a GDF15 polypeptide, construct comprising a GDF15 polypeptide or a mutant form thereof, that supports an observable level of one or more desired biological or medicinal response, for example lowering blood glucose, insulin, triglyceride, or cholesterol levels; reducing body weight; or improving glucose tolerance, energy expenditure, or insulin sensitivity.

It is noted that a therapeutically effective dose of a GDF15 polypeptide, construct comprising a GDF15 polypeptide or a mutant form thereof, can also vary with the desired result. Thus, for example, in situations in which a lower level of blood glucose is indicated a dose of a GDF15 mutant polypeptide will be correspondingly higher than a dose in which a comparatively lower level of blood glucose is desired. Conversely, in situations in which a higher level of blood glucose is indicated at a dose of a GDF15 polypeptide, construct comprising a GDF15 polypeptide or a mutant form thereof, will be correspondingly lower than a dose in which a comparatively higher level of blood glucose is desired.

In various embodiments, a subject is a human having a blood glucose level of 100 mg/dL or greater can be treated with a GDF15 polypeptide, construct comprising a GDF15 polypeptide or a mutant form thereof.

In one embodiment, a method of the instant disclosure comprises first measuring a baseline level of one or more metabolically-relevant compounds such as glucose, insulin, cholesterol, lipid in a subject. A pharmaceutical composition comprising a GDF15 polypeptide, construct comprising a GDF15 polypeptide or a mutant form thereof, is then administered to the subject. After a desired period of time, the level of the one or more metabolically-relevant compounds (e.g., blood glucose, insulin, cholesterol, lipid) in the subject is again measured. The two levels can then be compared in order to determine the relative change in the metabolically-relevant compound in the subject. Depending on the outcome of that comparison another dose of the pharmaceutical composition comprising a GDF15 polypeptide, construct comprising a GDF15 polypeptide or a mutant form thereof, can be administered to achieve a desired level of one or more metabolically-relevant compound.

It is noted that a pharmaceutical composition comprising a GDF15 polypeptide, construct comprising a GDF15 polypeptide or a mutant form thereof, can be co-administered with another compound. The identity and properties of compound co-administered with the GDF15 mutant polypeptide will depend on the nature of the condition to be treated or ameliorated. A non-limiting list of examples of compounds that can be administered in combination with a pharmaceutical composition comprising a GDF15 polypeptide, construct comprising a GDF15 polypeptide or a mutant form thereof, include rosiglitizone, pioglitizone, repaglinide, nateglitinide, metformin, exenatide, stiagliptin, pramlintide, glipizide, glimeprirideacarbose, and miglitol.

VI. KITS

Also provided are kits for practicing the disclosed methods. Such kits can comprise a pharmaceutical composition such as those described herein, including nucleic acids encoding the peptides or proteins provided herein, vectors and cells comprising such nucleic acids, and pharmaceutical compositions comprising such nucleic acid-containing compounds, which can be provided in a sterile container. Optionally, instructions on how to employ the provided pharmaceutical composition in the treatment of a metabolic disorder can also be included or be made available to a patient or a medical service provider.

In one aspect, a kit comprises (a) a pharmaceutical composition comprising a therapeutically effective amount of a GDF15 polypeptide, construct comprising a GDF15 polypeptide or a mutant form thereof; and (b) one or more containers for the pharmaceutical composition. Such a kit can also comprise instructions for the use thereof; the instructions can be tailored to the precise metabolic disorder being treated. The instructions can describe the use and nature of the materials provided in the kit. In certain embodiments, kits include instructions for a patient to carry out administration to treat a metabolic disorder, such as elevated glucose levels, elevated insulin levels, obesity, type 2 diabetes, dyslipidemia or diabetic nephropathy.

Instructions can be printed on a substrate, such as paper or plastic, etc, and can be present in the kits as a package insert, in the labeling of the container of the kit or components thereof (e.g., associated with the packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, such as over the internet, are provided. An example of this embodiment is a kit that includes a web address where the instructions can be viewed and/or from which the instructions can be downloaded.

Often it will be desirable that some or all components of a kit are packaged in suitable packaging to maintain sterility. The components of a kit can be packaged in a kit containment element to make a single, easily handled unit, where the kit containment element, e.g., box or analogous structure, may or may not be an airtight container, e.g., to further preserve the sterility of some or all of the components of the kit.

EXAMPLES

The following examples, including the experiments conducted and results achieved, are provided for illustrative purposes only and are not to be construed as limiting the present invention.

Example 1

Preparation of Native GDF15 Polypeptides

CHO—S stable cell line growth and transfection was carried out using six-well plates containing a transfection medium (CD-CHO, 4×L-Glutamine, 1×HT, 1×P/S/G). The day before transfection, cultured cells were split to a concentration of $5e^5$ viable cells (vc)/ml. A transfection complex formation was made using 4 µg Linear DNA/500 Optimem, 10 µl LF-LTX/500 µl Optimem, and a 20 minute incubation period. Cells were then prepared by centrifugation at $1e^6$ vc/well, washed in DPBS, and resuspend in 1 ml Optimem. Next, 1 ml of transfection complex was added to $1e^6$ cells in the 6-well plates and incubated for 6 hours with shaking followed by addition 2 ml of MIX-6 Media (w/o antibiotics). Selection was started on the second day using MIX-6 Media with 6 µg/ml Puromycin and replacing media every 2-3 days for 10-12 days by centrifugation of the cells and re-suspension in media.

Cells that were transformed with a GDF15 expression vector constructed with an affinity tag were grown to an optical density of 9 at 600 nm and then induced and harvested at an optical density of 63 by centrifugation 6 hours later. Frozen cell paste was thawed and re-suspended into buffer at 15% (wt./vol.) with a low shear homogenizer until the slurry was homogeneous. The cells were then subjected to high shear homogenization to break open and release product-containing inclusion bodies. The resulting homogenate was then centrifuged at 5,000×g for an hour at 5 C to harvest the inclusion bodies as a pellet, leaving the cytoplasmic contaminants in the discarded supernatant. The residual cytoplasm is washed from the inclusion bodies by homogeneously re-suspending the pellet to the original homogenate volume using chilled water and a low shear homogenizer followed by centrifugation as before. The resulting pellet, washed inclusion bodies (WIBS), is then frozen at −80 C.

A sufficient amount of WIBS and guanidine hydrochloride (GnHCl) was used at pH 8.5 in a reducing-solubilization to result in approximately 25 mg/ml reduced product and 6 M GnHCl final concentrations. The solubilization was then rapidly diluted 25-fold with stirring into a refolding buffer containing redox reagents, chaotrope and co-solvents at alkaline pH. The refold solution was allowed to gently stir and air oxidize at 6 C for 72 hours or until the solution was negative to Ellman's reagent. The refold solution at 5 C was then clarified by depth filtration to allow for a 10-fold ultra-filtration concentration and subsequent diafiltration into a buffer containing 50 mM sodium phosphate and low chaotrope concentration at pH 8.5. The subsequent retentate was warmed to 25 C and then the pH lowered into the acidic range to cause precipitation of contaminants. The precipitate was removed by centrifugation at 5,000×g for 30 min at 25 C and the resulting supernatant further clarified by 0.45 um filtration. The filtrate (AP) was then adjusted to pH 8.5, and low salt concentration to permit the first step of purification involving immobilized metal affinity chromatography (IMAC).

Following protein folding and AP, the GDF15 was purified using a two-step chromatography train. The adjusted AP was applied to an IMAC column that is equilibrated with buffered chaotrope containing a low salt concentration at pH 8.5. The column was next washed with equilibration buffer until a baseline ultraviolet (UV) level is obtained. Product and contaminants are eluted by step-wise increases in displacer concentration and the elutions were collected and subsequently assayed by Coomasie-stained SDS-PAGE (sodium dodecyl sulfate polyacrylamide gel electrophoresis) to identify which eluate fractions contained a polypeptide that migrates at the predicted molecular weight of GDF15. After the IMAC was completed, the pooled fraction containing product is adjusted to pH 7.2 and 5 mM EDTA at 25 C. The product was converted into the mature length GDF15 by adding a low concentration of an enzyme to cleave off the affinity tag at 25 C for several hours. The cleavage reaction mixture was adjusted with an organic modifier and acidic pH by the addition of acetic acid and organic solvent. This allowed for the final chromatography step consisting of a linear gradient elution of product from a reverse phase column conducted at 25 C. The elution from the chromatography was collected as fractions and then assayed by SDS-PAGE to determine the appropriate fractions to pool for homogeneous product. The resulting pool was buffer exchanged by diafiltration into a weakly acidic buffer, concentrated by ultra-filtration, sterile filtered, and finally stored at 5 C or frozen.

Example 2

Suppression of Food Intake in Hyperphagic Ob/Ob Mice by Fc Fusion GDF15 Proteins GDF15 reduces food intake in hyperphagic ob/ob mice, and a food intake assay was used to evaluate efficacy of different forms of GDF15 analogs. As the half-life of human GDF15 polypeptide in mouse was observed to be approximately 3 hours, an Fc fusion strategy was used to extend protein half-life. Different Fc fusion GDF15 polypeptides were generated and analyzed for in vivo GDF15 activity, by introducing the Fc fusion GDF15 and wild type GDF15 polypeptides into hyperphagic leptin-deficient ob/ob mice, and measuring the ability of a particular Fc fusion GDF15 polypeptide to suppress food intake in these animals. The Fc fusion GDF15 polypeptide to be tested was injected subcutaneously into a 7-8 week old ob/ob mouse (Jackson Laboratory) between 4-5 pm on day 0. Animals were transferred after injection to cages where food had been premeasured, and food intake was measured between 9-10 AM the next day.

The results of representative experiments for wild type GDF15 and each Fc fusion GDF15 polypeptide are provided in FIGS. 3-21, which show dose response curves in the food intake assay for the dimers of the charged pair (delHinge) constructs: DhCpmFc(−)-($G_4S$)$_4$-GDF15:DhCpmFc(+); DhCpmFc(+)-($G_4S$)$_4$-GDF15:DhCpmFc(−); DhCpmFc(−)-($G_4S$)$_4$-GDF15:DhCpmFc(+); DhCpmFc(+)-($G_4S$)$_4$-GDF15 (H6D):DhCpmFc(−); DhCpmFc(+)-($G_4S$)$_4$-GDF15 (N3Q):DhCpmFc(−); DhCpmFc(+)-GDF15:DhCpmFc(−); DhCpmFc(+)-$G_4$-GDF15:DhCpmFc(−); DhCpmFc(+)-($G_4S$)$_2$-GDF15:DhCpmFc(−); DhCpmFc(+)-($G_4Q$)$_4$-GDF15:DhCpmFc(−); DhCpmFc(+)-(1K)-GDF15:DhCpmFc(−); DhCpmFc(+)(L351C)-($G_4S$)$_4$-GDF15:DhCpmFc(−)(L351C); and DhCpmFc(+)(S354C)-($G_4S$)$_4$-GDF15:DhCpmFc(−) (Y349C); dimers of the charged pair construct DhCpmFc(+)(S354C)-($G_4S$)$_4$-GDF15:DhCpmFc(−) (Y349C); dimers of the hemiFc constructs Fc-($G_4S$)$_8$-Fc-GS($G_4S$)$_4$-GDF15; Fc-($G_4S$)$_3$-Fc-GS($G_4S$)$_4$-GDF15; and Fc-($G_4S$)$_5$-Fc-GS($G_4S$)$_4$-GDF15; native mature hGDF15 homodimer; and mature hGDF15(H6D) variant homodimer.

These experiments demonstrated that the dimers of the charged pair (delHinge), charged pair and hemiFc constructs exhibit a decrease in food intake in ob/ob mice, with greater potency than those of the native mature hGDF15 homodimer The food intake measurement was taken 17 hours after a single injection of the polypeptides, and the stronger potency and efficacy may have resulted from an extended half-life of the Fc fusion polypeptides.

Example 3

Improvement of Lipid Tolerance by Fc Fusion GDF15 Constructs

Dimers of charged pair (delHinge) and hemiFc constructs were analyzed for in vivo GDF15 activity, by introducing these constructs, as well as native mature hGDF15 homodimer, into obese B6D2F1 mice (obesity was induced by feeding the mice a 60% high fat diet), and measuring the ability of each particular polypeptide or construct to improve oral lipid tolerance in these animals.

Male B6D2F1 mice were fed 60% high fat diet (Research Diets D12492i) at 5 weeks old for 6-10 weeks and were stratified by body weight and 3 hour fasting serum triglyceride levels 2-4 days before study. On the day of the study, a dimer of the DhCpmFc(−)-($G_4S$)$_4$-GDF15:DhCpmFc(+) construct (see Section II.B.1), a dimer of Fc-($G_4S$)$_8$-Fc-GS($G_4S$)$_4$-GDF15 construct (see Section II.D.1), and native mature hGDF15 homodimer were injected intravenously into mice that had been fasted for 3 hours. In the dose response studies for native mature hGDF15 or or mature hGDF15(H6D) variant, proteins were injected subcutaneously. Three hours after protein injection, 20% Intralipid was orally administered at 20 ml/kg. Another 90 min later, blood samples were collected through tail bleeding and serum triglyceride levels were measured.

Figure 22:
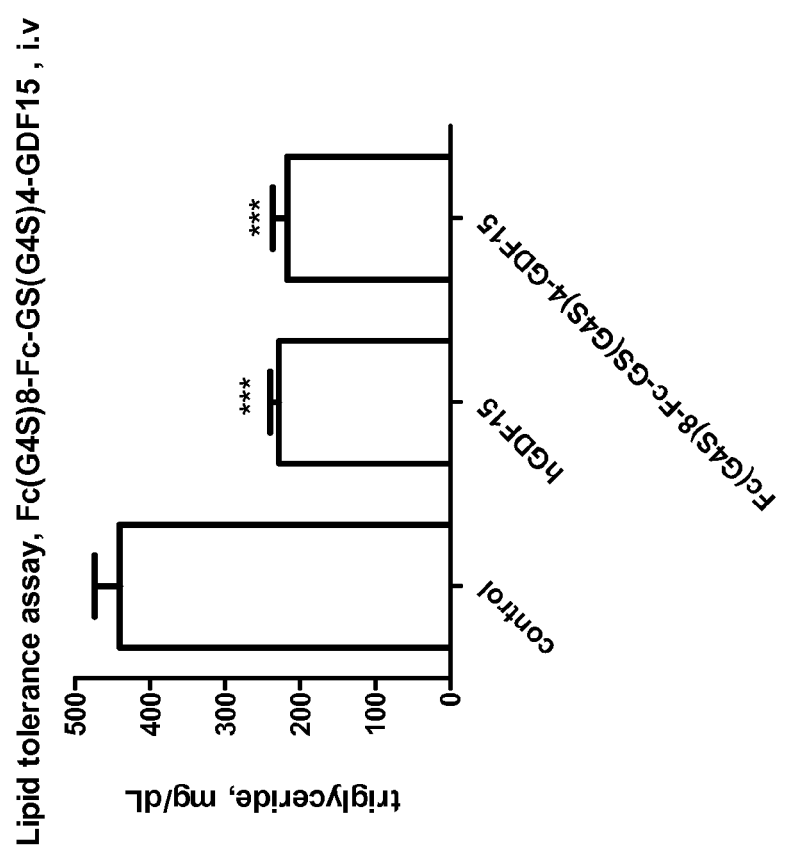
FIG. 22 is a bar graph of the results of a lipid tolerance assay showing the effect on triglyceride (mg/dL) for native mature GDF15 dimer (1 mg/kg, i.v.), a dimer of the Fc-($G_4S$)-8-Fc-GS($G_4S$)$_4$-GDF15 construct (1 mg/kg, i.v.) and control.
Figure 23:
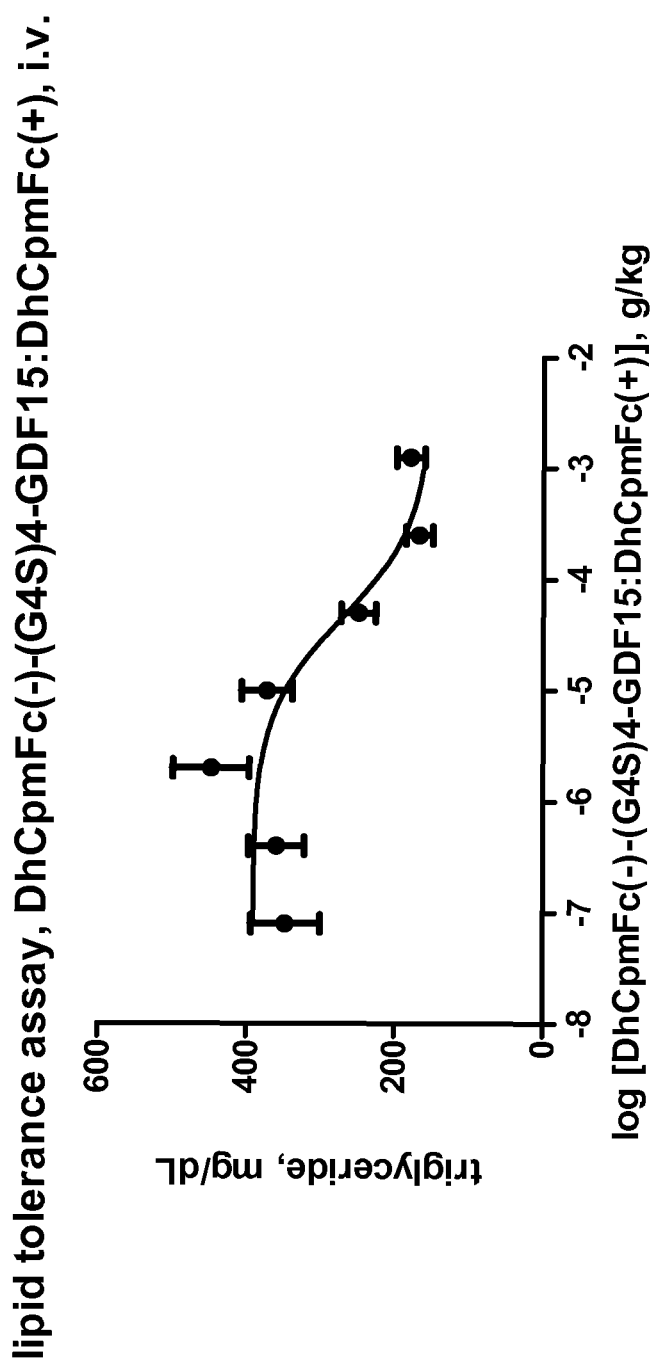
FIG. 23 is a plot of the results of a lipid tolerance assay using a dimer of the DhCpmFc(−)-($G_4S$)$_4$-GDF15:DhCpmFc(+) construct, showing effect on triglyceride (mg/dL) as a function of dose (log [g construct/kg BW]).
Figure 24:
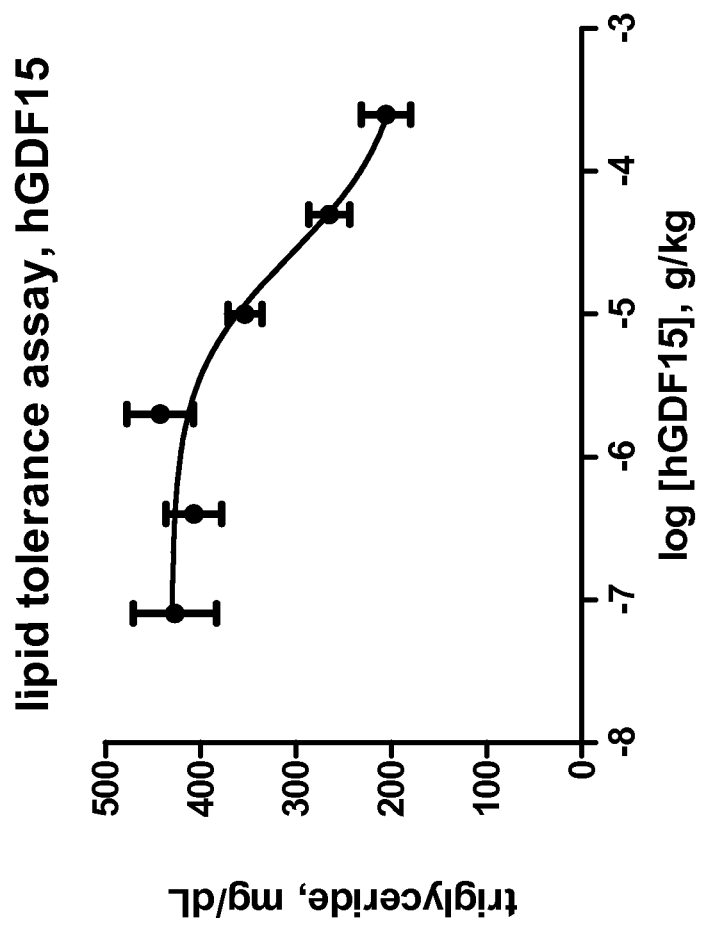
FIG. 24 is a plot showing the results of a lipid tolerance assay using a dimer of the native mature hGDF15.
Figure 25:
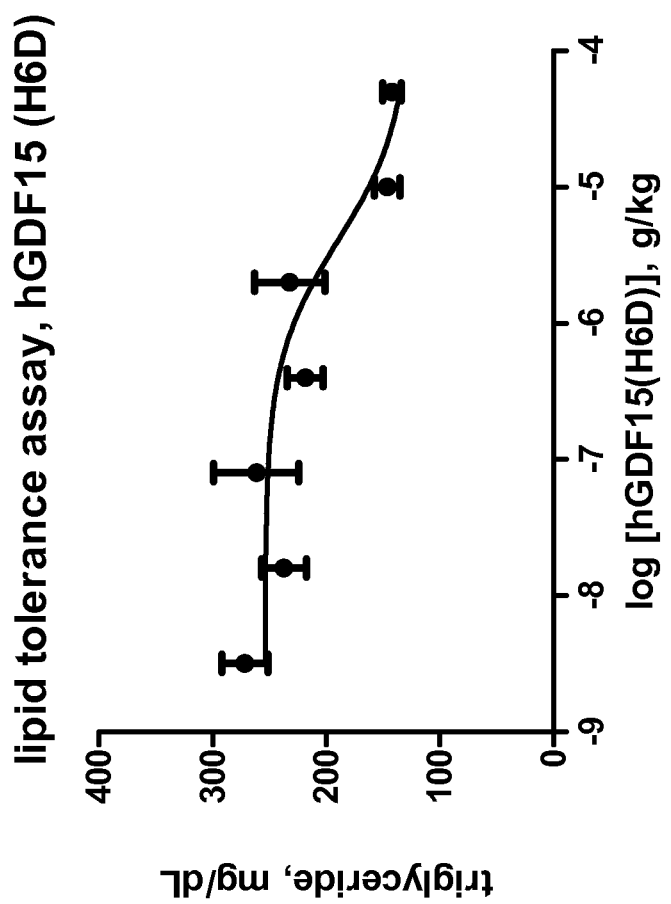
FIG. 25 is a plot showing the results of a lipid tolerance assay using a dimer of the mature hGDF15(H6D) variant.
Figure 26:
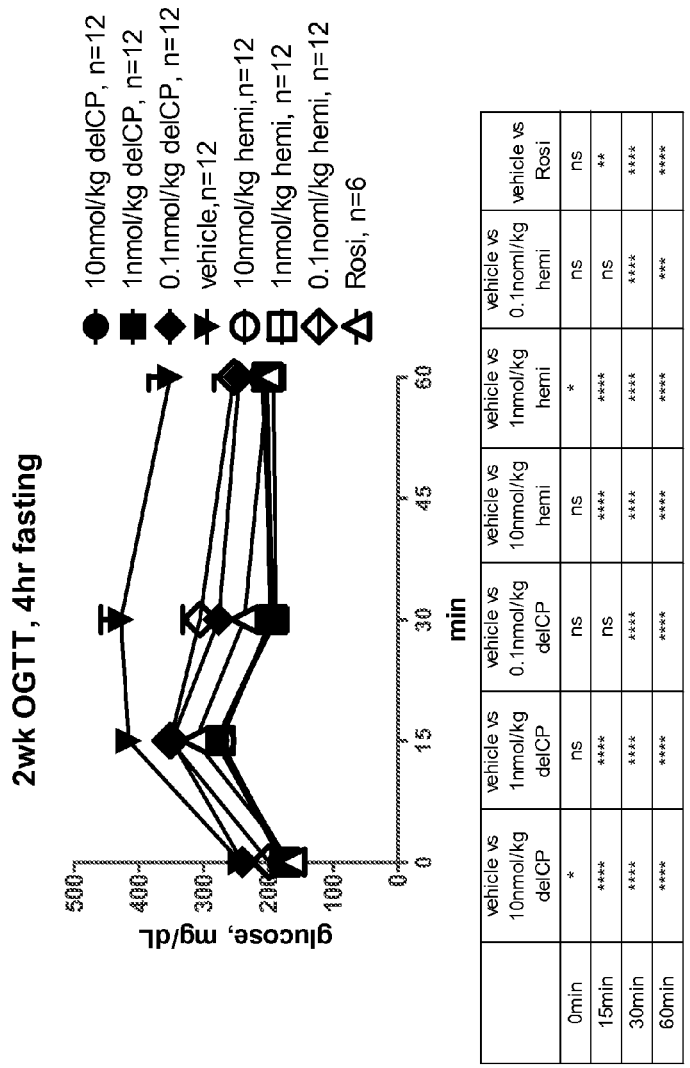
FIG. 26 is plot showing the results of a two week OGTT performed using a dimer of the DhCpmFc(−)-($G_4S$)$_4$-GDF15:DhCpmFc(+) construct, a dimer of the Fc-($G_4S$)$_8$-Fc-GS($G_4S$)$_4$-GDF15 construct and rosiglitizone (Rosi) in DIO (diet-induced obese) mice.
Figure 27:
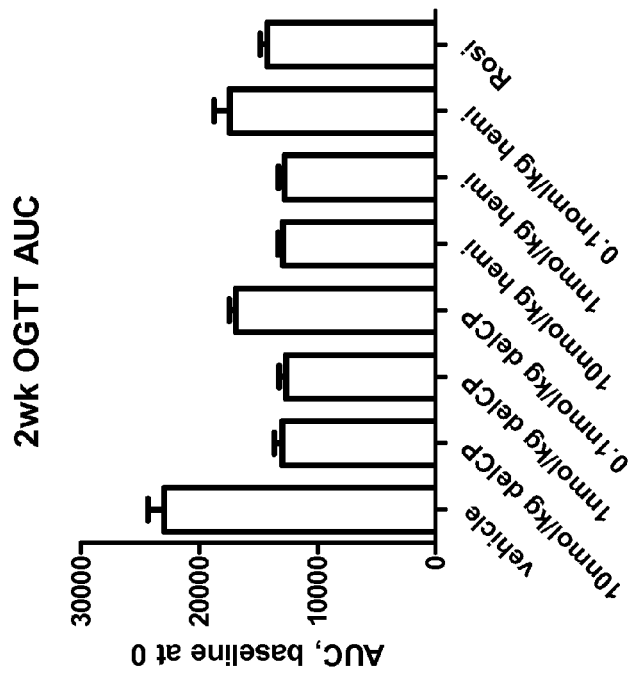
FIG. 27 is bar graph summarizing the data of FIG. 26 in the form of AUC data.

The results of representative experiments involving the native mature hGDF15 homodimer, the mature hGDF15 (H6D) variant homodimer, the dimer of the DhCpmFc(−)-($G_4S$)$_4$-GDF15:DhCpmFc(+) construct, and the dimer of the Fc-($G_4S$)$_8$-Fc-GS($G_4S$)$_4$-GDF15 construct are shown in FIGS. 22-25. In FIGS. 23-25, the native mature hGDF15 homodimer, the mature hGDF15(H6D) variant and the dimer of the DhCpmFc(−)-($G_4S$)$_4$-GDF15:DhCpmFc(+) construct improved lipid tolerance in a dose dependent fashion. In FIG. 22, the native mature hGDF15 homodimer and the dimer of the Fc-($G_4S$)$_8$-Fc-GS($G_4S$)$_4$-GDF15 construct are shown to be efficacious in the same assay at 1 mg/kg IV dose.

Example 4

Chronic Efficacy of hGDF15 and Constructs Comprising hGDF15 in DIO Mice

GDF15 lowers blood glucose, insulin, triglyceride, or cholesterol levels; reduces body weight; or improves glucose tolerance and insulin sensitivity. To assess the ability of hGDF15 and various Fc fusion GDF15 constructs to improve these parameters, chronic studies were performed.

Example 4.1 Study Design

Two separate studies were conducted to evaluate the chronic efficacy of different Fc fusion GDF15 polypeptides. The first study (Study #1) included the dimer of the DhCpmFc(−)-(G$_4$S)$_4$-GDF15:DhCpmFc(+) construct (see Section II.B.1) and the dimer of the Fc-(G$_4$S)$_8$-Fc-GS(G$_4$S)$_4$-GDF15 construct (see Section II.D.1). In this study, the dimer of the charged pair (delHinge) construct and the dimer of the hemiFc constructs were administered chronically and subcutaneously into male C57Bl/6 mice (HAR) fed 60 Kcal % high fat diet (Research Diets) at 4 weeks of age for 16 weeks. Animals were acclimated to single housing conditions for 6 weeks. Weekly handling and subcutaneous injection of saline were performed for 3 weeks prior to administration of any test compound. Mice were divided into 7 groups of 12 and one group of 6 based on weekly food intake, and body weight, 4 hr fasting blood glucose levels, 4 hr fasting serum insulin levels, triglyceride and cholesterol levels 2 days before the first protein injections. Three different dose levels were selected: 10, 1, 0.1 nmol/kg, which are equivalent to 1.29, 0.129, 0.0129 mg/kg for the dimer of the charged pair (delhinge) construct, or 1.35, 0.135, 0.0135 mg/kg for the dimer of the hemiFc construct. The dosing regimen of weekly dosing was selected based on mouse PK data. One group of 12 animals was subcutaneously injected with vehicle buffer weekly as control group. One group of 6 animals was subcutaneously injected with vehicle buffer and given diet containing 0.014% rosiglitazone to target 10 mg/kg oral daily dose as positive control. Studies were carried out for 5 weeks, with the last dose on day 28. The results are shown in FIGS. 26-38.

The second study (Study#2) included the dimer of the DhCpmFc(−)-(G$_4$S)$_4$-GDF15:DhCpmFc(+) construct (see Section II.B.1) and the dimer of the CpmFc(−)-(G$_4$S)$_4$-GDF15:CpmFc(+) construct (see Section II.C). In this study, the dimer of the charged pair (delHinge) construct and the dimer of the charged pair construct were administered chronically and subcutaneously into male C57Bl/6 mice (HAR) fed 60 Kcal % high fat diet (Research Diets) at 4 weeks of age for 15 weeks. Animals were acclimated to single housing conditions for 5 weeks. Weekly handling and subcutaneous injection of saline were performed for 3 weeks prior to administration of any test compound. Mice were divided into groups of 12 based on weekly food intake, and body weight, 4 hr fasting blood glucose levels, 4 hr fasting serum insulin, triglyceride and cholesterol levels 4 days before the first protein injection. Three different dose levels were selected at 10, 1, 0.1 nmol/kg, equivalent to 1.25, 0.125, 0.0125 mg/kg for the dimer of the charged pair construct. Two different dose levels were selected at 10 and 1 nmol/kg, equivalent to 1.29 and 0.129 mg/kg, for the dimer of the charged pair (delHinge) construct. Dosing regimen of weekly dosing was selected based on mouse PK data. One group of 12 animals was subcutaneously injected with vehicle buffer weekly as control group. One group of 6 animals was subcutaneously injected with vehicle buffer and given diet containing 0.014% rosiglitazone to target 10 mg/kg oral daily dose as positive control. Studies were carried for 5 weeks with the last dose on day 28. The results are shown in FIGS. 39-54.

Body weight and food intake were measured weekly throughout the study. One oral glucose tolerance tests (OGTT) was performed 2 weeks after the first protein injection in animals fasted for 4 hours. One oral glucose tolerance tests (OGTT) was performed 5 weeks after the first protein injection in animals fasted for 16 hours. Blood samples were collected from 4 hr fasted animals at 2 and 4 weeks after first protein injection, from animals with free access to food 3 weeks after the first protein injection, and from animals fasted for 16 hr 5 weeks after the first protein injection. Serum samples were used to measure insulin, triglyceride and cholesterol levels, as well as the levels of test compound.

Example 4.2 Effect of Test Compounds on Body Weight

Body weight was followed weekly throughout the study, both pre- and post-administration of test compounds. Body weight from baseline of the vehicle animals increased with time, whereas body weight of animals treated with 10 or 1 nmol/kg of the dimer of the charged pair (delHinge) construct, the dimer of the charged pair construct and the dimer of the hemiFc construct decreased over the course of the 5 week treatment period and started to come back during the compound wash-out phase, as shown in FIGS. 30 and 43. The change of body weight in animals treated with 1 nmol/kg of the dimer of the charged pair (delHinge) construct, the dimer of the charged pair construct and the dimer of the hemiFc constructs did not reach statistical significance.

Example 4.3 Effect of Test Compounds on Food Intake

Food intake was measured every week. Average daily food intake was calculated by dividing weekly food intake by 7. At 10 nmol/kg, the dimer of the charged pair (delHinge) construct, the dimer of the charged pair construct and the dimer of the hemiFc construct lowered food intake, with statistical significance in most weekly measurements, as demonstrated in FIGS. 31 and 44. The effect at 1 nmol/kg dose was less significant, but a trend was clear. The food intake in animals treated with 1 nmol/kg of each of the three constructs (i.e., the dimer of the charged pair (delHinge) construce, the dimer of the charged pair construct and the dimer of the hemiFc constructs) were lower compared to food intake in animals treated with vehicle buffer.

Example 4.4 Effect of Test Compounds on Glucose and OGTT

OGTTs (OGTT1 and OGTT2) were performed after treatment was initiated. OGTT1 was conducted 14 days after the first protein injection, in animals fasted for 4 hr from 6 am. 4 hr fasting glucose levels before the oral glucose challenge were compared with the baseline 4 hr fasting glucose levels measured 2 days or 4 days before protein injection (FIGS. 32 and 45). The glucose profile of OGTT1 is shown in FIGS. 26, 27, 39 and 40. Animals treated with 10 and 1 nmol/kg of the dimer of the charged pair (delHinge) construct, the dimer of the charged pair Fc-hGDF15 construct or the dimer of the hemiFc constructs exhibited improved glucose levels and oral glucose tolerance when compared to vehicle treated animals, as demonstrated by glucose levels before and during OGTT and glucose AUC during the OGTT. Animals treated with 0.1 nmol/kg of the dimer of the charged pair (delHinge) construct, the dimer of the charged pair construct and the dimer of the hemiFc construct exhibited improved glucose tolerance, but the improvement in glucose levels in these animals was not as significant. The improved glucose tolerance in 0.1 nmol/kg dimer of the hemiFc construct treated animals 2 weeks after the first protein injection is indicative of improved glucose tolerance independently from body weight or food intake changes, since these animals have similar body weight and food intake to vehicle treated animals.

OGTT2 was conducted 35 days after the first protein injection, 7 days after the last protein injection, in animals fasted for 16 hr from 5 pm the day before the oral glucose challenge. The glucose profile of OGTT2 is shown in FIGS. 28, 29, 41 and 42. Treatment with 10, 1, or 0.1 nmol/kg of each of the three constructs (i.e., the dimer of the charged pair (delHinge) construct, the dimer of the charged pair construct and the dimer of the hemiFc construct) for 5 weeks significantly improved oral glucose tolerance, as demonstrated by glucose levels and glucose curve AUC during the OGTT.

Example 4.5 Effect of Test Compounds on Insulin

Insulin levels were measured in blood samples that had been collected from 4 hr fasted animals on day 4, day 14 and day 28, from animals with free access to food on day 21, and from animals fasted for 16 hr on day 35. Mice consume majority of their food during the dark cycle. The protocol of 4 hr fasting from 6 am was used for longitudinal comparison within the same group to remove variation induced by nibbling of food during the light cycle. Observed insulin levels are shown in FIGS. 33, 34 and 46-48.

The 4 hr fasting insulin levels in vehicle treated animals increased over time, as insulin resistance further progresses in these animals. Treatment with 10 or 1 nmol/kg of the dimer of the charged pair (delHinge) construct, the dimer of the charged pair construct or the dimer of the hemiFc construct brought insulin levels to levels lower than where the animals started before the treatment was initiated, indicative of a reversal of high fat diet-induced insulin resistance. 0.1 nmol/kg dosage prevented the increase of insulin levels over time.

All three Fc fusion GDF15 constructs also demonstrated similar dose-dependent improvement in insulin levels in animals fasted overnight on day 35. Data collected for Study #2 demonstrated that the dimer of the charged pair (delHinge) construct and the dimer of the charged pair construct lower insulin levels in animals with free access to food.

Example 4.6 Effect of Test Compounds on Triglyceride Levels

Triglyceride levels were measured in blood samples that had been collected from 4 hr fasted animals at day −4, day 14 and day 28, from animals with free access to food on day 21, and from animals fasted for 16 hr on day 35. Mice consume majority of their food during the dark cycle. The protocol of 4 hr fasting from 6 am was used for longitudinal comparison within the same group to remove variation induced by nibbling of food during the light cycle.

The effect of the dimer of the charged pair (delHinge) construct, the dimer of the charged pair construct and the dimer of the hemiFc constructs on triglyceride levels in animals fasted for 4 hr or 16 hr were not robust but statistically significant, as demonstrated in FIGS. 35, 36, 49 and 51. At 10 nmol/kg, the dimer of the charged pair (delHinge) Fc-construct consistently lowered serum triglyceride levels at day 28 and day 35. Data collected from Study #2 demonstrated that in animals with free access to food, the effect of 10 and 1 nmol/kg of both the dimer of the charged pair (delHinge) construct and the dimer of the charged pair construct were statistically significant, as shown in FIG. 50. We have demonstrated in earlier sections that GDF15 improves oral lipid tolerance. The observation of more potent efficacy in lowering serum triglyceride levels in animals with free access food may indicate improvement of postprandial lipid profile and may have resulted from the improvement in oral/diet lipid tolerance.

Example 4.7 Effect of Test Compounds on Cholesterol Levels

Total cholesterol levels were measured in blood samples that had been collected from 4 hr fasted animals at day −4, day 14 and day 28, from animals with free access to food on day 21, and from animals fasted for 16 hr on day 35. Mice consume majority of their food during the dark cycle. The protocol of 4 hr fasting from 6 am was used for longitudinal comparison within the same group to remove variation induced by nibbling of food during the light cycle.

All three constructs (i.e., the dimer of the charged pair (delHinge) construct, the dimer of the charged pair construce and the dimer of the hemiFc construct) dose-dependently lowered total cholesterol levels, and this effect was impacted by the feeding state of the animals, as demonstrated in FIGS. 37, 38 and 52-54.

Conclusions From Example 4

All three constructs, namely the dimer of the charged pair (delHinge) construct, the dimer of the charged pair construct and the dimer of the hemiFc construct, demonstrated efficacy in improving various metabolic parameters, including body weight, blood glucose levels and glucose tolerance, serum insulin levels, serum cholesterol levels, serum triglyceride levels and oral lipid tolerance. The polypeptides were injected once per week, and efficacy was dose-dependent, with 10 nom/kg dosage demonstrating the most robust efficacy.

Example 5

Chronic Efficacy of hGDF15 and Constructs Comprising hGDF15 in Obese Cynomolgous Monkey The charged pair (delHinge) construct "DhCpmFc(−)-$(G_4S)_4$-GDF15:DhCpmFc(+)" and the hemiFc construct "Fc-$(G_4S)_8$-Fc-GS$(G_4S)_4$-GDF15" were analyzed for in vivo GDF15 activity by introducing these constructs, as well as vehicle (A4.5Su) into obese cynomolgous monkeys.

Example 5.1 Study Design

The study was conducted in cynomolgous monkeys. The monkeys were 11-14 years old. Their body weights ranged from 7-10 kg and BMI ranged from 38-58 kg/m$^2$. 40 monkeys were acclimated for 6 weeks prior to the initiation of compound administration. During the acclimation period, monkeys were trained 4 times a week for 6 weeks to familiarize the procedures including chair-restrain, subcutaneous injection (PBS, 0.1 ml/kg), gavage (Water, 10 ml/kg), blood drawn for non OGTT and OGTT samples. During 6 weeks of training, baseline OGTT and plasma metabolic parameters were measured. 30 out of 40 monkeys were selected and randomized into three treatment groups to achieve similar baseline levels of body weight, OGTT AUC response, and plasma glucose, insulin and triglyceride levels.

The study was conducted in a blind fashion. Vehicle (n=10), dimer of the DhCpmFc(−)-$(G_4S)_4$-GDF15:DhCpmFc(+) construct (n=10) and dimer of the Fc-$(G_4S)_8$-Fc-GS$(G_4S)_4$-GDF15 construct (n=10) were labeled as compound A, B and C and administered once a week via subcutaneous injection. Compounds were given at 1.5 mg/kg/week. After 6 weeks of compound treatments, animals were monitored for additional 5 weeks for compound washout and recovery from treatments. Food intake, body weight, clinical chemistry and OGTT were monitored throughout the study. Food intake was measured at every meal. Body weight was measured weekly. Blood samples were collected weekly 6 days post each injection to measure glucose, triglyceride. OGTTs were conducted on day 13, 34 and 55 after the initiation of treatments. The day starting the treatment is designated as 0 and the detailed study design is shown in FIG. 55.

The results shown in this example are data collected at the end of 6 weeks treatment and during the washout.

Example 5.2 Compounds Exposure

Compounds (dimer of the DhCpmFc(−)-$(G_4S)_4$-GDF15:DhCpmFc(+) construct and dimer of the Fc-$(G_4S)_8$-Fc-GS$(G_4S)_4$-GDF15 construct) exposure measurements were performed on samples collected after an overnight fast and the day after in non fasted animals. These measurements were made every week during the treatment and washout phase. The dimer of the DhCpmFc(−)-$(G_4S)_4$-GDF15:DhCpmFc(+) construct showed a greater exposure than the dimer of the Fc-$(G_4S)_8$-Fc-GS$(G_4S)_4$-GDF15 construct. Two out of ten animals in the dimer of the DhCpmFc(−)-$(G_4S)_4$-GDF15:DhCpmFc(+) construct group presented antibody whereas five out of ten animals were identified in the dimer of the Fc-$(G_4S)_8$-Fc-GS$(G_4S)_4$-GDF15 construct group. The loss of pharmacodynamic responses in suspected animals with antibody correlates with loss of drug exposure. The exposure levels for each compound are shown in FIG. 56.

Example 5.3 Effect of Test Compounds on Oral Glucose Tolerance Test (OGTT)

OGTTs were conducted before and after initiation of treatments. FIGS. 57-64 show pre- and post-OGTT area under the OGTT curve (AUC). Acclimation OGTT was performed before the treatment was initiated, post-dose OGTTs were performed on week 2 and week 5 and washout OGTT was performed on week 8 (3 weeks after the last dose). Glucose and insulin (AUC) were measured for glucose (FIGS. 57-60) and insulin (FIGS. 61-64). The dimer of the DhCpmFc(−)-$(G_4S)_4$-GDF15:DhCpmFc(+) construct significantly improved OGTT glucose AUC on week 2 and the dimer of the Fc-$(G_4S)_8$-Fc-GS$(G_4S)_4$-GDF15 construct on week 5. OGTT Glucose AUC was still improved on week 8 (during washout phase with the dimer of the Fc-$(G_4S)_8$-Fc-GS$(G_4S)_4$-GDF15) construct. OGTT insulin AUC was significantly ameliorated on week 2 and 5 for the dimer of the Fc-$(G_4S)_8$-Fc-GS$(G_4S)_4$-GDF15 construct and on week 2 only for the dimer of the DhCpmFc(−)-$(G_4S)_4$-GDF15:DhCpmFc(+) construct.

Example 5.4 Effect of Test Compounds on Fasting Insulin Levels

Blood was collected from overnight fasted animals. The blood drawn was conducted weekly at 6 days post each injection. Both the dimer of the DhCpmFc(−)-$(G_4S)_4$-GDF15:DhCpmFc(+) construct and the dimer of the Fc-$(G_4S)_8$-Fc-GS$(G_4S)_4$-GDF15 construct reduced fasting blood insulin levels. This effect was not seen during the washout period. FIG. 68 shows the levels of fasting insulin during the course of the study.

Example 5.5 Effect of Test Compounds on Food Intake

Animals were fed twice a day and food intake was recorded at each meal. The feeding times were from 8:00 AM to 9:00 AM (±30 minutes) and then from 4:00 PM to 5:00 PM (±30 minutes). Apple (150 g) was supplied to each animal at 1:30-2:30 PM (±30 minutes) every day.

Compared with vehicle, both the dimer of the DhCpmFc(−)-$(G_4S)_4$-GDF15:DhCpmFc(+) construct and the dimer of the Fc-$(G_4S)_8$-Fc-GS$(G_4S)_4$-GDF15 construct reduced food intake in monkeys (FIG. 66). However, the effect diminished and the food intake returned close to baseline or control levels after about 30 days of treatment.

Example 5.6 Effect of Test Compounds on Triglyceride Levels

Blood was collected from overnight fasted animals. The blood drawn was conducted weekly at 6 days post each injection. Triglyceride levels were significantly reduced in animals treated with the dimer of the DhCpmFc(−)-$(G_4S)_4$-GDF15:DhCpmFc(+) construct and the dimer of the Fc-$(G_4S)_8$-Fc-GS$(G_4S)_4$-GDF15 construct throughout the treatment phase. This effect diminished during the washout period. FIG. 67 shows the levels of fasting plasma triglycerides during the course of the study.

Example 5.7 Effect of Test Compounds on Body Weight

Body weight was monitored weekly throughout the study. Over the course of the 6 week treatments, the body weight of animals treated with vehicle remained constant or slightly increased while body weight of animals treated with the dimer of the DhCpmFc(−)-$(G_4S)_4$-GDF15:DhCpmFc(+) construct and the dimer of the Fc-$(G_4S)_8$-Fc-GS$(G_4S)_4$-GDF15 construct progressively decreased as shown in FIG. 65.

Conclusions from Example 5

In a study conducted in male obese cynomolgous monkeys, animals treated with the dimer of the DhCpmFc(−)-$(G_4S)_4$-GDF15:DhCpmFc(+) construct and the dimer of the Fc-$(G_4S)_8$-Fc-GS$(G_4S)_4$-GDF15 construct showed improved metabolic parameters. Body weight was reduced. Short-term reduction of food intake was observed and the effect diminished and the food intake recovered to baseline or control levels at the mid term of the study. Fasting triglyceride levels were also reduced by both compounds, the dimer of the DhCpmFc(−)-$(G_4S)_4$-GDF15:DhCpmFc(+) construct and the dimer of the Fc-$(G_4S)_8$-Fc-GS$(G_4S)_4$-GDF15 construct. OGTT glucose and insulin AUC were improved.

While the present invention has been described in terms of various embodiments, it is understood that variations and modifications will occur to those skilled in the art. Therefore, it is intended that the appended claims cover all such equivalent variations that come within the scope of the invention as claimed. In addition, the section headings used herein are for organizational purposes only and are not to be construed as limiting the subject matter described.

All references cited in this application are expressly incorporated by reference herein for any purpose.

```

What is claimed is:

1. A fusion protein comprising:
   (a) a GDF15 polypeptide comprising the amino acid sequence of SEQ ID NOs: 12, 14 or a variant thereof, wherein the variant is a GDF15(H6D) variant comprising the amino acid sequence of SEQ ID NO: 38, or a GDF15(N3Q) variant comprising the amino acid sequence of SEQ ID NO: 42: and
   (b) a negatively charged Fc sequence comprising two lysine-to-aspartate mutations.

2. The fusion protein of claim 1, wherein the Fc sequence comprises an amino acid sequence selected from the group consisting of SEQ ID NOs: 19, 23, 86, 91, 100, 108, 111, and 115.

3. A dimer comprising the fusion protein of claim 1, and a second Fc sequence comprising a charged pair mutation, wherein the second Fc sequence is a positively charged Fc sequence.

4. The fusion protein of claim 1, fused to a second Fc sequence comprising a charged pair mutation.

5. The fusion protein of claim 1, wherein the GDF15 polypeptide and the Fc sequence are joined by a linker.

6. The fusion protein of claim 5, wherein the fusion protein comprises an amino acid sequence selected from the group consisting of SEQ ID NOs: 44, 57, and 113.

7. The fusion protein of claim 4, wherein the second Fc sequence comprises an amino acid sequence selected from the group consisting of SEQ ID NOs:18, 19, 23, 85, 86, 89, 90, 91, 99, 100, 108, 109, 110, 111, 114 and 115.

8. The dimer of claim 3, wherein the second Fc sequence comprises an amino acid sequence the selected from the group consisting of SEQ ID NOs: 18, 85, 89, 90, 99, 109, 110, and 114.

9. The dimer of claim 8, comprising:
   (a) an Fc sequence comprising the amino acid sequence of SEQ ID NO: 18 and a fusion protein comprising the amino acid sequence of SEQ ID NO: 44;
   (b) an Fc sequence comprising the amino acid sequence of SEQ ID NO: 18 and a fusion protein comprising the amino acid sequence of SEQ NO: 113: or
   (c) an Fc sequence comprising the amino acid sequence of SEQ ID NO: 18 and a fusion protein comprising the amino acid sequence of SEQ ID NO: 57.

10. A tetramer comprising the dimer of claim 3.

11. The dimer of claim 3, wherein the dimer comprises an Fc sequence comprising the amino acid sequence of SEQ ID NO: 110 and a fusion protein comprising the amino acid sequence of SEQ ID NO: 113.

12. A tetramer comprising the dimer of claim 11.

13. The fusion protein of claim 5, wherein the linker comprises an amino acid sequence selected from the group consisting of SEQ ID NOs: 20, 31, 34, 80, 87, 88 and 131.

14. The fusion protein of claim 1, wherein the C-terminus of the GDF polypeptide is joined to the N-terminus of the Fc sequence.

15. The fusion protein of claim 14, further comprising a second Fc sequence, wherein the C-terminus of the fusion protein is joined to the C-terminus of the second Fc sequence.

16. The fusion protein of claim 15, wherein the fusion protein comprises an amino acid sequence selected from the group consisting of SEQ ID NOs: 33, 123, and 128.

17. The fusion protein of claim 3, wherein the charged pair mutation is an aspartic acid to lysine mutation or a glutamic acid to lysine mutation.

18. The fusion protein of claim 3, wherein the wherein the second Fc sequence comprises an aspartic acid to lysine mutation and a glutamic acid to lysine mutation.

* * * * *